US011292848B2

(12) United States Patent
Watkins et al.

(10) Patent No.: US 11,292,848 B2
(45) Date of Patent: Apr. 5, 2022

(54) HUMANIZED ANTIBODIES TO TNF-LIKE LIGAND 1A (TL1A) AND USES THEREOF

(71) Applicants: PROMETHEUS BIOSCIENCES, INC., San Diego, CA (US); CEDARS-SINAI MEDICAL CENTER, Los Angeles, CA (US)

(72) Inventors: Jeffry D. Watkins, Encinitas, CA (US); Cindy T. Dickerson, Encinitas, CA (US); Rafael Rojas, San Marcos, CA (US); Matthew Reissman, San Diego, CA (US); Patricia McNeeley, San Diego, CA (US); Janine Bilsborough, Adelaide (AU); Bradley Henkle, West Hollywood, CA (US); Stephan R. Targan, Santa Monica, CA (US)

(73) Assignees: Prometheus Biosciences, Inc., San Diego, CA (US); Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 17/110,004

(22) Filed: Dec. 2, 2020

(65) Prior Publication Data

US 2021/0122828 A1 Apr. 29, 2021

Related U.S. Application Data

(63) Continuation of application No. PCT/US2020/057119, filed on Oct. 23, 2020.

(60) Provisional application No. 62/925,736, filed on Oct. 24, 2019.

(51) Int. Cl.
| | | |
|---|---|---|
| C07K 16/24 | (2006.01) | |
| C07K 16/28 | (2006.01) | |
| A61P 1/04 | (2006.01) | |
| C07K 14/52 | (2006.01) | |
| C07K 14/525 | (2006.01) | |
| A61K 39/395 | (2006.01) | |

(52) U.S. Cl.
CPC ............ *C07K 16/2875* (2013.01); *A61P 1/04* (2018.01); *C07K 16/241* (2013.01); *C07K 2317/21* (2013.01); *C07K 2317/24* (2013.01); *C07K 2317/40* (2013.01); *C07K 2317/76* (2013.01)

(58) Field of Classification Search
CPC .............. C07K 2317/76; C07K 16/241; C07K 2317/565; C07K 2317/56; C07K 16/24; C07K 2317/567; A61K 2039/505; A61K 39/3955
See application file for complete search history.

(56) References Cited

U.S. PATENT DOCUMENTS

| | | |
|---|---|---|
| 4,518,584 A | 5/1985 | Mark et al. |
| 4,737,462 A | 4/1988 | Mark et al. |
| 4,946,778 A | 8/1990 | Ladner et al. |
| 5,225,539 A | 7/1993 | Winter |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,624,821 A | 4/1997 | Winter et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,861,155 A | 1/1999 | Lin |
| 5,885,793 A | 3/1999 | Griffiths et al. |
| 5,969,108 A | 10/1999 | McCafferty et al. |
| 6,172,197 B1 | 1/2001 | McCafferty et al. |
| 6,194,551 B1 | 2/2001 | Idusogie et al. |
| 6,297,367 B1 | 10/2001 | Tribouley |
| 6,300,064 B1 | 10/2001 | Knappik et al. |
| 6,407,213 B1 | 6/2002 | Carter et al. |
| 6,479,284 B1 | 11/2002 | Marasco et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,599,719 B2 | 7/2003 | Yu et al. |
| 6,632,976 B1 | 10/2003 | Tomizuka et al. |
| 6,653,068 B2 | 11/2003 | Frisch et al. |
| 6,706,484 B1 | 3/2004 | Knappik et al. |
| 6,824,767 B2 | 11/2004 | Yu et al. |
| 6,824,989 B1 | 11/2004 | Eisinger et al. |
| 6,835,823 B2 | 12/2004 | Le et al. |
| 7,264,963 B1 | 9/2007 | Knappik et al. |
| 7,597,886 B2 | 10/2009 | Yu et al. |

(Continued)

FOREIGN PATENT DOCUMENTS

| | | |
|---|---|---|
| EP | 2462165 B1 | 5/2016 |
| EP | 2638069 B1 | 1/2018 |

(Continued)

OTHER PUBLICATIONS

Kabat numbering for IGHV1-46*02; http://opig.stats.ox.ac.uk/webapps/newsabdab/sabpred/anarci/; accessed May 10, 2021.*
Kabat numbering for IGKV3-20*01; http://opig.stats.ox.ac.uk/webapps/newsabdab/sabpred/anarci/; accessed May 10, 2021.*
Adams et al., Two-stage genome-wide methylation profiling in childhood-onset Crohn's Disease implicates epigenetic alterations at the VMP1/MIR21 and HLA loci. Inflamm Bowel Dis. 20(10):1784-1793 (2014).

(Continued)

*Primary Examiner* — Bridget E Bunner
(74) *Attorney, Agent, or Firm* — Wilson Sonsini Goodrich & Rosati

(57) ABSTRACT

Described herein are humanized anti-TL1A antibodies and pharmaceutical compositions for the treatment of inflammatory bowel disease (IBD), such as Crohn's Disease (CD) and ulcerative colitis (UC).

20 Claims, 7 Drawing Sheets

Specification includes a Sequence Listing.

(56) References Cited

U.S. PATENT DOCUMENTS

| | | | |
|---|---|---|---|
| 7,612,181 | B2 | 11/2009 | Wu et al. |
| 7,700,739 | B2 | 4/2010 | Lacy et al. |
| 7,708,996 | B2 | 5/2010 | Yu et al. |
| 7,820,798 | B2 | 10/2010 | Yu et al. |
| 8,003,099 | B2 | 8/2011 | Auer et al. |
| 8,017,122 | B2 | 9/2011 | Siadak et al. |
| 8,093,363 | B2 | 1/2012 | Yu et al. |
| 8,263,743 | B2 | 9/2012 | Smith et al. |
| 8,409,577 | B2 | 4/2013 | Thompson et al. |
| 8,524,869 | B2 | 9/2013 | Smith et al. |
| 8,642,741 | B2 | 2/2014 | Classon et al. |
| 8,728,282 | B2 | 5/2014 | Niu |
| 8,728,475 | B2 | 5/2014 | Burkly et al. |
| 8,728,482 | B2 | 5/2014 | Smith et al. |
| 8,859,739 | B2 | 10/2014 | Kontermann et al. |
| 8,883,975 | B2 | 11/2014 | Brandt et al. |
| 9,017,679 | B2 | 4/2015 | Podack et al. |
| 9,068,003 | B2 | 6/2015 | Siegel et al. |
| 9,102,733 | B2 | 8/2015 | Endl et al. |
| 9,221,902 | B2 * | 12/2015 | Smider ............... C07K 16/00 |
| 9,290,576 | B2 | 3/2016 | Attinger et al. |
| 9,416,185 | B2 | 8/2016 | Smith et al. |
| 9,499,627 | B2 | 11/2016 | Podack et al. |
| 9,556,277 | B2 | 1/2017 | Classon et al. |
| 9,683,998 | B2 | 6/2017 | Arch et al. |
| 9,834,606 | B2 | 12/2017 | Li et al. |
| 9,839,670 | B2 | 12/2017 | Podack et al. |
| 9,896,511 | B2 | 2/2018 | Siegel et al. |
| 10,011,644 | B2 | 7/2018 | Rueger et al. |
| 10,138,296 | B2 | 11/2018 | Poulton et al. |
| 10,221,251 | B2 | 3/2019 | Humphreys et al. |
| 10,232,017 | B2 | 3/2019 | Gurney |
| 10,316,083 | B2 | 6/2019 | Michelsen et al. |
| 10,322,174 | B2 | 6/2019 | Bilsborough et al. |
| 10,464,981 | B2 | 11/2019 | Amann et al. |
| 10,526,413 | B2 | 1/2020 | Amann et al. |
| 10,689,439 | B2 | 6/2020 | Watkins et al. |
| 2002/0078757 | A1 | 6/2002 | Hines et al. |
| 2003/0017518 | A1 | 1/2003 | Lam et al. |
| 2003/0129189 | A1 | 7/2003 | Yu et al. |
| 2003/0166871 | A1 | 9/2003 | Barbas et al. |
| 2003/0198640 | A1 | 10/2003 | Yu et al. |
| 2004/0123343 | A1 | 6/2004 | La et al. |
| 2004/0132101 | A1 | 7/2004 | Lazar et al. |
| 2008/0177048 | A1 | 7/2008 | Gagnon |
| 2009/0042291 | A1 | 2/2009 | Chu et al. |
| 2009/0187005 | A1 | 7/2009 | Gagnon |
| 2009/0317388 | A1 | 12/2009 | Burkly et al. |
| 2011/0217310 | A1 | 9/2011 | Siegel et al. |
| 2011/0243951 | A1 | 10/2011 | Podack et al. |
| 2012/0014950 | A1 | 1/2012 | Migone et al. |
| 2012/0079611 | A1 | 3/2012 | Shih et al. |
| 2012/0114654 | A1 | 5/2012 | Classon et al. |
| 2012/0208900 | A1 | 8/2012 | Dubinsky et al. |
| 2012/0315282 | A1 | 12/2012 | Bedinger et al. |
| 2014/0255302 | A1 | 9/2014 | Poulton et al. |
| 2014/0308271 | A1 | 10/2014 | Attinger et al. |
| 2014/0315250 | A1 | 10/2014 | Smith et al. |
| 2015/0031972 | A1 | 1/2015 | Freeman et al. |
| 2015/0132311 | A1 | 5/2015 | Arch et al. |
| 2015/0299720 | A1 | 10/2015 | Cao et al. |
| 2015/0313904 | A1 | 11/2015 | Kolatch et al. |
| 2015/0344570 | A1 | 12/2015 | Igawa et al. |
| 2016/0009802 | A1 | 1/2016 | Longman et al. |
| 2016/0046678 | A1 | 2/2016 | Roschke et al. |
| 2016/0053007 | A1 | 2/2016 | Siegel et al. |
| 2016/0060330 | A1 | 3/2016 | Presta |
| 2016/0200833 | A1 | 7/2016 | Amann et al. |
| 2016/0333104 | A1 | 11/2016 | Poulton et al. |
| 2017/0073395 | A1 | 3/2017 | Finlay et al. |
| 2017/0081400 | A1 | 3/2017 | Poulton et al. |
| 2017/0096491 | A1 | 4/2017 | Classon et al. |
| 2017/0342128 | A1 | 11/2017 | Auer et al. |
| 2018/0021696 | A1 | 1/2018 | Wang et al. |
| 2018/0052175 | A1 | 2/2018 | Arch et al. |
| 2018/0064825 | A1 | 3/2018 | Olive |
| 2018/0078611 | A1 | 3/2018 | Podack et al. |
| 2018/0086840 | A1 | 3/2018 | Attinger et al. |
| 2018/0155451 | A1 | 6/2018 | Mimoto et al. |
| 2018/0179285 | A1 | 6/2018 | Bennett et al. |
| 2018/0186888 | A1 | 7/2018 | Siegel et al. |
| 2018/0237542 | A1 | 8/2018 | Kannan et al. |
| 2018/0251565 | A1 | 9/2018 | Harding et al. |
| 2018/0319889 | A1 | 11/2018 | Croft et al. |
| 2019/0071512 | A1 | 3/2019 | Lazar et al. |
| 2019/0106486 | A1 | 4/2019 | Poulton et al. |
| 2019/0106504 | A1 | 4/2019 | Wu et al. |
| 2019/0119407 | A1 | 4/2019 | Hsu et al. |
| 2019/0135928 | A1 | 5/2019 | Pashine et al. |
| 2019/0202937 | A1 | 7/2019 | Humphreys et al. |
| 2019/0218309 | A1 | 7/2019 | Igawa et al. |
| 2019/0247498 | A1 | 8/2019 | Bilsborough et al. |
| 2019/0331694 | A1 | 10/2019 | Arch et al. |
| 2019/0343425 | A1 | 11/2019 | Jones et al. |
| 2020/0140552 | A1 | 5/2020 | Wu et al. |
| 2020/0255510 | A1 | 8/2020 | Watkins et al. |
| 2021/0070871 | A1 | 3/2021 | Watkins et al. |

FOREIGN PATENT DOCUMENTS

| | | |
|---|---|---|
| WO | WO-9614328 A1 | 5/1996 |
| WO | WO-0066608 A1 | 11/2000 |
| WO | WO-0204643 A1 | 1/2002 |
| WO | WO-03068821 A2 | 8/2003 |
| WO | WO-2004035537 A2 | 4/2004 |
| WO | WO-2004050836 A2 | 6/2004 |
| WO | WO-2006017173 A1 | 2/2006 |
| WO | WO-2007005608 A2 | 1/2007 |
| WO | WO-2008106579 A2 | 9/2008 |
| WO | WO-2009064854 A2 | 5/2009 |
| WO | WO-2012161856 A1 | 11/2012 |
| WO | WO-2013044298 A1 | 4/2013 |
| WO | WO-2014051109 A1 | 4/2014 |
| WO | WO-2014106602 A1 | 7/2014 |
| WO | WO-2014160463 A1 | 10/2014 |
| WO | WO-2014197849 A2 | 12/2014 |
| WO | WO-2015073580 A1 | 5/2015 |
| WO | WO-2017049024 A1 | 3/2017 |
| WO | WO-2017076878 A1 | 5/2017 |
| WO | WO-2017077715 A1 | 5/2017 |
| WO | WO-2017106383 A1 | 6/2017 |
| WO | WO-2017189983 A1 | 11/2017 |
| WO | WO-2017196663 A1 | 11/2017 |
| WO | WO-2018081074 A1 | 5/2018 |
| WO | WO-2019121906 A1 | 6/2019 |
| WO | WO-2019209995 A2 | 10/2019 |
| WO | WO-2020011964 A1 | 1/2020 |
| WO | WO-2020011966 A1 | 1/2020 |
| WO | WO-2020011968 A1 | 1/2020 |
| WO | WO-2020011970 A1 | 1/2020 |
| WO | WO-2020011972 A1 | 1/2020 |
| WO | WO-2020011974 A1 | 1/2020 |
| WO | WO-2020011976 A1 | 1/2020 |
| WO | WO-2020086758 A1 | 4/2020 |

OTHER PUBLICATIONS

Aiba et al., The role of TL1A and DR3 in autoimmune and inflammatory diseases. Mediators Inflamm. 2013:#258164, 9 pages.

Al-Iazikani et al., Standard conformations for the canonical structures of immunoglobulins. J. Molec. Biol. 273:927-948, 1997.

Bamias et al. Circulating levels of TNF-like cytokine 1A (TL1A) and its decoy receptor 3 (DcR3) in rheumatoid arthritis. Clin Immunol 129:249-255, 2008.

Bamias et al.: Expression, localization, and functional activity of TL1A, a novel Th1-polarizing cytokine in inflammatory bowel disease. Journal of Immunology 171(9):4868-4874 (2003).

(56) References Cited

OTHER PUBLICATIONS

Barrett et al.: Constitutive TL1A Expression under Colitogenic Condition Modulates the Severity and Location of Gut Mucosal Inflammation and Induces Fibrostenosis, American Journal of Pathology, 180(2):636-649 (2012).
Bauer et al., A genetic enrichment for mutations constructed by oligodeoxynucleotide-directed mutagenesis. Gene, 37:73-81, 1985.
Benedict et al., Immunoglobulin Kappa light chain variable region, Partial (Mus musculus). GenBank: AAD39789.1, Jul. 26, 2016, 1 page.
Bird et al.: Single-chain antigen-binding proteins; Science, 242:423-42, 1988.
Brennan et al. Preparation of bispecific antibodies by chemical recombination of monoclonal immunoglobulin G1 fragments. Science 229:81-83, 1985.
Brummell et al. Probing the combining site of an anti-carbohydrate antibody by saturation-mutagenesis: Role of the heavy-chain CDR3 residues. Biochem. 32: 1180-1187, 1993.
Burks et al., In vitro scanning saturation mutagenesis of an antibody binding pocket. Proc. Natl. Acad. Sci. USA 94:412-417, 1997.
Camoglio et al.: Altered expression of interfero-gamma and interleukin-4 in inflammatory bowel disease; Inflamm Bowel Dis., 4(4): 285-290; Abstract only (1998).
Clarke et al. An anti-TL1A antibody for the treatment of asthma and inflammatory bowel disease. MAbs 10(4):664-677 (2018).
Craik, Charles. Use of oligonucleotides for site-specific mutagenesis. BioTechniques 1985 :12-19, 1985.
Erpenbeck et al. Segmental allergen challenge in patients with atopic asthma leads to increased IL-9 expression in bronchoalveolar lavage fluid lymphocytes. J Allergy Clin Immunol 111(6):1319-1327, 2003.
Fang et al., Essential role of TNF receptor superfamily 25 (TNFRS25) in the development of allergic lung inflammation. J.Exp. Med., 205(5):1037-1048, 2008.
Fitzpatrick, LR, Novel Pharmacological Approaches for Inflammatory Bowl Disease: Targeting Key Intracellular Pathways and the IL-23/IL-17 Axis, International Journal of Inflammation, vol. 2012, pp. 1-8.
Fransen et al., Inflammatory bowel disease: the genetic background and beyond. University of Groningen PhD Dissertation http://www.rug.nl/research/portal/files/12805965/Complete_dissertation.pdf (2014).
Heusch et al., IL-9 exacerbates colitis induced by CD4+ CD45RBhigh T cells transfer, via directed activation of in vivo antigen-experienced T cells. Cytokine 56:PS1-056, p. 31 (2011).
Hodgson, John. Making monoclonals in microbes. Bio/Technology 9:421-425, 1991.
Holliger et al.: Engineered antibody fragments and the rise of single domains. Nat. Biotechnol. 23(9):1126-36 (2005).
Hsu et al. The tale of TL1A in inflammation. Mucosal Immunol 4(4):368-370, 2011.
Hundorean et al., Functional relevance of T helper 17 (Th17) cells and the IL-17 cytokine family in inflammatory bowel disease. Inflammatory Bowel Disease 18:180-186 (2012).
Huse et al. Generation of a large combinatorial library of the immunoglobulin repertoire in phage lambda. Science 246:1275-1281, 1989.
Huston et al. Protein engineering of antibody binding sites: Recovery of specific activity in an anti-digoxin single-chain Fv analogue produced in *Escherichia coli*. Proc. Natl. Acad. Sci. USA 85:5879-5883, 1988.
Jones et al. Replacing the complementarity-determining regions in a human antibody with those from a mouse. Nature 321:522-525, 1986.
Kakuta et al., Su1746 Rare Variants of TNFSF15 Are Significantly Associated With Crohn's Disease in Non-Jewish Caucasian Independent of the Known Common Susceptibility SNPs, Gastroenterology, 144(5): S-466, 2013.
Kim et al. Effects of IL-9 blockade on chronic airway inflammation of murine asthma models. Allergy: Eur J Allergy Clin Immunol Suppl 96(67):448, Nov. 2012.
Kim et al. Effects of interleukin-9 blockade on chronic airway inflammation in murine asthma models. Allergy Asthma Immunol Res 5(4):197-206, 2013.
Kobayashi et al. Tryptophan H33 plays an important role in pyrimidine (6-4) pyrimidone photoproduct binding by a high-affinity antibody. Protein Eng. 12(10):879-884, 1999.
Koga et al., Transanal Delivery of Angiotensin Converting Enzyme Inhibitor Prevents Colonic Fibrosis in a Mouse Colitis Model: Development of a Unique Mode of Treatment, Surgery, 144(2):259-268, 2008.
Kohler et al.: Derivation of specific antibody-producing tissue culture and tumor lines by cell fusion. Eur. J. Immunol. 6: 511-519 (1976).
McGovern et al., Genetics of inflammatory bowel diseases. Gastroenterology 149(5):1163-1173 (2015).
Meylan et al., The TNF-family cytokine TL1A drives IL-13 dependent small intestinal inflammation. Muscosal Immunol., 4(2):172-185, 2011.
Migone et al., TL1A is a TNF-like Ligand for DR3 and TR6/DcR3 and Functions as a T cell Costimulator, Immunity, 16:479-492, 2002.
Morimoto et al. Single-step purification of F(ab')2 fragments of mouse monoclonal antibodies (immunoglobulins G1) by hydrophobic interaction high performance liquid chromatography using TSKgel Phenyl-5PW. J Biochem Biophys Methods 24:107-117 (1993).
Nalleweg et al., Inflammatory bowel disease patients failing anti-TNF therapy show activation of the Th9/TH17 pathway. Gastroenterol 142(5)(Suppl1):S867-868; Abstract No. Tu1878 (2012).
Takedatsu et al.: TL1A (TNFSF15) Regulates the Development of Chronic Colitis by Modulating both T helper (TH) 1 and TH17 Activation; Gastroenterology; HHS Public Access; 135(2): 552-567 (2008).
Nowak et al., IL-9 as a mediator of Th17-driven inflammatory disease. Journal of Experimental Medicine 206(8):1653-1660 (2009).
Oh et al., A randomized, controlled trial to evaluate the effect of an anti-interleukin-9 monoclonal antibody in adults with uncontrolled asthma. Respiratory Research 14:93 (2013).
Parente et al., Bowel Ultrasound in Assessment of Crohn's Disease and Detection of Related Small Bowel Strictures: A Prospective Comparative Study Versus X Ray and Intraoperative Findings, Gut, 50: 490-495, 2002.
PCT/US2009/069541 International Search Report dated Mar. 4, 2010.
PCT/US2017/023082 International Search Report and Written Opinion dated Aug. 15, 2017.
PCT/US2017/058019 International Preliminary Report on Patentability dated Apr. 30, 2019.
PCT/US2017/058019 International Search Report and Written Opinion dated Feb. 15, 2018.
PCT/US2019/028987 International Preliminary Report on Patentability dated Oct. 27, 2020.
PCT/US2019/028987 International Search Report and Written Opinion dated Oct. 29, 2019.
Pinchuk et al., Human Colonic Myofibroblast Promote Expansion of CD4+ CD25high Foxp3+ Regulatory T Cells, Gastroenterology, 140(7):2019-2030, pp. 1-19, and p. 8, 2011.
Queen et al. A humanized antibody that binds to the interleukin 2 receptor. PNAS USA 86:10029-10032 (1989).
R&D datasheet for human/mouse TL1A/TNFSF15 antibody, catalog No. MAB7441; clone #293327 (Feb. 7, 2018).
Reichwald et al. TL1A induces TCR independent IL-6 and TNF-alpha production and growth of PLZF leukocytes. PLOS ONE 9(1):e85793, 2013.
Richard et al. The TNF-family cytokine TL1A: from lymphocyte costimulator to disease co-conspirator. J Leukocyte Biol 98:333-345 2015.
Riechmann et al. Reshaping human antibodies for therapy. Nature, 332.6162:323-7 (1988).
Rothe et al., The human combinatorial antibody library HuCAL GOLD combines diversification of all six CDRs according to the natural immune system with a novel display method for efficient selection of high-affinity antibodies. J. Mol. Bio. 376:1182-1200, 2008.

(56) References Cited

OTHER PUBLICATIONS

Shih et al.: Constitutive TL1A (TNFSF15) Expression on Lymphoid or Myeloid Cells Leads to Mild Intestinal Inflammation and Fibrosis, PLOS One, 6(1), pp. 1-16, 2011.
Shih et al., Inhibition of a novel fibrogenic factor TI 1a reverses established colonic fibrosis. Mucosal Immunol., 7(6):1492-1503, 2014.
Shih et al. Reversal of murine colitis and fibrosis by neutralizing TL1A antibody: potential novel therapy to alter natural history of Crohn's disease. Gastroenterol 142(5):S84, Abstract #357, 2012.
Spinelli et al.: Intestinal Fibrosis in Crohn's Disease: Medical Treatment or Surgery?, Current Drug Targets, 11(2):242-248, 2010.
Strober et at, Proinflammatoly Cytokines in Pathogenesis of Inflammatory Bowel Diseases, Gastroenterology, 140(6):1756-1767, 2011.
Tomlinson et al.: Methods for generating multivalent and bispecific antibody fragments. Methods Enzymol 326:461-479 (2000).
UniprotKB Database, Q8NI17 (IL31R_Human), Retrieved online Sep. 5, 2019. Retrieved from < url https://www.uniprot.org/uniprot/Q8NI17 > . Jul. 31, 2019 < /url >.
U.S. Appl. No. 14/779,893 Final Office Action dated Apr. 26, 2019.
U.S. Appl. No. 14/779,893 Office Action dated Sep. 12, 2019.
U.S. Appl. No. 15/245,875 Office Action dated Jun. 12, 2018.
U.S. Appl. No. 15/792,266 Office Action dated Aug. 6, 2018.
U.S. Appl. No. 16/384,521 Office Action dated May 28, 2020.
Verhoeyen et al. Reshaping human antibodies: Grafting an antilysozyme activity. Science 239:1534-1536 (1988).
Walder et al. Oligodeoxynucleotide-directed mutagenesis using the yeast transformation system. Gene 42:133-139, 1986.
Ward et al. Binding activities of a repertoire of single immunoglobulin variable domains secreted from *Escherichia coli*. Nature 334:544-54, 1989.
Prometheus Biosciences, Inc. Form S-1 Registration Statement as filed with the Securities and Exchange Commission on Feb. 19, 2021 (246 pages).
Scheepers et al.: Ability to Develop Broadly Neutralizing HIV-1 Antibodies Is Not Restricted by the Germline Ig Gene Repertoire. J Immunol. 194(9):4371-4378 (2015).
PCT/US2020/057119 International Search Report and Written Opinion dated Mar. 10, 2021.

* cited by examiner

SEQUENCE LISTING

```
<160> NUMBER OF SEQ ID NOS: 1303

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1
```

Gly Phe Asp Ile Gln Asp Thr Tyr Met His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ile Asp Pro Ala Ser Gly His Thr Lys Tyr Asp Pro Lys Phe Gln
1               5                   10                  15

Val

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Ile Glu Pro Ala Ser Gly His Ile Lys Tyr Asp Pro Lys Phe Gln
1               5                   10                  15

Gly

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ile Asp Pro Ala Ser Gly His Ile Lys Tyr Asp Pro Lys Phe Gln
1               5                   10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ile Glu Pro Ala Ser Gly His Ile Lys Tyr Asp Pro Lys Phe Gln
1               5                   10                  15

Val

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Gly Gly Leu Pro Asp Val
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Arg Ser Gly Gly Leu Pro Asp Val
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Gly Gly Leu Pro Asp Trp
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Arg Ser Gly Gly Leu Pro Asp Trp
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ala Ser Ser Ser Val Ser Tyr Met Tyr
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Thr Ser Asn Leu Ala Ser
1               5

<210> SEQ ID NO 12
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 12

Gln Gln Trp Glu Gly Asn Pro Arg Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Gln Trp Lys Gly Asn Pro Arg Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Gln Trp Ser Gly Asn Pro Arg Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Gln Trp Ser Arg Asn Pro Arg Thr
1               5

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

```
<210> SEQ ID NO 20
<400> SEQUENCE: 20
000

<210> SEQ ID NO 21
<400> SEQUENCE: 21
000

<210> SEQ ID NO 22
<400> SEQUENCE: 22
000

<210> SEQ ID NO 23
<400> SEQUENCE: 23
000

<210> SEQ ID NO 24
<400> SEQUENCE: 24
000

<210> SEQ ID NO 25
<400> SEQUENCE: 25
000

<210> SEQ ID NO 26
<400> SEQUENCE: 26
000

<210> SEQ ID NO 27
<400> SEQUENCE: 27
000

<210> SEQ ID NO 28
<400> SEQUENCE: 28
000

<210> SEQ ID NO 29
<400> SEQUENCE: 29
000

<210> SEQ ID NO 30
<400> SEQUENCE: 30
000

<210> SEQ ID NO 31
```

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43
<400> SEQUENCE: 43
000

<210> SEQ ID NO 44
<400> SEQUENCE: 44
000

<210> SEQ ID NO 45
<400> SEQUENCE: 45
000

<210> SEQ ID NO 46
<400> SEQUENCE: 46
000

<210> SEQ ID NO 47
<400> SEQUENCE: 47
000

<210> SEQ ID NO 48
<400> SEQUENCE: 48
000

<210> SEQ ID NO 49
<400> SEQUENCE: 49
000

<210> SEQ ID NO 50
<400> SEQUENCE: 50
000

<210> SEQ ID NO 51
<400> SEQUENCE: 51
000

<210> SEQ ID NO 52
<400> SEQUENCE: 52
000

<210> SEQ ID NO 53
<400> SEQUENCE: 53
000

-continued

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77
<400> SEQUENCE: 77
000

<210> SEQ ID NO 78
<400> SEQUENCE: 78
000

<210> SEQ ID NO 79
<400> SEQUENCE: 79
000

<210> SEQ ID NO 80
<400> SEQUENCE: 80
000

<210> SEQ ID NO 81
<400> SEQUENCE: 81
000

<210> SEQ ID NO 82
<400> SEQUENCE: 82
000

<210> SEQ ID NO 83
<400> SEQUENCE: 83
000

<210> SEQ ID NO 84
<400> SEQUENCE: 84
000

<210> SEQ ID NO 85
<400> SEQUENCE: 85
000

<210> SEQ ID NO 86
<400> SEQUENCE: 86
000

<210> SEQ ID NO 87
<400> SEQUENCE: 87
000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 116
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 101

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Ile Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 102
<211> LENGTH: 116
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Met Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 103
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Arg Pro Gly Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Arg Ala Thr Ile Thr Thr Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 104
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Ile Thr Arg Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 105
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
        35                  40                  45

Gly Arg Ile Asp Pro Ala Ser Gly His Thr Lys Tyr Asp Pro Lys Phe
50                  55                  60

Gln Val Arg Ala Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 106
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Arg Pro Gly Gln Gly Leu Glu Trp Met
        35                  40                  45

Gly Arg Ile Asp Pro Ala Ser Gly His Thr Lys Tyr Asp Pro Lys Phe
50                  55                  60

Gln Val Arg Val Thr Ile Thr Thr Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 107
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Val Gln Leu Val Gln Ser Gly Ala Glu Val Lys Lys Pro Gly Ala
1               5                   10                  15

```
Ser Val Lys Val Ser Cys Lys Ala Ser Gly Phe Asp Ile Gln Asp Thr
            20                  25                  30

Tyr Met His Trp Val Arg Gln Arg Pro Gly Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Arg Ala Thr Ile Thr Thr Asp Thr Ser Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 108
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Arg Ala Thr Ile Thr Thr Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 109
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Ile
        35                  40                  45

Gly Arg Ile Asp Pro Ala Ser Gly His Thr Lys Tyr Asp Pro Lys Phe
    50                  55                  60
```

Gln Val Arg Ala Thr Ile Thr Thr Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 110
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Ile Thr Thr Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 111
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 112
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Arg Pro Gly Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 113
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Arg Pro Gly Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Arg Ala Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 114
<211> LENGTH: 116
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 114

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Ile Thr Arg Asp Thr Ser Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 115
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Arg Val Thr Ile Thr Thr Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 116
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr

```
            20                  25                  30
Tyr Met His Trp Val Lys Gln Ala Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 117
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 118
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Ile Thr Thr Asp Thr Ser Thr Ser Thr Ala Tyr
```

```
                65                  70                  75                  80
Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 119
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Ile Thr Arg Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 120
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
```

<210> SEQ ID NO 121
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Val Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 122
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Val Arg Ala Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 123
<211> LENGTH: 116
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 123

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Val Arg Val Thr Ile Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 124
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Val Arg Ala Thr Ile Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 125
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Ala Pro Gly Gln Gly Leu Glu Trp Met
            35                  40                  45

Gly Arg Ile Glu Pro Ala Ser Gly His Ile Lys Tyr Asp Pro Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
                100                 105                 110

Thr Val Ser Ser
        115

<210> SEQ ID NO 126
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Ala Pro Gly Gln Gly Leu Glu Trp Met
            35                  40                  45

Gly Arg Ile Asp Pro Ala Ser Gly His Ile Lys Tyr Asp Pro Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
                100                 105                 110

Thr Val Ser Ser
        115

<210> SEQ ID NO 127
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Ala Pro Gly Gln Gly Leu Glu Trp Met
            35                  40                  45

Gly Arg Ile Glu Pro Ala Ser Gly His Ile Lys Tyr Asp Pro Lys Phe
        50                  55                  60

Gln Gly Arg Ala Thr Met Thr Arg Asp Thr Ser Thr Ser Thr Val Tyr
65                  70                  75                  80

```
Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 128
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Gly Arg Ala Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 129
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Gly Arg Ala Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115
```

<210> SEQ ID NO 130
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Ile Lys Tyr Asp Pro Lys Phe
    50                  55                  60

Gln Gly Arg Ala Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 131
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Gly Arg Ala Thr Ile Thr Thr Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 132
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Gly Arg Ala Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 133
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Gly Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 134
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

```
Tyr Met His Trp Val Arg Gln Ala Pro Gly Gln Gly Leu Glu Trp Met
            35                  40                  45

Gly Arg Ile Glu Pro Ala Ser Gly His Ile Lys Tyr Asp Pro Lys Phe
 50                  55                  60

Gln Gly Arg Val Thr Met Thr Arg Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Gly Gly Leu Pro Asp Trp Trp Gly Gln Gly Thr Thr Val
                100                 105                 110

Thr Val Ser Ser
        115

<210> SEQ ID NO 135
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asp Ile Gln Asp Thr
                20                  25                  30

Tyr Met His Trp Val Arg Gln Ala Pro Gly Gln Gly Leu Glu Trp Met
            35                  40                  45

Gly Arg Ile Asp Pro Ala Ser Gly His Ile Lys Tyr Asp Pro Lys Phe
 50                  55                  60

Gln Gly Arg Val Thr Met Thr Arg Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Gly Gly Leu Pro Asp Trp Trp Gly Gln Gly Thr Thr Val
                100                 105                 110

Thr Val Ser Ser
        115

<210> SEQ ID NO 136
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asp Ile Gln Asp Thr
                20                  25                  30

Tyr Met His Trp Val Arg Gln Ala Pro Gly Gln Gly Leu Glu Trp Met
            35                  40                  45

Gly Arg Ile Glu Pro Ala Ser Gly His Ile Lys Tyr Asp Pro Lys Phe
 50                  55                  60

Gln Gly Arg Val Thr Met Thr Arg Asp Thr Ser Thr Ser Thr Val Tyr
 65                  70                  75                  80
```

```
Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 137
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Asp Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 138
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Ala Pro Gly Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Arg Ala Thr Ile Thr Thr Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115
```

<210> SEQ ID NO 139
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Arg Ala Thr Ile Thr Thr Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 140
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Ala Thr Ile Thr Thr Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 141
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Arg Ala Thr Ile Thr Thr Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 142
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Arg Ala Thr Ile Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 143
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Ile

```
                35                  40                  45
Gly Arg Ile Asp Pro Ala Ser Gly His Thr Lys Tyr Asp Pro Lys Phe
         50                  55                  60
Gln Val Arg Ala Thr Ile Thr Thr Asp Thr Ser Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Ser Gly Gly Leu Pro Asp Val Trp Gly Gln Gly Thr Thr Val
            100                 105                 110
Thr Val Ser Ser
        115

<210> SEQ ID NO 144
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gln Val Gln Leu Val Gln Ser Gly Ala Glu Val Lys Lys Pro Gly Ala
 1               5                  10                  15
Ser Val Lys Val Ser Cys Lys Ala Ser Gly Phe Asp Ile Gln Asp Thr
             20                  25                  30
Tyr Met His Trp Val Lys Gln Arg Pro Gly Gln Gly Leu Glu Trp Ile
         35                  40                  45
Gly Arg Ile Asp Pro Ala Ser Gly His Thr Lys Tyr Asp Pro Lys Phe
     50                  55                  60
Gln Val Arg Ala Thr Met Thr Thr Asp Thr Ser Thr Ser Thr Ala Tyr
 65                  70                  75                  80
Leu Glu Leu Ser Ser Leu Arg Ser Glu Asp Thr Ala Val Tyr Tyr Cys
                 85                  90                  95
Ala Arg Ser Gly Gly Leu Pro Asp Val Trp Gly Gln Gly Thr Thr Val
            100                 105                 110
Thr Val Ser Ser
        115

<210> SEQ ID NO 145
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gln Val Gln Leu Val Gln Ser Gly Ala Glu Val Lys Lys Pro Gly Ala
 1               5                  10                  15
Ser Val Lys Val Ser Cys Lys Ala Ser Gly Phe Asp Ile Gln Asp Thr
             20                  25                  30
Tyr Met His Trp Val Lys Gln Arg Pro Gly Gln Gly Leu Glu Trp Ile
         35                  40                  45
Gly Arg Ile Asp Pro Ala Ser Gly His Thr Lys Tyr Asp Pro Lys Phe
     50                  55                  60
Gln Val Arg Ala Thr Ile Thr Arg Asp Thr Ser Thr Ser Thr Ala Tyr
 65                  70                  75                  80
Leu Glu Leu Ser Ser Leu Arg Ser Glu Asp Thr Ala Val Tyr Tyr Cys
```

```
                    85                  90                  95

Ala Arg Ser Gly Gly Leu Pro Asp Val Trp Gly Gln Gly Thr Thr Val
                100                 105                 110

Thr Val Ser Ser
        115

<210> SEQ ID NO 146
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
                20                  25                  30

Tyr Met His Trp Val Lys Gln Arg Pro Gly Gln Gly Leu Glu Trp Ile
            35                  40                  45

Gly Arg Ile Asp Pro Ala Ser Gly His Thr Lys Tyr Asp Pro Lys Phe
    50                  55                  60

Gln Val Arg Val Thr Met Thr Thr Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
                100                 105                 110

Thr Val Ser Ser
        115

<210> SEQ ID NO 147
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
                20                  25                  30

Tyr Met His Trp Val Lys Gln Arg Pro Gly Gln Gly Leu Glu Trp Ile
            35                  40                  45

Gly Arg Ile Asp Pro Ala Ser Gly His Thr Lys Tyr Asp Pro Lys Phe
    50                  55                  60

Gln Val Arg Ala Thr Met Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
                100                 105                 110

Thr Val Ser Ser
        115
```

```
<210> SEQ ID NO 148
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Arg Val Thr Met Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 149
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Asp Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Arg Ala Thr Ile Thr Thr Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 150
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Arg Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 151
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Ile Lys Tyr Asp Pro Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 152
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Ile
        35                  40                  45
```

```
Gly Arg Ile Glu Pro Ala Ser Gly His Ile Lys Tyr Asp Pro Lys Phe
        50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
            115

<210> SEQ ID NO 153
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Ile
        35                  40                  45

Gly Arg Ile Asp Pro Ala Ser Gly His Ile Lys Tyr Asp Pro Lys Phe
    50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
            115

<210> SEQ ID NO 154
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Val Lys Tyr Asp Pro Lys Phe
    50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95
```

```
Ala Arg Ser Gly Gly Leu Pro Asp Trp Trp Gly Gln Gly Thr Thr Val
            100                 105                 110

Thr Val Ser Ser
        115

<210> SEQ ID NO 155
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Gly Arg Val Thr Ile Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 156
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 157
```

```
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Gly Arg Val Thr Met Thr Thr Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 158
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Gly Arg Val Thr Ile Thr Thr Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 159
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159
```

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Thr Lys Tyr Asp Pro Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Ser Gly Gly Leu Pro Asp Trp Trp Gly Gln Gly Thr Thr Val
                100                 105                 110

Thr Val Ser Ser
            115

<210> SEQ ID NO 160
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Gly Arg Ala Thr Ile Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Ser Gly Gly Leu Pro Asp Trp Trp Gly Gln Gly Thr Thr Val
                100                 105                 110

Thr Val Ser Ser
            115

<210> SEQ ID NO 161
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

```
Gly Arg Ile Glu Pro Ala Ser Gly His Ile Lys Tyr Asp Pro Lys Phe
        50                  55                  60

Gln Gly Arg Val Thr Met Thr Arg Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
                100                 105                 110

Thr Val Ser Ser
        115

<210> SEQ ID NO 162
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
                20                  25                  30

Tyr Met His Trp Val Arg Gln Ala Pro Gly Gln Gly Leu Glu Trp Met
            35                  40                  45

Gly Arg Ile Glu Pro Ala Ser Gly His Ile Lys Tyr Asp Pro Lys Phe
        50                  55                  60

Gln Gly Arg Val Thr Met Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
                100                 105                 110

Thr Val Ser Ser
        115

<210> SEQ ID NO 163
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
                20                  25                  30

Tyr Met His Trp Val Arg Gln Arg Pro Gly Gln Gly Leu Glu Trp Met
            35                  40                  45

Gly Arg Ile Asp Pro Ala Ser Gly His Thr Lys Tyr Asp Pro Lys Phe
        50                  55                  60

Gln Val Arg Ala Thr Ile Thr Thr Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95
```

Ala Arg Ser Gly Gly Leu Pro Asp Val Trp Gly Gln Gly Thr Thr Val
            100                 105                 110

Thr Val Ser Ser
        115

<210> SEQ ID NO 164
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Arg Pro Gly Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Arg Val Thr Ile Thr Thr Asp Thr Ser Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 165
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Ile Thr Thr Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 166
<211> LENGTH: 116

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Ile Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 167
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Met Thr Thr Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 168
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Gln Val Gln Leu Val Gln Ser Gly Ala Glu Val Lys Lys Pro Gly Ala
```

```
                1               5                   10                  15
            Ser Val Lys Val Ser Cys Lys Ala Ser Gly Phe Asp Ile Gln Asp Thr
                        20                  25                  30

Tyr Met His Trp Val Arg Gln Ala Pro Gly Gln Gly Leu Glu Trp Met
                        35                  40                  45

Gly Arg Ile Asp Pro Ala Ser Gly His Ile Lys Tyr Asp Pro Lys Phe
                        50                  55                  60

Gln Gly Arg Ala Thr Ile Thr Thr Asp Thr Ser Thr Ser Thr Val Tyr
            65                  70                  75                  80

Met Glu Leu Ser Ser Leu Arg Ser Glu Asp Thr Ala Val Tyr Tyr Cys
                        85                  90                  95

Ala Arg Ser Gly Gly Leu Pro Asp Trp Trp Gly Gln Gly Thr Thr Val
                        100                 105                 110

Thr Val Ser Ser
                    115
```

<210> SEQ ID NO 169
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

```
            Glu Val Gln Leu Val Gln Ser Gly Ala Glu Val Lys Lys Pro Gly Ala
            1               5                   10                  15

Ser Val Lys Val Ser Cys Lys Ala Ser Gly Phe Asp Ile Gln Asp Thr
                        20                  25                  30

Tyr Met His Trp Val Arg Gln Ala Pro Gly Gln Gly Leu Glu Trp Met
                        35                  40                  45

Gly Arg Ile Glu Pro Ala Ser Gly His Ile Lys Tyr Asp Pro Lys Phe
                        50                  55                  60

Gln Gly Arg Ala Thr Ile Thr Thr Asp Thr Ser Thr Ser Thr Val Tyr
            65                  70                  75                  80

Met Glu Leu Ser Ser Leu Arg Ser Glu Asp Thr Ala Val Tyr Tyr Cys
                        85                  90                  95

Ala Arg Ser Gly Gly Leu Pro Asp Trp Trp Gly Gln Gly Thr Thr Val
                        100                 105                 110

Thr Val Ser Ser
                    115
```

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196
<400> SEQUENCE: 196

000

<210> SEQ ID NO 197
<400> SEQUENCE: 197

000

<210> SEQ ID NO 198
<400> SEQUENCE: 198

000

<210> SEQ ID NO 199
<400> SEQUENCE: 199

000

<210> SEQ ID NO 200
<400> SEQUENCE: 200

000

<210> SEQ ID NO 201
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Pro Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Glu Gly Asn Pro Arg Thr
                85                  90                  95

Phe Gly Gly Gly Thr Lys Leu Glu Ile Lys
            100                 105

<210> SEQ ID NO 202
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 202

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Gly Asn Pro Arg Thr
                85                  90                  95

Phe Gly Gly Gly Thr Lys Leu Glu Ile Lys
            100                 105

<210> SEQ ID NO 203
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
            100                 105

<210> SEQ ID NO 204
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu

```
                65                  70                  75                  80
Asp Phe Ala Val Tyr Tyr Cys Gln Gln Trp Lys Gly Asn Pro Arg Thr
                    85                  90                  95

Phe Gly Gly Gly Thr Lys Leu Glu Ile Lys
                100                 105

<210> SEQ ID NO 205
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
                20                  25                  30

Tyr Trp Tyr Gln Gln Lys Pro Gly Gln Ala Pro Arg Pro Trp Ile Tyr
            35                  40                  45

Ala Thr Ser Asn Leu Ala Ser Gly Ile Pro Asp Arg Phe Ser Gly Ser
        50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Glu Gly Asn Pro Arg Thr
                    85                  90                  95

Phe Gly Gly Gly Thr Lys Leu Glu Ile Lys
                100                 105

<210> SEQ ID NO 206
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
                20                  25                  30

Tyr Trp Tyr Gln Gln Lys Pro Gly Gln Ala Pro Arg Pro Leu Ile Tyr
            35                  40                  45

Ala Thr Ser Asn Leu Ala Ser Gly Ile Pro Asp Arg Phe Ser Gly Ser
        50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Lys Gly Asn Pro Arg Thr
                    85                  90                  95

Phe Gly Gly Gly Thr Lys Leu Glu Ile Lys
                100                 105

<210> SEQ ID NO 207
<211> LENGTH: 106
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 207

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Arg Asn Pro Arg Thr
                85                  90                  95

Phe Gly Gly Gly Thr Lys Leu Glu Ile Lys
            100                 105

<210> SEQ ID NO 208
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Glu Ile Val Leu Thr Gln Ser Pro Gly Thr Leu Ser Ala Ser Pro Gly
1               5                   10                  15

Glu Arg Ala Thr Met Ser Cys Arg Ala Ser Ser Ser Val Ser Tyr Met
            20                  25                  30

Tyr Trp Tyr Gln Gln Lys Pro Gly Gln Ala Pro Arg Pro Trp Ile Tyr
        35                  40                  45

Ala Thr Ser Asn Leu Ala Ser Gly Val Pro Asp Arg Phe Ser Gly Ser
    50                  55                  60

Gly Ser Gly Thr Asp Tyr Thr Leu Thr Ile Ser Arg Val Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
            100                 105

<210> SEQ ID NO 209
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Val Pro Asp Arg Phe Ser Gly Ser
    50                  55                  60

```
Gly Ser Gly Thr Asp Phe Thr Leu Thr Ile Ser Arg Leu Glu Pro Glu
 65                  70                  75                  80

Asp Phe Ala Val Tyr Tyr Cys Gln Gln Trp Glu Gly Asn Pro Arg Thr
                 85                  90                  95

Phe Gly Gly Gly Thr Lys Leu Glu Ile Lys
            100                 105

<210> SEQ ID NO 210
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Glu Ile Val Leu Thr Gln Ser Pro Gly Thr Leu Ser Ala Ser Pro Gly
 1               5                  10                  15

Glu Arg Ala Thr Leu Ser Cys Arg Ala Ser Ser Val Ser Tyr Met
                 20                  25                  30

Tyr Trp Tyr Gln Gln Lys Pro Gly Gln Ala Pro Arg Pro Trp Ile Tyr
             35                  40                  45

Ala Thr Ser Asn Leu Ala Ser Gly Val Pro Asp Arg Phe Ser Gly Ser
         50                  55                  60

Gly Ser Gly Thr Asp Tyr Thr Leu Thr Ile Ser Arg Val Glu Pro Glu
 65                  70                  75                  80

Asp Phe Ala Val Tyr Tyr Cys Gln Gln Trp Ser Gly Asn Pro Arg Thr
                 85                  90                  95

Phe Gly Gly Gly Thr Lys Leu Glu Ile Lys
            100                 105

<210> SEQ ID NO 211
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Glu Ile Val Leu Thr Gln Ser Pro Gly Thr Leu Ser Ala Ser Pro Gly
 1               5                  10                  15

Glu Arg Ala Thr Met Ser Cys Arg Ala Ser Ser Val Ser Tyr Met
                 20                  25                  30

Tyr Trp Tyr Gln Gln Lys Pro Gly Gln Ala Pro Arg Leu Leu Ile Tyr
             35                  40                  45

Ala Thr Ser Asn Leu Ala Ser Gly Val Pro Asp Arg Phe Ser Gly Ser
         50                  55                  60

Gly Ser Gly Thr Asp Tyr Thr Leu Thr Ile Ser Arg Val Glu Pro Glu
 65                  70                  75                  80

Asp Phe Ala Val Tyr Tyr Cys Gln Gln Trp Ser Gly Asn Pro Arg Thr
                 85                  90                  95

Phe Gly Gly Gly Thr Lys Leu Glu Ile Lys
            100                 105

<210> SEQ ID NO 212
<211> LENGTH: 106
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 212

Glu Ile Val Leu Thr Gln Ser Pro Gly Thr Leu Ser Ala Ser Pro Gly
1               5                   10                  15

Glu Arg Ala Thr Met Ser Cys Arg Ala Ser Ser Val Ser Tyr Met
            20                  25                  30

Tyr Trp Tyr Gln Gln Lys Pro Gly Gln Ala Pro Arg Pro Trp Ile Tyr
        35                  40                  45

Ala Thr Ser Asn Leu Ala Ser Gly Val Pro Asp Arg Phe Ser Gly Ser
    50                  55                  60

Gly Ser Gly Thr Asp Phe Thr Leu Thr Ile Ser Arg Val Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
            100                 105

<210> SEQ ID NO 213
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Glu Ile Val Leu Thr Gln Ser Pro Gly Thr Leu Ser Ala Ser Pro Gly
1               5                   10                  15

Glu Arg Ala Thr Met Ser Cys Arg Ala Ser Ser Val Ser Tyr Met
            20                  25                  30

Tyr Trp Tyr Gln Gln Lys Pro Gly Gln Ala Pro Arg Pro Trp Ile Tyr
        35                  40                  45

Ala Thr Ser Asn Leu Ala Ser Gly Val Pro Asp Arg Phe Ser Gly Ser
    50                  55                  60

Gly Ser Gly Thr Asp Tyr Thr Leu Thr Ile Ser Arg Leu Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
            100                 105

<210> SEQ ID NO 214
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Glu Ile Val Leu Thr Gln Ser Pro Gly Thr Leu Ser Ala Ser Pro Gly
1               5                   10                  15

Glu Arg Ala Thr Met Ser Cys Arg Ala Ser Ser Val Ser Tyr Met
            20                  25                  30

Tyr Trp Tyr Gln Gln Lys Pro Gly Gln Ala Pro Arg Pro Trp Ile Tyr
        35                  40                  45
```

Ala Thr Ser Asn Leu Ala Ser Gly Val Pro Asp Arg Phe Ser Gly Ser
            50                  55                  60

Gly Ser Gly Thr Asp Phe Thr Leu Thr Ile Ser Arg Leu Glu Pro Glu
 65                  70                  75                  80

Asp Phe Ala Val Tyr Tyr Cys Gln Gln Trp Ser Gly Asn Pro Arg Thr
                 85                  90                  95

Phe Gly Gly Gly Thr Lys Leu Glu Ile Lys
            100                 105

<210> SEQ ID NO 215
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Glu Ile Val Leu Thr Gln Ser Pro Gly Thr Leu Ser Ala Ser Pro Gly
 1               5                  10                  15

Glu Arg Ala Thr Met Ser Cys Arg Ala Ser Ser Ser Val Ser Tyr Met
            20                  25                  30

Tyr Trp Tyr Gln Gln Lys Pro Gly Gln Ala Pro Arg Pro Trp Ile Tyr
            35                  40                  45

Ala Thr Ser Asn Leu Ala Ser Gly Ile Pro Asp Arg Phe Ser Gly Ser
            50                  55                  60

Gly Ser Gly Thr Asp Tyr Thr Leu Thr Ile Ser Arg Val Glu Pro Glu
 65                  70                  75                  80

Asp Phe Ala Val Tyr Tyr Cys Gln Gln Trp Ser Gly Asn Pro Arg Thr
                 85                  90                  95

Phe Gly Gly Gly Thr Lys Leu Glu Ile Lys
            100                 105

<210> SEQ ID NO 216
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
            35                  40                  45

Ala Thr Ser Asn Leu Ala Ser Gly Ile Pro Asp Arg Phe Ser Gly Ser
            50                  55                  60

Gly Ser Gly Thr Asp Tyr Thr Leu Thr Ile Ser Arg Leu Glu Pro Glu
 65                  70                  75                  80

Asp Phe Ala Val Tyr Tyr Cys Gln Gln Trp Glu Gly Asn Pro Arg Thr
                 85                  90                  95

Phe Gly Gly Gly Thr Lys Leu Glu Ile Lys
            100                 105

<210> SEQ ID NO 217
<211> LENGTH: 106

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Val Glu Pro Glu
65                  70                  75                  80

Asp Phe Ala Val Tyr Tyr Cys Gln Gln Trp Glu Gly Asn Pro Arg Thr
                85                  90                  95

Phe Gly Gly Gly Thr Lys Leu Glu Ile Lys
            100                 105

<210> SEQ ID NO 218
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Tyr Thr Leu Thr Ile Ser Arg Val Glu Pro Glu
65                  70                  75                  80

Asp Phe Ala Val Tyr Tyr Cys Gln Gln Trp Glu Gly Asn Pro Arg Thr
                85                  90                  95

Phe Gly Gly Gly Thr Lys Leu Glu Ile Lys
            100                 105

<210> SEQ ID NO 219
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Glu Ile Val Leu Thr Gln Ser Pro Gly Thr Leu Ser Ala Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr

```
            35                  40                  45
Ala Thr Ser Asn Leu Ala Ser Gly Ile Pro Asp Arg Phe Ser Gly Ser
        50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Glu Gly Asn Pro Arg Thr
                85                  90                  95

Phe Gly Gly Gly Thr Lys Leu Glu Ile Lys
            100                 105

<210> SEQ ID NO 220
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Glu Ile Val Leu Thr Gln Ser Pro Gly Thr Met Ser Leu Ser Pro Gly
1               5                   10                  15

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Leu Leu Ile Tyr
            35                  40                  45

Ala Thr Ser Asn Leu Ala Ser Gly Ile Pro Asp Arg Phe Ser Gly Ser
        50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Glu Gly Asn Pro Arg Thr
                85                  90                  95

Phe Gly Gly Gly Thr Lys Leu Glu Ile Lys
            100                 105

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225
```

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

```
<400> SEQUENCE: 293
000

<210> SEQ ID NO 294
<400> SEQUENCE: 294
000

<210> SEQ ID NO 295
<400> SEQUENCE: 295
000

<210> SEQ ID NO 296
<400> SEQUENCE: 296
000

<210> SEQ ID NO 297
<400> SEQUENCE: 297
000

<210> SEQ ID NO 298
<400> SEQUENCE: 298
000

<210> SEQ ID NO 299
<400> SEQUENCE: 299
000

<210> SEQ ID NO 300
<400> SEQUENCE: 300
000

<210> SEQ ID NO 301
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (40)..(40)
<223> OTHER INFORMATION: Any amino acid
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
```

-continued

```
<222> LOCATION: (50)..(66)
<223> OTHER INFORMATION: This region may encompass one of the following
      sequences: "RIDPASGHTKYDPKFQV" or "RIEPASGHIKYDPKFQG" or
      "RIDPASGHIKYDPKFQG" or "RIEPASGHIKYDPKFQV"
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (70)..(70)
<223> OTHER INFORMATION: Any amino acid
<220> FEATURE:
<221> NAME/KEY: MOD_RES
<222> LOCATION: (72)..(72)
<223> OTHER INFORMATION: Any amino acid
<220> FEATURE:
<221> NAME/KEY: MOD_RES
<222> LOCATION: (79)..(79)
<223> OTHER INFORMATION: Any amino acid
<220> FEATURE:
<221> NAME/KEY: MOD_RES
<222> LOCATION: (81)..(81)
<223> OTHER INFORMATION: Any amino acid
<220> FEATURE:
<221> NAME/KEY: MOD_RES
<222> LOCATION: (99)..(107)
<223> OTHER INFORMATION: This region may encompass one of the following
      sequences: "SGGLPDV" or "ARSGGLPDV" or "SGGLPDW" or "ARSGGLPDW"
<220> FEATURE:
<223> OTHER INFORMATION: See specification as filed for detailed
      description of substitutions and preferred embodiments

<400> SEQUENCE: 301

Xaa Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Xaa Gln Xaa Pro Gly Gln Gly Leu Glu Trp Xaa
        35                  40                  45

Gly Xaa Xaa Xaa Xaa Xaa Xaa Xaa Xaa Xaa Xaa Xaa Xaa Xaa Xaa Xaa
    50                  55                  60

Xaa Xaa Arg Xaa Thr Xaa Thr Xaa Asp Thr Ser Thr Ser Thr Xaa Tyr
65                  70                  75                  80

Xaa Glu Leu Ser Ser Leu Arg Ser Glu Asp Thr Ala Val Tyr Tyr Cys
            85                  90                  95

Ala Arg Xaa Xaa Xaa Xaa Xaa Xaa Xaa Xaa Xaa Trp Gly Gln Gly Thr
            100                 105                 110

Thr Val Thr Val Ser Ser
        115

<210> SEQ ID NO 302
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (40)..(40)
<223> OTHER INFORMATION: Any amino acid
```

```
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (50)..(66)
<223> OTHER INFORMATION: This region may encompass one of the following
      sequences: "RIDPASGHTKYDPKFQV" or "RIEPASGHIKYDPKFQG" or
      "RIDPASGHIKYDPKFQG" or "RIEPASGHIKYDPKFQV"
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (70)..(70)
<223> OTHER INFORMATION: Any amino acid
<220> FEATURE:
<221> NAME/KEY: MOD_RES
<222> LOCATION: (72)..(72)
<223> OTHER INFORMATION: Any amino acid
<220> FEATURE:
<221> NAME/KEY: MOD_RES
<222> LOCATION: (79)..(79)
<223> OTHER INFORMATION: Any amino acid
<220> FEATURE:
<221> NAME/KEY: MOD_RES
<222> LOCATION: (81)..(81)
<223> OTHER INFORMATION: Any amino acid
<220> FEATURE:
<221> NAME/KEY: MOD_RES
<222> LOCATION: (97)..(105)
<223> OTHER INFORMATION: This region may encompass one of the following
      sequences: "SGGLPDV" or "ARSGGLPDV" or "SGGLPDW" or "ARSGGLPDW"
<220> FEATURE:
<223> OTHER INFORMATION: See specification as filed for detailed
      description of substitutions and preferred embodiments

<400> SEQUENCE: 302

Xaa Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Xaa Gln Xaa Pro Gly Gln Gly Leu Glu Trp Xaa
        35                  40                  45

Gly Xaa Xaa Xaa Xaa Xaa Xaa Xaa Xaa Xaa Xaa Xaa Xaa Xaa Xaa Xaa
    50                  55                  60

Xaa Xaa Arg Xaa Thr Xaa Thr Xaa Asp Thr Ser Thr Ser Thr Xaa Tyr
65                  70                  75                  80

Xaa Glu Leu Ser Ser Leu Arg Ser Glu Asp Thr Ala Val Tyr Tyr Cys
            85                  90                  95

Xaa Xaa Xaa Xaa Xaa Xaa Xaa Xaa Xaa Trp Gly Gln Gly Thr Thr Val
            100                 105                 110

Thr Val Ser Ser
        115

<210> SEQ ID NO 303
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (45)..(46)
<223> OTHER INFORMATION: Any amino acid
<220> FEATURE:
<221> NAME/KEY: MOD_RES
```

```
<222> LOCATION: (88)..(96)
<223> OTHER INFORMATION: This region may encompass one of the following
      sequences: "QQWEGNPRT" or "QQWKGNPRT" or "QQWSGNPRT" or
      "QQWSRNPRT"
<220> FEATURE:
<223> OTHER INFORMATION: See specification as filed for detailed
      description of substitutions and preferred embodiments

<400> SEQUENCE: 303

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Xaa Xaa Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Xaa Xaa Xaa Xaa Xaa Xaa Xaa Xaa Xaa
                85                  90                  95

Phe Gly Gly Gly Thr Lys Leu Glu Ile Lys
            100                 105

<210> SEQ ID NO 304
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 305
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Trp Val Lys Gln Arg Pro Gly Gln Gly Leu Glu Trp Met Gly
1               5                   10

<210> SEQ ID NO 306
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Arg Val Thr Ile Thr Arg Asp Thr Ser Thr Ser Thr Val Tyr Leu Glu
1               5                   10                  15

Leu Ser Ser Leu Arg Ser Glu Asp Thr Ala Val Tyr Tyr Cys Ala Arg
            20                  25                  30
```

<210> SEQ ID NO 307
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Arg Val Thr Ile Thr Arg Asp Thr Ser Thr Ser Thr Val Tyr Leu Glu
1               5                   10                  15

Leu Ser Ser Leu Arg Ser Glu Asp Thr Ala Val Tyr Tyr Cys
            20                  25                  30

<210> SEQ ID NO 308
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Trp Gly Gln Gly Thr Thr Val Thr Val Ser Ser
1               5                   10

<210> SEQ ID NO 309
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 310
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Trp Tyr Gln Gln Lys Pro Gly Gln Ala Pro Arg Pro Leu Ile Tyr
1               5                   10                  15

<210> SEQ ID NO 311
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 312
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Phe Gly Gly Gly Thr Lys Leu Glu Ile Lys
1               5                   10

<210> SEQ ID NO 313
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Trp Val Arg Gln Arg Pro Gly Gln Gly Leu Glu Trp Ile Gly
1               5                   10

<210> SEQ ID NO 314
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Arg Ala Thr Ile Thr Thr Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 315
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Arg Ala Thr Ile Thr Thr Asp Thr Ser Thr Ser Thr Ala Tyr Leu Glu
1               5                   10                  15

Leu Ser Ser Leu Arg Ser Glu Asp Thr Ala Val Tyr Tyr Cys
            20                  25                  30

<210> SEQ ID NO 316
<211> LENGTH: 98
<212> TYPE: PRT
<213> ORGANISM: Homo sapiens

<400> SEQUENCE: 316

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
            50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 317
<211> LENGTH: 96
<212> TYPE: PRT
<213> ORGANISM: Homo sapiens

<400> SEQUENCE: 317

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

<210> SEQ ID NO 318

<400> SEQUENCE: 318

000

<210> SEQ ID NO 319
<211> LENGTH: 107
<212> TYPE: PRT
<213> ORGANISM: Homo sapiens

<400> SEQUENCE: 319

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
                 20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
         50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 320
<211> LENGTH: 330
<212> TYPE: PRT
<213> ORGANISM: Homo sapiens -continued

<400> SEQUENCE: 320

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 321
<211> LENGTH: 330
<212> TYPE: PRT
<213> ORGANISM: Homo sapiens

<400> SEQUENCE: 321

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 322
<211> LENGTH: 330
<212> TYPE: PRT
<213> ORGANISM: Homo sapiens

<400> SEQUENCE: 322

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 323
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys

```
                100                 105                 110
Pro Ala Pro Glu Leu Glu Gly Gly Pro Ser Val Phe Leu Phe Pro Pro
                115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
                195                 200                 205
Lys Ala Leu Pro Ala Pro Ile Glu Lys Thr Ile Ser Lys Ala Lys Gly
                210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
                275                 280                 285
Leu Tyr Ser Lys Leu Thr Val Asp Lys Ser Arg Trp Gln Gln Gly Asn
                290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 324
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
                100                 105                 110
Pro Ala Pro Glu Leu Glu Gly Gly Pro Ser Val Phe Leu Phe Pro Pro
                115                 120                 125
```

```
Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 325
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 326
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu

```
            180                 185                 190
His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 327
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 328
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

```
Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 329
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
                    260                 265                 270
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 330
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 331
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
Gln Lys Ser Leu Ser Leu Ser Pro Gly
                325

<210> SEQ ID NO 332
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

-continued

```
<210> SEQ ID NO 333
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 334
<211> LENGTH: 330
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 334

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 335
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Ser Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 336
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
              35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
                100                 105                 110

Pro Ala Pro Glu Phe Glu Gly Gly Pro Ser Val Phe Leu Phe Pro Pro
                115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Ser Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 337
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser

```
            50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Phe Glu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 338
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65                  70                  75                  80
```

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 339
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

```
Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 340
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
```

```
                130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 341
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175
Glu Gln Tyr Asn Ser Thr Tyr Arg Val Val Ser Val Leu Thr Val Leu
        180                 185                 190
His Gln Asp Trp Leu Asn Gly Lys Glu Tyr Lys Cys Lys Val Ser Asn
    195                 200                 205
Lys Ala Leu Pro Ala Ser Ile Glu Lys Thr Ile Ser Lys Ala Lys Gly
210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly
                325

<210> SEQ ID NO 342
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
                100                 105                 110
Pro Ala Pro Glu Ala Glu Gly Ala Pro Ser Val Phe Leu Phe Pro Pro
            115                 120                 125
Lys Pro Lys Asp Thr Leu Met Ile Ser Arg Thr Pro Glu Val Thr Cys
        130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
                195                 200                 205

Lys Ala Leu Pro Ala Ser Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 343
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
                195                 200                 205

Lys Ala Leu Pro Ala Ser Ile Glu Lys Thr Ile Ser Lys Ala Lys Gly

```
            210                 215                 220
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 344
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Ala Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240
```

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 345
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Ala Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 346
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Ala Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
```

```
                    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 347
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

Gln Lys Ser Leu Ser Leu Ser Pro Gly Lys
            325                 330

<210> SEQ ID NO 348
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 349

<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 349

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 350
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 350

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Gly Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 351
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 351

Ala Ser Thr Lys Gly Pro Ser Val Phe Pro Leu Ala Pro Ser Ser Lys

```
                1               5                  10                 15
            Ser Thr Ser Gly Gly Thr Ala Ala Leu Gly Cys Leu Val Lys Asp Tyr
                            20                  25                 30

Phe Pro Glu Pro Val Thr Val Ser Trp Asn Ser Gly Ala Leu Thr Ser
                            35                  40                 45

Gly Val His Thr Phe Pro Ala Val Leu Gln Ser Ser Gly Leu Tyr Ser
                            50                  55                 60

Leu Ser Ser Val Val Thr Val Pro Ser Ser Leu Gly Thr Gln Thr
            65                  70                  75                 80

Tyr Ile Cys Asn Val Asn His Lys Pro Ser Asn Thr Lys Val Asp Lys
                            85                  90                 95

Arg Val Glu Pro Lys Ser Cys Asp Lys Thr His Thr Cys Pro Pro Cys
                            100                 105                110

Pro Ala Pro Glu Leu Leu Gly Gly Pro Ser Val Phe Leu Phe Pro Pro
                            115                 120                125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
            145                 150                 155                160

Tyr Val Asp Gly Val Glu Val His Asn Ala Lys Thr Lys Pro Arg Glu
                            165                 170                175

Glu Gln Tyr Gly Ser Thr Tyr Arg Val Val Ser Val Leu Thr Val Leu
                            180                 185                190

His Gln Asp Trp Leu Asn Gly Lys Glu Tyr Lys Cys Lys Val Ser Asn
                            195                 200                205

Lys Ala Leu Pro Ala Pro Ile Glu Lys Thr Ile Ser Lys Ala Lys Gly
                            210                 215                220

Gln Pro Arg Glu Pro Gln Val Tyr Thr Leu Pro Pro Ser Arg Glu Glu
            225                 230                 235                240

Met Thr Lys Asn Gln Val Ser Leu Thr Cys Leu Val Lys Gly Phe Tyr
                            245                 250                255

Pro Ser Asp Ile Ala Val Glu Trp Glu Ser Asn Gly Gln Pro Glu Asn
                            260                 265                270

Asn Tyr Lys Thr Thr Pro Pro Val Leu Asp Ser Asp Gly Ser Phe Phe
                            275                 280                285

Leu Tyr Ser Lys Leu Thr Val Asp Lys Ser Arg Trp Gln Gln Gly Asn
                            290                 295                300

Val Phe Ser Cys Ser Val Met His Glu Ala Leu His Asn His Tyr Thr
            305                 310                 315                320

Gln Lys Ser Leu Ser Leu Ser Pro Gly Lys
                            325                 330

<210> SEQ ID NO 352
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 353
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 353

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60
```

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 354
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
            85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 355
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 356
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

```
Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Gly Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 357
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

165                 170                 175
Glu Gln Tyr Gly Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 358
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
            130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 359
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 360
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

-continued

```
                    245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
            325                 330

<210> SEQ ID NO 361
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Ala Gly Ala Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 362
<211> LENGTH: 327
<212> TYPE: PRT
<213> ORGANISM: Homo sapiens

<400> SEQUENCE: 362

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320
```

```
Leu Ser Leu Ser Leu Gly Lys
            325
```

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

-continued

<210> SEQ ID NO 385
<400> SEQUENCE: 385
000

<210> SEQ ID NO 386
<400> SEQUENCE: 386
000

<210> SEQ ID NO 387
<400> SEQUENCE: 387
000

<210> SEQ ID NO 388
<400> SEQUENCE: 388
000

<210> SEQ ID NO 389
<400> SEQUENCE: 389
000

<210> SEQ ID NO 390
<400> SEQUENCE: 390
000

<210> SEQ ID NO 391
<400> SEQUENCE: 391
000

<210> SEQ ID NO 392
<400> SEQUENCE: 392
000

<210> SEQ ID NO 393
<400> SEQUENCE: 393
000

<210> SEQ ID NO 394
<400> SEQUENCE: 394
000

<210> SEQ ID NO 395
<400> SEQUENCE: 395
000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 401

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 402
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 402

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Leu Glu Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly

```
                210                 215                 220
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 403
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 403

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 404
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 404

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 405
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 405

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Ala Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
```

```
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 406
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 406

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Ala Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320
```

Gln Lys Ser Leu Ser Leu Ser Pro Gly Lys
            325                 330

<210> SEQ ID NO 407
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 407

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Ala Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 408

```
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Glu Phe Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 409
<211> LENGTH: 330
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 409

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 410
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 410

Ala Ser Thr Lys Gly Pro Ser Val Phe Pro Leu Ala Pro Ser Ser Lys

```
              1               5                  10                 15
           Ser Thr Ser Gly Gly Thr Ala Ala Leu Gly Cys Leu Val Lys Asp Tyr
                           20                  25                 30

Phe Pro Glu Pro Val Thr Val Ser Trp Asn Ser Gly Ala Leu Thr Ser
                           35                  40                 45

Gly Val His Thr Phe Pro Ala Val Leu Gln Ser Ser Gly Leu Tyr Ser
                           50                  55                 60

Leu Ser Ser Val Val Thr Val Pro Ser Ser Leu Gly Thr Gln Thr
            65                  70                  75                 80

Tyr Ile Cys Asn Val Asn His Lys Pro Ser Asn Thr Lys Val Asp Lys
                           85                  90                 95

Lys Val Glu Pro Lys Ser Cys Asp Lys Thr His Thr Cys Pro Pro Cys
                           100                 105                110

Pro Ala Pro Glu Leu Leu Gly Gly Pro Ser Val Phe Leu Phe Pro Pro
                           115                 120                125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
            145                 150                 155                160

Tyr Val Asp Gly Val Glu Val His Asn Ala Lys Thr Lys Pro Arg Glu
                           165                 170                175

Glu Gln Tyr Gly Ser Thr Tyr Arg Val Val Ser Val Leu Thr Val Leu
                           180                 185                 190

His Gln Asp Trp Leu Asn Gly Lys Glu Tyr Lys Cys Lys Val Ser Asn
                           195                 200                 205

Lys Ala Leu Pro Ala Pro Ile Glu Lys Thr Ile Ser Lys Ala Lys Gly
                           210                 215                 220

Gln Pro Arg Glu Pro Gln Val Tyr Thr Leu Pro Pro Ser Arg Asp Glu
            225                 230                 235                240

Leu Thr Lys Asn Gln Val Ser Leu Thr Cys Leu Val Lys Gly Phe Tyr
                           245                 250                 255

Pro Ser Asp Ile Ala Val Glu Trp Glu Ser Asn Gly Gln Pro Glu Asn
                           260                 265                 270

Asn Tyr Lys Thr Thr Pro Pro Val Leu Asp Ser Asp Gly Ser Phe Phe
                           275                 280                 285

Leu Tyr Ser Lys Leu Thr Val Asp Lys Ser Arg Trp Gln Gln Gly Asn
                           290                 295                 300

Val Phe Ser Cys Ser Val Met His Glu Ala Leu His Asn His Tyr Thr
            305                 310                 315                320

Gln Lys Ser Leu Ser Leu Ser Pro Gly Lys
                           325                 330

<210> SEQ ID NO 411
           <211> LENGTH: 327
           <212> TYPE: PRT
           <213> ORGANISM: Artificial Sequence
           <220> FEATURE:
           <223> OTHER INFORMATION: Description of Artificial Sequence: Synthetic
                 polypeptide

<400> SEQUENCE: 411

Ala Ser Thr Lys Gly Pro Ser Val Phe Pro Leu Ala Pro Cys Ser Arg
            1               5                   10                 15

Ser Thr Ser Glu Ser Thr Ala Ala Leu Gly Cys Leu Val Lys Asp Tyr
                           20                  25                 30
```

```
Phe Pro Glu Pro Val Thr Val Ser Trp Asn Ser Gly Ala Leu Thr Ser
             35                   40                  45

Gly Val His Thr Phe Pro Ala Val Leu Gln Ser Ser Gly Leu Tyr Ser
     50                   55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 412
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 412

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
     50                  55                  60
```

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 413
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 413

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys

```
                        85                  90                  95
Arg Val Glu Ser Lys Tyr Gly Pro Pro Cys Pro Cys Pro Ala Pro
                100                 105                 110
Glu Ala Ala Gly Gly Pro Ser Val Phe Leu Phe Pro Pro Lys Pro Lys
                115                 120                 125
Asp Thr Leu Met Ile Ser Arg Thr Pro Glu Val Thr Cys Val Val Val
                130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
                180                 185                 190
Trp Leu Asn Gly Lys Glu Tyr Lys Cys Lys Val Ser Asn Lys Gly Leu
                195                 200                 205
Pro Ser Ser Ile Glu Lys Thr Ile Ser Lys Ala Lys Gly Gln Pro Arg
                210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
                260                 265                 270
Thr Thr Pro Pro Val Leu Asp Ser Asp Gly Ser Phe Phe Leu Tyr Ser
                275                 280                 285
Arg Leu Thr Val Asp Lys Ser Arg Trp Gln Glu Gly Asn Val Phe Ser
                290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 414

<400> SEQUENCE: 414

000

<210> SEQ ID NO 415

<400> SEQUENCE: 415

000

<210> SEQ ID NO 416

<400> SEQUENCE: 416

000

<210> SEQ ID NO 417

<400> SEQUENCE: 417

000

<210> SEQ ID NO 418

<400> SEQUENCE: 418
```

000

<210> SEQ ID NO 419
<400> SEQUENCE: 419
000

<210> SEQ ID NO 420
<400> SEQUENCE: 420
000

<210> SEQ ID NO 421
<400> SEQUENCE: 421
000

<210> SEQ ID NO 422
<400> SEQUENCE: 422
000

<210> SEQ ID NO 423
<400> SEQUENCE: 423
000

<210> SEQ ID NO 424
<400> SEQUENCE: 424
000

<210> SEQ ID NO 425
<400> SEQUENCE: 425
000

<210> SEQ ID NO 426
<400> SEQUENCE: 426
000

<210> SEQ ID NO 427
<400> SEQUENCE: 427
000

<210> SEQ ID NO 428
<400> SEQUENCE: 428
000

<210> SEQ ID NO 429
<400> SEQUENCE: 429
000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464
<400> SEQUENCE: 464
000

<210> SEQ ID NO 465
<400> SEQUENCE: 465
000

<210> SEQ ID NO 466
<400> SEQUENCE: 466
000

<210> SEQ ID NO 467
<400> SEQUENCE: 467
000

<210> SEQ ID NO 468
<400> SEQUENCE: 468
000

<210> SEQ ID NO 469
<400> SEQUENCE: 469
000

<210> SEQ ID NO 470
<400> SEQUENCE: 470
000

<210> SEQ ID NO 471
<400> SEQUENCE: 471
000

<210> SEQ ID NO 472
<400> SEQUENCE: 472
000

<210> SEQ ID NO 473
<400> SEQUENCE: 473
000

<210> SEQ ID NO 474
<400> SEQUENCE: 474
000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

```
<400> SEQUENCE: 486
000

<210> SEQ ID NO 487
<400> SEQUENCE: 487
000

<210> SEQ ID NO 488
<400> SEQUENCE: 488
000

<210> SEQ ID NO 489
<400> SEQUENCE: 489
000

<210> SEQ ID NO 490
<400> SEQUENCE: 490
000

<210> SEQ ID NO 491
<400> SEQUENCE: 491
000

<210> SEQ ID NO 492
<400> SEQUENCE: 492
000

<210> SEQ ID NO 493
<400> SEQUENCE: 493
000

<210> SEQ ID NO 494
<400> SEQUENCE: 494
000

<210> SEQ ID NO 495
<400> SEQUENCE: 495
000

<210> SEQ ID NO 496
<400> SEQUENCE: 496
000

<210> SEQ ID NO 497
<400> SEQUENCE: 497
```

000

<210> SEQ ID NO 498

<400> SEQUENCE: 498

000

<210> SEQ ID NO 499

<400> SEQUENCE: 499

000

<210> SEQ ID NO 500

<400> SEQUENCE: 500

000

<210> SEQ ID NO 501
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 501

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Ile Thr Arg Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

```
Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 502
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 502

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Ile Thr Arg Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
```

```
             145                 150                 155                 160
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
210                 215                 220

Cys Pro Pro Cys Pro Ala Pro Glu Leu Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 503
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 503

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
                20                  25                  30

Tyr Met His Trp Val Lys Gln Arg Pro Gly Gln Gly Leu Glu Trp Met
                35                  40                  45

Gly Arg Ile Asp Pro Ala Ser Gly His Thr Lys Tyr Asp Pro Lys Phe
            50                  55                  60
```

```
Gln Val Arg Val Thr Ile Thr Arg Asp Thr Ser Thr Thr Val Tyr
 65                  70                  75                  80

Leu Glu Leu Ser Ser Leu Arg Ser Glu Asp Thr Ala Val Tyr Tyr Cys
                 85                  90                  95

Ala Arg Ser Gly Gly Leu Pro Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Ala Ala Gly Ala Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 504
<211> LENGTH: 446
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 504

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Ile Thr Arg Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Glu Gly Ala Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

```
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 505
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 505

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Ile Thr Arg Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Ala Leu Ala Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 506
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 506

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
            35                  40                  45

Gly Arg Ile Asp Pro Ala Ser Gly His Thr Lys Tyr Asp Pro Lys Phe
    50                  55                  60

Gln Val Arg Val Thr Ile Thr Arg Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
```

```
                  225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
                290                 295                 300

Leu Thr Val Leu His Gln Asp Trp Leu Asn Gly Lys Glu Tyr Lys Cys
305                 310                 315                 320

Lys Val Ser Asn Lys Ala Leu Ala Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 507
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 507

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
                20                  25                  30

Tyr Met His Trp Val Lys Gln Arg Pro Gly Gln Gly Leu Glu Trp Met
                35                  40                  45

Gly Arg Ile Asp Pro Ala Ser Gly His Thr Lys Tyr Asp Pro Lys Phe
            50                  55                  60

Gln Val Arg Val Thr Ile Thr Arg Asp Thr Ser Thr Ser Thr Val Tyr
65              70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
                100                 105                 110

Thr Val Ser Ser Ala Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
                130                 135                 140
```

```
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Ala Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 508
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 508

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60
```

Gln Val Arg Val Thr Ile Thr Arg Asp Thr Ser Thr Ser Thr Val Tyr
65                  70                  75                  80

Leu Glu Leu Ser Ser Leu Arg Ser Glu Asp Thr Ala Val Tyr Tyr Cys
            85                  90                  95

Ala Arg Ser Gly Gly Leu Pro Asp Val Trp Gly Gln Gly Thr Thr Val
        100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Phe Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 509
<211> LENGTH: 446
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 509

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Ile Thr Arg Asp Thr Ser Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Ala Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Gly Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400
```

```
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 510
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 510

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
            35                  40                  45

Gly Arg Ile Asp Pro Ala Ser Gly His Thr Lys Tyr Asp Pro Lys Phe
    50                  55                  60

Gln Val Arg Val Thr Ile Thr Arg Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Gly Ser Thr Tyr Arg Val Val Ser Val
    290                 295                 300

Leu Thr Val Leu His Gln Asp Trp Leu Asn Gly Lys Glu Tyr Lys Cys
```

```
                305                 310                 315                 320
Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 511
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 511

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Ile Thr Arg Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220
```

```
Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Asp Val Ser Gln Glu Asp Pro Glu Val Gln Phe Asn
        260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 512
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 512

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Ile Thr Arg Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140
```

```
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Lys Thr Tyr Thr Cys Asn Val Asp His Lys Pro Ser Asn Thr
    195                 200                 205

Lys Val Asp Lys Arg Val Glu Ser Lys Tyr Gly Pro Pro Cys Pro Pro
210                 215                 220

Cys Pro Ala Pro Glu Phe Glu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 513
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 513

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Lys Gln Arg Pro Gly Gln Gly Leu Glu Trp Met
        35                  40                  45

Gly Arg Ile Asp Pro Ala Ser Gly His Thr Lys Tyr Asp Pro Lys Phe
```

```
            50                  55                  60
Gln Val Arg Val Thr Ile Thr Arg Asp Thr Ser Thr Ser Thr Val Tyr
 65                  70                  75                  80

Leu Glu Leu Ser Ser Leu Arg Ser Glu Asp Thr Ala Val Tyr Tyr Cys
                 85                  90                  95

Ala Arg Ser Gly Gly Leu Pro Asp Val Trp Gly Gln Gly Thr Thr Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Pro
210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
            290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
            435                 440

<210> SEQ ID NO 514
<211> LENGTH: 213
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 514

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Pro Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Glu Gly Asn Pro Arg Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 515

<400> SEQUENCE: 515

000

<210> SEQ ID NO 516

<400> SEQUENCE: 516

000

<210> SEQ ID NO 517

<400> SEQUENCE: 517

000

<210> SEQ ID NO 518

<400> SEQUENCE: 518

000

<210> SEQ ID NO 519

<400> SEQUENCE: 519

000

<210> SEQ ID NO 520

<400> SEQUENCE: 520

000

<210> SEQ ID NO 521

<400> SEQUENCE: 521

000

<210> SEQ ID NO 522

<400> SEQUENCE: 522

000

<210> SEQ ID NO 523

<400> SEQUENCE: 523

000

<210> SEQ ID NO 524

<400> SEQUENCE: 524

000

<210> SEQ ID NO 525

<400> SEQUENCE: 525

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000

<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

<400> SEQUENCE: 549

000

<210> SEQ ID NO 550

<400> SEQUENCE: 550

000

<210> SEQ ID NO 551

<400> SEQUENCE: 551

000

<210> SEQ ID NO 552

<400> SEQUENCE: 552

000

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561

<400> SEQUENCE: 561

000

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565
<400> SEQUENCE: 565
000

<210> SEQ ID NO 566
<400> SEQUENCE: 566
000

<210> SEQ ID NO 567
<400> SEQUENCE: 567
000

<210> SEQ ID NO 568
<400> SEQUENCE: 568
000

<210> SEQ ID NO 569
<400> SEQUENCE: 569
000

<210> SEQ ID NO 570
<400> SEQUENCE: 570
000

<210> SEQ ID NO 571
<400> SEQUENCE: 571
000

<210> SEQ ID NO 572
<400> SEQUENCE: 572
000

<210> SEQ ID NO 573
<400> SEQUENCE: 573
000

<210> SEQ ID NO 574
<400> SEQUENCE: 574
000

<210> SEQ ID NO 575
<400> SEQUENCE: 575
000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600

<400> SEQUENCE: 600

000

<210> SEQ ID NO 601

<400> SEQUENCE: 601

000

<210> SEQ ID NO 602

<400> SEQUENCE: 602

000

<210> SEQ ID NO 603

<400> SEQUENCE: 603

000

<210> SEQ ID NO 604

<400> SEQUENCE: 604

000

<210> SEQ ID NO 605

<400> SEQUENCE: 605

000

<210> SEQ ID NO 606

<400> SEQUENCE: 606

000

<210> SEQ ID NO 607

<400> SEQUENCE: 607

000

<210> SEQ ID NO 608

<400> SEQUENCE: 608

000

<210> SEQ ID NO 609

<400> SEQUENCE: 609

000

<210> SEQ ID NO 610
<400> SEQUENCE: 610
000

<210> SEQ ID NO 611
<400> SEQUENCE: 611
000

<210> SEQ ID NO 612
<400> SEQUENCE: 612
000

<210> SEQ ID NO 613
<400> SEQUENCE: 613
000

<210> SEQ ID NO 614
<400> SEQUENCE: 614
000

<210> SEQ ID NO 615
<400> SEQUENCE: 615
000

<210> SEQ ID NO 616
<400> SEQUENCE: 616
000

<210> SEQ ID NO 617
<400> SEQUENCE: 617
000

<210> SEQ ID NO 618
<400> SEQUENCE: 618
000

<210> SEQ ID NO 619
<400> SEQUENCE: 619
000

<210> SEQ ID NO 620
<400> SEQUENCE: 620
000

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629

<400> SEQUENCE: 629

000

<210> SEQ ID NO 630

<400> SEQUENCE: 630

000

<210> SEQ ID NO 631

<400> SEQUENCE: 631

000

<210> SEQ ID NO 632

<400> SEQUENCE: 632

000

<210> SEQ ID NO 633

<400> SEQUENCE: 633

000

<210> SEQ ID NO 634

<400> SEQUENCE: 634

000

<210> SEQ ID NO 635

<400> SEQUENCE: 635

000

<210> SEQ ID NO 636

<400> SEQUENCE: 636

000

<210> SEQ ID NO 637

<400> SEQUENCE: 637

000

<210> SEQ ID NO 638

<400> SEQUENCE: 638

000

<210> SEQ ID NO 639

<400> SEQUENCE: 639

000

<210> SEQ ID NO 640

<400> SEQUENCE: 640

000

<210> SEQ ID NO 641

<400> SEQUENCE: 641

000

<210> SEQ ID NO 642

<400> SEQUENCE: 642

000

<210> SEQ ID NO 643

<400> SEQUENCE: 643

000

<210> SEQ ID NO 644
<400> SEQUENCE: 644
000

<210> SEQ ID NO 645
<400> SEQUENCE: 645
000

<210> SEQ ID NO 646
<400> SEQUENCE: 646
000

<210> SEQ ID NO 647
<400> SEQUENCE: 647
000

<210> SEQ ID NO 648
<400> SEQUENCE: 648
000

<210> SEQ ID NO 649
<400> SEQUENCE: 649
000

<210> SEQ ID NO 650
<400> SEQUENCE: 650
000

<210> SEQ ID NO 651
<400> SEQUENCE: 651
000

<210> SEQ ID NO 652
<400> SEQUENCE: 652
000

<210> SEQ ID NO 653
<400> SEQUENCE: 653
000

<210> SEQ ID NO 654
<400> SEQUENCE: 654
000

-continued

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

<210> SEQ ID NO 666

<400> SEQUENCE: 666

000

<210> SEQ ID NO 667

<400> SEQUENCE: 667

000

<210> SEQ ID NO 668

<400> SEQUENCE: 668

000

<210> SEQ ID NO 669

<400> SEQUENCE: 669

000

<210> SEQ ID NO 670

<400> SEQUENCE: 670

000

<210> SEQ ID NO 671

<400> SEQUENCE: 671

000

<210> SEQ ID NO 672

<400> SEQUENCE: 672

000

<210> SEQ ID NO 673

<400> SEQUENCE: 673

000

<210> SEQ ID NO 674

<400> SEQUENCE: 674

000

<210> SEQ ID NO 675

<400> SEQUENCE: 675

000

<210> SEQ ID NO 676

<400> SEQUENCE: 676

000

<210> SEQ ID NO 677

-continued

<400> SEQUENCE: 677

000

<210> SEQ ID NO 678

<400> SEQUENCE: 678

000

<210> SEQ ID NO 679

<400> SEQUENCE: 679

000

<210> SEQ ID NO 680

<400> SEQUENCE: 680

000

<210> SEQ ID NO 681

<400> SEQUENCE: 681

000

<210> SEQ ID NO 682

<400> SEQUENCE: 682

000

<210> SEQ ID NO 683

<400> SEQUENCE: 683

000

<210> SEQ ID NO 684

<400> SEQUENCE: 684

000

<210> SEQ ID NO 685

<400> SEQUENCE: 685

000

<210> SEQ ID NO 686

<400> SEQUENCE: 686

000

<210> SEQ ID NO 687

<400> SEQUENCE: 687

000

<210> SEQ ID NO 688

<400> SEQUENCE: 688

-continued

000

<210> SEQ ID NO 689

<400> SEQUENCE: 689

000

<210> SEQ ID NO 690

<400> SEQUENCE: 690

000

<210> SEQ ID NO 691

<400> SEQUENCE: 691

000

<210> SEQ ID NO 692

<400> SEQUENCE: 692

000

<210> SEQ ID NO 693

<400> SEQUENCE: 693

000

<210> SEQ ID NO 694

<400> SEQUENCE: 694

000

<210> SEQ ID NO 695

<400> SEQUENCE: 695

000

<210> SEQ ID NO 696

<400> SEQUENCE: 696

000

<210> SEQ ID NO 697

<400> SEQUENCE: 697

000

<210> SEQ ID NO 698

<400> SEQUENCE: 698

000

<210> SEQ ID NO 699

<400> SEQUENCE: 699

000

<210> SEQ ID NO 700
<400> SEQUENCE: 700
000

<210> SEQ ID NO 701
<400> SEQUENCE: 701
000

<210> SEQ ID NO 702
<400> SEQUENCE: 702
000

<210> SEQ ID NO 703
<400> SEQUENCE: 703
000

<210> SEQ ID NO 704
<400> SEQUENCE: 704
000

<210> SEQ ID NO 705
<400> SEQUENCE: 705
000

<210> SEQ ID NO 706
<400> SEQUENCE: 706
000

<210> SEQ ID NO 707
<400> SEQUENCE: 707
000

<210> SEQ ID NO 708
<400> SEQUENCE: 708
000

<210> SEQ ID NO 709
<400> SEQUENCE: 709
000

<210> SEQ ID NO 710
<400> SEQUENCE: 710
000

<210> SEQ ID NO 711

```
<400> SEQUENCE: 711

000

<210> SEQ ID NO 712

<400> SEQUENCE: 712

000

<210> SEQ ID NO 713

<400> SEQUENCE: 713

000

<210> SEQ ID NO 714

<400> SEQUENCE: 714

000

<210> SEQ ID NO 715

<400> SEQUENCE: 715

000

<210> SEQ ID NO 716

<400> SEQUENCE: 716

000

<210> SEQ ID NO 717

<400> SEQUENCE: 717

000

<210> SEQ ID NO 718

<400> SEQUENCE: 718

000

<210> SEQ ID NO 719

<400> SEQUENCE: 719

000

<210> SEQ ID NO 720

<400> SEQUENCE: 720

000

<210> SEQ ID NO 721

<400> SEQUENCE: 721

000

<210> SEQ ID NO 722

<400> SEQUENCE: 722
```

000

<210> SEQ ID NO 723

<400> SEQUENCE: 723

000

<210> SEQ ID NO 724

<400> SEQUENCE: 724

000

<210> SEQ ID NO 725

<400> SEQUENCE: 725

000

<210> SEQ ID NO 726

<400> SEQUENCE: 726

000

<210> SEQ ID NO 727

<400> SEQUENCE: 727

000

<210> SEQ ID NO 728

<400> SEQUENCE: 728

000

<210> SEQ ID NO 729

<400> SEQUENCE: 729

000

<210> SEQ ID NO 730

<400> SEQUENCE: 730

000

<210> SEQ ID NO 731

<400> SEQUENCE: 731

000

<210> SEQ ID NO 732

<400> SEQUENCE: 732

000

<210> SEQ ID NO 733

<400> SEQUENCE: 733

000

<210> SEQ ID NO 734

<400> SEQUENCE: 734

000

<210> SEQ ID NO 735

<400> SEQUENCE: 735

000

<210> SEQ ID NO 736

<400> SEQUENCE: 736

000

<210> SEQ ID NO 737

<400> SEQUENCE: 737

000

<210> SEQ ID NO 738

<400> SEQUENCE: 738

000

<210> SEQ ID NO 739

<400> SEQUENCE: 739

000

<210> SEQ ID NO 740

<400> SEQUENCE: 740

000

<210> SEQ ID NO 741

<400> SEQUENCE: 741

000

<210> SEQ ID NO 742

<400> SEQUENCE: 742

000

<210> SEQ ID NO 743

<400> SEQUENCE: 743

000

<210> SEQ ID NO 744

<400> SEQUENCE: 744

000

-continued

<210> SEQ ID NO 745

<400> SEQUENCE: 745

000

<210> SEQ ID NO 746

<400> SEQUENCE: 746

000

<210> SEQ ID NO 747

<400> SEQUENCE: 747

000

<210> SEQ ID NO 748

<400> SEQUENCE: 748

000

<210> SEQ ID NO 749

<400> SEQUENCE: 749

000

<210> SEQ ID NO 750

<400> SEQUENCE: 750

000

<210> SEQ ID NO 751

<400> SEQUENCE: 751

000

<210> SEQ ID NO 752

<400> SEQUENCE: 752

000

<210> SEQ ID NO 753

<400> SEQUENCE: 753

000

<210> SEQ ID NO 754

<400> SEQUENCE: 754

000

<210> SEQ ID NO 755

<400> SEQUENCE: 755

000

<210> SEQ ID NO 756

```
<400> SEQUENCE: 756
000

<210> SEQ ID NO 757
<400> SEQUENCE: 757
000

<210> SEQ ID NO 758
<400> SEQUENCE: 758
000

<210> SEQ ID NO 759
<400> SEQUENCE: 759
000

<210> SEQ ID NO 760
<400> SEQUENCE: 760
000

<210> SEQ ID NO 761
<400> SEQUENCE: 761
000

<210> SEQ ID NO 762
<400> SEQUENCE: 762
000

<210> SEQ ID NO 763
<400> SEQUENCE: 763
000

<210> SEQ ID NO 764
<400> SEQUENCE: 764
000

<210> SEQ ID NO 765
<400> SEQUENCE: 765
000

<210> SEQ ID NO 766
<400> SEQUENCE: 766
000

<210> SEQ ID NO 767
<400> SEQUENCE: 767
```

000

<210> SEQ ID NO 768

<400> SEQUENCE: 768

000

<210> SEQ ID NO 769

<400> SEQUENCE: 769

000

<210> SEQ ID NO 770

<400> SEQUENCE: 770

000

<210> SEQ ID NO 771

<400> SEQUENCE: 771

000

<210> SEQ ID NO 772

<400> SEQUENCE: 772

000

<210> SEQ ID NO 773

<400> SEQUENCE: 773

000

<210> SEQ ID NO 774

<400> SEQUENCE: 774

000

<210> SEQ ID NO 775

<400> SEQUENCE: 775

000

<210> SEQ ID NO 776

<400> SEQUENCE: 776

000

<210> SEQ ID NO 777

<400> SEQUENCE: 777

000

<210> SEQ ID NO 778

<400> SEQUENCE: 778

000

<210> SEQ ID NO 779

<400> SEQUENCE: 779

000

<210> SEQ ID NO 780

<400> SEQUENCE: 780

000

<210> SEQ ID NO 781

<400> SEQUENCE: 781

000

<210> SEQ ID NO 782

<400> SEQUENCE: 782

000

<210> SEQ ID NO 783

<400> SEQUENCE: 783

000

<210> SEQ ID NO 784

<400> SEQUENCE: 784

000

<210> SEQ ID NO 785

<400> SEQUENCE: 785

000

<210> SEQ ID NO 786

<400> SEQUENCE: 786

000

<210> SEQ ID NO 787

<400> SEQUENCE: 787

000

<210> SEQ ID NO 788

<400> SEQUENCE: 788

000

<210> SEQ ID NO 789

<400> SEQUENCE: 789

000

<210> SEQ ID NO 790

```
<400> SEQUENCE: 790
000

<210> SEQ ID NO 791
<400> SEQUENCE: 791
000

<210> SEQ ID NO 792
<400> SEQUENCE: 792
000

<210> SEQ ID NO 793
<400> SEQUENCE: 793
000

<210> SEQ ID NO 794
<400> SEQUENCE: 794
000

<210> SEQ ID NO 795
<400> SEQUENCE: 795
000

<210> SEQ ID NO 796
<400> SEQUENCE: 796
000

<210> SEQ ID NO 797
<400> SEQUENCE: 797
000

<210> SEQ ID NO 798
<400> SEQUENCE: 798
000

<210> SEQ ID NO 799
<400> SEQUENCE: 799
000

<210> SEQ ID NO 800
<400> SEQUENCE: 800
000

<210> SEQ ID NO 801
<400> SEQUENCE: 801
```

000

<210> SEQ ID NO 802

<400> SEQUENCE: 802

000

<210> SEQ ID NO 803

<400> SEQUENCE: 803

000

<210> SEQ ID NO 804

<400> SEQUENCE: 804

000

<210> SEQ ID NO 805

<400> SEQUENCE: 805

000

<210> SEQ ID NO 806

<400> SEQUENCE: 806

000

<210> SEQ ID NO 807

<400> SEQUENCE: 807

000

<210> SEQ ID NO 808

<400> SEQUENCE: 808

000

<210> SEQ ID NO 809

<400> SEQUENCE: 809

000

<210> SEQ ID NO 810

<400> SEQUENCE: 810

000

<210> SEQ ID NO 811

<400> SEQUENCE: 811

000

<210> SEQ ID NO 812

<400> SEQUENCE: 812

000

<210> SEQ ID NO 813

<400> SEQUENCE: 813

000

<210> SEQ ID NO 814

<400> SEQUENCE: 814

000

<210> SEQ ID NO 815

<400> SEQUENCE: 815

000

<210> SEQ ID NO 816

<400> SEQUENCE: 816

000

<210> SEQ ID NO 817

<400> SEQUENCE: 817

000

<210> SEQ ID NO 818

<400> SEQUENCE: 818

000

<210> SEQ ID NO 819

<400> SEQUENCE: 819

000

<210> SEQ ID NO 820

<400> SEQUENCE: 820

000

<210> SEQ ID NO 821

<400> SEQUENCE: 821

000

<210> SEQ ID NO 822

<400> SEQUENCE: 822

000

<210> SEQ ID NO 823

<400> SEQUENCE: 823

000

<210> SEQ ID NO 824
<400> SEQUENCE: 824
000

<210> SEQ ID NO 825
<400> SEQUENCE: 825
000

<210> SEQ ID NO 826
<400> SEQUENCE: 826
000

<210> SEQ ID NO 827
<400> SEQUENCE: 827
000

<210> SEQ ID NO 828
<400> SEQUENCE: 828
000

<210> SEQ ID NO 829
<400> SEQUENCE: 829
000

<210> SEQ ID NO 830
<400> SEQUENCE: 830
000

<210> SEQ ID NO 831
<400> SEQUENCE: 831
000

<210> SEQ ID NO 832
<400> SEQUENCE: 832
000

<210> SEQ ID NO 833
<400> SEQUENCE: 833
000

<210> SEQ ID NO 834
<400> SEQUENCE: 834
000

<210> SEQ ID NO 835

<400> SEQUENCE: 835

000

<210> SEQ ID NO 836

<400> SEQUENCE: 836

000

<210> SEQ ID NO 837

<400> SEQUENCE: 837

000

<210> SEQ ID NO 838

<400> SEQUENCE: 838

000

<210> SEQ ID NO 839

<400> SEQUENCE: 839

000

<210> SEQ ID NO 840

<400> SEQUENCE: 840

000

<210> SEQ ID NO 841

<400> SEQUENCE: 841

000

<210> SEQ ID NO 842

<400> SEQUENCE: 842

000

<210> SEQ ID NO 843

<400> SEQUENCE: 843

000

<210> SEQ ID NO 844

<400> SEQUENCE: 844

000

<210> SEQ ID NO 845

<400> SEQUENCE: 845

000

<210> SEQ ID NO 846

<400> SEQUENCE: 846

000

<210> SEQ ID NO 847

<400> SEQUENCE: 847

000

<210> SEQ ID NO 848

<400> SEQUENCE: 848

000

<210> SEQ ID NO 849

<400> SEQUENCE: 849

000

<210> SEQ ID NO 850

<400> SEQUENCE: 850

000

<210> SEQ ID NO 851

<400> SEQUENCE: 851

000

<210> SEQ ID NO 852

<400> SEQUENCE: 852

000

<210> SEQ ID NO 853

<400> SEQUENCE: 853

000

<210> SEQ ID NO 854

<400> SEQUENCE: 854

000

<210> SEQ ID NO 855

<400> SEQUENCE: 855

000

<210> SEQ ID NO 856

<400> SEQUENCE: 856

000

<210> SEQ ID NO 857

<400> SEQUENCE: 857

000

<210> SEQ ID NO 858

<400> SEQUENCE: 858

000

<210> SEQ ID NO 859

<400> SEQUENCE: 859

000

<210> SEQ ID NO 860

<400> SEQUENCE: 860

000

<210> SEQ ID NO 861

<400> SEQUENCE: 861

000

<210> SEQ ID NO 862

<400> SEQUENCE: 862

000

<210> SEQ ID NO 863

<400> SEQUENCE: 863

000

<210> SEQ ID NO 864

<400> SEQUENCE: 864

000

<210> SEQ ID NO 865

<400> SEQUENCE: 865

000

<210> SEQ ID NO 866

<400> SEQUENCE: 866

000

<210> SEQ ID NO 867

<400> SEQUENCE: 867

000

<210> SEQ ID NO 868

<400> SEQUENCE: 868

000

<210> SEQ ID NO 869

```
<400> SEQUENCE: 869

000

<210> SEQ ID NO 870

<400> SEQUENCE: 870

000

<210> SEQ ID NO 871

<400> SEQUENCE: 871

000

<210> SEQ ID NO 872

<400> SEQUENCE: 872

000

<210> SEQ ID NO 873

<400> SEQUENCE: 873

000

<210> SEQ ID NO 874

<400> SEQUENCE: 874

000

<210> SEQ ID NO 875

<400> SEQUENCE: 875

000

<210> SEQ ID NO 876

<400> SEQUENCE: 876

000

<210> SEQ ID NO 877

<400> SEQUENCE: 877

000

<210> SEQ ID NO 878

<400> SEQUENCE: 878

000

<210> SEQ ID NO 879

<400> SEQUENCE: 879

000

<210> SEQ ID NO 880

<400> SEQUENCE: 880
```

000

<210> SEQ ID NO 881

<400> SEQUENCE: 881

000

<210> SEQ ID NO 882

<400> SEQUENCE: 882

000

<210> SEQ ID NO 883

<400> SEQUENCE: 883

000

<210> SEQ ID NO 884

<400> SEQUENCE: 884

000

<210> SEQ ID NO 885

<400> SEQUENCE: 885

000

<210> SEQ ID NO 886

<400> SEQUENCE: 886

000

<210> SEQ ID NO 887

<400> SEQUENCE: 887

000

<210> SEQ ID NO 888

<400> SEQUENCE: 888

000

<210> SEQ ID NO 889

<400> SEQUENCE: 889

000

<210> SEQ ID NO 890

<400> SEQUENCE: 890

000

<210> SEQ ID NO 891

<400> SEQUENCE: 891

000

<210> SEQ ID NO 892

<400> SEQUENCE: 892

000

<210> SEQ ID NO 893

<400> SEQUENCE: 893

000

<210> SEQ ID NO 894

<400> SEQUENCE: 894

000

<210> SEQ ID NO 895

<400> SEQUENCE: 895

000

<210> SEQ ID NO 896

<400> SEQUENCE: 896

000

<210> SEQ ID NO 897

<400> SEQUENCE: 897

000

<210> SEQ ID NO 898

<400> SEQUENCE: 898

000

<210> SEQ ID NO 899

<400> SEQUENCE: 899

000

<210> SEQ ID NO 900

<400> SEQUENCE: 900

000

<210> SEQ ID NO 901

<400> SEQUENCE: 901

000

<210> SEQ ID NO 902

<400> SEQUENCE: 902

000

<210> SEQ ID NO 903

<400> SEQUENCE: 903

000

<210> SEQ ID NO 904

<400> SEQUENCE: 904

000

<210> SEQ ID NO 905

<400> SEQUENCE: 905

000

<210> SEQ ID NO 906

<400> SEQUENCE: 906

000

<210> SEQ ID NO 907

<400> SEQUENCE: 907

000

<210> SEQ ID NO 908

<400> SEQUENCE: 908

000

<210> SEQ ID NO 909

<400> SEQUENCE: 909

000

<210> SEQ ID NO 910

<400> SEQUENCE: 910

000

<210> SEQ ID NO 911

<400> SEQUENCE: 911

000

<210> SEQ ID NO 912

<400> SEQUENCE: 912

000

<210> SEQ ID NO 913

<400> SEQUENCE: 913

000

<210> SEQ ID NO 914

-continued

<400> SEQUENCE: 914

000

<210> SEQ ID NO 915

<400> SEQUENCE: 915

000

<210> SEQ ID NO 916

<400> SEQUENCE: 916

000

<210> SEQ ID NO 917

<400> SEQUENCE: 917

000

<210> SEQ ID NO 918

<400> SEQUENCE: 918

000

<210> SEQ ID NO 919

<400> SEQUENCE: 919

000

<210> SEQ ID NO 920

<400> SEQUENCE: 920

000

<210> SEQ ID NO 921

<400> SEQUENCE: 921

000

<210> SEQ ID NO 922

<400> SEQUENCE: 922

000

<210> SEQ ID NO 923

<400> SEQUENCE: 923

000

<210> SEQ ID NO 924

<400> SEQUENCE: 924

000

<210> SEQ ID NO 925

<400> SEQUENCE: 925

000

<210> SEQ ID NO 926

<400> SEQUENCE: 926

000

<210> SEQ ID NO 927

<400> SEQUENCE: 927

000

<210> SEQ ID NO 928

<400> SEQUENCE: 928

000

<210> SEQ ID NO 929

<400> SEQUENCE: 929

000

<210> SEQ ID NO 930

<400> SEQUENCE: 930

000

<210> SEQ ID NO 931

<400> SEQUENCE: 931

000

<210> SEQ ID NO 932

<400> SEQUENCE: 932

000

<210> SEQ ID NO 933

<400> SEQUENCE: 933

000

<210> SEQ ID NO 934

<400> SEQUENCE: 934

000

<210> SEQ ID NO 935

<400> SEQUENCE: 935

000

<210> SEQ ID NO 936

<400> SEQUENCE: 936

000

<210> SEQ ID NO 937

<400> SEQUENCE: 937

000

<210> SEQ ID NO 938

<400> SEQUENCE: 938

000

<210> SEQ ID NO 939

<400> SEQUENCE: 939

000

<210> SEQ ID NO 940

<400> SEQUENCE: 940

000

<210> SEQ ID NO 941

<400> SEQUENCE: 941

000

<210> SEQ ID NO 942

<400> SEQUENCE: 942

000

<210> SEQ ID NO 943

<400> SEQUENCE: 943

000

<210> SEQ ID NO 944

<400> SEQUENCE: 944

000

<210> SEQ ID NO 945

<400> SEQUENCE: 945

000

<210> SEQ ID NO 946

<400> SEQUENCE: 946

000

<210> SEQ ID NO 947

<400> SEQUENCE: 947

000

<210> SEQ ID NO 948

<400> SEQUENCE: 948

000

<210> SEQ ID NO 949

<400> SEQUENCE: 949

000

<210> SEQ ID NO 950

<400> SEQUENCE: 950

000

<210> SEQ ID NO 951

<400> SEQUENCE: 951

000

<210> SEQ ID NO 952

<400> SEQUENCE: 952

000

<210> SEQ ID NO 953

<400> SEQUENCE: 953

000

<210> SEQ ID NO 954

<400> SEQUENCE: 954

000

<210> SEQ ID NO 955

<400> SEQUENCE: 955

000

<210> SEQ ID NO 956

<400> SEQUENCE: 956

000

<210> SEQ ID NO 957

<400> SEQUENCE: 957

000

<210> SEQ ID NO 958

<400> SEQUENCE: 958

000

<210> SEQ ID NO 959

<400> SEQUENCE: 959

000

<210> SEQ ID NO 960

<400> SEQUENCE: 960

000

<210> SEQ ID NO 961

<400> SEQUENCE: 961

000

<210> SEQ ID NO 962

<400> SEQUENCE: 962

000

<210> SEQ ID NO 963

<400> SEQUENCE: 963

000

<210> SEQ ID NO 964

<400> SEQUENCE: 964

000

<210> SEQ ID NO 965

<400> SEQUENCE: 965

000

<210> SEQ ID NO 966

<400> SEQUENCE: 966

000

<210> SEQ ID NO 967

<400> SEQUENCE: 967

000

<210> SEQ ID NO 968

<400> SEQUENCE: 968

000

<210> SEQ ID NO 969

<400> SEQUENCE: 969

000

<210> SEQ ID NO 970

<400> SEQUENCE: 970

000

<210> SEQ ID NO 971

<400> SEQUENCE: 971

000

<210> SEQ ID NO 972

<400> SEQUENCE: 972

000

<210> SEQ ID NO 973

<400> SEQUENCE: 973

000

<210> SEQ ID NO 974

<400> SEQUENCE: 974

000

<210> SEQ ID NO 975

<400> SEQUENCE: 975

000

<210> SEQ ID NO 976

<400> SEQUENCE: 976

000

<210> SEQ ID NO 977

<400> SEQUENCE: 977

000

<210> SEQ ID NO 978

<400> SEQUENCE: 978

000

<210> SEQ ID NO 979

<400> SEQUENCE: 979

000

<210> SEQ ID NO 980

<400> SEQUENCE: 980

000

<210> SEQ ID NO 981

<400> SEQUENCE: 981

000

<210> SEQ ID NO 982

<400> SEQUENCE: 982

000

<210> SEQ ID NO 983

<400> SEQUENCE: 983

000

<210> SEQ ID NO 984

<400> SEQUENCE: 984

000

<210> SEQ ID NO 985

<400> SEQUENCE: 985

000

<210> SEQ ID NO 986

<400> SEQUENCE: 986

000

<210> SEQ ID NO 987

<400> SEQUENCE: 987

000

<210> SEQ ID NO 988

<400> SEQUENCE: 988

000

<210> SEQ ID NO 989

<400> SEQUENCE: 989

000

<210> SEQ ID NO 990

<400> SEQUENCE: 990

000

<210> SEQ ID NO 991

<400> SEQUENCE: 991

000

<210> SEQ ID NO 992

<400> SEQUENCE: 992

000

<210> SEQ ID NO 993

<400> SEQUENCE: 993

000

<210> SEQ ID NO 994

<400> SEQUENCE: 994

000

<210> SEQ ID NO 995

<400> SEQUENCE: 995

000

<210> SEQ ID NO 996

<400> SEQUENCE: 996

000

<210> SEQ ID NO 997

<400> SEQUENCE: 997

000

<210> SEQ ID NO 998

<400> SEQUENCE: 998

000

<210> SEQ ID NO 999

<400> SEQUENCE: 999

000

<210> SEQ ID NO 1000

<400> SEQUENCE: 1000

000

<210> SEQ ID NO 1001

<400> SEQUENCE: 1001

000

<210> SEQ ID NO 1002

<400> SEQUENCE: 1002

000

<210> SEQ ID NO 1003

<400> SEQUENCE: 1003

000

<210> SEQ ID NO 1004

<400> SEQUENCE: 1004

000

<210> SEQ ID NO 1005

<400> SEQUENCE: 1005

000

<210> SEQ ID NO 1006

<400> SEQUENCE: 1006

000

<210> SEQ ID NO 1007

<400> SEQUENCE: 1007

000

<210> SEQ ID NO 1008

<400> SEQUENCE: 1008

000

<210> SEQ ID NO 1009

<400> SEQUENCE: 1009

000

<210> SEQ ID NO 1010

<400> SEQUENCE: 1010

000

<210> SEQ ID NO 1011

<400> SEQUENCE: 1011

000

<210> SEQ ID NO 1012

<400> SEQUENCE: 1012

000

<210> SEQ ID NO 1013

<400> SEQUENCE: 1013

000

<210> SEQ ID NO 1014

<400> SEQUENCE: 1014

000

<210> SEQ ID NO 1015

<400> SEQUENCE: 1015

000

<210> SEQ ID NO 1016

<400> SEQUENCE: 1016

000

<210> SEQ ID NO 1017

<400> SEQUENCE: 1017

000

<210> SEQ ID NO 1018

<400> SEQUENCE: 1018

000

<210> SEQ ID NO 1019

<400> SEQUENCE: 1019

000

<210> SEQ ID NO 1020

<400> SEQUENCE: 1020

000

<210> SEQ ID NO 1021

<400> SEQUENCE: 1021

000

<210> SEQ ID NO 1022

<400> SEQUENCE: 1022

000

<210> SEQ ID NO 1023

<400> SEQUENCE: 1023

000

<210> SEQ ID NO 1024

<400> SEQUENCE: 1024

000

<210> SEQ ID NO 1025

<400> SEQUENCE: 1025

000

<210> SEQ ID NO 1026

<400> SEQUENCE: 1026

000

<210> SEQ ID NO 1027

<400> SEQUENCE: 1027

000

<210> SEQ ID NO 1028

<400> SEQUENCE: 1028

000

<210> SEQ ID NO 1029

<400> SEQUENCE: 1029

000

<210> SEQ ID NO 1030

<400> SEQUENCE: 1030

000

<210> SEQ ID NO 1031

<400> SEQUENCE: 1031

000

<210> SEQ ID NO 1032

<400> SEQUENCE: 1032

000

<210> SEQ ID NO 1033

<400> SEQUENCE: 1033

000

<210> SEQ ID NO 1034

<400> SEQUENCE: 1034

000

<210> SEQ ID NO 1035

<400> SEQUENCE: 1035

000

<210> SEQ ID NO 1036

<400> SEQUENCE: 1036

000

<210> SEQ ID NO 1037

<400> SEQUENCE: 1037

000

<210> SEQ ID NO 1038

<400> SEQUENCE: 1038

000

<210> SEQ ID NO 1039

<400> SEQUENCE: 1039

000

<210> SEQ ID NO 1040

<400> SEQUENCE: 1040

000

<210> SEQ ID NO 1041

<400> SEQUENCE: 1041

000

<210> SEQ ID NO 1042

<400> SEQUENCE: 1042

000

<210> SEQ ID NO 1043

<400> SEQUENCE: 1043

000

<210> SEQ ID NO 1044

<400> SEQUENCE: 1044

000

<210> SEQ ID NO 1045

<400> SEQUENCE: 1045

000

<210> SEQ ID NO 1046

<400> SEQUENCE: 1046

000

<210> SEQ ID NO 1047

<400> SEQUENCE: 1047

000

<210> SEQ ID NO 1048

<400> SEQUENCE: 1048

000

<210> SEQ ID NO 1049

<400> SEQUENCE: 1049

000

<210> SEQ ID NO 1050

<400> SEQUENCE: 1050

000

<210> SEQ ID NO 1051

<400> SEQUENCE: 1051

000

<210> SEQ ID NO 1052

<400> SEQUENCE: 1052

000

<210> SEQ ID NO 1053

<400> SEQUENCE: 1053

000

<210> SEQ ID NO 1054

<400> SEQUENCE: 1054

000

<210> SEQ ID NO 1055

<400> SEQUENCE: 1055

000

<210> SEQ ID NO 1056

<400> SEQUENCE: 1056

000

<210> SEQ ID NO 1057

<400> SEQUENCE: 1057

000

<210> SEQ ID NO 1058

<400> SEQUENCE: 1058

000

<210> SEQ ID NO 1059

<400> SEQUENCE: 1059

000

<210> SEQ ID NO 1060

<400> SEQUENCE: 1060

000

<210> SEQ ID NO 1061

<400> SEQUENCE: 1061

000

<210> SEQ ID NO 1062

<400> SEQUENCE: 1062

000

<210> SEQ ID NO 1063

<400> SEQUENCE: 1063

000

<210> SEQ ID NO 1064

<400> SEQUENCE: 1064

000

<210> SEQ ID NO 1065

<400> SEQUENCE: 1065

000

<210> SEQ ID NO 1066

<400> SEQUENCE: 1066

000

<210> SEQ ID NO 1067

<400> SEQUENCE: 1067

000

<210> SEQ ID NO 1068

<400> SEQUENCE: 1068

000

<210> SEQ ID NO 1069

<400> SEQUENCE: 1069

000

<210> SEQ ID NO 1070

<400> SEQUENCE: 1070

000

<210> SEQ ID NO 1071

<400> SEQUENCE: 1071

000

<210> SEQ ID NO 1072

```
<400> SEQUENCE: 1072

000

<210> SEQ ID NO 1073

<400> SEQUENCE: 1073

000

<210> SEQ ID NO 1074

<400> SEQUENCE: 1074

000

<210> SEQ ID NO 1075

<400> SEQUENCE: 1075

000

<210> SEQ ID NO 1076

<400> SEQUENCE: 1076

000

<210> SEQ ID NO 1077

<400> SEQUENCE: 1077

000

<210> SEQ ID NO 1078

<400> SEQUENCE: 1078

000

<210> SEQ ID NO 1079

<400> SEQUENCE: 1079

000

<210> SEQ ID NO 1080

<400> SEQUENCE: 1080

000

<210> SEQ ID NO 1081

<400> SEQUENCE: 1081

000

<210> SEQ ID NO 1082

<400> SEQUENCE: 1082

000

<210> SEQ ID NO 1083

<400> SEQUENCE: 1083
```

-continued

000

<210> SEQ ID NO 1084

<400> SEQUENCE: 1084

000

<210> SEQ ID NO 1085

<400> SEQUENCE: 1085

000

<210> SEQ ID NO 1086

<400> SEQUENCE: 1086

000

<210> SEQ ID NO 1087

<400> SEQUENCE: 1087

000

<210> SEQ ID NO 1088

<400> SEQUENCE: 1088

000

<210> SEQ ID NO 1089

<400> SEQUENCE: 1089

000

<210> SEQ ID NO 1090

<400> SEQUENCE: 1090

000

<210> SEQ ID NO 1091

<400> SEQUENCE: 1091

000

<210> SEQ ID NO 1092

<400> SEQUENCE: 1092

000

<210> SEQ ID NO 1093

<400> SEQUENCE: 1093

000

<210> SEQ ID NO 1094

<400> SEQUENCE: 1094

000

<210> SEQ ID NO 1095

<400> SEQUENCE: 1095

000

<210> SEQ ID NO 1096

<400> SEQUENCE: 1096

000

<210> SEQ ID NO 1097

<400> SEQUENCE: 1097

000

<210> SEQ ID NO 1098

<400> SEQUENCE: 1098

000

<210> SEQ ID NO 1099

<400> SEQUENCE: 1099

000

<210> SEQ ID NO 1100

<400> SEQUENCE: 1100

000

<210> SEQ ID NO 1101

<400> SEQUENCE: 1101

000

<210> SEQ ID NO 1102

<400> SEQUENCE: 1102

000

<210> SEQ ID NO 1103

<400> SEQUENCE: 1103

000

<210> SEQ ID NO 1104

<400> SEQUENCE: 1104

000

<210> SEQ ID NO 1105

<400> SEQUENCE: 1105

000

<210> SEQ ID NO 1106

-continued

<400> SEQUENCE: 1106

000

<210> SEQ ID NO 1107

<400> SEQUENCE: 1107

000

<210> SEQ ID NO 1108

<400> SEQUENCE: 1108

000

<210> SEQ ID NO 1109

<400> SEQUENCE: 1109

000

<210> SEQ ID NO 1110

<400> SEQUENCE: 1110

000

<210> SEQ ID NO 1111

<400> SEQUENCE: 1111

000

<210> SEQ ID NO 1112

<400> SEQUENCE: 1112

000

<210> SEQ ID NO 1113

<400> SEQUENCE: 1113

000

<210> SEQ ID NO 1114

<400> SEQUENCE: 1114

000

<210> SEQ ID NO 1115

<400> SEQUENCE: 1115

000

<210> SEQ ID NO 1116

<400> SEQUENCE: 1116

000

<210> SEQ ID NO 1117

<400> SEQUENCE: 1117

000

<210> SEQ ID NO 1118

<400> SEQUENCE: 1118

000

<210> SEQ ID NO 1119

<400> SEQUENCE: 1119

000

<210> SEQ ID NO 1120

<400> SEQUENCE: 1120

000

<210> SEQ ID NO 1121

<400> SEQUENCE: 1121

000

<210> SEQ ID NO 1122

<400> SEQUENCE: 1122

000

<210> SEQ ID NO 1123

<400> SEQUENCE: 1123

000

<210> SEQ ID NO 1124

<400> SEQUENCE: 1124

000

<210> SEQ ID NO 1125

<400> SEQUENCE: 1125

000

<210> SEQ ID NO 1126

<400> SEQUENCE: 1126

000

<210> SEQ ID NO 1127

<400> SEQUENCE: 1127

000

<210> SEQ ID NO 1128

<400> SEQUENCE: 1128

000

<210> SEQ ID NO 1129

<400> SEQUENCE: 1129

000

<210> SEQ ID NO 1130

<400> SEQUENCE: 1130

000

<210> SEQ ID NO 1131

<400> SEQUENCE: 1131

000

<210> SEQ ID NO 1132

<400> SEQUENCE: 1132

000

<210> SEQ ID NO 1133

<400> SEQUENCE: 1133

000

<210> SEQ ID NO 1134

<400> SEQUENCE: 1134

000

<210> SEQ ID NO 1135

<400> SEQUENCE: 1135

000

<210> SEQ ID NO 1136

<400> SEQUENCE: 1136

000

<210> SEQ ID NO 1137

<400> SEQUENCE: 1137

000

<210> SEQ ID NO 1138

<400> SEQUENCE: 1138

000

<210> SEQ ID NO 1139

<400> SEQUENCE: 1139

000

```
<210> SEQ ID NO 1140
<400> SEQUENCE: 1140
000

<210> SEQ ID NO 1141
<400> SEQUENCE: 1141
000

<210> SEQ ID NO 1142
<400> SEQUENCE: 1142
000

<210> SEQ ID NO 1143
<400> SEQUENCE: 1143
000

<210> SEQ ID NO 1144
<400> SEQUENCE: 1144
000

<210> SEQ ID NO 1145
<400> SEQUENCE: 1145
000

<210> SEQ ID NO 1146
<400> SEQUENCE: 1146
000

<210> SEQ ID NO 1147
<400> SEQUENCE: 1147
000

<210> SEQ ID NO 1148
<400> SEQUENCE: 1148
000

<210> SEQ ID NO 1149
<400> SEQUENCE: 1149
000

<210> SEQ ID NO 1150
<400> SEQUENCE: 1150
000

<210> SEQ ID NO 1151
```

<400> SEQUENCE: 1151

000

<210> SEQ ID NO 1152

<400> SEQUENCE: 1152

000

<210> SEQ ID NO 1153

<400> SEQUENCE: 1153

000

<210> SEQ ID NO 1154

<400> SEQUENCE: 1154

000

<210> SEQ ID NO 1155

<400> SEQUENCE: 1155

000

<210> SEQ ID NO 1156

<400> SEQUENCE: 1156

000

<210> SEQ ID NO 1157

<400> SEQUENCE: 1157

000

<210> SEQ ID NO 1158

<400> SEQUENCE: 1158

000

<210> SEQ ID NO 1159

<400> SEQUENCE: 1159

000

<210> SEQ ID NO 1160

<400> SEQUENCE: 1160

000

<210> SEQ ID NO 1161

<400> SEQUENCE: 1161

000

<210> SEQ ID NO 1162

<400> SEQUENCE: 1162

000

<210> SEQ ID NO 1163

<400> SEQUENCE: 1163

000

<210> SEQ ID NO 1164

<400> SEQUENCE: 1164

000

<210> SEQ ID NO 1165

<400> SEQUENCE: 1165

000

<210> SEQ ID NO 1166

<400> SEQUENCE: 1166

000

<210> SEQ ID NO 1167

<400> SEQUENCE: 1167

000

<210> SEQ ID NO 1168

<400> SEQUENCE: 1168

000

<210> SEQ ID NO 1169

<400> SEQUENCE: 1169

000

<210> SEQ ID NO 1170

<400> SEQUENCE: 1170

000

<210> SEQ ID NO 1171

<400> SEQUENCE: 1171

000

<210> SEQ ID NO 1172

<400> SEQUENCE: 1172

000

<210> SEQ ID NO 1173

<400> SEQUENCE: 1173

000

<210> SEQ ID NO 1174

<400> SEQUENCE: 1174

000

<210> SEQ ID NO 1175

<400> SEQUENCE: 1175

000

<210> SEQ ID NO 1176

<400> SEQUENCE: 1176

000

<210> SEQ ID NO 1177

<400> SEQUENCE: 1177

000

<210> SEQ ID NO 1178

<400> SEQUENCE: 1178

000

<210> SEQ ID NO 1179

<400> SEQUENCE: 1179

000

<210> SEQ ID NO 1180

<400> SEQUENCE: 1180

000

<210> SEQ ID NO 1181

<400> SEQUENCE: 1181

000

<210> SEQ ID NO 1182

<400> SEQUENCE: 1182

000

<210> SEQ ID NO 1183

<400> SEQUENCE: 1183

000

<210> SEQ ID NO 1184

<400> SEQUENCE: 1184

000

<210> SEQ ID NO 1185

<400> SEQUENCE: 1185

000

<210> SEQ ID NO 1186

<400> SEQUENCE: 1186

000

<210> SEQ ID NO 1187

<400> SEQUENCE: 1187

000

<210> SEQ ID NO 1188

<400> SEQUENCE: 1188

000

<210> SEQ ID NO 1189

<400> SEQUENCE: 1189

000

<210> SEQ ID NO 1190

<400> SEQUENCE: 1190

000

<210> SEQ ID NO 1191

<400> SEQUENCE: 1191

000

<210> SEQ ID NO 1192

<400> SEQUENCE: 1192

000

<210> SEQ ID NO 1193

<400> SEQUENCE: 1193

000

<210> SEQ ID NO 1194

<400> SEQUENCE: 1194

000

<210> SEQ ID NO 1195

<400> SEQUENCE: 1195

000

<210> SEQ ID NO 1196

<400> SEQUENCE: 1196

000

<210> SEQ ID NO 1197

<400> SEQUENCE: 1197

000

<210> SEQ ID NO 1198

<400> SEQUENCE: 1198

000

<210> SEQ ID NO 1199

<400> SEQUENCE: 1199

000

<210> SEQ ID NO 1200

<400> SEQUENCE: 1200

000

<210> SEQ ID NO 1201

<400> SEQUENCE: 1201

000

<210> SEQ ID NO 1202

<400> SEQUENCE: 1202

000

<210> SEQ ID NO 1203

<400> SEQUENCE: 1203

000

<210> SEQ ID NO 1204

<400> SEQUENCE: 1204

000

<210> SEQ ID NO 1205

<400> SEQUENCE: 1205

000

<210> SEQ ID NO 1206

<400> SEQUENCE: 1206

000

<210> SEQ ID NO 1207

<400> SEQUENCE: 1207

000

<210> SEQ ID NO 1208

<400> SEQUENCE: 1208

000

<210> SEQ ID NO 1209

<400> SEQUENCE: 1209

000

<210> SEQ ID NO 1210

<400> SEQUENCE: 1210

000

<210> SEQ ID NO 1211

<400> SEQUENCE: 1211

000

<210> SEQ ID NO 1212

<400> SEQUENCE: 1212

000

<210> SEQ ID NO 1213

<400> SEQUENCE: 1213

000

<210> SEQ ID NO 1214

<400> SEQUENCE: 1214

000

<210> SEQ ID NO 1215

<400> SEQUENCE: 1215

000

<210> SEQ ID NO 1216

<400> SEQUENCE: 1216

000

<210> SEQ ID NO 1217

<400> SEQUENCE: 1217

000

<210> SEQ ID NO 1218

<400> SEQUENCE: 1218

000

```
<210> SEQ ID NO 1219
<400> SEQUENCE: 1219
000

<210> SEQ ID NO 1220
<400> SEQUENCE: 1220
000

<210> SEQ ID NO 1221
<400> SEQUENCE: 1221
000

<210> SEQ ID NO 1222
<400> SEQUENCE: 1222
000

<210> SEQ ID NO 1223
<400> SEQUENCE: 1223
000

<210> SEQ ID NO 1224
<400> SEQUENCE: 1224
000

<210> SEQ ID NO 1225
<400> SEQUENCE: 1225
000

<210> SEQ ID NO 1226
<400> SEQUENCE: 1226
000

<210> SEQ ID NO 1227
<400> SEQUENCE: 1227
000

<210> SEQ ID NO 1228
<400> SEQUENCE: 1228
000

<210> SEQ ID NO 1229
<400> SEQUENCE: 1229
000

<210> SEQ ID NO 1230
```

```
<400> SEQUENCE: 1230
000

<210> SEQ ID NO 1231
<400> SEQUENCE: 1231
000

<210> SEQ ID NO 1232
<400> SEQUENCE: 1232
000

<210> SEQ ID NO 1233
<400> SEQUENCE: 1233
000

<210> SEQ ID NO 1234
<400> SEQUENCE: 1234
000

<210> SEQ ID NO 1235
<400> SEQUENCE: 1235
000

<210> SEQ ID NO 1236
<400> SEQUENCE: 1236
000

<210> SEQ ID NO 1237
<400> SEQUENCE: 1237
000

<210> SEQ ID NO 1238
<400> SEQUENCE: 1238
000

<210> SEQ ID NO 1239
<400> SEQUENCE: 1239
000

<210> SEQ ID NO 1240
<400> SEQUENCE: 1240
000

<210> SEQ ID NO 1241
<400> SEQUENCE: 1241
```

000

<210> SEQ ID NO 1242
<400> SEQUENCE: 1242
000

<210> SEQ ID NO 1243
<400> SEQUENCE: 1243
000

<210> SEQ ID NO 1244
<400> SEQUENCE: 1244
000

<210> SEQ ID NO 1245
<400> SEQUENCE: 1245
000

<210> SEQ ID NO 1246
<400> SEQUENCE: 1246
000

<210> SEQ ID NO 1247
<400> SEQUENCE: 1247
000

<210> SEQ ID NO 1248
<400> SEQUENCE: 1248
000

<210> SEQ ID NO 1249
<400> SEQUENCE: 1249
000

<210> SEQ ID NO 1250
<400> SEQUENCE: 1250
000

<210> SEQ ID NO 1251
<400> SEQUENCE: 1251
000

<210> SEQ ID NO 1252
<400> SEQUENCE: 1252
000

<210> SEQ ID NO 1253

<400> SEQUENCE: 1253

000

<210> SEQ ID NO 1254

<400> SEQUENCE: 1254

000

<210> SEQ ID NO 1255

<400> SEQUENCE: 1255

000

<210> SEQ ID NO 1256

<400> SEQUENCE: 1256

000

<210> SEQ ID NO 1257

<400> SEQUENCE: 1257

000

<210> SEQ ID NO 1258

<400> SEQUENCE: 1258

000

<210> SEQ ID NO 1259

<400> SEQUENCE: 1259

000

<210> SEQ ID NO 1260

<400> SEQUENCE: 1260

000

<210> SEQ ID NO 1261

<400> SEQUENCE: 1261

000

<210> SEQ ID NO 1262

<400> SEQUENCE: 1262

000

<210> SEQ ID NO 1263

<400> SEQUENCE: 1263

000

<210> SEQ ID NO 1264

<400> SEQUENCE: 1264

000

<210> SEQ ID NO 1265

<400> SEQUENCE: 1265

000

<210> SEQ ID NO 1266

<400> SEQUENCE: 1266

000

<210> SEQ ID NO 1267

<400> SEQUENCE: 1267

000

<210> SEQ ID NO 1268

<400> SEQUENCE: 1268

000

<210> SEQ ID NO 1269

<400> SEQUENCE: 1269

000

<210> SEQ ID NO 1270

<400> SEQUENCE: 1270

000

<210> SEQ ID NO 1271

<400> SEQUENCE: 1271

000

<210> SEQ ID NO 1272

<400> SEQUENCE: 1272

000

<210> SEQ ID NO 1273

<400> SEQUENCE: 1273

000

<210> SEQ ID NO 1274

<400> SEQUENCE: 1274

000

<210> SEQ ID NO 1275

<400> SEQUENCE: 1275

000

<210> SEQ ID NO 1276

<400> SEQUENCE: 1276

000

<210> SEQ ID NO 1277

<400> SEQUENCE: 1277

000

<210> SEQ ID NO 1278

<400> SEQUENCE: 1278

000

<210> SEQ ID NO 1279

<400> SEQUENCE: 1279

000

<210> SEQ ID NO 1280

<400> SEQUENCE: 1280

000

<210> SEQ ID NO 1281

<400> SEQUENCE: 1281

000

<210> SEQ ID NO 1282

<400> SEQUENCE: 1282

000

<210> SEQ ID NO 1283

<400> SEQUENCE: 1283

000

<210> SEQ ID NO 1284

<400> SEQUENCE: 1284

000

<210> SEQ ID NO 1285

<400> SEQUENCE: 1285

000

<210> SEQ ID NO 1286

<400> SEQUENCE: 1286

000

<210> SEQ ID NO 1287

<400> SEQUENCE: 1287

000

<210> SEQ ID NO 1288

<400> SEQUENCE: 1288

000

<210> SEQ ID NO 1289

<400> SEQUENCE: 1289

000

<210> SEQ ID NO 1290

<400> SEQUENCE: 1290

000

<210> SEQ ID NO 1291

<400> SEQUENCE: 1291

000

<210> SEQ ID NO 1292

<400> SEQUENCE: 1292

000

<210> SEQ ID NO 1293

<400> SEQUENCE: 1293

000

<210> SEQ ID NO 1294

<400> SEQUENCE: 1294

000

<210> SEQ ID NO 1295

<400> SEQUENCE: 1295

000

<210> SEQ ID NO 1296

<400> SEQUENCE: 1296

000

<210> SEQ ID NO 1297

<400> SEQUENCE: 1297

000

```
<210> SEQ ID NO 1298

<400> SEQUENCE: 1298

000

<210> SEQ ID NO 1299

<400> SEQUENCE: 1299

000

<210> SEQ ID NO 1300

<400> SEQUENCE: 1300

000

<210> SEQ ID NO 1301
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (50)..(66)
<223> OTHER INFORMATION: This region may encompass one of the following
      sequences: "RIDPASGHTKYDPKFQV" or "RIEPASGHIKYDPKFQG" or
      "RIDPASGHIKYDPKFQG" or "RIEPASGHIKYDPKFQV"
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (70)..(70)
<223> OTHER INFORMATION: Any amino acid
<220> FEATURE:
<221> NAME/KEY: MOD_RES
<222> LOCATION: (72)..(72)
<223> OTHER INFORMATION: Any amino acid
<220> FEATURE:
<221> NAME/KEY: MOD_RES
<222> LOCATION: (79)..(79)
<223> OTHER INFORMATION: Any amino acid
<220> FEATURE:
<221> NAME/KEY: MOD_RES
<222> LOCATION: (81)..(81)
<223> OTHER INFORMATION: Any amino acid
<220> FEATURE:
<221> NAME/KEY: MOD_RES
<222> LOCATION: (99)..(107)
<223> OTHER INFORMATION: This region may encompass one of the following
      sequences: "SGGLPDV" or "ARSGGLPDV" or "SGGLPDW" or "ARSGGLPDW"
<220> FEATURE:
<223> OTHER INFORMATION: See specification as filed for detailed
      description of substitutions and preferred embodiments

<400> SEQUENCE: 1301

Xaa Val Gln Leu Val Gln Ser Gly Ala Glu Val Lys Lys Pro Gly Ala
1               5                   10                  15
```

```
Ser Val Lys Val Ser Cys Lys Ala Ser Gly Phe Asp Ile Gln Asp Thr
            20                  25                  30

Tyr Met His Trp Val Xaa Gln Arg Pro Gly Gln Gly Leu Glu Trp Xaa
            35                  40                  45

Gly Xaa Xaa Xaa Xaa Xaa Xaa Xaa Xaa Xaa Xaa Xaa Xaa Xaa Xaa Xaa
        50                  55                  60

Xaa Xaa Arg Xaa Thr Xaa Thr Xaa Asp Thr Ser Thr Ser Thr Xaa Tyr
65                  70                  75                  80

Xaa Glu Leu Ser Ser Leu Arg Ser Glu Asp Thr Ala Val Tyr Tyr Cys
            85                  90                  95

Ala Arg Xaa Xaa Xaa Xaa Xaa Xaa Xaa Xaa Xaa Trp Gly Gln Gly Thr
            100                 105                 110

Thr Val Thr Val Ser Ser
        115
```

```
<210> SEQ ID NO 1302
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (50)..(66)
<223> OTHER INFORMATION: This region may encompass one of the following
      sequences: "RIDPASGHTKYDPKFQV" or "RIEPASGHIKYDPKFQG" or
      "RIDPASGHIKYDPKFQG" or "RIEPASGHIKYDPKFQV"
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (70)..(70)
<223> OTHER INFORMATION: Any amino acid
<220> FEATURE:
<221> NAME/KEY: MOD_RES
<222> LOCATION: (72)..(72)
<223> OTHER INFORMATION: Any amino acid
<220> FEATURE:
<221> NAME/KEY: MOD_RES
<222> LOCATION: (79)..(79)
<223> OTHER INFORMATION: Any amino acid
<220> FEATURE:
<221> NAME/KEY: MOD_RES
<222> LOCATION: (81)..(81)
<223> OTHER INFORMATION: Any amino acid
<220> FEATURE:
<221> NAME/KEY: MOD_RES
<222> LOCATION: (97)..(105)
<223> OTHER INFORMATION: This region may encompass one of the following
      sequences: "SGGLPDV" or "ARSGGLPDV" or "SGGLPDW" or "ARSGGLPDW"
<220> FEATURE:
<223> OTHER INFORMATION: See specification as filed for detailed
      description of substitutions and preferred embodiments

<400> SEQUENCE: 1302
```

```
Xaa Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Xaa Gln Arg Pro Gly Gln Gly Leu Glu Trp Xaa
        35                  40                  45

Gly Xaa Xaa Xaa Xaa Xaa Xaa Xaa Xaa Xaa Xaa Xaa Xaa Xaa Xaa Xaa
    50                  55                  60

Xaa Xaa Arg Xaa Thr Xaa Thr Xaa Asp Thr Ser Thr Ser Thr Xaa Tyr
65                  70                  75                  80

Xaa Glu Leu Ser Ser Leu Arg Ser Glu Asp Thr Ala Val Tyr Tyr Cys
                85                  90                  95

Xaa Xaa Xaa Xaa Xaa Xaa Xaa Xaa Xaa Trp Gly Gln Gly Thr Thr Val
            100                 105                 110

Thr Val Ser Ser
        115

<210> SEQ ID NO 1303
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1303

His His His His His His
1               5
```

HUMANIZED ANTIBODIES TO TNF-LIKE LIGAND 1A (TL1A) AND USES THEREOF

CROSS-REFERENCE

This application is a continuation application of International Application No. PCT/US20/57119 filed Oct. 23, 2020, which claims the benefit of U.S. Provisional Application No. 62/925,736, filed Oct. 24, 2019, both of which are incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 1, 2020, is named 56884-767_301_SL.txt and is 376,991 bytes in size.

BACKGROUND

Inflammatory bowel disease (IBD) refers to a collection of intestinal disorders causing inflammatory conditions in the gastrointestinal tract. The primary types of IBD are ulcerative colitis (UC) and Crohn's Disease (CD). These diseases are prevalent, with about 1.86 million people diagnosed globally with UC, and about 1.3 million people diagnosed globally with CD. Severe forms of IBD may be characterized by intestinal fibrosis, which is the accumulation of scar tissue in the intestinal wall. There are a limited number of therapies available for IBD patients, and the development of new therapeutics has been hampered by sub-optimal results in clinical trials. Furthermore, a significant number of patients experience a lack of response or a loss of response to existing anti-inflammatory therapies. While the patient is treated with this ineffective anti-inflammatory therapy, the disease worsens. Currently the only treatment for patients that do not respond to first line therapies is surgery, in the form of structureplasty (reshaping of the intestine) or resection (removal of the intestine). Surgical treatments for IBD are invasive, causing post-operative risks for an estimated one-third of patients undergoing surgery, such as anastomotic leak, infection, and bleeding.

The pathogenesis of IBD is thought to involve an uncontrolled immune response that may be triggered by certain environmental factors in a genetically susceptible host. The heterogeneity of disease pathogenesis and clinical course, combined with the variable response to treatment and its associated side effects, suggests a targeted therapeutic approach to treating these diseases is a desirable treatment strategy. Yet there are very few targeted therapies available to IBD patients, especially those patients who may be non-responsive to existing IBD therapies. Accordingly, there is a need for novel therapeutics to treat IBD that specifically target IBD pathogenesis.

SUMMARY

The present disclosure provides tumor necrosis factor ligand 1A (TL1A) binding antibodies for the treatment of IBD, including severe forms of IBD characterized by intestinal fibrosis. In various aspects, antibodies described herein possess features useful for therapeutic application such as low immunogenicity, and/or features that facilitate antibody manufacture, such as high percentage of monomeric fraction as measured by size-exclusion chromatography, and/or high expression.

In one aspect, provided herein, is an antibody or antigen binding fragment thereof that binds to TL1A, comprising a heavy chain variable framework region comprising a human IGHV1-46*02 framework or a modified human IGHV1-46*02 framework, and a light chain variable framework region comprising a human IGKV3-20 framework or a modified human IGKV3-20 framework; wherein the heavy chain variable framework region and the light chain variable framework region collectively comprise less than 9 amino acid modifications from the human IGHV1-46*02 framework and the human IGKV3-20 framework. In some embodiments, the amino acid modification comprises: (a) a modification at amino acid position 47 in the heavy chain variable region; (b) a modification at amino acid position 45 in the heavy chain variable region; (c) a modification at amino acid position 55 in the heavy chain variable region; (d) a modification at amino acid position 78 in the heavy chain variable region; (e) a modification at amino acid position 80 in the heavy chain variable region; (f) a modification at amino acid position 82 in the heavy chain variable region; (g) a modification at amino acid position 89 in the heavy chain variable region; or (h) a modification at amino acid position 91 in the heavy chain variable region; per Kabat numbering; or a combination of two or more modifications selected from (a) to (h). In some embodiments, (a) the amino acid modification is at position 47 in the heavy chain variable region, and the amino acid at position 47 is R, N, D, C, Q, E, G, H, I, L, K, M, F, P, S, T, W, Y, or V; (b) the amino acid modification is at position 45 in the heavy chain variable region, and the amino acid at position 45 is A, N, D, C, Q, E, G, H, I, L, K, M, F, P, S, T, W, Y, or V; (c) the amino acid modification is at position 55 in the heavy chain variable region, and the amino acid at position 55 is A, R, N, D, C, Q, E, G, H, I, L, K, F, P, S, T, W, Y, or V; (d) the amino acid modification is at position 78 in the heavy chain variable region, and the amino acid at position 78 is A, R, N, D, C, Q, E, G, H, I, L, K, M, F, P, S, T, W, or Y; (e) the amino acid modification is at position 80 in the heavy chain variable region, and the amino acid at position 80 is A, R, N, D, C, Q, E, G, H, I, L, K, F, P, S, T, W, Y, or V; (f) the amino acid modification is at position 82 in the heavy chain variable region, and the amino acid at position 82 is A, N, D, C, Q, E, G, H, I, L, K, M, F, P, S, T, W, Y, or V; (g) the amino acid modification is at position 89 in the heavy chain variable region, and the amino acid at position 89 is A, R, N, D, C, Q, E, G, H, I, L, K, M, F, P, S, T, W, or Y; or (h) the amino acid modification is at position 91 in the heavy chain variable region, and the amino acid at position 91 is A, R, N, D, C, Q, E, G, H, I, L, K, F, P, S, T, W, Y, or V; or a combination of two or more modifications selected from (a) to (h). In some embodiments, the amino acid modifications comprise one or more of: A47R, R45K, M55I, V78A, M80I, R82T, V89A, M91L in the heavy chain variable region, per Aho numbering. In some embodiments, the amino acid modification comprises: (a) a modification at amino acid position 54 in the light chain variable region; and/or (b) a modification at amino acid position 55 in the light chain variable region; per Kabat numbering. In some embodiments, (a) the amino acid modification is at position 54 of the light chain variable region, and the amino acid at position 54 is A, R, N, D, C, Q, E, G, H, I, K, M, F, P, S, T, W, Y, or V; and/or (b) the amino acid modification is at position 55 of the light chain variable region, and the amino acid at position 55 is A, R, N, D, C, Q, E, G, H, I, K, M, F, P, S, T, W, Y, or V. In some embodiments, the amino acid modifications comprise L54P and/or L55W in the light chain variable region, per Aho numbering. In some embodiments, the antibody or antigen binding fragment comprises a heavy chain CDR1 as set forth by SEQ ID NO: 1, a heavy chain CDR2 as set forth by any one of SEQ ID NOS: 2-5, a heavy chain CDR3 as set forth by any one of SEQ ID NOS: 6-9, a light chain CDR1 as set forth by SEQ ID NO: 10, a light chain CDR2 as set forth by SEQ ID NO: 11, and a light chain CDR3 as set forth by any one of SEQ ID NOS: 12-15. In some embodiments, the antibody or antigen binding fragment comprises a heavy chain CDR1 as set forth by SEQ ID NO: 1, a heavy chain CDR2 as set forth by SEQ ID NO: 2, a heavy chain CDR3 as set forth by SEQ ID NO: 6, a light chain CDR1 as set forth by SEQ ID NO: 10, a light chain CDR2 as set forth by SEQ ID NO: 11, and a light chain CDR3 as set forth by SEQ ID NO: 12. In some embodiments, the antibody or antigen binding fragment comprises comprising a heavy chain framework (FR) 1 as set forth by SEQ ID NO: 304, a heavy chain FR2 as set forth by SEQ ID NO: 305 or SEQ ID NO: 313, a heavy chain FR3 as set forth by any one of SEQ ID NOS: 306, 307, 314, or 315, a heavy chain FR4 as set forth by SEQ ID NO: 308, a light chain FR1 as set forth by SEQ ID NO: 309, a light chain FR2 as set forth by SEQ ID NO: 310, a light chain FR3 as set forth by SEQ ID NO: 311, or a light chain FR4 as set forth by SEQ ID NO: 312, or a combination thereof. In some embodiments, the antibody or antigen binding fragment comprises a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of two or more selected from (a)-(uu), per Kabat numbering. In some embodiments, the antibody or antigen binding fragment comprises a human IgG4 Fc region. In some embodiments, the antibody or antigen binding fragment comprises a Fc region comprising a sequence at least about 90%, 91%, 92%, 93%, 94%, 95%, 96%, 97%, 98%, 99%, or 100% identical to any one of SEQ ID NOS: 320-362. In some embodiments, the antibody or antigen binding fragment comprises at least about 80% monomeric fraction as determined by size exclusion chromatography. In some embodiments, the antibody or antigen binding fragment expresses at least about 20 ug/ml total antibody, optionally about 20 ug/ml and 70 ug/mL total antibody.

In another aspect, provided herein is an antibody or antigen binding fragment thereof that binds to tumor necrosis factor-like protein 1A (TL1A), comprising a heavy chain variable domain comprising an amino acid sequence at least 96% identical to SEQ ID NO: 104, and a light chain variable domain comprising an amino acid sequence at least 97% identical to SEQ ID NO: 201. In some embodiments, the heavy chain variable domain comprises an amino acid sequence at least 97% identical to SEQ ID NO: 104. In some embodiments, the heavy chain variable domain comprises an amino acid sequence at least 98% identical to SEQ ID NO: 104. In some embodiments, the heavy chain variable domain comprises an amino acid sequence at least 99% identical to SEQ ID NO: 104. In some embodiments, the heavy chain variable domain comprises SEQ ID NO: 104. In some embodiments, the light chain variable domain comprises an amino acid sequence at least 98% identical to SEQ ID NO: 201. In some embodiments, the light chain variable domain comprises an amino acid sequence at least about 99% identical to SEQ ID NO: 201. In some embodiments, the light chain variable domain comprises SEQ ID NO: 201.

In another aspect, provided herein is an antibody or antigen binding fragment thereof that binds to tumor necrosis factor-like protein 1A (TL1A), comprising a heavy chain variable domain comprising an amino acid sequence at least about 99% identical to any one of SEQ ID NOS: 101-135, and a light chain variable domain comprising an amino acid sequence at least about 99% identical to any one of SEQ ID NOS: 201-206.

In some embodiments, antibodies or antigen binding fragments described herein comprise a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of two or more selected from (a)-(uu), per Kabat numbering. In some embodiments, antibodies or antigen binding fragments described herein comprise a human IgG4 Fc region. In some embodiments, antibodies or antigen binding fragments described herein comprise a Fc region comprising a sequence at least about 90%, 91%, 92%, 93%, 94%, 95%, 96%, 97%, 98%, 99%, or 100% identical to any one of SEQ ID NOS: 320-362. In some embodiments, antibodies or antigen binding fragments described herein comprise at least about 80% monomeric fraction as determined by size exclusion chromatography. In some embodiments, antibodies or antigen binding fragments described herein express at least about 20 ug/ml total antibody, optionally about 20 ug/ml and 70 ug/mL total antibody.

In another aspect, provided herein is an antibody or antigen binding fragment thereof that binds to TL1A, comprising a heavy chain variable region comprising: (a) an HCDR1 comprising an amino acid sequence set forth by SEQ ID NO: 1; (b) an HCDR2 comprising an amino acid sequence set forth by any one of SEQ ID NOS: 2-5; and (c) an HCDR3 comprising an amino acid sequence set forth by any one of SEQ ID NOS: 6-9; and the light chain variable region comprises: (d) an LCDR1 comprising an amino acid sequence set forth by SEQ ID NO: 10; (e) an LCDR2 comprising an amino acid sequence set forth by SEQ ID NO: 11; (f) an LCDR3 comprising an amino acid sequence set forth by any one of SEQ ID NOS: 12-15; and a fragment crystallizable (Fc) region comprising reduced antibody-dependent cell-mediated cytotoxicity (ADCC) function as compared to human IgG1 and/or reduced complement-dependent cytotoxicity (CDC) as compared to human IgG1. In some embodiments, the human IgG1 comprises SEQ ID NO: 320. In some embodiments, the ADCC function of the Fc region comprising reduced ADCC is at least about 50% reduced as compared to human IgG1. In some embodiments, the CDC function of the Fc region comprising reduced CDC is at least about 50% reduced as compared to human IgG1. In some embodiments, the Fc region comprises a human IgG1 comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some embodiments, the antibody or antigen binding fragment comprises a (i) human IgG4 Fc region or (ii) a human IgG4 Fc region comprising (a) S228P, (b) S228P and L235E, or (c) S228P, F234A, and L235A, per Kabat numbering. In some embodiments, the antibody or antigen binding fragment comprises a human IgG2 Fc region; IgG2-IgG4 cross-subclass Fc region; IgG2-IgG3 cross-subclass Fc region; IgG2 comprising H268Q, V309L, A330S, P331S (IgG2m4); or IgG2 comprising V234A, G237A, P238S, H268A, V309L, A330S, P331S (IgG2σ). In some embodiments, the Fc region comprises a human IgG1 with a substitution selected from 329A, 329G, 329Y, 331S, 236F, 236R, 238A, 238E, 238G, 238H, 238I, 238V, 238W, 238Y, 248A, 254D, 254E, 254G, 254H, 254I, 254N, 254P, 254Q, 254T, 254V, 264S, 265H, 265K, 265S, 265Y, 265A, 267G, 267H, 267I, 267K, 434I, 438G, 439E, 439H, 439Q, 440A, 440D, 440E, 440F, 440M, 440T, and 440V, per Kabat numbering. In some embodiments, the antibody or antigen binding fragment comprises a sequence at least about 90%, 91%, 92%, 93%, 94%, 95%, 96%, 97%, 98%, 99%, or 100% identical to any one of SEQ ID NOS: 320-362. In some embodiments, the HCDR1 comprises SEQ ID NO: 1, HCDR2 comprises any one of SEQ ID NOS: 2-5, HCDR3 comprises any one of SEQ ID NOS: 6-9, LCDR1 comprises SEQ ID NO: 10, LCDR2 comprises SEQ ID NO: 11, and LCDR3 comprises any one of SEQ ID NOS: 12-15. In some embodiments, the Fc region comprises any one of SEQ ID NOs: 401-413 or a sequence at least about 90%, 91%, 92%, 93%, 94%, 95%, 96%, 97%, 98%, or 99% identical to any one of SEQ ID NOs: 401-413. In some embodiments, the heavy chain comprises any one of SEQ ID NOs: 501-513 or a sequence at least about 90%, 91%, 92%, 93%, 94%, 95%, 96%, 97%, 98%, or 99% identical to any one of SEQ ID NOs: 501-513. In some embodiments, the light chain comprises any one of SEQ ID NO: 514 or a sequence at least about 90%, 91%, 92%, 93%, 94%, 95%, 96%, 97%, 98%, or 99% identical to any one of SEQ ID NO: 514. In some embodiments, the HCDR2 comprises SEQ ID NO: 2, the HCDR3 comprises SEQ ID NO: 6, and the LCDR3 comprises SEQ ID NO: 12, and wherein the Fc region comprises any one of SEQ ID NOs: 401-413 or a sequence at least about 90%, 91%, 92%, 93%, 94%, 95%, 96%, 97%, 98%, or 99% identical to any one of SEQ ID NOs: 401-413. In some embodiments, the antibody or antigen binding fragment comprises at least about 80% monomeric fraction as determined by size exclusion chromatography. In some embodiments, the antibody or antigen binding fragment expresses at least about 20 ug/ml total antibody, optionally about 20 ug/ml and 70 ug/mL total antibody.

Further provided are methods of treating fibrosis or an intestinal inflammatory condition, disease, or disorder in a subject in need thereof, the method comprising administering to the subject an antibody or antigen binding fragment of any antibody or antigen binding fragment disclosed herein. In some embodiments, the subject has fibrosis. In some embodiments, the subject has an intestinal inflammatory condition, disease, or disorder. In some embodiments, the intestinal inflammatory condition, disease, or disorder comprises inflammatory bowel disease (IBD). In some embodiments, the IBD comprises Crohn's Disease. In some embodiments, the IBD comprises ulcerative colitis.

In some embodiments, antibodies or antigen binding fragments described herein comprise are present in a liquid composition a concentration of the antibody or antigen binding fragment of 10 mg/ml to 170 mg/ml. In some embodiments, the antibody or antigen binding fragment thereof is at a concentration of 10 mg/ml to 170 mg/ml. In some embodiments, the viscosity is from about 4 to about 30 mPa·s (millipascal-second (mPa·s)). In some embodiments, the viscosity is from about 4 to about 10 mPa·s (millipascal-second (mPa·s)).

In another aspect, provided herein, is an antibody or antigen binding fragment thereof that binds to TL1A, comprising a heavy chain variable framework region comprising a human IGHV1-46*02 framework or a modified human IGHV1-46*02 framework, and a light chain variable framework region comprising a human IGKV3-20 framework or a modified human IGKV3-20 framework; wherein the heavy chain variable framework region and the light chain variable framework region collectively comprise less than about 14 amino acid modifications from the human IGHV1-46*02 framework and the human IGKV3-20 framework. In some embodiments, the heavy chain variable framework region and the light chain variable framework region collectively comprise 13, 12, 11, 10, 9, 8, 7, 6, 5, 4, 3, 2, 1, or no amino acid modifications from the human IGHV1-46*02 framework and the human IGKV3-20 framework. In some embodiments, the amino acid modification comprises a modification at amino acid position 1 in the heavy chain variable region, per Kabat numbering. In some embodiments, the amino acid at position 1 comprises A, R, N, D, C, E, G, H, I, L, K, M, F, P, S, T, W, Y, or V. In some embodiments, the amino acid at position 1 comprises a hydrophobic amino acid, a hydrophilic amino acid, or an amphipathic amino acid. In some embodiments, the amino acid at position 1 comprises an aliphatic amino acid, an aromatic amino acid, an acidic amino acid, a basic amino acid, a hydroxylic amino acid, a sulfur-containing amino acid, or an amidic amino acid. In some embodiments, the amino acid at position 1 comprises E. In some embodiments, the amino acid modification comprises a modification at amino acid position 45 in the heavy chain variable region, per Kabat numbering. In some embodiments, the amino acid at position 45 comprises A, N, D, C, Q, E, G, H, I, L, K, M, F, P, S, T, W, Y, or V. In some embodiments, the amino acid at position 45 comprises a hydrophobic amino acid, a hydrophilic amino acid, or an amphipathic amino acid. In some embodiments, the amino acid at position 45 comprises an aliphatic amino acid, an aromatic amino acid, an acidic amino acid, a basic amino acid, a hydroxylic amino acid, a sulfur-containing amino acid, or an amidic amino acid. In some embodiments, the amino acid at position 45 comprises K. In some embodiments, the amino acid modification comprises a modification at amino acid position 47 in the heavy chain variable region, per Kabat numbering. In some embodiments, the amino acid at position 47 comprises R, N, D, C, Q, E, G, H, I, L, K, M, F, P, S, T, W, Y, or V. In some embodiments, the amino acid at position 47 comprises a hydrophobic amino acid, a hydrophilic amino acid, or an amphipathic amino acid. In some embodiments, the amino acid at position 47 comprises an aliphatic amino acid, an aromatic amino acid, an acidic amino acid, a basic amino acid, a hydroxylic amino acid, a sulfur-containing amino acid, or an amidic amino acid. In some embodiments, the amino acid at position 47 comprises R. In some embodiments, the amino acid modification comprises a modification at amino acid position 55 in the heavy chain variable region, per Kabat numbering. In some embodiments, the amino acid at position 55 comprises A, R, N, D, C, Q, E, G, H, I, L, K, F, P, S, T, W, Y, or V. In some embodiments, the amino acid at position 55 comprises a hydrophobic amino acid, a hydrophilic amino acid, or an amphipathic amino acid. In some embodiments, the amino acid at position 55 comprises an aliphatic amino acid, an aromatic amino acid, an acidic amino acid, a basic amino acid, a hydroxylic amino acid, a sulfur-containing amino acid, or an amidic amino acid. In some embodiments, the amino acid at position 55 comprises I. In some embodiments, the amino acid modification comprises a modification at amino acid position 78 in the heavy chain variable region, per Kabat numbering. In some embodiments, the amino acid at position 78 comprises A, R, N, D, C, Q, E, G, H, I, L, K, M, F, P, S, T, W, or Y.

In some embodiments, the amino acid at position 78 comprises a hydrophobic amino acid, a hydrophilic amino acid, or an amphipathic amino acid. In some embodiments, the amino acid at position 78 comprises an aliphatic amino acid, an aromatic amino acid, an acidic amino acid, a basic amino acid, a hydroxylic amino acid, a sulfur-containing amino acid, or an amidic amino acid. In some embodiments, the amino acid at position 78 comprises A. In some embodiments, the amino acid modification comprises a modification at amino acid position 80 in the heavy chain variable region, per Kabat numbering. In some embodiments, the amino acid at position 80 comprises A, R, N, D, C, Q, E, G, H, I, L, K, F, P, S, T, W, Y, or V. In some embodiments, the amino acid at position 80 comprises a hydrophobic amino acid, a hydrophilic amino acid, or an amphipathic amino acid. In some embodiments, the amino acid at position 80 comprises an aliphatic amino acid, an aromatic amino acid, an acidic amino acid, a basic amino acid, a hydroxylic amino acid, a sulfur-containing amino acid, or an amidic amino acid. In some embodiments, the amino acid at position 80 comprises I. In some embodiments, the amino acid modification comprises a modification at amino acid position 82 in the heavy chain variable region, per Kabat numbering. In some embodiments, the amino acid at position 82 comprises A, N, D, C, Q, E, G, H, I, L, K, M, F, P, S, T, W, Y, or V. In some embodiments, the amino acid at position 82 comprises a hydrophobic amino acid, a hydrophilic amino acid, or an amphipathic amino acid. In some embodiments, the amino acid at position 82 comprises an aliphatic amino acid, an aromatic amino acid, an acidic amino acid, a basic amino acid, a hydroxylic amino acid, a sulfur-containing amino acid, or an amidic amino acid. In some embodiments, the amino acid at position 82 comprises T. In some embodiments, the amino acid modification comprises a modification at amino acid position 89 in the heavy chain variable region, per Kabat numbering. In some embodiments, the amino acid at position 89 comprises A, R, N, D, C, Q, E, G, H, I, L, K, M, F, P, S, T, W, or Y. In some embodiments, the amino acid at position 89 comprises a hydrophobic amino acid, a hydrophilic amino acid, or an amphipathic amino acid. In some embodiments, the amino acid at position 89 comprises an aliphatic amino acid, an aromatic amino acid, an acidic amino acid, a basic amino acid, a hydroxylic amino acid, a sulfur-containing amino acid, or an amidic amino acid. In some embodiments, the amino acid at position 89 comprises A. In some embodiments, the amino acid modification comprises a modification at amino acid position 91 in the heavy chain variable region, per Kabat numbering. In some embodiments, the amino acid at position 91 comprises A, R, N, D, C, Q, E, G, H, I, L, K, F, P, S, T, W, Y, or V. In some embodiments, the amino acid at position 91 comprises a hydrophobic amino acid, a hydrophilic amino acid, or an amphipathic amino acid. In some embodiments, the amino acid at position 91 comprises an aliphatic amino acid, an aromatic amino acid, an acidic amino acid, a basic amino acid, a hydroxylic amino acid, a sulfur-containing amino acid, or an amidic amino acid. In some embodiments, the amino acid at position 91 comprises L.

In some embodiments, the amino acid modifications comprise one or more of: Q1E, R45K, A47R, M55I, V78A, M80I, R82T, V89A, M91L in the heavy chain variable region, per Aho numbering. In some embodiments, the amino acid modifications comprise Q1E. In some embodiments, the amino acid modifications comprise R45K. In some embodiments, the amino acid modifications comprise A47R. In some embodiments, the amino acid modifications comprise M55I. In some embodiments, the amino acid modifications comprise V78A. In some embodiments, the amino acid modifications comprise M80I. In some embodiments, the amino acid modifications comprise R82T. In some embodiments, the amino acid modifications comprise V89A. In some embodiments, the amino acid modifications comprise M91L.

In some embodiments, the amino acid modification comprises a modification at amino acid position 54 in the light chain variable region, per Kabat numbering. In some embodiments, the amino acid at position 54 comprises A, R, N, D, C, Q, E, G, H, I, K, M, F, P, S, T, W, Y, or V. In some embodiments, the amino acid at position 54 comprises a hydrophobic amino acid, a hydrophilic amino acid, or an amphipathic amino acid. In some embodiments, the amino acid at position 54 comprises an aliphatic amino acid, an aromatic amino acid, an acidic amino acid, a basic amino acid, a hydroxylic amino acid, a sulfur-containing amino acid, or an amidic amino acid. In some embodiments, the amino acid at position 54 comprises P. In some embodiments, the amino acid modification comprises a modification at amino acid position 55 in the light chain variable region, per Kabat numbering. In some embodiments, the amino acid at position 55 comprises A, R, N, D, C, Q, E, G, H, I, K, M, F, P, S, T, W, Y, or V. In some embodiments, the amino acid at position 55 comprises a hydrophobic amino acid, a hydrophilic amino acid, or an amphipathic amino acid. In some embodiments, the amino acid at position 55 comprises an aliphatic amino acid, an aromatic amino acid, an acidic amino acid, a basic amino acid, a hydroxylic amino acid, a sulfur-containing amino acid, or an amidic amino acid. In some embodiments, the amino acid at position 55 comprises W.

In some embodiments, the amino acid modifications comprise L54P and/or L55W in the light chain variable region, per Aho numbering. In some embodiments, the amino acid modifications comprise L54P. In some embodiments, the amino acid modifications comprise L55W.

In some embodiments, the antibody or antigen binding fragment comprises a heavy chain CDR1 as set forth by SEQ ID NO: 1. In some embodiments, the antibody or antigen binding fragment comprises a heavy chain CDR2 as set forth by SEQ ID NO: 2. In some embodiments, the antibody or antigen binding fragment comprises a heavy chain CDR2 as set forth by SEQ ID NO: 3. In some embodiments, the antibody or antigen binding fragment comprises a heavy chain CDR2 as set forth by SEQ ID NO: 4. In some embodiments, the antibody or antigen binding fragment comprises a heavy chain CDR2 as set forth by SEQ ID NO: 5. In some embodiments, the antibody or antigen binding fragment comprises a heavy chain CDR3 as set forth by SEQ ID NO: 6. In some embodiments, the antibody or antigen binding fragment comprises a heavy chain CDR3 as set forth by SEQ ID NO: 7. In some embodiments, the antibody or antigen binding fragment comprises a heavy chain CDR3 as set forth by SEQ ID NO: 8. In some embodiments, the antibody or antigen binding fragment comprises a heavy chain CDR3 as set forth by SEQ ID NO: 9. In some embodiments, the antibody or antigen binding fragment comprises a light chain CDR1 as set forth by SEQ ID NO: 10. In some embodiments, the antibody or antigen binding fragment comprises a light chain CDR2 as set forth by SEQ ID NO: 11. In some embodiments, the antibody or antigen binding fragment comprises a light chain CDR3 as set forth by SEQ ID NO: 12. In some embodiments, the antibody or antigen binding fragment comprises a light chain CDR3 as set forth by SEQ ID NO: 13. In some embodiments, the antibody or antigen binding fragment comprises a light chain CDR3 as set forth by SEQ ID NO: 14. In some embodiments, the antibody or antigen binding fragment comprises a light chain CDR3 as set forth by SEQ ID NO: 15.

In some embodiments, the antibody or antigen binding fragment comprises a heavy chain FR1 as set forth by SEQ ID NO: 304. In some embodiments, the antibody or antigen binding fragment comprises a heavy chain FR2 as set forth by SEQ ID NO: 305. In some embodiments, the antibody or antigen binding fragment comprises a heavy chain FR2 as set forth by SEQ ID NO: 313. In some embodiments, the antibody or antigen binding fragment comprises a heavy chain FR3 as set forth by SEQ ID NO: 306. In some embodiments, the antibody or antigen binding fragment comprises a heavy chain FR3 as set forth by SEQ ID NO: 307. In some embodiments, the antibody or antigen binding fragment comprises a heavy chain FR3 as set forth by SEQ ID NO: 314. In some embodiments, the antibody or antigen binding fragment comprises a heavy chain FR3 as set forth by SEQ ID NO: 315. In some embodiments, the antibody or antigen binding fragment comprises a heavy chain FR4 as set forth by SEQ ID NO: 308. In some embodiments, the antibody or antigen binding fragment comprises a light chain FR1 as set forth by SEQ ID NO: 309. In some embodiments, the antibody or antigen binding fragment comprises a light chain FR2 as set forth by SEQ ID NO: 310. In some embodiments, the antibody or antigen binding fragment comprises a light chain FR3 as set forth by SEQ ID NO: 311. In some embodiments, the antibody or antigen binding fragment comprises a light chain FR4 as set forth by SEQ ID NO: 312.

In another aspect, provided herein is an antibody or antigen binding fragment thereof that binds to TL1A, comprising: (a) a heavy chain variable region comprising SEQ ID NO: 301 (X1VQLVQSGAEVKKPGASVKVSCKAS[HCDR1]WVX2QX3PGQGLEWX4G[HCDR2]RX5TX6TX7DTSTSTX8YX9ELSSLRSEDTAVYYCAR[HCDR3]WGQGTTVTVSS), and (b) a light chain variable region comprising SEQ ID NO: 303 (EIVLTQSPGTLSLSPGERATLSC[LCDR1]WYQQKPGQAPRX10X11IY[LCDR2]GIPDR FSGSGSGTDFTLTISRLEPEDFAVYYC[LCDR3]FGGGTKLEIK), wherein each of X1-X11 is independently selected from A, R, N, D, C, Q, E, G, H, I, L, K, M, F, P, S, T, W, Y, or V.

In some embodiments, X1 comprises a hydrophobic amino acid, a hydrophilic amino acid, or an amphipathic amino acid. In some embodiments, X1 comprises an aliphatic amino acid, an aromatic amino acid, an acidic amino acid, a basic amino acid, a hydroxylic amino acid, a sulfur-containing amino acid, or an amidic amino acid. In some embodiments, X2 comprises a hydrophobic amino acid, a hydrophilic amino acid, or an amphipathic amino acid. In some embodiments, X2 comprises an aliphatic amino acid, an aromatic amino acid, an acidic amino acid, a basic amino acid, a hydroxylic amino acid, a sulfur-containing amino acid, or an amidic amino acid. In some embodiments, X3 comprises a hydrophobic amino acid, a hydrophilic amino acid, or an amphipathic amino acid. In some embodiments, X3 comprises an aliphatic amino acid, an aromatic amino acid, an acidic amino acid, a basic amino acid, a hydroxylic amino acid, a sulfur-containing amino acid, or an amidic amino acid. In some embodiments, X4 comprises a hydrophobic amino acid, a hydrophilic amino acid, or an amphipathic amino acid. In some embodiments, X4 comprises an aliphatic amino acid, an aromatic amino acid, an acidic amino acid, a basic amino acid, a hydroxylic amino acid, a sulfur-containing amino acid, or an amidic amino acid. In some embodiments, X5 comprises a hydrophobic amino acid, a hydrophilic amino acid, or an amphipathic amino acid. In some embodiments, X5 comprises an aliphatic amino acid, an aromatic amino acid, an acidic amino acid, a basic amino acid, a hydroxylic amino acid, a sulfur-containing amino acid, or an amidic amino acid. In some embodiments, X6 comprises a hydrophobic amino acid, a hydrophilic amino acid, or an amphipathic amino acid. In some embodiments, X6 comprises an aliphatic amino acid, an aromatic amino acid, an acidic amino acid, a basic amino acid, a hydroxylic amino acid, a sulfur-containing amino acid, or an amidic amino acid. In some embodiments, X7 comprises a hydrophobic amino acid, a hydrophilic amino acid, or an amphipathic amino acid. In some embodiments, X7 comprises an aliphatic amino acid, an aromatic amino acid, an acidic amino acid, a basic amino acid, a hydroxylic amino acid, a sulfur-containing amino acid, or an amidic amino acid. In some embodiments, X8 comprises a hydrophobic amino acid, a hydrophilic amino acid, or an amphipathic amino acid. In some embodiments, X8 comprises an aliphatic amino acid, an aromatic amino acid, an acidic amino acid, a basic amino acid, a hydroxylic amino acid, a sulfur-containing amino acid, or an amidic amino acid. In some embodiments, X9 comprises a hydrophobic amino acid, a hydrophilic amino acid, or an amphipathic amino acid. In some embodiments, X9 comprises an aliphatic amino acid, an aromatic amino acid, an acidic amino acid, a basic amino acid, a hydroxylic amino acid, a sulfur-containing amino acid, or an amidic amino acid. In some embodiments, X10 comprises a hydrophobic amino acid, a hydrophilic amino acid, or an amphipathic amino acid. In some embodiments, X10 comprises an aliphatic amino acid, an aromatic amino acid, an acidic amino acid, a basic amino acid, a hydroxylic amino acid, a sulfur-containing amino acid, or an amidic amino acid. In some embodiments, X11 comprises a hydrophobic amino acid, a hydrophilic amino acid, or an amphipathic amino acid. In some embodiments, X11 comprises an aliphatic amino acid, an aromatic amino acid, an acidic amino acid, a basic amino acid, a hydroxylic amino acid, a sulfur-containing amino acid, or an amidic amino acid.

In some embodiments, X1=Q or E, X2=R or K, X3=A or R, X4=M or I, X5=V or A, X6=M or I, X7=R or T, X8=V or A, X9=M or L, X10=L or P, and X11=L or W. In some embodiments, X1=Q. In some embodiments, X1=E. In some embodiments, X2=R. In some embodiments, X2=K. In some embodiments, X3=A. In some embodiments, X3=R. In some embodiments, X4=M. In some embodiments, X4=I. In some embodiments, X5=V. In some embodiments, X5=A. In some embodiments, X6=M. In some embodiments, X6=I. In some embodiments, X7=R. In some embodiments, X7=T. In some embodiments, X8=V. In some embodiments, X8=A. In some embodiments, X9=M. In some embodiments, X9=L. In some embodiments, X10=L. In some embodiments, X10=P. In some embodiments, X11=L. In some embodiments, X11=W.

In some embodiments, HCDR1 comprises SEQ ID NO: 1. In some embodiments, HCDR2 comprises SEQ ID NO: 2. In some embodiments, HCDR2 comprises SEQ ID NO: 3. In some embodiments, HCDR2 comprises SEQ ID NO: 4. In some embodiments, HCDR2 comprises SEQ ID NO: 5. In some embodiments, HCDR3 comprises SEQ ID NO: 6. In some embodiments, HCDR3 comprises SEQ ID NO: 7. In some embodiments, HCDR3 comprises SEQ ID NO: 8. In some embodiments, HCDR3 comprises SEQ ID NO: 9. In some embodiments, LCDR1 comprises SEQ ID NO: 10. In some embodiments, LCDR2 comprises SEQ ID NO: 11. In some embodiments, LCDR3 comprises SEQ ID NO: 12. In some embodiments, LCDR3 comprises SEQ ID NO: 13. In some embodiments, LCDR3 comprises SEQ ID NO: 14. In some embodiments, the antibody or antigen binding fragment comprises a light chain CDR3 as set forth by SEQ ID NO: 15.

In another aspect, provided herein is an antibody or antigen binding fragment thereof that binds to TL1A, comprising: (a) a heavy chain variable region comprising SEQ ID NO: 302 (X1VQLVQSGAEVKKPGASVKVSCKAS[HCDR1]WVX2QX3PGQGLEWX4G[HCDR2]RX5TX6TX7DTSTSTX8YX9ELSSLRSEDTAVYYC[HCDR3]WGQGTTVTVSS), and (b) a light chain variable region comprising SEQ ID NO: 303 (EIVLTQSPGTLSLSPGERATLSC[LCDR1]WYQQKPGQAPRX10X11IY[LCDR2]GIPDR FSGSGSGTDFTLTISRLEPEDFAVYYC[LCDR3]FGGGTKLEIK), wherein each of X1-X11 is independently selected from A, R, N, D, C, Q, E, G, H, I, L, K, M, F, P, S, T, W, Y, or V.

In some embodiments, X1 comprises a hydrophobic amino acid, a hydrophilic amino acid, or an amphipathic amino acid. In some embodiments, X1 comprises an aliphatic amino acid, an aromatic amino acid, an acidic amino acid, a basic amino acid, a hydroxylic amino acid, a sulfur-containing amino acid, or an amidic amino acid. In some embodiments, X2 comprises a hydrophobic amino acid, a hydrophilic amino acid, or an amphipathic amino acid. In some embodiments, X2 comprises an aliphatic amino acid, an aromatic amino acid, an acidic amino acid, a basic amino acid, a hydroxylic amino acid, a sulfur-containing amino acid, or an amidic amino acid. In some embodiments, X3 comprises a hydrophobic amino acid, a hydrophilic amino acid, or an amphipathic amino acid. In some embodiments, X3 comprises an aliphatic amino acid, an aromatic amino acid, an acidic amino acid, a basic amino acid, a hydroxylic amino acid, a sulfur-containing amino acid, or an amidic amino acid. In some embodiments, X4 comprises a hydrophobic amino acid, a hydrophilic amino acid, or an amphipathic amino acid. In some embodiments, X4 comprises an aliphatic amino acid, an aromatic amino acid, an acidic amino acid, a basic amino acid, a hydroxylic amino acid, a sulfur-containing amino acid, or an amidic amino acid. In some embodiments, X5 comprises a hydrophobic amino acid, a hydrophilic amino acid, or an amphipathic amino acid. In some embodiments, X5 comprises an aliphatic amino acid, an aromatic amino acid, an acidic amino acid, a basic amino acid, a hydroxylic amino acid, a sulfur-containing amino acid, or an amidic amino acid. In some embodiments, X6 comprises a hydrophobic amino acid, a hydrophilic amino acid, or an amphipathic amino acid. In some embodiments, X6 comprises an aliphatic amino acid, an aromatic amino acid, an acidic amino acid, a basic amino acid, a hydroxylic amino acid, a sulfur-containing amino acid, or an amidic amino acid. In some embodiments, X7 comprises a hydrophobic amino acid, a hydrophilic amino acid, or an amphipathic amino acid. In some embodiments, X7 comprises an aliphatic amino acid, an aromatic amino acid, an acidic amino acid, a basic amino acid, a hydroxylic amino acid, a sulfur-containing amino acid, or an amidic amino acid. In some embodiments, X8 comprises a hydrophobic amino acid, a hydrophilic amino acid, or an amphipathic amino acid. In some embodiments, X8 comprises an aliphatic amino acid, an aromatic amino acid, an acidic amino acid, a basic amino acid, a hydroxylic amino acid, a sulfur-containing amino acid, or an amidic amino acid. In some embodiments, X9 comprises a hydrophobic amino acid, a hydrophilic amino acid, or an amphipathic amino acid. In some embodiments, X9 comprises an aliphatic amino acid, an aromatic amino acid, an acidic amino acid, a basic amino acid, a hydroxylic amino acid, a sulfur-containing amino acid, or an amidic amino acid. In some embodiments, X10 comprises a hydrophobic amino acid, a hydrophilic amino acid, or an amphipathic amino acid. In some embodiments, X10 comprises an aliphatic amino acid, an aromatic amino acid, an acidic amino acid, a basic amino acid, a hydroxylic amino acid, a sulfur-containing amino acid, or an amidic amino acid. In some embodiments, X11 comprises a hydrophobic amino acid, a hydrophilic amino acid, or an amphipathic amino acid. In some embodiments, X11 comprises an aliphatic amino acid, an aromatic amino acid, an acidic amino acid, a basic amino acid, a hydroxylic amino acid, a sulfur-containing amino acid, or an amidic amino acid.

In some embodiments, X1=Q or E, X2=R or K, X3=A or R, X4=M or I, X5=V or A, X6=M or I, X7=R or T, X8=V or A, X9=M or L, X10=L or P, and X11=L or W. In some embodiments, X1=Q. In some embodiments, X1=E. In some embodiments, X2=R. In some embodiments, X2=K. In some embodiments, X3=A. In some embodiments, X3=R. In some embodiments, X4=M. In some embodiments, X4=I. In some embodiments, X5=V. In some embodiments, X5=A. In some embodiments, X6=M. In some embodiments, X6=I. In some embodiments, X7=R. In some embodiments, X7=T. In some embodiments, X8=V. In some embodiments, X8=A. In some embodiments, X9=M. In some embodiments, X9=L. In some embodiments, X10=L. In some embodiments, X10=P. In some embodiments, X11=L. In some embodiments, X11=W.

In some embodiments, HCDR1 comprises SEQ ID NO: 1. In some embodiments, HCDR2 comprises SEQ ID NO: 2. In some embodiments, HCDR2 comprises SEQ ID NO: 3. In some embodiments, HCDR2 comprises SEQ ID NO: 4. In some embodiments, HCDR2 comprises SEQ ID NO: 5. In some embodiments, HCDR3 comprises SEQ ID NO: 6. In some embodiments, HCDR3 comprises SEQ ID NO: 7. In some embodiments, HCDR3 comprises SEQ ID NO: 8. In some embodiments, HCDR3 comprises SEQ ID NO: 9. In some embodiments, LCDR1 comprises SEQ ID NO: 10. In some embodiments, LCDR2 comprises SEQ ID NO: 11. In some embodiments, LCDR3 comprises SEQ ID NO: 12. In some embodiments, LCDR3 comprises SEQ ID NO: 13. In some embodiments, LCDR3 comprises SEQ ID NO: 14. In some embodiments, LCDR3 comprises SEQ ID NO: 15.

In some embodiments, the heavy chain variable region comprises SEQ ID NO: 101. In some embodiments, the heavy chain variable region comprises SEQ ID NO: 102. In some embodiments, the heavy chain variable region comprises SEQ ID NO: 103. In some embodiments, the heavy chain variable region comprises SEQ ID NO: 104. In some embodiments, the heavy chain variable region comprises SEQ ID NO: 105. In some embodiments, the heavy chain variable region comprises SEQ ID NO: 106. In some embodiments, the heavy chain variable region comprises SEQ ID NO: 107. In some embodiments, the heavy chain variable region comprises SEQ ID NO: 108. In some embodiments, the heavy chain variable region comprises SEQ ID NO: 109. In some embodiments, the heavy chain variable region comprises SEQ ID NO: 110. In some embodiments, the heavy chain variable region comprises SEQ ID NO: 111. In some embodiments, the heavy chain variable region comprises SEQ ID NO: 112. In some embodiments, the heavy chain variable region comprises SEQ ID NO: 113. In some embodiments, the heavy chain variable region comprises SEQ ID NO: 114. In some embodiments, the heavy chain variable region comprises SEQ ID NO: 115. In some embodiments, the heavy chain variable region comprises SEQ ID NO: 116. In some embodiments, the heavy chain variable region comprises SEQ ID NO: 117. In some embodiments, the heavy chain variable region comprises SEQ ID NO: 118. In some embodiments, the heavy chain variable region comprises SEQ ID NO: 119. In some embodiments, the heavy chain variable region comprises SEQ ID NO: 120. In some embodiments, the heavy chain variable region comprises SEQ ID NO: 121. In some embodiments, the heavy chain variable region comprises SEQ ID NO: 122. In some embodiments, the heavy chain variable region comprises SEQ ID NO: 123. In some embodiments, the heavy chain variable region comprises SEQ ID NO: 124. In some embodiments, the heavy chain variable region comprises SEQ ID NO: 125. In some embodiments, the heavy chain variable region comprises SEQ ID NO: 126. In some embodiments, the heavy chain variable region comprises SEQ ID NO: 127. In some embodiments, the heavy chain variable region comprises SEQ ID NO: 128. In some embodiments, the heavy chain variable region comprises SEQ ID NO: 129. In some embodiments, the heavy chain variable region comprises SEQ ID NO: 130. In some embodiments, the heavy chain variable region comprises SEQ ID NO: 131. In some embodiments, the heavy chain variable region comprises SEQ ID NO: 132. In some embodiments, the heavy chain variable region comprises SEQ ID NO: 133. In some embodiments, the heavy chain variable region comprises SEQ ID NO: 134. In some embodiments, the heavy chain variable region comprises SEQ ID NO: 135. In some embodiments, the light chain variable region comprises SEQ ID NO: 201. In some embodiments, the light chain variable region comprises SEQ ID NO: 202. In some embodiments, the light chain variable region comprises SEQ ID NO: 203. In some embodiments, the light chain variable region comprises SEQ ID NO: 204. In some embodiments, the light chain variable region comprises SEQ ID NO: 205. In some embodiments, the light chain variable region comprises SEQ ID NO: 206.

Further provided herein is an antibody or antigen binding fragment thereof that binds to tumor necrosis factor-like protein 1A (TL1A), comprising a heavy chain variable domain comprising an amino acid sequence at least about 96% identical to SEQ ID NO: 104, and a light chain variable domain comprising an amino acid sequence at least about 97% identical to SEQ ID NO: 201. In some embodiments, the heavy chain variable domain comprises an amino acid sequence at least about 97% identical to SEQ ID NO: 104. In some embodiments, the heavy chain variable domain comprises an amino acid sequence at least about 98% identical to SEQ ID NO: 104. In some embodiments, the heavy chain variable domain comprises an amino acid sequence at least about 99% identical to SEQ ID NO: 104. In some embodiments, the heavy chain variable domain comprises SEQ ID NO: 104. In some embodiments, the light chain variable domain comprises an amino acid sequence at least about 98% identical to SEQ ID NO: 201. In some embodiments, the light chain variable domain comprises an amino acid sequence at least about 99% identical to SEQ ID NO: 201. In some embodiments, the light chain variable domain comprises SEQ ID NO: 201.

Further provided herein is an antibody or antigen binding fragment thereof that binds to tumor necrosis factor-like protein 1A (TL1A), comprising a heavy chain variable domain comprising an amino acid sequence at least about 99% identical to SEQ ID NO: 107, and a light chain variable domain comprising an amino acid sequence at least about 97% identical to SEQ ID NO: 201. In some embodiments, the heavy chain variable domain comprises SEQ ID NO: 107. In some embodiments, the light chain variable domain comprises an amino acid sequence at least about 98% identical to SEQ ID NO: 201. In some embodiments, the light chain variable domain comprises an amino acid sequence at least about 99% identical to SEQ ID NO: 201. In some embodiments, the light chain variable domain comprises SEQ ID NO: 201.

Further provided herein is an antibody or antigen binding fragment thereof that binds to tumor necrosis factor-like protein 1A (TL1A), comprising a heavy chain variable domain comprising an amino acid sequence at least about 95%, 96%, 97%, 98%, 99%, or 100% identical to any one of SEQ ID NOS: 101-135, and a light chain variable domain comprising an amino acid sequence at least about 95%, 96%, 97%, 98%, 99%, or 100% identical to any one of SEQ ID NOS: 201-206. In some embodiments, the heavy chain variable domain comprises a sequence at least about 95%, 96%, 97%, 98%, 99%, or 100% identical to SEQ ID NO: 101. In some embodiments, the heavy chain variable domain comprises a sequence at least about 95%, 96%, 97%, 98%, 99%, or 100% identical to SEQ ID NO: 102. In some embodiments, the heavy chain variable domain comprises a sequence at least about 95%, 96%, 97%, 98%, 99%, or 100% identical to SEQ ID NO: 103. In some embodiments, the heavy chain variable domain comprises a sequence at least about 95%, 96%, 97%, 98%, 99%, or 100% identical to SEQ ID NO: 104. In some embodiments, the heavy chain variable domain comprises a sequence at least about 95%, 96%, 97%, 98%, 99%, or 100% identical to SEQ ID NO: 105. In some embodiments, the heavy chain variable domain comprises a sequence at least about 95%, 96%, 97%, 98%, 99%, or 100% identical to SEQ ID NO: 106. In some embodiments, the heavy chain variable domain comprises a sequence at least about 95%, 96%, 97%, 98%, 99%, or 100% identical to SEQ ID NO: 107. In some embodiments, the heavy chain variable domain comprises a sequence at least about 95%, 96%, 97%, 98%, 99%, or 100% identical to SEQ ID NO: 108. In some embodiments, the heavy chain variable domain comprises a sequence at least about 95%, 96%, 97%, 98%, 99%, or 100% identical to SEQ ID NO: 109. In some embodiments, the heavy chain variable domain comprises a sequence at least about 95%, 96%, 97%, 98%, 99%, or 100% identical to SEQ ID NO: 110. In some embodiments, the heavy chain variable domain comprises a sequence at least about 95%, 96%, 97%, 98%, 99%, or 100% identical to SEQ ID NO: 111. In some embodiments, the heavy chain variable domain comprises a sequence at least about 95%, 96%, 97%, 98%, 99%, or 100% identical to SEQ ID NO: 112. In some embodiments, the heavy chain variable domain comprises a sequence at least about 95%, 96%, 97%, 98%, 99%, or 100% identical to SEQ ID NO: 113. In some embodiments, the heavy chain variable domain comprises a sequence at least about 95%, 96%, 97%, 98%, 99%, or 100% identical to SEQ ID NO: 114. In some embodiments, the heavy chain variable domain comprises a sequence at least about 95%, 96%, 97%, 98%, 99%, or 100% identical to SEQ ID NO: 115. In some embodiments, the heavy chain variable domain comprises a sequence at least about 95%, 96%, 97%, 98%, 99%, or 100% identical to SEQ ID NO: 116. In some embodiments, the heavy chain variable domain comprises a sequence at least about 95%, 96%, 97%, 98%, 99%, or 100% identical to SEQ ID NO: 117. In some embodiments, the heavy chain variable domain comprises a sequence at least about 95%, 96%, 97%, 98%, 99%, or 100% identical to SEQ ID NO: 118. In some embodiments, the heavy chain variable domain comprises a sequence at least about 95%, 96%, 97%, 98%, 99%, or 100% identical to SEQ ID NO: 119. In some embodiments, the heavy chain variable domain comprises a sequence at least about 95%, 96%, 97%, 98%, 99%, or 100% identical to SEQ ID NO: 120. In some embodiments, the heavy chain variable domain comprises a sequence at least about 95%, 96%, 97%, 98%, 99%, or 100% identical to SEQ ID NO: 121. In some embodiments, the heavy chain variable domain comprises a sequence at least about 95%, 96%, 97%, 98%, 99%, or 100% identical to SEQ ID NO: 122. In some embodiments, the heavy chain variable domain comprises a sequence at least about 95%, 96%, 97%, 98%, 99%, or 100% identical to SEQ ID NO: 123. In some embodiments, the heavy chain variable domain comprises a sequence at least about 95%, 96%, 97%, 98%, 99%, or 100% identical to SEQ ID NO: 124. In some embodiments, the heavy chain variable domain comprises a sequence at least about 95%, 96%, 97%, 98%, 99%, or 100% identical to SEQ ID NO: 125. In some embodiments, the heavy chain variable domain comprises a sequence at least about 95%, 96%, 97%, 98%, 99%, or 100% identical to SEQ ID NO: 126. In some embodiments, the heavy chain variable domain comprises a sequence at least about 95%, 96%, 97%, 98%, 99%, or 100% identical to SEQ ID NO: 127. In some embodiments, the heavy chain variable domain comprises a sequence at least about 95%, 96%, 97%, 98%, 99%, or 100% identical to SEQ ID NO: 128. In some embodiments, the heavy chain variable domain comprises a sequence at least about 95%, 96%, 97%, 98%, 99%, or 100% identical to SEQ ID NO: 129. In some embodiments, the heavy chain variable domain comprises a sequence at least about 95%, 96%, 97%, 98%, 99%, or 100% identical to SEQ ID NO: 130. In some embodiments, the heavy chain variable domain comprises a sequence at least about 95%, 96%, 97%, 98%, 99%, or 100% identical to SEQ ID NO: 131. In some embodiments, the heavy chain variable domain comprises a sequence at least about 95%, 96%, 97%, 98%, 99%, or 100% identical to SEQ ID NO: 132. In some embodiments, the heavy chain variable domain comprises a sequence at least about 95%, 96%, 97%, 98%, 99%, or 100% identical to SEQ ID NO: 133. In some embodiments, the heavy chain variable domain comprises a sequence at least about 95%, 96%, 97%, 98%, 99%, or 100% identical to SEQ ID NO: 134. In some embodiments, the heavy chain variable domain comprises a sequence at least about 95%, 96%, 97%, 98%, 99%, or 100% identical to SEQ ID NO: 135. In some embodiments, the light chain variable domain comprises a sequence at least about 95%, 96%, 97%, 98%, 99%, or 100% identical to SEQ ID NO: 201. In some embodiments, the light chain variable domain comprises a sequence at least about 95%, 96%, 97%, 98%, 99%, or 100% identical to SEQ ID NO: 202. In some embodiments, the light chain variable domain comprises a sequence at least about 95%, 96%, 97%, 98%, 99%, or 100% identical to SEQ ID NO: 203. In some embodiments, the light chain variable domain comprises a sequence at least about 95%, 96%, 97%, 98%, 99%, or 100% identical to SEQ ID NO: 204. In some embodiments, the light chain variable domain comprises a sequence at least about 95%, 96%, 97%, 98%, 99%, or 100% identical to SEQ ID NO: 205. In some embodiments, the light chain variable domain comprises a sequence at least about 95%, 96%, 97%, 98%, 99%, or 100% identical to SEQ ID NO: 206.

Further provided herein is an antibody or antigen binding fragment thereof that binds to tumor necrosis factor-like protein 1A (TL1A), comprising a heavy chain variable domain comprising SEQ ID NO: 101, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 102, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 103, and a light chain variable domain comprising SEQ ID NOS: 202.

Further provided herein is an antibody or antigen binding fragment thereof that binds to tumor necrosis factor-like protein 1A (TL1A), comprising a heavy chain variable domain comprising SEQ ID NO: 104, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 105, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 103, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 106, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 107, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 108, and a light chain variable domain comprising SEQ ID NOS: 202.

Further provided herein is an antibody or antigen binding fragment thereof that binds to tumor necrosis factor-like protein 1A (TL1A), comprising a heavy chain variable domain comprising SEQ ID NO: 109, and a light chain variable domain comprising SEQ ID NOS: 202.

Further provided herein is an antibody or antigen binding fragment thereof that binds to tumor necrosis factor-like protein 1A (TL1A), comprising a heavy chain variable domain comprising SEQ ID NO: 108, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 109, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 108, and a light chain variable domain comprising SEQ ID NOS: 203.

Further provided herein is an antibody or antigen binding fragment thereof that binds to tumor necrosis factor-like protein 1A (TL1A), comprising a heavy chain variable domain comprising SEQ ID NO: 108, and a light chain variable domain comprising SEQ ID NOS: 204.

Further provided herein is an antibody or antigen binding fragment thereof that binds to tumor necrosis factor-like protein 1A (TL1A), comprising a heavy chain variable domain comprising SEQ ID NO: 107, and a light chain variable domain comprising SEQ ID NOS: 204.

Further provided herein is an antibody or antigen binding fragment thereof that binds to tumor necrosis factor-like protein 1A (TL1A), comprising a heavy chain variable domain comprising SEQ ID NO: 107, and a light chain variable domain comprising SEQ ID NOS: 202.

Further provided herein is an antibody or antigen binding fragment thereof that binds to tumor necrosis factor-like protein 1A (TL1A), comprising a heavy chain variable domain comprising SEQ ID NO: 110, and a light chain variable domain comprising SEQ ID NOS: 204.

Further provided herein is an antibody or antigen binding fragment thereof that binds to tumor necrosis factor-like protein 1A (TL1A), comprising a heavy chain variable domain comprising SEQ ID NO: 111, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 112, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 113, and a light chain variable domain comprising SEQ ID NOS: 204.

Further provided herein is an antibody or antigen binding fragment thereof that binds to tumor necrosis factor-like protein 1A (TL1A), comprising a heavy chain variable domain comprising SEQ ID NO: 114, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 115, and a light chain variable domain comprising SEQ ID NOS: 202.

Further provided herein is an antibody or antigen binding fragment thereof that binds to tumor necrosis factor-like protein 1A (TL1A), comprising a heavy chain variable domain comprising SEQ ID NO: 116, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 117, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 118, and a light chain variable domain comprising SEQ ID NOS: 204.

Further provided herein is an antibody or antigen binding fragment thereof that binds to tumor necrosis factor-like protein 1A (TL1A), comprising a heavy chain variable domain comprising SEQ ID NO: 114, and a light chain variable domain comprising SEQ ID NOS: 204.

Further provided herein is an antibody or antigen binding fragment thereof that binds to tumor necrosis factor-like protein 1A (TL1A), comprising a heavy chain variable domain comprising SEQ ID NO: 102, and a light chain variable domain comprising SEQ ID NOS: 204.

Further provided herein is an antibody or antigen binding fragment thereof that binds to tumor necrosis factor-like protein 1A (TL1A), comprising a heavy chain variable domain comprising SEQ ID NO: 104, and a light chain variable domain comprising SEQ ID NOS: 204.

Further provided herein is an antibody or antigen binding fragment thereof that binds to tumor necrosis factor-like protein 1A (TL1A), comprising a heavy chain variable domain comprising SEQ ID NO: 119, and a light chain variable domain comprising SEQ ID NOS: 204.

Further provided herein is an antibody or antigen binding fragment thereof that binds to tumor necrosis factor-like protein 1A (TL1A), comprising a heavy chain variable domain comprising SEQ ID NO: 119, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 101, and a light chain variable domain comprising SEQ ID NOS: 204.

Further provided herein is an antibody or antigen binding fragment thereof that binds to tumor necrosis factor-like protein 1A (TL1A), comprising a heavy chain variable domain comprising SEQ ID NO: 105, and a light chain variable domain comprising SEQ ID NOS: 204.

Further provided herein is an antibody or antigen binding fragment thereof that binds to tumor necrosis factor-like protein 1A (TL1A), comprising a heavy chain variable domain comprising SEQ ID NO: 120, and a light chain variable domain comprising SEQ ID NOS: 204.

Further provided herein is an antibody or antigen binding fragment thereof that binds to tumor necrosis factor-like protein 1A (TL1A), comprising a heavy chain variable domain comprising SEQ ID NO: 121, and a light chain variable domain comprising SEQ ID NOS: 202.

Further provided herein is an antibody or antigen binding fragment thereof that binds to tumor necrosis factor-like protein 1A (TL1A), comprising a heavy chain variable domain comprising SEQ ID NO: 122, and a light chain variable domain comprising SEQ ID NOS: 202.

Further provided herein is an antibody or antigen binding fragment thereof that binds to tumor necrosis factor-like protein 1A (TL1A), comprising a heavy chain variable domain comprising SEQ ID NO: 122, and a light chain variable domain comprising SEQ ID NOS: 204.

Further provided herein is an antibody or antigen binding fragment thereof that binds to tumor necrosis factor-like protein 1A (TL1A), comprising a heavy chain variable domain comprising SEQ ID NO: 123, and a light chain variable domain comprising SEQ ID NOS: 202.

Further provided herein is an antibody or antigen binding fragment thereof that binds to tumor necrosis factor-like protein 1A (TL1A), comprising a heavy chain variable domain comprising SEQ ID NO: 124, and a light chain variable domain comprising SEQ ID NOS: 202.

Further provided herein is an antibody or antigen binding fragment thereof that binds to tumor necrosis factor-like protein 1A (TL1A), comprising a heavy chain variable domain comprising SEQ ID NO: 125, and a light chain variable domain comprising SEQ ID NOS: 205.

Further provided herein is an antibody or antigen binding fragment thereof that binds to tumor necrosis factor-like protein 1A (TL1A), comprising a heavy chain variable domain comprising SEQ ID NO: 116, and a light chain variable domain comprising SEQ ID NOS: 205.

Further provided herein is an antibody or antigen binding fragment thereof that binds to tumor necrosis factor-like protein 1A (TL1A), comprising a heavy chain variable domain comprising SEQ ID NO: 117, and a light chain variable domain comprising SEQ ID NOS: 205.

Further provided herein is an antibody or antigen binding fragment thereof that binds to tumor necrosis factor-like protein 1A (TL1A), comprising a heavy chain variable domain comprising SEQ ID NO: 126, and a light chain variable domain comprising SEQ ID NOS: 205.

Further provided herein is an antibody or antigen binding fragment thereof that binds to tumor necrosis factor-like protein 1A (TL1A), comprising a heavy chain variable domain comprising SEQ ID NO: 127, and a light chain variable domain comprising SEQ ID NOS: 205.

Further provided herein is an antibody or antigen binding fragment thereof that binds to tumor necrosis factor-like protein 1A (TL1A), comprising a heavy chain variable domain comprising SEQ ID NO: 127, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 121, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 122, and a light chain variable domain comprising SEQ ID NOS: 205.

Further provided herein is an antibody or antigen binding fragment thereof that binds to tumor necrosis factor-like protein 1A (TL1A), comprising a heavy chain variable domain comprising SEQ ID NO: 122, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 122, and a light chain variable domain comprising SEQ ID NOS: 206.

Further provided herein is an antibody or antigen binding fragment thereof that binds to tumor necrosis factor-like protein 1A (TL1A), comprising a heavy chain variable domain comprising SEQ ID NO: 124, and a light chain variable domain comprising SEQ ID NOS: 205.

Further provided herein is an antibody or antigen binding fragment thereof that binds to tumor necrosis factor-like protein 1A (TL1A), comprising a heavy chain variable domain comprising SEQ ID NO: 124, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 128, and a light chain variable domain comprising SEQ ID NOS: 205.

Further provided herein is an antibody or antigen binding fragment thereof that binds to tumor necrosis factor-like protein 1A (TL1A), comprising a heavy chain variable domain comprising SEQ ID NO: 128, and a light chain variable domain comprising SEQ ID NOS: 206.

Further provided herein is an antibody or antigen binding fragment thereof that binds to tumor necrosis factor-like protein 1A (TL1A), comprising a heavy chain variable domain comprising SEQ ID NO: 129, and a light chain variable domain comprising SEQ ID NOS: 205.

Further provided herein is an antibody or antigen binding fragment thereof that binds to tumor necrosis factor-like protein 1A (TL1A), comprising a heavy chain variable domain comprising SEQ ID NO: 130, and a light chain variable domain comprising SEQ ID NOS: 205.

Further provided herein is an antibody or antigen binding fragment thereof that binds to tumor necrosis factor-like protein 1A (TL1A), comprising a heavy chain variable domain comprising SEQ ID NO: 131, and a light chain variable domain comprising SEQ ID NOS: 205.

Further provided herein is an antibody or antigen binding fragment thereof that binds to tumor necrosis factor-like protein 1A (TL1A), comprising a heavy chain variable domain comprising SEQ ID NO: 132, and a light chain variable domain comprising SEQ ID NOS: 205.

Further provided herein is an antibody or antigen binding fragment thereof that binds to tumor necrosis factor-like protein 1A (TL1A), comprising a heavy chain variable domain comprising SEQ ID NO: 133, and a light chain variable domain comprising SEQ ID NOS: 205.

Further provided herein is an antibody or antigen binding fragment thereof that binds to tumor necrosis factor-like protein 1A (TL1A), comprising a heavy chain variable domain comprising SEQ ID NO: 134, and a light chain variable domain comprising SEQ ID NOS: 205.

Further provided herein is an antibody or antigen binding fragment thereof that binds to tumor necrosis factor-like protein 1A (TL1A), comprising a heavy chain variable domain comprising SEQ ID NO: 135, and a light chain variable domain comprising SEQ ID NOS: 205.

Further provided herein is an antibody or antigen binding fragment thereof that binds to tumor necrosis factor-like protein 1A (TL1A), comprising a heavy chain variable domain comprising SEQ ID NO: 132, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 126, and a light chain variable domain comprising SEQ ID NOS: 201.

Further provided herein is an antibody or antigen binding fragment thereof that binds to tumor necrosis factor-like protein 1A (TL1A), comprising a heavy chain variable domain comprising SEQ ID NO: 130, and a light chain variable domain comprising SEQ ID NOS: 201.

Further provided herein is an antibody or antigen binding fragment thereof that binds to tumor necrosis factor-like protein 1A (TL1A), comprising a heavy chain domain comprising any one of SEQ ID NOs: 501-513, and a light chain domain comprising SEQ ID NOS: 514.

In another aspect, provided herein is an antibody or antigen binding fragment thereof that binds to TL1A, comprising a heavy chain variable region comprising: (a) an HCDR1 comprising an amino acid sequence set forth by SEQ ID NO: 1; (b) an HCDR2 comprising an amino acid sequence set forth by any one of SEQ ID NOS: 2-5; and (c) an HCDR3 comprising an amino acid sequence set forth by any one of SEQ ID NOS: 6-9; and the light chain variable region comprises: (d) an LCDR1 comprising an amino acid sequence set forth by SEQ ID NO: 10; (e) an LCDR2 comprising an amino acid sequence set forth by SEQ ID NO: 11; (f) an LCDR3 comprising an amino acid sequence set forth by any one of SEQ ID NOS: 12-15; and a fragment crystallizable (Fc) region comprising reduced antibody-dependent cell-mediated cytotoxicity (ADCC) function as compared to human IgG1 and/or reduced complement-dependent cytotoxicity (CDC) as compared to human IgG1. In some embodiments, the human IgG1 comprises SEQ ID NO: 320. In some embodiments, the ADCC function of the Fc region comprising reduced ADCC is at least about 50% reduced as compared to human IgG1. In some embodiments, the CDC function of the Fc region comprising reduced ADCC is at least about 50% reduced as compared to human IgG1. In some embodiments, the Fc region comprises a human IgG1 comprising (a) 297A, 297Q, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some embodiments, the antibody of antigen binding fragment comprises a (i) human IgG4 Fc region or (ii) a human IgG4 Fc region comprising (a) S228P and L235E, or (b) S228P, F234A, and L235A, per Kabat numbering. In some embodiments, the antibody of antigen binding fragment comprises a human IgG2 Fc region; IgG2-IgG4 cross-subclass Fc region; IgG2-IgG3 cross-subclass Fc region; IgG2 comprising H268Q, V309L, A330S, P331S (IgG2m4); or IgG2 comprising V234A, G237A, P238S, H268A, V309L, A330S, P331S (IgG2σ). In some embodiments, the antibody of antigen binding fragment comprises a human Fc region comprising high mannose glycosylation. In some embodiments, the Fc region comprises a human IgG1 with a substitution selected from 297A, 297Q, 297D, 279F, 279K, 279L, 228P, 235A, 235E, 235G, 235Q, 235R, 235S, 237A, 237E, 237K, 237N, 237R, 268K, 269N, 269Q, 270A, 270G, 270M, 270N, 424H, 424M, and 424V, per Kabat numbering. In some embodiments, the Fc region comprises a human IgG1 with a substitution selected from 271T, 272N, 292E, 292F, 292G, 292I, 293S, 301W, 304E, 311E, 311G, 311S, 255N, 256H, 256K, 256R, 256V, 316F, 328V, 330R, 339E, 339L, 343I, 343V, 373A, 373G, 373S, 376E, 376W, 376Y, 380D, 382D, 382P, 385P, 234A, 234V, 234F, 233P, 328A, 327Q and 327T, per Kabat numbering. In some embodiments, the Fc region comprises a human IgG1 with a substitution selected from 329A, 329G, 329Y, 331S, 236F, 236R, 238A, 238E, 238G, 238H, 238I, 238V, 238W, 238Y, 248A, 254D, 254E, 254G, 254H, 254I, 254N, 254P, 254Q, 254T, 254V, 264S, 265H, 265K, 265S, 265Y, 265A, 267G, 267H, 267I, 267K, 434I, 438G, 439E, 439H, 439Q, 440A, 440D, 440E, 440F, 440M, 440T, and 440V, per Kabat numbering. In some embodiments, the antibody or antigen binding fragment comprises a sequence at least about 90%, 91%, 92%, 93%, 94%, 95%, 96%, 97%, 98%, 99%, or 100% identical to any one of SEQ ID NOS: 320-362. In some embodiments, HCDR1 comprises SEQ ID NO: 1. In some embodiments, HCDR2 comprises SEQ ID NO: 2. In some embodiments, HCDR2 comprises SEQ ID NO: 3. In some embodiments, HCDR2 comprises SEQ ID NO: 4. In some embodiments, HCDR2 comprises SEQ ID NO: 5. In some embodiments, HCDR3 comprises SEQ ID NO: 6. In some embodiments, HCDR3 comprises SEQ ID NO: 7. In some embodiments, HCDR3 comprises SEQ ID NO: 8. In some embodiments, HCDR3 comprises SEQ ID NO: 9. In some embodiments, LCDR1 comprises SEQ ID NO: 10. In some embodiments, LCDR2 comprises SEQ ID NO: 11. In some embodiments, LCDR3 comprises SEQ ID NO: 12. In some embodiments, LCDR3 comprises SEQ ID NO: 13. In some embodiments, LCDR3 comprises SEQ ID NO: 14. In some embodiments, LCDR3 comprises SEQ ID NO: 15.

In another aspect, provided herein is an antibody or antigen binding fragment thereof that binds to TL1A, comprising a heavy chain variable region comprising: (a) an HCDR1 comprising an amino acid sequence set forth by SEQ ID NO: 1; (b) an HCDR2 comprising an amino acid sequence set forth by any one of SEQ ID NOS: 2-5; and (c) an HCDR3 comprising an amino acid sequence set forth by any one of SEQ ID NOS: 6-9; and the light chain variable region comprises: (d) an LCDR1 comprising an amino acid sequence set forth by SEQ ID NO: 10; (e) an LCDR2 comprising an amino acid sequence set forth by SEQ ID NO: 11; and (f) an LCDR3 comprising an amino acid sequence set forth by any one of SEQ ID NOS: 12-15. In some embodiments, the heavy chain variable region comprises human IGHV1-46*02 framework or a modified human IGHV1-46*02 framework. In some embodiments, the light chain variable framework region comprising a human IGKV3-20 framework or a modified human IGKV3-20 framework. In some embodiments, the heavy chain variable region comprises one of more of the following amino acids: 1E, 45K, 47R, 55I, 78A, 80I, 82T, 89A, 91L, per Kabat numbering. In some embodiments, the heavy chain variable region comprises 1E. In some embodiments, the heavy chain variable region comprises 45K. In some embodiments, the heavy chain variable region comprises 47R. In some embodiments, the heavy chain variable region comprises 55I. In some embodiments, the heavy chain variable region comprises 78A. In some embodiments, the heavy chain variable region comprises 80I. In some embodiments, the heavy chain variable region comprises 82T. In some embodiments, the heavy chain variable region comprises 89A. In some embodiments, the heavy chain variable region comprises 91L. In some embodiments, the light chain variable region comprises one or more of the following amino acids: 54P and 55W, per Kabat numbering. In some embodiments, the light chain variable region comprises 54P. In some embodiments, the light chain variable region comprises 55W. In some embodiments, the HCDR2 comprises SEQ ID NO: 2. In some embodiments, the HCDR2 comprises SEQ ID NO: 3. In some embodiments, the HCDR2 comprises SEQ ID NO: 4. In some embodiments, the HCDR2 comprises SEQ ID NO: 5. In some embodiments, the HCDR3 comprises SEQ ID NO: 6. In some embodiments, the HCDR3 comprises SEQ ID NO: 7. In some embodiments, the HCDR3 comprises SEQ ID NO: 8. In some embodiments, the HCDR3 comprises SEQ ID NO: 9. In some embodiments, the LCDR3 comprises SEQ ID NO: 12. In some embodiments, the LCDR3 comprises SEQ ID NO: 13. In some embodiments, the LCDR3 comprises SEQ ID NO: 14. In some embodiments, LCDR3 comprises SEQ ID NO: 15.

In some embodiments, an antibody or antigen binding fragment described herein comprises a human IgG1 Fc region comprising (a) 297A, 297Q, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some embodiments, an antibody of antigen binding fragment herein comprises a (i) human IgG4 Fc region or (ii) a human IgG4 Fc region comprising (a) S228P and L235E, or (b) S228P, F234A, and L235A, per Kabat numbering. In some embodiments, an antibody of antigen binding fragment herein comprises a human IgG2 Fc region; IgG2-IgG4 cross-subclass Fc region; IgG2-IgG3 cross-subclass Fc region; IgG2 comprising H268Q, V309L, A330S, P331S (IgG2m4); or IgG2 comprising V234A, G237A, P238S, H268A, V309L, A330S, P331S (IgG2σ). In some embodiments, an antibody of antigen binding fragment herein comprises a human Fc region comprising high mannose glycosylation. In some embodiments, any of the antibody or antigen binding fragments described herein comprise a human IgG4 Fc region.

In some embodiments, an antibody or antigen binding fragment described herein comprises a human IgG1 with a substitution selected from 297A, 297Q, 297D, 279F, 279K, 279L, 228P, 235A, 235E, 235G, 235Q, 235R, 235S, 237A, 237E, 237K, 237N, 237R, 268K, 269N, 269Q, 270A, 270G, 270M, 270N, 424H, 424M, and 424V, per Kabat numbering. In some embodiments, an antibody or antigen binding fragment described herein comprises a human IgG1 with a substitution selected from 271T, 272N, 292E, 292F, 292G, 292I, 293S, 301W, 304E, 311E, 311G, 311S, 255N, 256H, 256K, 256R, 256V, 316F, 328V, 330R, 339E, 339L, 343I, 343V, 373A, 373G, 373S, 376E, 376W, 376Y, 380D, 382D, 382P, 385P, 234A, 234V, 234F, 233P, 328A, 327Q and 327T, per Kabat numbering. In some embodiments, an antibody or antigen binding fragment described herein comprises a human IgG1 with a substitution selected from 329A, 329G, 329Y, 331S, 236F, 236R, 238A, 238E, 238G, 238H, 238I, 238V, 238W, 238Y, 248A, 254D, 254E, 254G, 254H, 254I, 254N, 254P, 254Q, 254T, 254V, 264S, 265H, 265K, 265S, 265Y, 265A, 267G, 267H, 267I, 267K, 434I, 438G, 439E, 439H, 439Q, 440A, 440D, 440E, 440F, 440M, 440T, and 440V, per Kabat numbering.

In some embodiments, an antibody or antigen binding fragment described herein comprises a Fc region comprising a sequence at least about 90%, 91%, 92%, 93%, 94%, 95%, 96%, 97%, 98%, 99%, or 100% identical to any one of SEQ ID NOS: 320-362.

In some embodiments, an antibody or antigen binding fragment described herein comprises at least about 80% monomeric fraction as determined by size exclusion chromatography. In some embodiments, an antibody or antigen binding fragment described herein comprises at least about 85%, 90%, 91%, 92%, 93%, 94%, 95%, 96%, 97%, 98%, or 99% monomeric fraction. In some embodiments, the size exclusion chromatography comprises injecting purified antibody or antigen binding fragment onto a size exclusion column, wherein the antibody or antigen binding fragment is purified by protein A. In some embodiments, the antibody or antigen binding fragment is purified as described in Example 2. In some embodiments, the antibody or antigen binding fragment is expressed under conditions described in Example 2. In some embodiments, the size exclusion chromatography column has an inner diameter of 4.6 mm. In some embodiments, the size exclusion chromatography column has a length of 150 mm. In some embodiments, the size exclusion chromatography column has a pore size of 200 Å. In some embodiments, the size exclusion chromatography column has a particle size of 1.7 micrometer. In some embodiments, the size exclusion chromatography column is ACQUITY UPLC BEH200 SEC column. In some embodiments, the antibody or antigen binding fragment is injected at a total volume of 15 μL. In some embodiments, the antibody or antigen binding fragment is injected at a concentration of about 0.1 μg/μL to about 1.0 μg/μL. In some embodiments, the size exclusion chromatography is performed on a Shimadzu UPLC instrument. In some embodiments, the size exclusion chromatography is performed at a flow rate of 0.2 mL/min. In some embodiments, the size exclusion chromatography is performed at a column oven temperature of 30° C. In some embodiments, the percentage of monomer is calculated using Shimadzu software. In some embodiments, the size exclusion chromatography is performed as described in Example 2.

In some embodiments, an antibody or antigen binding fragment described herein expresses at least about 20 ug/ml total antibody. In some embodiments, an antibody or antigen binding fragment described herein expresses between about 20 ug/ml and 70 ug/mL total antibody. In some embodiments, the antibody or antigen binding fragment is expressed in FreeStyle 293-F cells. In some embodiments, the antibody or antigen binding fragment is expressed as described in Example 2. In some embodiments, the antibody or antigen binding fragment expression level is quantified using Enzyme-Linked Immunosorbent assay (ELISA). In some embodiments, the ELISA comprises coating a surface of a substrate with a capture antibody that binds to a human or humanized antibody, applying the antibody or antigen binding fragment to the substrate, and applying to the substrate a second antibody that binds to a human or humanized antibody. In some embodiments, the capture antibody comprises an anti-kappa antibody. In some embodiments, the second antibody comprises an anti-Fc antibody. In some embodiments, the ELISA is performed as described in Example 2.

Further provided herein are methods of treating inflammatory bowel disease (IBD) in a subject in need thereof, the method comprising administering to the subject an antibody or antigen binding fragment described herein. In some embodiments, the IBD comprises Crohn's Disease. In some embodiments, the IBD comprises ulcerative colitis.

BRIEF DESCRIPTION OF THE FIGURES

Exemplary embodiments are illustrated in referenced figures. It is intended that the embodiments and figures disclosed herein are to be considered illustrative rather than restrictive.

FIG. 3A shows a PLS graph, FIG. 3B shows a model of the predicted viscosity versus anti-TL1A antibody concentration in mg/mL, and FIG. 3C shows a model of the estimated viscosity versus actual viscosity. Viscosity units are in mPa-s.

DESCRIPTION OF THE INVENTION

Figure 1A:
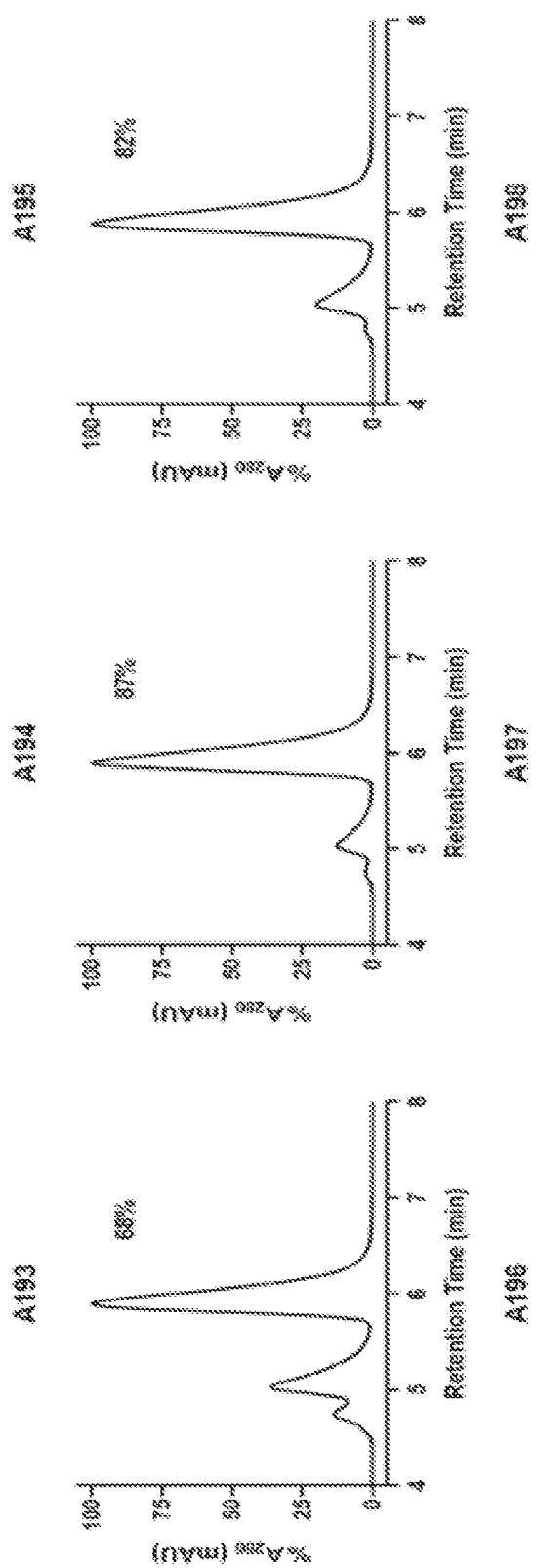
FIGS. 1A-1C show chromatograms for analytical size exclusion chromatography of anti-TL1A antibodies.

Tumor necrosis factor-like protein 1A (TL1A) is a proinflammatory molecule which stimulates proliferation and effector functions of CD8 (+) cytotoxic T cells as well as Th1, Th2, and Th17 cells in the presence of TCR stimulation. TL1A has been associated with the development and severity of inflammatory bowel disease (IBD), such as Crohn's Disease (CD) and ulcerative colitis. TL1A is believed to be involved in the pathogenesis of IBD by bridging the innate and adaptive immune response, modulating adaptive immunity by augmenting Th1, Th2, and Th17 effector cell function, and T-cell accumulation and immunopathology of inflamed tissue. TL1A is a target associated with both intestinal inflammation and intestinal fibrosis, which was clinically validated in a Phase 2a clinical trial in UC. In addition, preclinical and human genetic association data suggests that TL1A is a potential therapeutic target in CD. The present disclosure describes optimized antibodies against TL1A and offers novel therapeutics for the treatment of IBD. The anti-TL1A antibodies described herein may substantially improve outcomes for moderate-to-severe IBD patients who are predisposed to increased TL1A expression. As an example, the patients are selected for treatment with an anti-TL1A antibody herein based on increased expression of TL1A in the patient as compared to a reference level (e.g., from a subject who does not have IBD). The patients may be selected for increased TL1A expression as determined by a genotyping assay to determine the presence of a genotype associated with increased TL1A expression. TL1A and nucleic acids encoding TL1A (Tumor Necrosis Factor Ligand Superfamily Member 15 (TNFSF15)) are provided as set forth by Entrez Gene: 9966; UniProtKB: 095150. Accordingly, the present disclosure further provides methods of treating subjects having a increased TL1A expression with an antibody described herein.

Antibodies

In one aspect, provided herein are antibodies and antigen-binding fragments. In some embodiments, an antibody comprises an antigen-binding fragment that refers to a portion of an antibody having antigenic determining variable regions of an antibody. Examples of antigen-binding fragments include, but are not limited to Fab, Fab', F(ab')$_2$, and Fv fragments, linear antibodies, single chain antibodies, and multispecific antibodies formed from antibody fragments. In some embodiments, an antibody refers to an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. In some embodiments, an antibody includes intact polyclonal antibodies, intact monoclonal antibodies, antibody fragments (such as Fab, Fab', F(ab')$_2$, and Fv fragments), single chain Fv (scFv) mutants, a CDR-grafted antibody, multispecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules such as toxins, radioisotopes, etc.

In some embodiments, a humanized antibody refers to forms of non-human (e.g., murine) antibodies having specific immunoglobulin chains, chimeric immunoglobulins, or fragments thereof that contain minimal non-human (e.g., murine) sequences. In a non-limiting example, a humanized antibody comprises less than about 40% non-human sequence in the variable region. In some cases, a humanized antibody comprises less than about 20% non-human sequence in a full-length antibody sequence. In a further non-limiting example, a humanized antibody comprises less than about 20% non-human sequence in the framework region of each of the heavy chain and light chain variable regions. For instance, the humanized antibody comprises less than about 20%, 19%, 18%, 17%, 16%, 15%, 14%, 13%, 12%, 11%, 10%, 9%, 8%, 7%, 6%, 5%, 4%, 3%, 2%, or 1% non-human sequence in the framework region of each of the heavy chain and light chain variable regions. As another example, the humanized antibody comprises about or less than about 15, 14, 13, 12, 11, 10, 9, 8, 7, 6, 5, 4, 3, 2, or 1 non-human sequences in the framework region of each of the heavy chain and light chain variable regions. In some cases, humanized antibodies are human immunoglobulins in which residues from the complementarity determining region (CDR) are replaced by residues from the CDR of a non-human species (e.g., mouse, rat, rabbit, hamster) that have the desired specificity, affinity, and capability. These humanized antibodies may contain one or more non-human species mutations, e.g., the heavy chain comprises about 1, 2, 3, 4, 5, 6, 7, 8, 9, 10, 11, 12, 13, 14, or 15 non-human species mutations in the framework region, and the light chain comprises about 1, 2, 3, 4, 5, 6, 7, 8, 9, 10, 11, 12, 13, 14, or 15 non-human species mutations in the framework region. The humanized heavy chain variable domain may comprise IGHV1-46*02 framework with no or fewer than about 10, 9, 8, 7, 6, 5, 4, 3, 2, or 1 amino acid mutations. The humanized light chain variable domain may comprise IGKV3-20 framework with no or fewer than about 10, 9, 8, 7, 6, 5, 4, 3, 2, or 1 amino acid mutations.

In some embodiments, chimeric antibodies refer to antibodies wherein the sequence of the immunoglobulin molecule is derived from two or more species. As a non-limiting example, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

The terms "complementarity determining region," and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) *JMB* 273,927-948 ("Chothia" numbering scheme); MacCallum et al., *J. Mol. Biol.* 262:732-745 (1996), "Antibody-antigen interactions: Contact analysis and binding site topography," *J. Mol. Biol.* 262, 732-745." ("Contact" numbering scheme); Lefranc M P et al., "IMGT unique numbering for immunoglobulin and T cell receptor variable domains and Ig superfamily V-like domains," *Dev Comp Immunol*, 2003 January; 27(1):55-77 ("IMGT" numbering scheme); Honegger A and Plückthun A, "Yet another numbering scheme for immunoglobulin variable domains: an automatic modeling and analysis tool," *J Mol Biol*, 2001 Jun. 8; 309(3):657-70, ("Aho" numbering scheme); and Whitelegg N R and Rees A R, "WAM: an improved algorithm for modelling antibodies on the WEB," *Protein Eng.* 2000 December; 13(12):819-24 ("AbM" numbering scheme. In certain embodiments, the CDRs of the antibodies described herein can be defined by a method selected from Kabat, Chothia, IMGT, Aho, AbM, or combinations thereof.

In some embodiments, an antibody that specifically binds to a protein indicates that the antibody reacts or associates more frequently, more rapidly, with greater duration, with greater affinity, or with some combination of the above to the protein than with alternative substances, including unrelated proteins.

In some embodiments, the terms "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as fusion with another polypeptide and/or conjugation, e.g., with a labeling component. Also included within the definition are, for example, polypeptides containing one or more analogs of an amino acid (for example, unnatural amino acids, etc.), as well as other modifications known in the art.

In some embodiments, a protein such as an antibody described herein comprises a hydrophobic amino acid. Non-limiting exemplary hydrophobic amino acids include glycine (Gly), proline (Pro), phenylalanine (Phe), alanine (Ala), isoleucine (Ile), leucine (Leu), and valine (Val). In some embodiments, a protein such as an antibody described herein comprises a hydrophilic amino acid. Non-limiting exemplary hydrophilic amino acids include serine (Ser), threonine (Thr), aspartic acid (Asp), glutamic acid (Glu), cysteine (Cys), asparagine (Asn), glutamine (Gln), arginine (Arg), and histidine (His). In some embodiments, a protein such as an antibody described herein comprises an amphipathic amino acid. Non-limiting exemplary amphipathic amino acids include lysine (Lys), tryptophan (Trp), tyrosine (Tyr), and methionine (Met). In some embodiments, a protein such as an antibody described herein comprises an aliphatic amino acid. Non-limiting exemplary aliphatic amino acids include alanine (Ala), isoleucine (Ile), leucine (Leu) and valine (Val). In some embodiments, a protein such as an antibody described herein comprises an aromatic amino acid. Non-limiting exemplary aromatic amino acids include phenylalanine (Phe), tryptophan (Trp), and tyrosine (Tyr). In some embodiments, a protein such as an antibody described herein comprises an acidic amino acid. Non-limiting exemplary acidic amino acids include aspartic acid (Asp) and glutamic acid (Glu). In some embodiments, a protein such as an antibody described herein comprises a basic amino acid. Non-limiting exemplary basic amino acids include arginine (Arg), histidine (His), and lysine (Lys). In some embodiments, a protein such as an antibody described herein comprises a hydroxylic amino acid. Non-limiting exemplary hydroxylic amino acids include serine (Ser) and threonine (Thr). In some embodiments, a protein such as an antibody described herein comprises a sulfur-containing amino acid. Non-limiting exemplary sulfur-containing amino acids include cysteine (Cys) and methionine (Met). In some embodiments, a protein such as an antibody described herein comprises an amidic amino acid. Non-limiting exemplary amidic amino acids include asparagine (Asn) and glutamine (Gln).

In some embodiments, "polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as, but not limited to methylated nucleotides and their analogs or non-nucleotide components. Modifications to the nucleotide structure may be imparted before or after assembly of the polymer. A polynucleotide may be further modified after polymerization, such as by conjugation with a labeling component.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In some embodiments, the term "about" means within 10% of the stated amount. For instance, an antibody variable region comprising about 80% identity to a reference variable region may comprise 72% to 88% identity to the reference variable region.

In certain aspects, antibodies are described herein that specifically bind to TL1A (Entrez Gene: 9966; UniProtKB: O95150). In some embodiments, the antibodies specifically bind to soluble TL1A. In some embodiments, the antibodies specifically bind to membrane bound TL1A. In some embodiments, an anti-TL1A antibody is provided having a heavy chain comprising four heavy chain framework regions (HCFR) and three heavy chain complementarity-determining regions (HCDR): HCFR1, HCDR1, HCFR2, HCDR2, HCFR3, HCDR3, and HCFR4; and a light chain comprising four light chain framework regions (LCFR) and three light chain complementarity-determining regions (LCDR): LCFR1, LCDR1, LCFR2, LCDR2, LCFR3, LCDR3, and LCFR4. An anti-TL1A antibody may comprise any region provided herein, for example, as provided in Tables 6-11, the examples, and the sequences.

Exemplary Anti-TL1A CDRs

In certain embodiments, an anti-TL1A antibody comprises a HCDR1 as set forth by SEQ ID NO: 1. In certain embodiments, an anti-TL1A antibody comprises a HCDR2 as set forth by any one of SEQ ID NOS: 2-5. In certain embodiments, an anti-TL1A antibody comprises a HCDR3 as set forth by any one of SEQ ID NOS: 6-9. In certain embodiments, an anti-TL1A antibody comprises a LCDR1 as set forth by SEQ ID NO: 10. In certain embodiments, an anti-TL1A antibody comprises a LCDR2 as set forth by SEQ ID NO: 11. In certain embodiments, an anti-TL1A antibody comprises a LCDR3 as set forth by any one of SEQ ID NOS: 12-15.

In certain embodiments, an anti-TL1A antibody comprises a HCDR1, HCDR2, HCDR3, LCDR1, LCDR2, LCDR3 selected from Table 6. In certain embodiments, an anti-TL1A antibody comprises the CDRs set forth in antibody A as shown in Table 10. In certain embodiments, an anti-TL1A antibody comprises the CDRs set forth in antibody B as shown in Table 10. In certain embodiments, an anti-TL1A antibody comprises the CDRs set forth in antibody C as shown in Table 10. In certain embodiments, an anti-TL1A antibody comprises the CDRs set forth in antibody D as shown in Table 10. In certain embodiments, an anti-TL1A antibody comprises the CDRs set forth in antibody E as shown in Table 10. In certain embodiments, an anti-TL1A antibody comprises the CDRs set forth in antibody F as shown in Table 10. In certain embodiments, an anti-TL1A antibody comprises the CDRs set forth in antibody G as shown in Table 10. In certain embodiments, an anti-TL1A antibody comprises the CDRs set forth in antibody H as shown in Table 10. In certain embodiments, an anti-TL1A antibody comprises the CDRs set forth in antibody A2 as shown in Table 10. In certain embodiments, an anti-TL1A antibody comprises the CDRs set forth in antibody B2 as shown in Table 10. In certain embodiments, an anti-TL1A antibody comprises the CDRs set forth in antibody C2 as shown in Table 10. In certain embodiments, an anti-TL1A antibody comprises the CDRs set forth in antibody D2 as shown in Table 10. In certain embodiments, an anti-TL1A antibody comprises the CDRs set forth in antibody E2 as shown in Table 10. In certain embodiments, an anti-TL1A antibody comprises the CDRs set forth in antibody F2 as shown in Table 10. In certain embodiments, an anti-TL1A antibody comprises the CDRs set forth in antibody G2 as shown in Table 10. In certain embodiments, an anti-TL1A antibody comprises the CDRs set forth in antibody H2 as shown in Table 10. In certain embodiments, an anti-TL1A antibody comprises the CDRs set forth in antibody I as shown in Table 10. In certain embodiments, an anti-TL1A antibody comprises the CDRs set forth in antibody 12 as shown in Table 10.

In certain embodiments, an anti-TL1A antibody comprises the CDRs set forth in any one of the antibodies in Table 1. In certain embodiments, an anti-TL1A antibody comprises the CDRs set forth in antibody A217, wherein the CDRs are defined by the Kabat, Chothia, or IMGT method. In certain embodiments, an anti-TL1A antibody comprises the CDRs set forth in antibody A220, wherein the CDRs are defined by the Kabat, Chothia, or IMGT method. In certain embodiments, an anti-TL1A antibody comprises the CDRs set forth in antibody A223, wherein the CDRs are defined by the Kabat, Chothia, or IMGT method. In certain embodiments, an anti-TL1A antibody comprises the CDRs set forth in antibody A219, wherein the CDRs are defined by the Kabat, Chothia, or IMGT method. In certain embodiments, an anti-TL1A antibody comprises the CDRs set forth in antibody A221, wherein the CDRs are defined by the Kabat, Chothia, or IMGT method. In certain embodiments, an anti-TL1A antibody comprises the CDRs set forth in antibody A200, wherein the CDRs are defined by the Kabat, Chothia, or IMGT method. In certain embodiments, an anti-TL1A antibody comprises the CDRs set forth in antibody A213, wherein the CDRs are defined by the Kabat, Chothia, or IMGT method. In certain embodiments, an anti-TL1A antibody comprises the CDRs set forth in antibody A212, wherein the CDRs are defined by the Kabat, Chothia, or IMGT method. In certain embodiments, an anti-TL1A antibody comprises the CDRs set forth in antibody A107, wherein the CDRs are defined by the Kabat, Chothia, or IMGT method. In certain embodiments, an anti-TL1A antibody comprises the CDRs set forth in antibody A205, wherein the CDRs are defined by the Kabat, Chothia, or IMGT method. In certain embodiments, an anti-TL1A antibody comprises the CDRs set forth in antibody A211, wherein the CDRs are defined by the Kabat, Chothia, or IMGT method. In certain embodiments, an anti-TL1A antibody comprises the CDRs set forth in antibody A199, wherein the CDRs are defined by the Kabat, Chothia, or IMGT method. In certain embodiments, an anti-TL1A antibody comprises the CDRs set forth in antibody A15, wherein the CDRs are defined by the Kabat, Chothia, or IMGT method. In certain embodiments, an anti-TL1A antibody comprises the CDRs set forth in antibody A30, wherein the CDRs are defined by the Kabat, Chothia, or IMGT method. In certain embodiments, an anti-TL1A antibody comprises the CDRs set forth in antibody A100, wherein the CDRs are defined by the Kabat, Chothia, or IMGT method. In certain embodiments, an anti-TL1A antibody comprises the CDRs set forth in antibody A181, wherein the CDRs are defined by the Kabat, Chothia, or IMGT method. In certain embodiments, an anti-TL1A antibody comprises the CDRs set forth in antibody A129, wherein the CDRs are defined by the Kabat, Chothia, or IMGT method. In certain embodiments, an anti-TL1A antibody comprises the CDRs set forth in antibody A214, wherein the CDRs are defined by the Kabat, Chothia, or IMGT method. In certain embodiments, an anti-TL1A antibody comprises the CDRs set forth in antibody A216, wherein the CDRs are defined by the Kabat, Chothia, or IMGT method. In certain embodiments, an anti-TL1A antibody comprises the CDRs set forth in antibody A122, wherein the CDRs are defined by the Kabat, Chothia, or IMGT method. In certain embodiments, an anti-TL1A antibody comprises the CDRs set forth in antibody A222, wherein the CDRs are defined by the Kabat, Chothia, or IMGT method. In certain embodiments, an anti-TL1A antibody comprises the CDRs set forth in antibody A188, wherein the CDRs are defined by the Kabat, Chothia, or IMGT method. In certain embodiments, an anti-TL1A antibody comprises the CDRs set forth in antibody A203, wherein the CDRs are defined by the Kabat, Chothia, or IMGT method. In certain embodiments, an anti-TL1A antibody comprises the CDRs set forth in antibody A147, wherein the CDRs are defined by the Kabat, Chothia, or IMGT method. In certain embodiments, an anti-TL1A antibody comprises the CDRs set forth in antibody A127, wherein the CDRs are defined by the Kabat, Chothia, or IMGT method. In certain embodiments, an anti-TL1A antibody comprises the CDRs set forth in antibody A126, wherein the CDRs are defined by the Kabat, Chothia, or IMGT method. In certain embodiments, an anti-TL1A antibody comprises the CDRs set forth in antibody A160, wherein the CDRs are defined by the Kabat, Chothia, or IMGT method. In certain embodiments, an anti-TL1A antibody comprises the CDRs set forth in antibody A157, wherein the CDRs are defined by the Kabat, Chothia, or IMGT method. In certain embodiments, an anti-TL1A antibody comprises the CDRs set forth in antibody A159, wherein the CDRs are defined by the Kabat, Chothia, or IMGT method. In certain embodiments, an anti-TL1A antibody comprises the CDRs set forth in antibody A218, wherein the CDRs are defined by the Kabat, Chothia, or IMGT method. In certain embodiments, an anti-TL1A antibody comprises the CDRs set forth in antibody A158, wherein the CDRs are defined by the Kabat, Chothia, or IMGT method. In certain embodiments, an anti-TL1A antibody comprises the CDRs set forth in antibody A125, wherein the CDRs are defined by the Kabat, Chothia, or IMGT method. In certain embodiments, an anti-TL1A antibody comprises the CDRs set forth in antibody A103, wherein the CDRs are defined by the Kabat, Chothia, or IMGT method. In certain embodiments, an anti-TL1A antibody comprises the CDRs set forth in antibody A64, wherein the CDRs are defined by the Kabat, Chothia, or IMGT method. In certain embodiments, an anti-TL1A antibody comprises the CDRs set forth in antibody A67, wherein the CDRs are defined by the Kabat, Chothia, or IMGT method. In certain embodiments, an anti-TL1A antibody comprises the CDRs set forth in antibody A138, wherein the CDRs are defined by the Kabat, Chothia, or IMGT method. In certain embodiments, an anti-TL1A antibody comprises the CDRs set forth in antibody A68, wherein the CDRs are defined by the Kabat, Chothia, or IMGT method. In certain embodiments, an anti-TL1A antibody comprises the CDRs set forth in antibody A94, wherein the CDRs are defined by the Kabat, Chothia, or IMGT method. In certain embodiments, an anti-TL1A antibody comprises the CDRs set forth in antibody A110, wherein the CDRs are defined by the Kabat, Chothia, or IMGT method. In certain embodiments, an anti-TL1A antibody comprises the CDRs set forth in antibody A197, wherein the CDRs are defined by the Kabat, Chothia, or IMGT method. In certain embodiments, an anti-TL1A antibody comprises the CDRs set forth in antibody A112, wherein the CDRs are defined by the Kabat, Chothia, or IMGT method. In certain embodiments, an anti-TL1A antibody comprises the CDRs set forth in antibody A169, wherein the CDRs are defined by the Kabat, Chothia, or IMGT method. In certain embodiments, an anti-TL1A antibody comprises the CDRs set forth in antibody A173, wherein the CDRs are defined by the Kabat, Chothia, or IMGT method. In certain embodiments, an anti-TL1A antibody comprises the CDRs set forth in antibody A179, wherein the CDRs are defined by the Kabat, Chothia, or IMGT method. In certain embodiments, an anti-TL1A antibody comprises the CDRs set forth in antibody A148, wherein the CDRs are defined by the Kabat, Chothia, or IMGT method. In certain embodiments, an anti-TL1A antibody comprises the CDRs set forth in antibody A115, wherein the CDRs are defined by the Kabat, Chothia, or IMGT method. In certain embodiments, an anti-TL1A antibody comprises the CDRs set forth in antibody A149, wherein the CDRs are defined by the Kabat, Chothia, or IMGT method. In certain embodiments, an anti-TL1A antibody comprises the CDRs set forth in antibody A134, wherein the CDRs are defined by the Kabat, Chothia, or IMGT method. In certain embodiments, an anti-TL1A antibody comprises the CDRs set forth in antibody A113, wherein the CDRs are defined by the Kabat, Chothia, or IMGT method. In certain embodiments, an anti-TL1A antibody comprises the CDRs set forth in antibody A151, wherein the CDRs are defined by the Kabat, Chothia, or IMGT method. In certain embodiments, an anti-TL1A antibody comprises the CDRs set forth in antibody A96, wherein the CDRs are defined by the Kabat, Chothia, or IMGT method. In certain embodiments, an anti-TL1A antibody comprises the CDRs set forth in antibody A132, wherein the CDRs are defined by the Kabat, Chothia, or IMGT method. In certain embodiments, an anti-TL1A antibody comprises the CDRs set forth in antibody A196, wherein the CDRs are defined by the Kabat, Chothia, or IMGT method. In certain embodiments, an anti-TL1A antibody comprises the CDRs set forth in antibody A172, wherein the CDRs are defined by the Kabat, Chothia, or IMGT method. In certain embodiments, an anti-TL1A antibody comprises the CDRs set forth in antibody A75, wherein the CDRs are defined by the Kabat, Chothia, or IMGT method. In certain embodiments, an anti-TL1A antibody comprises the CDRs set forth in antibody A174, wherein the CDRs are defined by the Kabat, Chothia, or IMGT method. In certain embodiments, an anti-TL1A antibody comprises the CDRs set forth in antibody A109, wherein the CDRs are defined by the Kabat, Chothia, or IMGT method. In certain embodiments, an anti-TL1A antibody comprises the CDRs set forth in antibody A198, wherein the CDRs are defined by the Kabat, Chothia, or IMGT method. In certain embodiments, an anti-TL1A antibody comprises the CDRs set forth in antibody A170, wherein the CDRs are defined by the Kabat, Chothia, or IMGT method.

Exemplary Anti-TL1A Framework Regions

Tables 7-9A and Table 11 provides exemplary framework and variable region sequences.

In some embodiments, an anti-TL1A antibody comprises a heavy chain framework comprising SEQ ID NO: 301 ($X_1$VQLVQSGAEVKKPGASVKVSCKAS[HCDR1]WV$X_2$Q$X_3$PGQGLEW$X_4$G[HCDR2]R$X_5$T$X_6$T$X_7$DTSTST$X_8$Y$X_9$ELSSLRSEDTAVYYCAR[HCDR3]WGQGTTVTVSS). In some cases, $X_1$ is Q. In some cases, $X_1$=E. In some cases, $X_2$=R. In some cases, $X_2$=K. In some cases, $X_3$=A. In some cases, $X_3$=R. In some cases, $X_4$=M. In some cases, $X_4$=I. In some cases, $X_5$=V. In some cases, $X_5$=A. In some cases, $X_6$=M. In some cases, $X_6$=I. In some cases, $X_7$=R. In some cases, $X_7$=T. In some cases, $X_8$=V. In some cases, $X_8$=A. In some cases, $X_9$=M. In some cases, $X_9$=L. In some embodiments, $X_1$ is at position 1 of IGHV1-46*02 as determined by Aho numbering. In some embodiments, $X_2$ is at position 45 of IGHV1-46*02 as determined by Aho numbering. In some embodiments, $X_3$ is at position 47 of IGHV1-46*02 as determined by Aho numbering. In some embodiments, $X_4$ is at position 55 of IGHV1-46*02 as determined by Aho numbering. In some embodiments, $X_5$ is at position 78 of IGHV1-46*02 as determined by Aho numbering. In some embodiments, $X_6$ is at position 80 of IGHV1-46*02 as determined by Aho numbering. In some embodiments, $X_7$ is at position 82 of IGHV1-46*02 as determined by Aho numbering. In some embodiments, $X_8$ is at position 89 of IGHV1-46*02 as determined by Aho numbering. In some embodiments, $X_9$ is at position 91 of IGHV1-46*02 as determined by Aho numbering.

In one aspect, provided herein is a first embodiment of an anti-TL1A antibody comprising a heavy chain framework comprising IGHV1-46*02, or a variant thereof, wherein the variant comprises between about 1 and about 9 amino acid substitutions, or between about 1 and about 20 amino acid substitutions, or about 1, 2, 3, 4, 5, 6, 7, 8, 9, 10, 11, 12, 13, 14, 15, 16, 17, 18, 19, or 20 amino acid substitutions from IGHV1-46*02 framework. Additional embodiments include: (2) The anti-TL1A of embodiment (1), wherein the heavy chain framework comprises SEQ ID NO: 301. (3) The anti-TL1A of embodiment 2, wherein $X_1$=Q. (4) The anti-TL1A of embodiment 2, wherein $X_1$=E. (5) The anti-TL1A of any one of embodiments 2-4, wherein $X_2$=R. (6) The anti-TL1A of any one of embodiments 2-4, wherein $X_2$=K. (7) The anti-TL1A of any one of embodiments 2-6, wherein $X_3$=A. (8) The anti-TL1A of any one of embodiments 2-6, wherein $X_3$=R. (9) The anti-TL1A of any one of embodiments 2-8, wherein $X_4$=M. (10) The anti-TL1A of any one of embodiments 2-8, wherein $X_4$=I. (11) The anti-TL1A of any one of embodiments 2-10, wherein $X_5$=V. (12) The anti-TL1A of any one of embodiments 2-10, wherein $X_5$=A. (13) The anti-TL1A of any one of embodiments 2-12, wherein X6=M. (14) The anti-TL1A of any one of embodiments 2-12, wherein X6=I. (15) The anti-TL1A of any one of embodiments 2-14, wherein X7=R. (16) The anti-TL1A of any one of embodiments 2-14, wherein X7=T. (17) The anti-TL1A of any one of embodiments 2-16, wherein X8=V. (18) The anti-TL1A of any one of embodiments 2-16, wherein X8=A. (19) The anti-TL1A of any one of embodiments 2-18, wherein X9=M. (20) The anti-TL1A of any one of embodiments 2-4, wherein X9=L. (21) The anti-TL1A of any one of embodiments 1-20, comprising antibody A. (22) The anti-TL1A of any one of embodiments 1-20, comprising antibody B. (23) The anti-TL1A of any one of embodiments 1-20, comprising antibody C. (24) The anti-TL1A of any one of embodiments 1-20, comprising antibody D. (25) The anti-TL1A of any one of embodiments 1-20, comprising antibody E. (26) The anti-TL1A of any one of embodiments 1-20, comprising antibody F. (27) The anti-TL1A of any one of embodiments 1-20, comprising antibody G or I. (28) The anti-TL1A of any one of embodiments 1-20, comprising antibody H. (29) The anti-TL1A of any one of embodiments 1-28, comprising a human IgG1 Fc region comprising: (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. As used herein, any combination of a group, such as (a) to (uu), includes at least about two or more items from the group, e.g., any combination of a group of (a) to (uu) includes 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, and up to 47 or all of the members of the group. (30) The anti-TL1A of any one of embodiments 1-28, comprising a (i) human IgG4 Fc region or (ii) a human IgG4 Fc region comprising (a) S228P, (b) S228P and L235E, or (c) S228P, F234A, and L235A, per Kabat numbering. (31) The anti-TL1A of any one of embodiments 1-28, comprising a human IgG2 Fc region; IgG2-IgG4 cross-subclass Fc region; IgG2-IgG3 cross-subclass Fc region; IgG2 comprising H268Q, V309L, A330S, P331S (IgG2m4); or IgG2 comprising V234A, G237A, P238S, H268A, V309L, A330S, P331S (IgG2σ). (32) The anti-TL1A of any one of embodiments 1-31, comprising a heavy chain Fc region comprising any one of SEQ ID NOS: 320-362. (33) The anti-TL1A of any one of embodiments 1-32, comprising a light chain constant region comprising SEQ ID NO: 319. (34) The anti-TL1A of any one of embodiments 1-33, comprising a light chain comprising a light chain framework comprising IGKV3-20*01, or a variant thereof, wherein the variant comprises between about 1 and about 2 substitutions, or between about 1 and about 20 amino acid substitutions, or about 1, 2, 3, 4, 5, 6, 7, 8, 9, 10, 11, 12, 13, 14, 15, 16, 17, 18, 19, or 20 amino acid substitutions in the framework. (35) The anti-TL1A antibody of embodiment 34, wherein X10 is L. (36) The anti-TL1A antibody of embodiment 34, wherein X10 is P. (37) The anti-TL1A antibody of any one of embodiments 34-36, wherein X11 is L. (38) The anti-TL1A antibody of any one of embodiments 34-36, wherein X11 is W.

In some embodiments, an anti-TL1A antibody comprises a heavy chain framework comprising SEQ ID NO: 302 (X1VQLVQSGAEVKKPGASVKVSCKAS[HCDR1]WVX2QX3PGQGLEWX4G[HCDR2]RX5TX6TX7DTSTSTX8YX9ELSSLRSEDTAVYYC[HCDR3]WGQGTTVTVSS). In some cases, X1 is Q. In some cases, X1=E. In some cases, X2=R. In some cases, X2=K. In some cases, X3=A. In some cases, X3=R. In some cases, X4=M. In some cases, X4=I. In some cases, X5=V. In some cases, X5=A. In some cases, X6=M. In some cases, X6=I. In some cases, X7=R. In some cases, X7=T. In some cases, X8=V. In some cases, X8=A. In some cases, X9=M. In some cases, X9=L. In some embodiments, X1 is at position 1 of IGHV1-46*02 as determined by Aho numbering. In some embodiments, X2 is at position 45 of IGHV1-46*02 as determined by Aho numbering. In some embodiments, X3 is at position 47 of IGHV1-46*02 as determined by Aho numbering. In some embodiments, X4 is at position 55 of IGHV1-46*02 as determined by Aho numbering. In some embodiments, X5 is at position 78 of IGHV1-46*02 as determined by Aho numbering. In some embodiments, X6 is at position 80 of IGHV1-46*02 as determined by Aho numbering. In some embodiments, X7 is at position 82 of IGHV1-46*02 as determined by Aho numbering. In some embodiments, X8 is at position 89 of IGHV1-46*02 as determined by Aho numbering. In some embodiments, X9 is at position 91 of IGHV1-46*02 as determined by Aho numbering.

In one aspect, provided herein is another first embodiment of an anti-TL1A antibody comprising a heavy chain framework comprising IGHV1-46*02, or a variant thereof, wherein the variant comprises between about 1 and about 9 amino acid substitutions, or between about 1 and about 20 amino acid substitutions, or about 1, 2, 3, 4, 5, 6, 7, 8, 9, 10, 11, 12, 13, 14, 15, 16, 17, 18, 19, or 20 amino acid substitutions from IGHV1-46*02 framework. Additional embodiments include: (2) The anti-TL1A of embodiment (1), wherein the heavy chain framework comprises SEQ ID NO: 302. (3) The anti-TL1A of embodiment 2, wherein X1=Q. (4) The anti-TL1A of embodiment 2, wherein X1=E. (5) The anti-TL1A of any one of embodiments 2-4, wherein X2=R. (6) The anti-TL1A of any one of embodiments 2-4, wherein X2=K. (7) The anti-TL1A of any one of embodiments 2-6, wherein X3=A. (8) The anti-TL1A of any one of embodiments 2-6, wherein X3=R. (9) The anti-TL1A of any one of embodiments 2-8, wherein X4=M. (10) The anti-TL1A of any one of embodiments 2-8, wherein X4=I. (11) The anti-TL1A of any one of embodiments 2-10, wherein X5=V. (12) The anti-TL1A of any one of embodiments 2-10, wherein X5=A. (13) The anti-TL1A of any one of embodiments 2-12, wherein X6=M. (14) The anti-TL1A of any one of embodiments 2-12, wherein X6=I. (15) The anti-TL1A of any one of embodiments 2-14, wherein X7=R. (16) The anti-TL1A of any one of embodiments 2-14, wherein X7=T. (17) The anti-TL1A of any one of embodiments 2-16, wherein X8=V. (18) The anti-TL1A of any one of embodiments 2-16, wherein X8=A. (19) The anti-TL1A of any one of embodiments 2-18, wherein X9=M. (20) The anti-TL1A of any one of embodiments 2-4, wherein X9=L. (21) The anti-TL1A of any one of embodiments 1-20, comprising antibody A. (22) The anti-TL1A of any one of embodiments 1-20, comprising antibody B. (23) The anti-TL1A of any one of embodiments 1-20, comprising antibody C. (24) The anti-TL1A of any one of embodiments 1-20, comprising antibody D. (25) The anti-TL1A of any one of embodiments 1-20, comprising antibody E. (26) The anti-TL1A of any one of embodiments 1-20, comprising antibody F. (27) The anti-TL1A of any one of embodiments 1-20, comprising antibody G or I. (28) The anti-TL1A of any one of embodiments 1-20, comprising antibody H. (29) The anti-TL1A of any one of embodiments 1-28, comprising a human IgG1 Fc region comprising: (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 3431 or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. (30) The anti-TL1A of any one of embodiments 1-28, comprising a (i) human IgG4 Fc region or (ii) a human IgG4 Fc region comprising (a) S228P and L235E, or (b) S228P, F234A, and L235A, per Kabat numbering. (31) The anti-TL1A of any one of embodiments 1-28, comprising a human IgG2 Fc region; IgG2-IgG4 cross-subclass Fc region; IgG2-IgG3 cross-subclass Fc region; IgG2 comprising H268Q, V309L, A330S, P331S (IgG2m4); or IgG2 comprising V234A, G237A, P238S, H268A, V309L, A330S, P331S (IgG2σ). (32) The anti-TL1A of any one of embodiments 1-31, comprising a heavy chain Fc region comprising any one of SEQ ID NOS: 320-362. (33) The anti-TL1A of any one of embodiments 1-32, comprising a light chain constant region comprising SEQ ID NO: 319. (34) The anti-TL1A of any one of embodiments 1-33, comprising a light chain comprising a light chain framework comprising IGKV3-20*01, or a variant thereof, wherein the variant comprises between about 1 and about 2 substitutions, or between about 1 and about 20 amino acid substitutions, or about 1, 2, 3, 4, 5, 6, 7, 8, 9, 10, 11, 12, 13, 14, 15, 16, 17, 18, 19, or 20 amino acid substitutions in the framework. (35) The anti-TL1A antibody of embodiment 34, wherein X10 is L. (36) The anti-TL1A antibody of embodiment 34, wherein X10 is P. (37) The anti-TL1A antibody of any one of embodiments 34-36, wherein X11 is L. (38) The anti-TL1A antibody of any one of embodiments 34-36, wherein X11 is W.

In some embodiments, an anti-TL1A antibody comprises a light chain framework comprising SEQ ID NO: 303 (EIVLTQSPGTLSLSPGERATLSC[LCDR1] WYQQKPGQAPRX10X11IY[LCDR2]GIPDR FSGSGSGTDFTLTISRLEPEDFAVYYC[LCDR3] FGGGTKLEIK). In some cases, X10 is L. In some cases, X10 is P. In some cases, X11 is L. In some cases, X11 is W. In some embodiments, X10 is at position 54 of IGKV3-20*01 as determined by Aho numbering. In some embodiments, X11 is at position 55 of IGKV3-20*01 as determined by Aho numbering.

In some embodiments, an anti-TL1A antibody comprises a heavy chain framework comprising IGHV1-46*02. In some embodiments, an anti-TL1A antibody comprises a heavy chain framework comprising a variant of IGHV1-46*02 comprising between about 1 and about 20 amino acid substitutions from SEQ ID NO: 316. In some embodiments, an anti-TL1A antibody comprises a heavy chain framework comprising a variant of IGHV1-46*02 comprising between about 1 and about 9 amino acid substitutions from SEQ ID NO: 316. In some embodiments, an anti-TL1A antibody comprises a heavy chain framework comprising a variant of IGHV1-46*02 comprising about 1, 2, 3, 4, 5, 6, 7, 8, 9, 10, 11, 12, 13, 14, 15, 16, 17, 18, 19, or 20 amino acid substitutions from SEQ ID NO: 316 in the framework. In some cases, the heavy chain framework substitution comprises Q1E, as determined by Aho numbering. In some cases, the heavy chain framework substitution comprises R45K, as determined by Aho numbering. In some cases, the heavy chain framework substitution comprises A47R, as determined by Aho numbering. In some cases, the heavy chain framework substitution comprises M55I, as determined by Aho numbering. In some cases, the heavy chain framework substitution comprises V78A, as determined by Aho numbering. In some cases, the heavy chain framework substitution comprises M80I, as determined by Aho numbering. In some cases, the heavy chain framework substitution comprises R82T, as determined by Aho numbering. In some cases, the heavy chain framework substitution comprises V89A, as determined by Aho numbering. In some cases, the heavy chain framework substitution comprises M91L, as determined by Aho numbering.

In some embodiments, an anti-TL1A antibody comprises a light chain framework comprising IGKV3-20*01. In some embodiments, an anti-TL1A antibody comprises a variant of IGKV3-20*01 comprising between about 1 and about 20 amino acid substitutions from SEQ ID NO: 317. In some embodiments, an anti-TL1A antibody comprises a variant of IGKV3-20*01 comprising about 1 amino acid substitution from SEQ ID NO: 317. In some embodiments, an anti-TL1A antibody comprises a light chain framework comprising a variant of IGKV3-20*01 comprising about 2 amino acid substitutions from SEQ ID NO: 317. In some embodiments, an anti-TL1A antibody comprises a light chain framework comprising a variant of IGKV3-20*01 comprising about 1, 2, 3, 4, 5, 6, 7, 8, 9, 10, 11, 12, 13, 14, 15, 16, 17, 18, 19, or 20 amino acid substitutions from SEQ ID NO: 317 in the framework. In some cases, the light chain framework substitution comprises Q1E, as determined by Aho numbering. In some cases, the light chain framework substitution comprises R45K, as determined by Aho numbering.

In some embodiments, an anti-TL1A antibody comprises a heavy chain FR1 as set forth by SEQ ID NO: 304. In some embodiments, an anti-TL1A antibody comprises a heavy chain FR2 as set forth by SEQ ID NO: 305. In some embodiments, an anti-TL1A antibody comprises a heavy chain FR2 as set forth by SEQ ID NO: 313. In some embodiments, an anti-TL1A antibody comprises a heavy chain FR3 as set forth by SEQ ID NO: 306. In some embodiments, an anti-TL1A antibody comprises a heavy chain FR3 as set forth by SEQ ID NO: 307. In some embodiments, an anti-TL1A antibody comprises a heavy chain FR3 as set forth by SEQ ID NO: 314. In some embodiments, an anti-TL1A antibody comprises a heavy chain FR3 as set forth by SEQ ID NO: 315. In some embodiments, an anti-TL1A antibody comprises a heavy chain FR4 as set forth by SEQ ID NO: 308. In some embodiments, an anti-TL1A antibody comprises a light chain FR1 as set forth by SEQ ID NO: 309. In some embodiments, an anti-TL1A antibody comprises a light chain FR2 as set forth by SEQ ID NO: 310. In some embodiments, an anti-TL1A antibody comprises a light chain FR3 as set forth by SEQ ID NO: 311. In some embodiments, an anti-TL1A antibody comprises a light chain FR4 as set forth by SEQ ID NO: 312.

In certain embodiments, an anti-TL1A antibody comprises the framework regions set forth in any one of the antibodies in Table 1, wherein the framework regions are defined by the Kabat, Chothia, or IMGT method. In certain embodiments, an anti-TL1A antibody comprises the framework regions set forth in antibody A217, wherein the framework regions are defined by the Kabat, Chothia, or IMGT method. In certain embodiments, an anti-TL1A antibody comprises the framework regions set forth in antibody A220, wherein the framework regions are defined by the Kabat, Chothia, or IMGT method. In certain embodiments, an anti-TL1A antibody comprises the framework regions set forth in antibody A223, wherein the framework regions are defined by the Kabat, Chothia, or IMGT method. In certain embodiments, an anti-TL1A antibody comprises the framework regions set forth in antibody A219, wherein the framework regions are defined by the Kabat, Chothia, or IMGT method. In certain embodiments, an anti-TL1A antibody comprises the framework regions set forth in antibody A221, wherein the framework regions are defined by the Kabat, Chothia, or IMGT method. In certain embodiments, an anti-TL1A antibody comprises the framework regions set forth in antibody A200, wherein the framework regions are defined by the Kabat, Chothia, or IMGT method. In certain embodiments, an anti-TL1A antibody comprises the framework regions set forth in antibody A213, wherein the framework regions are defined by the Kabat, Chothia, or IMGT method. In certain embodiments, an anti-TL1A antibody comprises the framework regions set forth in antibody A212, wherein the framework regions are defined by the Kabat, Chothia, or IMGT method. In certain embodiments, an anti-TL1A antibody comprises the framework regions set forth in antibody A107, wherein the framework regions are defined by the Kabat, Chothia, or IMGT method. In certain embodiments, an anti-TL1A antibody comprises the framework regions set forth in antibody A205, wherein the framework regions are defined by the Kabat, Chothia, or IMGT method. In certain embodiments, an anti-TL1A antibody comprises the framework regions set forth in antibody A211, wherein the framework regions are defined by the Kabat, Chothia, or IMGT method. In certain embodiments, an anti-TL1A antibody comprises the framework regions set forth in antibody A199, wherein the framework regions are defined by the Kabat, Chothia, or IMGT method. In certain embodiments, an anti-TL1A antibody comprises the framework regions set forth in antibody A15, wherein the framework regions are defined by the Kabat, Chothia, or IMGT method. In certain embodiments, an anti-TL1A antibody comprises the framework regions set forth in antibody A30, wherein the framework regions are defined by the Kabat, Chothia, or IMGT method. In certain embodiments, an anti-TL1A antibody comprises the framework regions set forth in antibody A100, wherein the framework regions are defined by the Kabat, Chothia, or IMGT method. In certain embodiments, an anti-TL1A antibody comprises the framework regions set forth in antibody A181, wherein the framework regions are defined by the Kabat, Chothia, or IMGT method. In certain embodiments, an anti-TL1A antibody comprises the framework regions set forth in antibody A129, wherein the framework regions are defined by the Kabat, Chothia, or IMGT method. In certain embodiments, an anti-TL1A antibody comprises the framework regions set forth in antibody A214, wherein the framework regions are defined by the Kabat, Chothia, or IMGT method. In certain embodiments, an anti-TL1A antibody comprises the framework regions set forth in antibody A216, wherein the framework regions are defined by the Kabat, Chothia, or IMGT method. In certain embodiments, an anti-TL1A antibody comprises the framework regions set forth in antibody A122, wherein the framework regions are defined by the Kabat, Chothia, or IMGT method. In certain embodiments, an anti-TL1A antibody comprises the framework regions set forth in antibody A222, wherein the framework regions are defined by the Kabat, Chothia, or IMGT method. In certain embodiments, an anti-TL1A antibody comprises the framework regions set forth in antibody A188, wherein the framework regions are defined by the Kabat, Chothia, or IMGT method. In certain embodiments, an anti-TL1A antibody comprises the framework regions set forth in antibody A203, wherein the framework regions are defined by the Kabat, Chothia, or IMGT method. In certain embodiments, an anti-TL1A antibody comprises the framework regions set forth in antibody A147, wherein the framework regions are defined by the Kabat, Chothia, or IMGT method. In certain embodiments, an anti-TL1A antibody comprises the framework regions set forth in antibody A127, wherein the framework regions are defined by the Kabat, Chothia, or IMGT method. In certain embodiments, an anti-TL1A antibody comprises the framework regions set forth in antibody A126, wherein the framework regions are defined by the Kabat, Chothia, or IMGT method. In certain embodiments, an anti-TL1A antibody comprises the framework regions set forth in antibody A160, wherein the framework regions are defined by the Kabat, Chothia, or IMGT method. In certain embodiments, an anti-TL1A antibody comprises the framework regions set forth in antibody A157, wherein the framework regions are defined by the Kabat, Chothia, or IMGT method. In certain embodiments, an anti-TL1A antibody comprises the framework regions set forth in antibody A159, wherein the framework regions are defined by the Kabat, Chothia, or IMGT method. In certain embodiments, an anti-TL1A antibody comprises the framework regions set forth in antibody A218, wherein the framework regions are defined by the Kabat, Chothia, or IMGT method. In certain embodiments, an anti-TL1A antibody comprises the framework regions set forth in antibody A158, wherein the framework regions are defined by the Kabat, Chothia, or IMGT method. In certain embodiments, an anti-TL1A antibody comprises the framework regions set forth in antibody A125, wherein the framework regions are defined by the Kabat, Chothia, or IMGT method. In certain embodiments, an anti-TL1A antibody comprises the framework regions set forth in antibody A103, wherein the framework regions are defined by the Kabat, Chothia, or IMGT method. In certain embodiments, an anti-TL1A antibody comprises the framework regions set forth in antibody A64, wherein the framework regions are defined by the Kabat, Chothia, or IMGT method. In certain embodiments, an anti-TL1A antibody comprises the framework regions set forth in antibody A67, wherein the framework regions are defined by the Kabat, Chothia, or IMGT method. In certain embodiments, an anti-TL1A antibody comprises the framework regions set forth in antibody A138, wherein the framework regions are defined by the Kabat, Chothia, or IMGT method. In certain embodiments, an anti-TL1A antibody comprises the framework regions set forth in antibody A68, wherein the framework regions are defined by the Kabat, Chothia, or IMGT method. In certain embodiments, an anti-TL1A antibody comprises the framework regions set forth in antibody A94, wherein the framework regions are defined by the Kabat, Chothia, or IMGT method. In certain embodiments, an anti-TL1A antibody comprises the framework regions set forth in antibody A110, wherein the framework regions are defined by the Kabat, Chothia, or IMGT method. In certain embodiments, an anti-TL1A antibody comprises the framework regions set forth in antibody A197, wherein the framework regions are defined by the Kabat, Chothia, or IMGT method. In certain embodiments, an anti-TL1A antibody comprises the framework regions set forth in antibody A112, wherein the framework regions are defined by the Kabat, Chothia, or IMGT method. In certain embodiments, an anti-TL1A antibody comprises the framework regions set forth in antibody A169, wherein the framework regions are defined by the Kabat, Chothia, or IMGT method. In certain embodiments, an anti-TL1A antibody comprises the framework regions set forth in antibody A173, wherein the framework regions are defined by the Kabat, Chothia, or IMGT method. In certain embodiments, an anti-TL1A antibody comprises the framework regions set forth in antibody A179, wherein the framework regions are defined by the Kabat, Chothia, or IMGT method. In certain embodiments, an anti-TL1A antibody comprises the framework regions set forth in antibody A148, wherein the framework regions are defined by the Kabat, Chothia, or IMGT method. In certain embodiments, an anti-TL1A antibody comprises the framework regions set forth in antibody A115, wherein the framework regions are defined by the Kabat, Chothia, or IMGT method. In certain embodiments, an anti-TL1A antibody comprises the framework regions set forth in antibody A149, wherein the framework regions are defined by the Kabat, Chothia, or IMGT method. In certain embodiments, an anti-TL1A antibody comprises the framework regions set forth in antibody A134, wherein the framework regions are defined by the Kabat, Chothia, or IMGT method. In certain embodiments, an anti-TL1A antibody comprises the framework regions set forth in antibody A113, wherein the framework regions are defined by the Kabat, Chothia, or IMGT method. In certain embodiments, an anti-TL1A antibody comprises the framework regions set forth in antibody A151, wherein the framework regions are defined by the Kabat, Chothia, or IMGT method. In certain embodiments, an anti-TL1A antibody comprises the framework regions set forth in antibody A96, wherein the framework regions are defined by the Kabat, Chothia, or IMGT method. In certain embodiments, an anti-TL1A antibody comprises the framework regions set forth in antibody A132, wherein the framework regions are defined by the Kabat, Chothia, or IMGT method. In certain embodiments, an anti-TL1A antibody comprises the framework regions set forth in antibody A196, wherein the framework regions are defined by the Kabat, Chothia, or IMGT method. In certain embodiments, an anti-TL1A antibody comprises the framework regions set forth in antibody A172, wherein the framework regions are defined by the Kabat, Chothia, or IMGT method. In certain embodiments, an anti-TL1A antibody comprises the framework regions set forth in antibody A75, wherein the framework regions are defined by the Kabat, Chothia, or IMGT method. In certain embodiments, an anti-TL1A antibody comprises the framework regions set forth in antibody A174, wherein the framework regions are defined by the Kabat, Chothia, or IMGT method. In certain embodiments, an anti-TL1A antibody comprises the framework regions set forth in antibody A109, wherein the framework regions are defined by the Kabat, Chothia, or IMGT method. In certain embodiments, an anti-TL1A antibody comprises the framework regions set forth in antibody A198, wherein the framework regions are defined by the Kabat, Chothia, or IMGT method. In certain embodiments, an anti-TL1A antibody comprises the framework regions set forth in antibody A170, wherein the framework regions are defined by the Kabat, Chothia, or IMGT method.

Exemplary Anti-TL1A Variable Regions

In one aspect, provided herein is an anti-TL1A antibody comprising a heavy chain variable region comprising an amino acid sequence at least about 85%, 90%, 91%, 92%, 93%, 94%, 95%, 96%, 97%, 98%, 99%, or 100% identical to any one of SEQ ID NOS: 101-135; and a light chain variable region at least about 85%, 90%, 91%, 92%, 93%, 94%, 95%, 96%, 97%, 98%, 99%, or 100% identical to any one of SEQ ID NOS: 201-206.

Further provided herein is a first embodiment of an anti-TL1A antibody comprising a heavy chain variable region and a light chain variable region. Non-limiting additional embodiments include: (Embodiment 2) The anti-TL1A antibody of embodiment 1, wherein the heavy chain variable region comprises SEQ ID NO: 101. (Embodiment 3) The anti-TL1A antibody of embodiment 1, wherein the heavy chain variable region comprises a sequence at least about 90%, 95%, 96%, 97%, 98%, 99%, or 100% identical to SEQ ID NO: 101. (Embodiment 4) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 101. (Embodiment 5) The anti-TL1A antibody of embodiment 1, wherein the heavy chain variable region comprises SEQ ID NO: 102. (Embodiment 6) The anti-TL1A antibody of embodiment 1, wherein the heavy chain variable region comprises a sequence at least about 90%, 95%, 96%, 97%, 98%, 99%, or 100% identical to SEQ ID NO: 102. (Embodiment 7) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 102. (Embodiment 8) The anti-TL1A antibody of embodiment 1, wherein the heavy chain variable region comprises SEQ ID NO: 103. (Embodiment 9) The anti-TL1A antibody of embodiment 1, wherein the heavy chain variable region comprises a sequence at least about 90%, 95%, 96%, 97%, 98%, 99%, or 100% identical to SEQ ID NO: 103. (Embodiment 10) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 103.

(Embodiment 11) The anti-TL1A antibody of embodiment 1, wherein the heavy chain variable region comprises SEQ ID NO: 104. (Embodiment 12) The anti-TL1A antibody of embodiment 1, wherein the heavy chain variable region comprises a sequence at least about 90%, 95%, 96%, 97%, 98%, 99%, or 100% identical to SEQ ID NO: 104. (Embodiment 13) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 104. (Embodiment 14) The anti-TL1A antibody of embodiment 1, wherein the heavy chain variable region comprises SEQ ID NO: 105. (Embodiment 15) The anti-TL1A antibody of embodiment 1, wherein the heavy chain variable region comprises a sequence at least about 90%, 95%, 96%, 97%, 98%, 99%, or 100% identical to SEQ ID NO: 105. (Embodiment 16) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 105. (Embodiment 17) The anti-TL1A antibody of embodiment 1, wherein the heavy chain variable region comprises SEQ ID NO: 106. (Embodiment 18) The anti-TL1A antibody of embodiment 1, wherein the heavy chain variable region comprises a sequence at least about 90%, 95%, 96%, 97%, 98%, 99%, or 100% identical to SEQ ID NO: 106. (Embodiment 19) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 106. (Embodiment 20) The anti-TL1A antibody of embodiment 1, wherein the heavy chain variable region comprises SEQ ID NO: 107. (Embodiment 21) The anti-TL1A antibody of embodiment 1, wherein the heavy chain variable region comprises a sequence at least about 90%, 95%, 96%, 97%, 98%, 99%, or 100% identical to SEQ ID NO: 107. (Embodiment 22) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 107.

(Embodiment 23) The anti-TL1A antibody of embodiment 1, wherein the heavy chain variable region comprises SEQ ID NO: 108. (Embodiment 24) The anti-TL1A antibody of embodiment 1, wherein the heavy chain variable region comprises a sequence at least about 90%, 95%, 96%, 97%, 98%, 99%, or 100% identical to SEQ ID NO: 108. (Embodiment 25) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 108. (Embodiment 26) The anti-TL1A antibody of embodiment 1, wherein the heavy chain variable region comprises SEQ ID NO: 109. (Embodiment 27) The anti-TL1A antibody of embodiment 1, wherein the heavy chain variable region comprises a sequence at least about 90%, 95%, 96%, 97%, 98%, 99%, or 100% identical to SEQ ID NO: 109. (Embodiment 28) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 109. (Embodiment 29) The anti-TL1A antibody of embodiment 1, wherein the heavy chain variable region comprises SEQ ID NO: 110. (Embodiment 30) The anti-TL1A antibody of embodiment 1, wherein the heavy chain variable region comprises a sequence at least about 90%, 95%, 96%, 97%, 98%, 99%, or 100% identical to SEQ ID NO: 110.

(Embodiment 31) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 110. (Embodiment 32) The anti-TL1A antibody of embodiment 1, wherein the heavy chain variable region comprises SEQ ID NO: 111. (Embodiment 33) The anti-TL1A antibody of embodiment 1, wherein the heavy chain variable region comprises a sequence at least about 90%, 95%, 96%, 97%, 98%, 99%, or 100% identical to SEQ ID NO: 111. (Embodiment 34) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 111. (Embodiment 35) The anti-TL1A antibody of embodiment 1, wherein the heavy chain variable region comprises SEQ ID NO: 112. (Embodiment 36) The anti-TL1A antibody of embodiment 1, wherein the heavy chain variable region comprises a sequence at least about 90%, 95%, 96%, 97%, 98%, 99%, or 100% identical to SEQ ID NO: 112. (Embodiment 37) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 112. (Embodiment 38) The anti-TL1A antibody of embodiment 1, wherein the heavy chain variable region comprises SEQ ID NO: 113. (Embodiment 39) The anti-TL1A antibody of embodiment 1, wherein the heavy chain variable region comprises a sequence at least about 90%, 95%, 96%, 97%, 98%, 99%, or 100% identical to SEQ ID NO: 113. (Embodiment 40) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 113.

(Embodiment 41) The anti-TL1A antibody of embodiment 1, wherein the heavy chain variable region comprises SEQ ID NO: 114. (Embodiment 42) The anti-TL1A antibody of embodiment 1, wherein the heavy chain variable region comprises a sequence at least about 90%, 95%, 96%, 97%, 98%, 99%, or 100% identical to SEQ ID NO: 114. (Embodiment 43) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 114. (Embodiment 44) The anti-TL1A antibody of embodiment 1, wherein the heavy chain variable region comprises SEQ ID NO: 115. (Embodiment 45) The anti-TL1A antibody of embodiment 1, wherein the heavy chain variable region comprises a sequence at least about 90%, 95%, 96%, 97%, 98%, 99%, or 100% identical to SEQ ID NO: 115. (Embodiment 46) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 115. (Embodiment 47) The anti-TL1A antibody of embodiment 1, wherein the heavy chain variable region comprises SEQ ID NO: 116. (Embodiment 48) The anti-TL1A antibody of embodiment 1, wherein the heavy chain variable region comprises a sequence at least about 90%, 95%, 96%, 97%, 98%, 99%, or 100% identical to SEQ ID NO: 116. (Embodiment 49) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 116. (Embodiment 50) The anti-TL1A antibody of embodiment 1, wherein the heavy chain variable region comprises SEQ ID NO: 117. (Embodiment 51) The anti-TL1A antibody of embodiment 1, wherein the heavy chain variable region comprises a sequence at least about 90%, 95%, 96%, 97%, 98%, 99%, or 100% identical to SEQ ID NO: 117. (Embodiment 52) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 117.

(Embodiment 53) The anti-TL1A antibody of embodiment 1, wherein the heavy chain variable region comprises SEQ ID NO: 118. (Embodiment 54) The anti-TL1A antibody of embodiment 1, wherein the heavy chain variable region comprises a sequence at least about 90%, 95%, 96%, 97%, 98%, 99%, or 100% identical to SEQ ID NO: 118. (Embodiment 55) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 118. (Embodiment 56) The anti-TL1A antibody of embodiment 1, wherein the heavy chain variable region comprises SEQ ID NO: 119. (Embodiment 57) The anti-TL1A antibody of embodiment 1, wherein the heavy chain variable region comprises a sequence at least about 90%, 95%, 96%, 97%, 98%, 99%, or 100% identical to SEQ ID NO: 119. (Embodiment 58) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 119. (Embodiment 59) The anti-TL1A antibody of embodiment 1, wherein the heavy chain variable region comprises SEQ ID NO: 120. (Embodiment 60) The anti-TL1A antibody of embodiment 1, wherein the heavy chain variable region comprises a sequence at least about 90%, 95%, 96%, 97%, 98%, 99%, or 100% identical to SEQ ID NO: 120. (Embodiment 61) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 120.

(Embodiment 62) The anti-TL1A antibody of embodiment 1, wherein the heavy chain variable region comprises SEQ ID NO: 121. (Embodiment 63) The anti-TL1A antibody of embodiment 1, wherein the heavy chain variable region comprises a sequence at least about 90%, 95%, 96%, 97%, 98%, 99%, or 100% identical to SEQ ID NO: 121. (Embodiment 64) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 121. (Embodiment 65) The anti-TL1A antibody of embodiment 1, wherein the heavy chain variable region comprises SEQ ID NO: 122. (Embodiment 66) The anti-TL1A antibody of embodiment 1, wherein the heavy chain variable region comprises a sequence at least about 90%, 95%, 96%, 97%, 98%, 99%, or 100% identical to SEQ ID NO: 122. (Embodiment 67) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 122. (Embodiment 68) The anti-TL1A antibody of embodiment 1, wherein the heavy chain variable region comprises SEQ ID NO: 123. (Embodiment 69) The anti-TL1A antibody of embodiment 1, wherein the heavy chain variable region comprises a sequence at least about 90%, 95%, 96%, 97%, 98%, 99%, or 100% identical to SEQ ID NO: 123. (Embodiment 70) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 123. (Embodiment 71) The anti-TL1A antibody of embodiment 1, wherein the heavy chain variable region comprises SEQ ID NO: 124. (Embodiment 72) The anti-TL1A antibody of embodiment 1, wherein the heavy chain variable region comprises a sequence at least about 90%, 95%, 96%, 97%, 98%, 99%, or 100% identical to SEQ ID NO: 124. (Embodiment 73) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 124.

(Embodiment 74) The anti-TL1A antibody of embodiment 1, wherein the heavy chain variable region comprises SEQ ID NO: 125. (Embodiment 75) The anti-TL1A antibody of embodiment 1, wherein the heavy chain variable region comprises a sequence at least about 90%, 95%, 96%, 97%, 98%, 99%, or 100% identical to SEQ ID NO: 125. (Embodiment 76) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 125. (Embodiment 77) The anti-TL1A antibody of embodiment 1, wherein the heavy chain variable region comprises SEQ ID NO: 126. (Embodiment 78) The anti-TL1A antibody of embodiment 1, wherein the heavy chain variable region comprises a sequence at least about 90%, 95%, 96%, 97%, 98%, 99%, or 100% identical to SEQ ID NO: 126. (Embodiment 79) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 126. (Embodiment 80) The anti-TL1A antibody of embodiment 1, wherein the heavy chain variable region comprises SEQ ID NO: 127. (Embodiment 81) The anti-TL1A antibody of embodiment 1, wherein the heavy chain variable region comprises a sequence at least about 90%, 95%, 96%, 97%, 98%, 99%, or 100% identical to SEQ ID NO: 127. (Embodiment 82) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 127. (Embodiment 83) The anti-TL1A antibody of embodiment 1, wherein the heavy chain variable region comprises SEQ ID NO: 128. (Embodiment 84) The anti-TL1A antibody of embodiment 1, wherein the heavy chain variable region comprises a sequence at least about 90%, 95%, 96%, 97%, 98%, 99%, or 100% identical to SEQ ID NO: 128. (Embodiment 85) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 128.

(Embodiment 86) The anti-TL1A antibody of embodiment 1, wherein the heavy chain variable region comprises SEQ ID NO: 129. (Embodiment 87) The anti-TL1A antibody of embodiment 1, wherein the heavy chain variable region comprises a sequence at least about 90%, 95%, 96%, 97%, 98%, 99%, or 100% identical to SEQ ID NO: 129. (Embodiment 88) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 129. (Embodiment 89) The anti-TL1A antibody of embodiment 1, wherein the heavy chain variable region comprises SEQ ID NO: 130. (Embodiment 90) The anti-TL1A antibody of embodiment 1, wherein the heavy chain variable region comprises a sequence at least about 90%, 95%, 96%, 97%, 98%, 99%, or 100% identical to SEQ ID NO: 130. (Embodiment 91) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 130. (Embodiment 92) The anti-TL1A antibody of embodiment 1, wherein the heavy chain variable region comprises SEQ ID NO: 131. (Embodiment 93) The anti-TL1A antibody of embodiment 1, wherein the heavy chain variable region comprises a sequence at least about 90%, 95%, 96%, 97%, 98%, 99%, or 100% identical to SEQ ID NO: 131. (Embodiment 94) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 131. (Embodiment 95) The anti-TL1A antibody of embodiment 1, wherein the heavy chain variable region comprises SEQ ID NO: 132. (Embodiment 96) The anti-TL1A antibody of embodiment 1, wherein the heavy chain variable region comprises a sequence at least about 90%, 95%, 96%, 97%, 98%, 99%, or 100% identical to SEQ ID NO: 132. (Embodiment 97) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 132.

(Embodiment 98) The anti-TL1A antibody of embodiment 1, wherein the heavy chain variable region comprises SEQ ID NO: 133. (Embodiment 99) The anti-TL1A antibody of embodiment 1, wherein the heavy chain variable region comprises a sequence at least about 90%, 95%, 96%, 97%, 98%, 99%, or 100% identical to SEQ ID NO: 133. (Embodiment 100) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 133. (Embodiment 101) The anti-TL1A antibody of embodiment 1, wherein the heavy chain variable region comprises SEQ ID NO: 134. (Embodiment 102) The anti-TL1A antibody of embodiment 1, wherein the heavy chain variable region comprises a sequence at least about 90%, 95%, 96%, 97%, 98%, 99%, or 100% identical to SEQ ID NO: 134. (Embodiment 103) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 134. (Embodiment 104) The anti-TL1A antibody of embodiment 1, wherein the heavy chain variable region comprises SEQ ID NO: 135. (Embodiment 105) The anti-TL1A antibody of embodiment 1, wherein the heavy chain variable region comprises a sequence at least about 90%, 95%, 96%, 97%, 98%, 99%, or 100% identical to SEQ ID NO: 135. (Embodiment 106) The anti-TL1A antibody of embodiment 1, wherein the heavy chain variable region comprises a sequence having about 1, 2, 3, 4, 5, 6, 7, 8, 9 or 10 amino acid substitutions or deletions as compared to SEQ ID NO: 135.

(Embodiment 107) The anti-TL1A antibody of any one of embodiments 1-106, wherein the light chain variable region comprises SEQ ID NO: 201. (Embodiment 108) The anti-TL1A antibody of any one of embodiments 1-106, wherein the light chain variable region comprises a sequence at least about 90%, 95%, 96%, 97%, 98%, 99%, or 100% identical to SEQ ID NO: 201. (Embodiment 109) The anti-TL1A antibody of any one of embodiments 1-106, wherein the light chain variable region comprises a sequence having about 1, 2, 3, 4, 5, 6, 7, 8, 9 or 10 amino acid substitutions or deletions as compared to SEQ ID NO: 201. (Embodiment 110) The anti-TL1A antibody of any one of embodiments 1-106, wherein the light chain variable region comprises SEQ ID NO: 202. (Embodiment 111) The anti-TL1A antibody of any one of embodiments 1-106, wherein the light chain variable region comprises a sequence at least about 90%, 95%, 96%, 97%, 98%, 99%, or 100% identical to SEQ ID NO: 202. (Embodiment 112) The anti-TL1A antibody of any one of embodiments 1-106, wherein the light chain variable region comprises a sequence having about 1, 2, 3, 4, 5, 6, 7, 8, 9 or 10 amino acid substitutions or deletions as compared to SEQ ID NO: 202. (Embodiment 113) The anti-TL1A antibody of any one of embodiments 1-106, wherein the light chain variable region comprises SEQ ID NO: 203. (Embodiment 114) The anti-TL1A antibody of any one of embodiments 1-106, wherein the light chain variable region comprises a sequence at least about 90%, 95%, 96%, 97%, 98%, 99%, or 100% identical to SEQ ID NO: 203. (Embodiment 115) The anti-TL1A antibody of any one of embodiments 1-106, wherein the light chain variable region comprises a sequence having about 1, 2, 3, 4, 5, 6, 7, 8, 9 or 10 amino acid substitutions or deletions as compared to SEQ ID NO: 203. (Embodiment 116) The anti-TL1A antibody of any one of embodiments 1-106, wherein the light chain variable region comprises SEQ ID NO: 204. (Embodiment 117) The anti-TL1A antibody of any one of embodiments 1-106, wherein the light chain variable region comprises a sequence at least about 90%, 95%, 96%, 97%, 98%, 99%, or 100% identical to SEQ ID NO: 204. (Embodiment 118) The anti-TL1A antibody of any one of embodiments 1-106, wherein the light chain variable region comprises a sequence having about 1, 2, 3, 4, 5, 6, 7, 8, 9 or 10 amino acid substitutions or deletions as compared to SEQ ID NO: 204. (Embodiment 119) The anti-TL1A antibody of any one of embodiments 1-106, wherein the light chain variable region comprises SEQ ID NO: 205. (Embodiment 120) The anti-TL1A antibody of any one of embodiments 1-106, wherein the light chain variable region comprises a sequence at least about 90%, 95%, 96%, 97%, 98%, 99%, or 100% identical to SEQ ID NO: 205. (Embodiment 121) The anti-TL1A antibody of any one of embodiments 1-106, wherein the light chain variable region comprises a sequence having about 1, 2, 3, 4, 5, 6, 7, 8, 9 or 10 amino acid substitutions or deletions as compared to SEQ ID NO: 205. (Embodiment 122) The anti-TL1A antibody of any one of embodiments 1-106, wherein the light chain variable region comprises SEQ ID NO: 206. (Embodiment 123) The anti-TL1A antibody of any one of embodiments 1-106, wherein the light chain variable region comprises a sequence at least about 90%, 95%, 96%, 97%, 98%, 99%, or 100% identical to SEQ ID NO: 206. (Embodiment 124) The anti-TL1A antibody of any one of embodiments 1-106, wherein the light chain variable region comprises a sequence having about 1, 2, 3, 4, 5, 6, 7, 8, 9 or 10 amino acid substitutions or deletions as compared to SEQ ID NO: 206.

(Embodiment 125) The anti-TL1A antibody of embodiment 1, comprising A217. (Embodiment 126) The anti-TL1A antibody of embodiment 1, wherein the heavy chain variable region comprises a sequence at least about 90%, 95%, 96%, 97%, 98%, 99%, or 100% identical to SEQ ID NO: 101, and the light chain variable region comprises a sequence at least about 90%, 95%, 96%, 97%, 98%, 99%, or 100% identical to SEQ ID NO: 201. (Embodiment 127) The anti-TL1A antibody of embodiment 1, comprising A220.

(Embodiment 128) The anti-TL1A antibody of embodiment 1, wherein the heavy chain variable region comprises a sequence at least about 90%, 95%, 96%, 97%, 98%, 99%, or 100% identical to SEQ ID NO: 102, and the light chain variable region comprises a sequence at least about 90%, 95%, 96%, 97%, 98%, 99%, or 100% identical to SEQ ID NO: 201. (Embodiment 129) The anti-TL1A antibody of embodiment 1, comprising A223. (Embodiment 130) The anti-TL1A antibody of embodiment 1, wherein the heavy chain variable region comprises a sequence at least about 90%, 95%, 96%, 97%, 98%, 99%, or 100% identical to SEQ ID NO: 103, and the light chain variable region comprises a sequence at least about 90%, 95%, 96%, 97%, 98%, 99%, or 100% identical to SEQ ID NO: 202. (Embodiment 131) The anti-TL1A antibody of embodiment 1, comprising A219. (Embodiment 132) The anti-TL1A antibody of embodiment 1, wherein the heavy chain variable region comprises a sequence at least about 90%, 95%, 96%, 97%, 98%, 99%, or 100% identical to SEQ ID NO: 104, and the light chain variable region comprises a sequence at least about 90%, 95%, 96%, 97%, 98%, 99%, or 100% identical to SEQ ID NO: 201. (Embodiment 133) The anti-TL1A antibody of embodiment 1, comprising A221. (Embodiment 134) The anti-TL1A antibody of embodiment 1, wherein the heavy chain variable region comprises a sequence at least about 90%, 95%, 96%, 97%, 98%, 99%, or 100% identical to SEQ ID NO: 105, and the light chain variable region comprises a sequence at least about 90%, 95%, 96%, 97%, 98%, 99%, or 100% identical to SEQ ID NO: 201.

(Embodiment 135) The anti-TL1A antibody of embodiment 1, comprising A200. (Embodiment 136) The anti-TL1A antibody of embodiment 1, wherein the heavy chain variable region comprises a sequence at least about 90%, 95%, 96%, 97%, 98%, 99%, or 100% identical to SEQ ID NO: 103, and the light chain variable region comprises a sequence at least about 90%, 95%, 96%, 97%, 98%, 99%, or 100% identical to SEQ ID NO: 201. (Embodiment 137) The anti-TL1A antibody of embodiment 1, comprising A213. (Embodiment 138) The anti-TL1A antibody of embodiment 1, wherein the heavy chain variable region comprises a sequence at least about 90%, 95%, 96%, 97%, 98%, 99%, or 100% identical to SEQ ID NO: 106, and the light chain variable region comprises a sequence at least about 90%, 95%, 96%, 97%, 98%, 99%, or 100% identical to SEQ ID NO: 201. (Embodiment 139) The anti-TL1A antibody of embodiment 1, comprising A212. (Embodiment 140) The anti-TL1A antibody of embodiment 1, wherein the heavy chain variable region comprises a sequence at least about 90%, 95%, 96%, 97%, 98%, 99%, or 100% identical to SEQ ID NO: 107, and the light chain variable region comprises a sequence at least about 90%, 95%, 96%, 97%, 98%, 99%, or 100% identical to SEQ ID NO: 202. (Embodiment 141) The anti-TL1A antibody of embodiment 1, comprising A107. (Embodiment 142) The anti-TL1A antibody of embodiment 1, wherein the heavy chain variable region comprises a sequence at least about 90%, 95%, 96%, 97%, 98%, 99%, or 100% identical to SEQ ID NO: 108, and the light chain variable region comprises a sequence at least about 90%, 95%, 96%, 97%, 98%, 99%, or 100% identical to SEQ ID NO: 202. (Embodiment 143) The anti-TL1A antibody of embodiment 1, comprising A205. (Embodiment 144) The anti-TL1A antibody of embodiment 1, wherein the heavy chain variable region comprises a sequence at least about 90%, 95%, 96%, 97%, 98%, 99%, or 100% identical to SEQ ID NO: 109, and the light chain variable region comprises a sequence at least about 90%, 95%, 96%, 97%, 98%, 99%, or 100% identical to SEQ ID NO: 202.

(Embodiment 145) The anti-TL1A antibody of embodiment 1, comprising A211. (Embodiment 146) The anti-TL1A antibody of embodiment 1, wherein the heavy chain variable region comprises a sequence at least about 90%, 95%, 96%, 97%, 98%, 99%, or 100% identical to SEQ ID NO: 108, and the light chain variable region comprises a sequence at least about 90%, 95%, 96%, 97%, 98%, 99%, or 100% identical to SEQ ID NO: 201. (Embodiment 147) The anti-TL1A antibody of embodiment 1, comprising A199. (Embodiment 148) The anti-TL1A antibody of embodiment 1, wherein the heavy chain variable region comprises a sequence at least about 90%, 95%, 96%, 97%, 98%, 99%, or 100% identical to SEQ ID NO: 109, and the light chain variable region comprises a sequence at least about 90%, 95%, 96%, 97%, 98%, 99%, or 100% identical to SEQ ID NO: 201. (Embodiment 149) The anti-TL1A antibody of embodiment 1, comprising A15. (Embodiment 150) The anti-TL1A antibody of embodiment 1, wherein the heavy chain variable region comprises a sequence at least about 90%, 95%, 96%, 97%, 98%, 99%, or 100% identical to SEQ ID NO: 108, and the light chain variable region comprises a sequence at least about 90%, 95%, 96%, 97%, 98%, 99%, or 100% identical to SEQ ID NO: 203. (Embodiment 151) The anti-TL1A antibody of embodiment 1, comprising A30. (Embodiment 152) The anti-TL1A antibody of embodiment 1, wherein the heavy chain variable region comprises a sequence at least about 90%, 95%, 96%, 97%, 98%, 99%, or 100% identical to SEQ ID NO: 108, and the light chain variable region comprises a sequence at least about 90%, 95%, 96%, 97%, 98%, 99%, or 100% identical to SEQ ID NO: 204. (Embodiment 153) The anti-TL1A antibody of embodiment 1, comprising A100. (Embodiment 154) The anti-TL1A antibody of embodiment 1, wherein the heavy chain variable region comprises a sequence at least about 90%, 95%, 96%, 97%, 98%, 99%, or 100% identical to SEQ ID NO: 107, and the light chain variable region comprises a sequence at least about 90%, 95%, 96%, 97%, 98%, 99%, or 100% identical to SEQ ID NO: 204.

(Embodiment 155) The anti-TL1A antibody of embodiment 1, comprising A181. (Embodiment 156) The anti-TL1A antibody of embodiment 1, wherein the heavy chain variable region comprises a sequence at least about 90%, 95%, 96%, 97%, 98%, 99%, or 100% identical to SEQ ID NO: 107, and the light chain variable region comprises a sequence at least about 90%, 95%, 96%, 97%, 98%, 99%, or 100% identical to SEQ ID NO: 202. (Embodiment 157) The anti-TL1A antibody of embodiment 1, comprising A129. (Embodiment 158) The anti-TL1A antibody of embodiment 1, wherein the heavy chain variable region comprises a sequence at least about 90%, 95%, 96%, 97%, 98%, 99%, or 100% identical to SEQ ID NO: 110, and the light chain variable region comprises a sequence at least about 90%, 95%, 96%, 97%, 98%, 99%, or 100% identical to SEQ ID NO: 204. (Embodiment 159) The anti-TL1A antibody of embodiment 1, comprising A214. (Embodiment 160) The anti-TL1A antibody of embodiment 1, wherein the heavy chain variable region comprises a sequence at least about 90%, 95%, 96%, 97%, 98%, 99%, or 100% identical to SEQ ID NO: 111, and the light chain variable region comprises a sequence at least about 90%, 95%, 96%, 97%, 98%, 99%, or 100% identical to SEQ ID NO: 201. (Embodiment 161) The anti-TL1A antibody of embodiment 1, comprising A216. (Embodiment 162) The anti-TL1A antibody of embodiment 1, wherein the heavy chain variable region comprises a sequence at least about 90%, 95%, 96%, 97%, 98%, 99%, or 100% identical to SEQ ID NO: 112, and the light chain variable region comprises a sequence at least about 90%, 95%, 96%, 97%, 98%, 99%, or 100% identical to SEQ ID NO: 201. (Embodiment 163) The anti-TL1A antibody of embodiment 1, comprising A122. (Embodiment 164) The anti-TL1A antibody of embodiment 1, wherein the heavy chain variable region comprises a sequence at least about 90%, 95%, 96%, 97%, 98%, 99%, or 100% identical to SEQ ID NO: 113, and the light chain variable region comprises a sequence at least about 90%, 95%, 96%, 97%, 98%, 99%, or 100% identical to SEQ ID NO: 204.

(Embodiment 165) The anti-TL1A antibody of embodiment 1, comprising A222. (Embodiment 166) The anti-TL1A antibody of embodiment 1, wherein the heavy chain variable region comprises a sequence at least about 90%, 95%, 96%, 97%, 98%, 99%, or 100% identical to SEQ ID NO: 114, and the light chain variable region comprises a sequence at least about 90%, 95%, 96%, 97%, 98%, 99%, or 100% identical to SEQ ID NO: 201. (Embodiment 167) The anti-TL1A antibody of embodiment 1, comprising A188. (Embodiment 168) The anti-TL1A antibody of embodiment 1, wherein the heavy chain variable region comprises a sequence at least about 90%, 95%, 96%, 97%, 98%, 99%, or 100% identical to SEQ ID NO: 115, and the light chain variable region comprises a sequence at least about 90%, 95%, 96%, 97%, 98%, 99%, or 100% identical to SEQ ID NO: 202. (Embodiment 169) The anti-TL1A antibody of embodiment 1, comprising A203. (Embodiment 170) The anti-TL1A antibody of embodiment 1, wherein the heavy chain variable region comprises a sequence at least about 90%, 95%, 96%, 97%, 98%, 99%, or 100% identical to SEQ ID NO: 116, and the light chain variable region comprises a sequence at least about 90%, 95%, 96%, 97%, 98%, 99%, or 100% identical to SEQ ID NO: 201. (Embodiment 171) The anti-TL1A antibody of embodiment 1, comprising A147. (Embodiment 172) The anti-TL1A antibody of embodiment 1, wherein the heavy chain variable region comprises a sequence at least about 90%, 95%, 96%, 97%, 98%, 99%, or 100% identical to SEQ ID NO: 117, and the light chain variable region comprises a sequence at least about 90%, 95%, 96%, 97%, 98%, 99%, or 100% identical to SEQ ID NO: 201. (Embodiment 173) The anti-TL1A antibody of embodiment 1, comprising A127. (Embodiment 174) The anti-TL1A antibody of embodiment 1, wherein the heavy chain variable region comprises a sequence at least about 90%, 95%, 96%, 97%, 98%, 99%, or 100% identical to SEQ ID NO: 118, and the light chain variable region comprises a sequence at least about 90%, 95%, 96%, 97%, 98%, 99%, or 100% identical to SEQ ID NO: 204.

(Embodiment 175) The anti-TL1A antibody of embodiment 1, comprising A126. (Embodiment 176) The anti-TL1A antibody of embodiment 1, wherein the heavy chain variable region comprises a sequence at least about 90%, 95%, 96%, 97%, 98%, 99%, or 100% identical to SEQ ID NO: 114, and the light chain variable region comprises a sequence at least about 90%, 95%, 96%, 97%, 98%, 99%, or 100% identical to SEQ ID NO: 204. (Embodiment 177) The anti-TL1A antibody of embodiment 1, comprising A160. (Embodiment 178) The anti-TL1A antibody of embodiment 1, wherein the heavy chain variable region comprises a sequence at least about 90%, 95%, 96%, 97%, 98%, 99%, or 100% identical to SEQ ID NO: 102, and the light chain variable region comprises a sequence at least about 90%, 95%, 96%, 97%, 98%, 99%, or 100% identical to SEQ ID NO: 204. (Embodiment 179) The anti-TL1A antibody of embodiment 1, comprising A157. (Embodiment 180) The anti-TL1A antibody of embodiment 1, wherein the heavy chain variable region comprises a sequence at least about 90%, 95%, 96%, 97%, 98%, 99%, or 100% identical to SEQ ID NO: 104, and the light chain variable region comprises a sequence at least about 90%, 95%, 96%, 97%, 98%, 99%, or 100% identical to SEQ ID NO: 204. (Embodiment 181) The anti-TL1A antibody of embodiment 1, comprising A159. (Embodiment 182) The anti-TL1A antibody of embodiment 1, wherein the heavy chain variable region comprises a sequence at least about 90%, 95%, 96%, 97%, 98%, 99%, or 100% identical to SEQ ID NO: 119, and the light chain variable region comprises a sequence at least about 90%, 95%, 96%, 97%, 98%, 99%, or 100% identical to SEQ ID NO: 204. (Embodiment 183) The anti-TL1A antibody of embodiment 1, comprising A218. (Embodiment 184) The anti-TL1A antibody of embodiment 1, wherein the heavy chain variable region comprises a sequence at least about 90%, 95%, 96%, 97%, 98%, 99%, or 100% identical to SEQ ID NO: 119, and the light chain variable region comprises a sequence at least about 90%, 95%, 96%, 97%, 98%, 99%, or 100% identical to SEQ ID NO: 201.

(Embodiment 185) The anti-TL1A antibody of embodiment 1, comprising A158. (Embodiment 186) The anti-TL1A antibody of embodiment 1, wherein the heavy chain variable region comprises a sequence at least about 90%, 95%, 96%, 97%, 98%, 99%, or 100% identical to SEQ ID NO: 101, and the light chain variable region comprises a sequence at least about 90%, 95%, 96%, 97%, 98%, 99%, or 100% identical to SEQ ID NO: 204. (Embodiment 187) The anti-TL1A antibody of embodiment 1, comprising A125. (Embodiment 188) The anti-TL1A antibody of embodiment 1, wherein the heavy chain variable region comprises a sequence at least about 90%, 95%, 96%, 97%, 98%, 99%, or 100% identical to SEQ ID NO: 105, and the light chain variable region comprises a sequence at least about 90%, 95%, 96%, 97%, 98%, 99%, or 100% identical to SEQ ID NO: 204. (Embodiment 189) The anti-TL1A antibody of embodiment 1, comprising A103. (Embodiment 190) The anti-TL1A antibody of embodiment 1, wherein the heavy chain variable region comprises a sequence at least about 90%, 95%, 96%, 97%, 98%, 99%, or 100% identical to SEQ ID NO: 120, and the light chain variable region comprises a sequence at least about 90%, 95%, 96%, 97%, 98%, 99%, or 100% identical to SEQ ID NO: 204. (Embodiment 191) The anti-TL1A antibody of embodiment 1, comprising A64. (Embodiment 192) The anti-TL1A antibody of embodiment 1, wherein the heavy chain variable region comprises a sequence at least about 90%, 95%, 96%, 97%, 98%, 99%, or 100% identical to SEQ ID NO: 121, and the light chain variable region comprises a sequence at least about 90%, 95%, 96%, 97%, 98%, 99%, or 100% identical to SEQ ID NO: 202. (Embodiment 193) The anti-TL1A antibody of embodiment 1, comprising A67. (Embodiment 194) The anti-TL1A antibody of embodiment 1, wherein the heavy chain variable region comprises a sequence at least about 90%, 95%, 96%, 97%, 98%, 99%, or 100% identical to SEQ ID NO: 122, and the light chain variable region comprises a sequence at least about 90%, 95%, 96%, 97%, 98%, 99%, or 100% identical to SEQ ID NO: 202.

(Embodiment 195) The anti-TL1A antibody of embodiment 1, comprising A138. (Embodiment 196) The anti-TL1A antibody of embodiment 1, wherein the heavy chain variable region comprises a sequence at least about 90%, 95%, 96%, 97%, 98%, 99%, or 100% identical to SEQ ID NO: 122, and the light chain variable region comprises a sequence at least about 90%, 95%, 96%, 97%, 98%, 99%, or 100% identical to SEQ ID NO: 204. (Embodiment 197) The anti-TL1A antibody of embodiment 1, comprising A68. (Embodiment 198) The anti-TL1A antibody of embodiment 1, wherein the heavy chain variable region comprises a sequence at least about 90%, 95%, 96%, 97%, 98%, 99%, or 100% identical to SEQ ID NO: 123, and the light chain variable region comprises a sequence at least about 90%, 95%, 96%, 97%, 98%, 99%, or 100% identical to SEQ ID NO: 202. (Embodiment 199) The anti-TL1A antibody of embodiment 1, comprising A94. (Embodiment 200) The anti-TL1A antibody of embodiment 1, wherein the heavy chain variable region comprises a sequence at least about 90%, 95%, 96%, 97%, 98%, 99%, or 100% identical to SEQ ID NO: 124, and the light chain variable region comprises a sequence at least about 90%, 95%, 96%, 97%, 98%, 99%, or 100% identical to SEQ ID NO: 202. (Embodiment 201) The anti-TL1A antibody of embodiment 1, comprising A110. (Embodiment 202) The anti-TL1A antibody of embodiment 1, wherein the heavy chain variable region comprises a sequence at least about 90%, 95%, 96%, 97%, 98%, 99%, or 100% identical to SEQ ID NO: 125, and the light chain variable region comprises a sequence at least about 90%, 95%, 96%, 97%, 98%, 99%, or 100% identical to SEQ ID NO: 205. (Embodiment 203) The anti-TL1A antibody of embodiment 1, comprising A197. (Embodiment 204) The anti-TL1A antibody of embodiment 1, wherein the heavy chain variable region comprises a sequence at least about 90%, 95%, 96%, 97%, 98%, 99%, or 100% identical to SEQ ID NO: 116, and the light chain variable region comprises a sequence at least about 90%, 95%, 96%, 97%, 98%, 99%, or 100% identical to SEQ ID NO: 205.

(Embodiment 205) The anti-TL1A antibody of embodiment 1, comprising A112. (Embodiment 206) The anti-TL1A antibody of embodiment 1, wherein the heavy chain variable region comprises a sequence at least about 90%, 95%, 96%, 97%, 98%, 99%, or 100% identical to SEQ ID NO: 117, and the light chain variable region comprises a sequence at least about 90%, 95%, 96%, 97%, 98%, 99%, or 100% identical to SEQ ID NO: 205. (Embodiment 207) The anti-TL1A antibody of embodiment 1, comprising A169. (Embodiment 208) The anti-TL1A antibody of embodiment 1, wherein the heavy chain variable region comprises a sequence at least about 90%, 95%, 96%, 97%, 98%, 99%, or 100% identical to SEQ ID NO: 126, and the light chain variable region comprises a sequence at least about 90%, 95%, 96%, 97%, 98%, 99%, or 100% identical to SEQ ID NO: 205. (Embodiment 209) The anti-TL1A antibody of embodiment 1, comprising A173. (Embodiment 210) The anti-TL1A antibody of embodiment 1, wherein the heavy chain variable region comprises a sequence at least about 90%, 95%, 96%, 97%, 98%, 99%, or 100% identical to SEQ ID NO: 127, and the light chain variable region comprises a sequence at least about 90%, 95%, 96%, 97%, 98%, 99%, or 100% identical to SEQ ID NO: 205. (Embodiment 211) The anti-TL1A antibody of embodiment 1, comprising A179. (Embodiment 212) The anti-TL1A antibody of embodiment 1, wherein the heavy chain variable region comprises a sequence at least about 90%, 95%, 96%, 97%, 98%, 99%, or 100% identical to SEQ ID NO: 127, and the light chain variable region comprises a sequence at least about 90%, 95%, 96%, 97%, 98%, 99%, or 100% identical to SEQ ID NO: 201. (Embodiment 213) The anti-TL1A antibody of embodiment 1, comprising A148. (Embodiment 214) The anti-TL1A antibody of embodiment 1, wherein the heavy chain variable region comprises a sequence at least about 90%, 95%, 96%, 97%, 98%, 99%, or 100% identical to SEQ ID NO: 121, and the light chain variable region comprises a sequence at least about 90%, 95%, 96%, 97%, 98%, 99%, or 100% identical to SEQ ID NO: 201.

(Embodiment 215) The anti-TL1A antibody of embodiment 1, comprising A115. (Embodiment 216) The anti-TL1A antibody of embodiment 1, wherein the heavy chain variable region comprises a sequence at least about 90%, 95%, 96%, 97%, 98%, 99%, or 100% identical to SEQ ID NO: 122, and the light chain variable region comprises a sequence at least about 90%, 95%, 96%, 97%, 98%, 99%, or 100% identical to SEQ ID NO: 205. (Embodiment 217) The anti-TL1A antibody of embodiment 1, comprising A149. (Embodiment 218) The anti-TL1A antibody of embodiment 1, wherein the heavy chain variable region comprises a sequence at least about 90%, 95%, 96%, 97%, 98%, 99%, or 100% identical to SEQ ID NO: 122, and the light chain variable region comprises a sequence at least about 90%, 95%, 96%, 97%, 98%, 99%, or 100% identical to SEQ ID NO: 201. (Embodiment 219) The anti-TL1A antibody of embodiment 1, comprising A134. (Embodiment 220) The anti-TL1A antibody of embodiment 1, wherein the heavy chain variable region comprises a sequence at least about 90%, 95%, 96%, 97%, 98%, 99%, or 100% identical to SEQ ID NO: 122, and the light chain variable region comprises a sequence at least about 90%, 95%, 96%, 97%, 98%, 99%, or 100% identical to SEQ ID NO: 206. (Embodiment 221) The anti-TL1A antibody of embodiment 1, comprising A113. (Embodiment 222) The anti-TL1A antibody of embodiment 1, wherein the heavy chain variable region comprises a sequence at least about 90%, 95%, 96%, 97%, 98%, 99%, or 100% identical to SEQ ID NO: 124, and the light chain variable region comprises a sequence at least about 90%, 95%, 96%, 97%, 98%, 99%, or 100% identical to SEQ ID NO: 205. (Embodiment 223) The anti-TL1A antibody of embodiment 1, comprising A151. (Embodiment 224) The anti-TL1A antibody of embodiment 1, wherein the heavy chain variable region comprises a sequence at least about 90%, 95%, 96%, 97%, 98%, 99%, or 100% identical to SEQ ID NO: 124, and the light chain variable region comprises a sequence at least about 90%, 95%, 96%, 97%, 98%, 99%, or 100% identical to SEQ ID NO: 201.

(Embodiment 225) The anti-TL1A antibody of embodiment 1, comprising A96. (Embodiment 226) The anti-TL1A antibody of embodiment 1, wherein the heavy chain variable region comprises a sequence at least about 90%, 95%, 96%, 97%, 98%, 99%, or 100% identical to SEQ ID NO: 128, and the light chain variable region comprises a sequence at least about 90%, 95%, 96%, 97%, 98%, 99%, or 100% identical to SEQ ID NO: 205. (Embodiment 227) The anti-TL1A antibody of embodiment 1, comprising A132. (Embodiment 228) The anti-TL1A antibody of embodiment 1, wherein the heavy chain variable region comprises a sequence at least about 90%, 95%, 96%, 97%, 98%, 99%, or 100% identical to SEQ ID NO: 128, and the light chain variable region comprises a sequence at least about 90%, 95%, 96%, 97%, 98%, 99%, or 100% identical to SEQ ID NO: 206. (Embodiment 229) The anti-TL1A antibody of embodiment 1, comprising A196. (Embodiment 230) The anti-TL1A antibody of embodiment 1, wherein the heavy chain variable region comprises a sequence at least about 90%, 95%, 96%, 97%, 98%, 99%, or 100% identical to SEQ ID NO: 129, and the light chain variable region comprises a sequence at least about 90%, 95%, 96%, 97%, 98%, 99%, or 100% identical to SEQ ID NO: 205. (Embodiment 231) The anti-TL1A antibody of embodiment 1, comprising A172. (Embodiment 232) The anti-TL1A antibody of embodiment 1, wherein the heavy chain variable region comprises a sequence at least about 90%, 95%, 96%, 97%, 98%, 99%, or 100% identical to SEQ ID NO: 130, and the light chain variable region comprises a sequence at least about 90%, 95%, 96%, 97%, 98%, 99%, or 100% identical to SEQ ID NO: 205. (Embodiment 233) The anti-TL1A antibody of embodiment 1, comprising A75. (Embodiment 234) The anti-TL1A antibody of embodiment 1, wherein the heavy chain variable region comprises a sequence at least about 90%, 95%, 96%, 97%, 98%, 99%, or 100% identical to SEQ ID NO: 131, and the light chain variable region comprises a sequence at least about 90%, 95%, 96%, 97%, 98%, 99%, or 100% identical to SEQ ID NO: 205.

(Embodiment 235) The anti-TL1A antibody of embodiment 1, comprising A174. (Embodiment 236) The anti-TL1A antibody of embodiment 1, wherein the heavy chain variable region comprises a sequence at least about 90%, 95%, 96%, 97%, 98%, 99%, or 100% identical to SEQ ID NO: 132, and the light chain variable region comprises a sequence at least about 90%, 95%, 96%, 97%, 98%, 99%, or 100% identical to SEQ ID NO: 205. (Embodiment 237) The anti-TL1A antibody of embodiment 1, comprising A109. (Embodiment 238) The anti-TL1A antibody of embodiment 1, wherein the heavy chain variable region comprises a sequence at least about 90%, 95%, 96%, 97%, 98%, 99%, or 100% identical to SEQ ID NO: 133, and the light chain variable region comprises a sequence at least about 90%, 95%, 96%, 97%, 98%, 99%, or 100% identical to SEQ ID NO: 205. (Embodiment 239) The anti-TL1A antibody of embodiment 1, comprising A198. (Embodiment 240) The anti-TL1A antibody of embodiment 1, wherein the heavy chain variable region comprises a sequence at least about 90%, 95%, 96%, 97%, 98%, 99%, or 100% identical to SEQ ID NO: 134, and the light chain variable region comprises a sequence at least about 90%, 95%, 96%, 97%, 98%, 99%, or 100% identical to SEQ ID NO: 205. (Embodiment 241) The anti-TL1A antibody of embodiment 1, comprising A170. (Embodiment 242) The anti-TL1A antibody of embodiment 1, wherein the heavy chain variable region comprises a sequence at least about 90%, 95%, 96%, 97%, 98%, 99%, or 100% identical to SEQ ID NO: 135, and the light chain variable region comprises a sequence at least about 90%, 95%, 96%, 97%, 98%, 99%, or 100% identical to SEQ ID NO: 205. (Embodiment 243) The anti-TL1A antibody of embodiment 1, comprising A500. (Embodiment 244) The anti-TL1A antibody of embodiment 1, comprising A501.

(Embodiment 245) The anti-TL1A of any one of embodiments 1-244, comprising a human IgG1 Fc region comprising: (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. (Embodiment 246) The anti-TL1A of any one of embodiments 1-244, comprising a (i) human IgG4 Fc region or (ii) a human IgG4 Fc region comprising (a) S228P and L235E, or (b) S228P, F234A, and L235A, per Kabat numbering. (Embodiment 247) The anti-TL1A of any one of embodiments 1-244, comprising a human IgG2 Fc region; IgG2-IgG4 cross-subclass Fc region; IgG2-IgG3 cross-subclass Fc region; IgG2 comprising H268Q, V309L, A330S, P331S (IgG2m4); or IgG2 comprising V234A, G237A, P238S, H268A, V309L, A330S, P331S (IgG2σ). (Embodiment 248) The anti-TL1A of any one of embodiments 1-247, comprising a heavy chain Fc region comprising any one of SEQ ID NOS: 320-362. (Embodiment 249) The anti-TL1A of any one of embodiments 1-248, comprising a light chain constant region comprising SEQ ID NO: 319.

(Embodiment 250) The anti-TL1A of any one of embodiments 1-249, comprising at least about 80% monomeric fraction as determined by the size exclusion chromatography method described herein. (Embodiment 251) The anti-TL1A of any one of embodiments 1-250, comprising at least about 81%, at least about 82%, at least about 83%, or at least about 84% monomeric fraction as determined by the size exclusion chromatography method described herein. (Embodiment 252) The anti-TL1A of any one of embodiments 1-251, comprising at least about 85% monomeric fraction as determined by the size exclusion chromatography method described herein. (Embodiment 253) The anti-TL1A of any one of embodiments 1-252, comprising at least about 86%, at least about 87%, at least about 88%, or at least about 89% monomeric fraction as determined by the size exclusion chromatography method described herein. (Embodiment 254) The anti-TL1A of any one of embodiments 1-253, comprising at least about 90% monomeric fraction as determined by the size exclusion chromatography method described herein. (Embodiment 255) The anti-TL1A of any one of embodiments 1-254, comprising at least about 91%, at least about 92%, at least about 93%, or at least about 94% monomeric fraction as determined by the size exclusion chromatography method described herein. (Embodiment 256) The anti-TL1A of any one of embodiments 1-255, comprising at least about 95% monomeric fraction as determined by the size exclusion chromatography method described herein. (Embodiment 257) The anti-TL1A of any one of embodiments 1-256, comprising at least about 96%, at least about 97%, at least about 98%, or at least about 99% monomeric fraction as determined by the size exclusion chromatography method described herein.

(Embodiment 258) The anti-TL1A of any one of embodiments 1-257, comprising at least about 2 μg/mL expression as determined by the method disclosed herein. (Embodiment 259) The anti-TL1A of any one of embodiments 1-258, comprising between about 2 μg/mL and about 60 μg/mL expression as determined by the method disclosed herein. (Embodiment 260) The anti-TL1A of any one of embodiments 1-259, comprising between about 5 μg/mL and about 60 μg/mL expression as determined by the method disclosed herein. (Embodiment 261) The anti-TL1A of any one of embodiments 1-260, comprising between about 10 μg/mL and about 60 μg/mL expression as determined by the method disclosed herein. (Embodiment 262) The anti-TL1A of any one of embodiments 1-261, comprising at least about 5 μg/mL expression as determined by the method disclosed herein. (Embodiment 263) The anti-TL1A of any one of embodiments 1-262, comprising at least about 10 μg/mL expression as determined by the method disclosed herein. (Embodiment 264) The anti-TL1A of any one of embodiments 1-263, comprising at least about 15 μg/mL expression as determined by the method disclosed herein. (Embodiment 265) The anti-TL1A of any one of embodiments 1-264, comprising at least about 20 μg/mL expression as determined by the method disclosed herein.

Exemplary Anti-TL1A Constant Regions

In some embodiments, one or more amino acid modifications may be introduced into the Fragment crystallizable (Fc) region of a human or humanized antibody, thereby generating an Fc region variant. An Fc region may comprise a C-terminal region of an immunoglobulin heavy chain that comprises a hinge region, CH2 domain, CH3 domain, or any combination thereof. As used herein, an Fc region includes native sequence Fc regions and variant Fc regions. The Fc region variant may comprise a human Fc region sequence (e.g., a human IgG1, IgG2, IgG3 or IgG4 Fc region) comprising an amino acid modification (e.g., a substitution, addition, or deletion) at one or more amino acid positions. In an exemplary embodiment, the Fc region comprises any one of SEQ ID NOS: 320-362.

In some embodiments, antibodies of this disclosure have a reduced effector function as compared to a human IgG. Effector function refers to a biological event resulting from the interaction of an antibody Fc region with an Fc receptor or ligand. Non-limiting effector functions include C1q binding, complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation. In some cases, antibody-dependent cell-mediated cytotoxicity (ADCC) refers to a cell-mediated reaction in which nonspecific cytotoxic cells expressing Fc receptors (e.g., natural killer cells, neutrophils, macrophages) recognize bound antibody on a target cell, subsequently causing lysis of the target cell. In some cases, complement dependent cytotoxicity (CDC) refers to lysing of a target cells in the presence of complement, where the complement action pathway is initiated by the binding of C1q to antibody bound with the target.

Some Fc regions have a natural lack of effector function, and some Fc regions can comprise mutations that reduce effector functions. For instance, IgG4 has low ADCC and CDC activities and IgG2 has low ADCC activity.

The disclosure provides antibodies comprising Fc regions characterized by exhibiting ADCC that is reduced by at least about 30%, at least about 40%, at least about 50%, at least about 60%, at least about 70% or more as compared to an antibody comprising a non-variant Fc region, i.e., an antibody with the same sequence identity but for the substitution(s) that decrease ADCC (such as human IgG1, SEQ ID NO: 320). The disclosure provides antibodies comprising Fc regions characterized by exhibiting CDC that is reduced by at least about 30%, at least about 40%, at least about 50%, at least about 60%, at least about 70% or more as compared to an antibody comprising a non-variant Fc region, i.e., an antibody with the same sequence identity but for the substitution(s) that decrease CDC (such as human IgG1, SEQ ID NO: 320). In certain embodiments, the antibodies of this disclosure have reduced effector function as compared with human IgG1. Measurement of effector function may be performed as described in Example 3.

Non-limiting examples of Fc mutations in IgG1 that may reduce ADCC and/or CDC include substitutions at one or more of positions: 231, 232, 234, 235, 236, 237, 238, 239, 264, 265, 267, 269, 270, 297, 299, 318, 320, 322, 325, 327, 328, 329, 330, and 331 in IgG1, where the numbering system of the constant region is that of the EU index as set forth by Kabat. In certain embodiments, the antibodies of this disclosure have reduced effector function as compared with human IgG1.

In some embodiments, an antibody comprises an IgG1 Fc region comprising an N297A substitution, according to the Kabat numbering system. In some embodiments, an antibody comprises an IgG1 Fc region comprising an N297Q substitution, according to the Kabat numbering system. In some embodiments, an antibody comprises an IgG1 Fc region comprising an N297D substitution, according to the Kabat numbering system. In some embodiments, an antibody comprises an IgG1 Fc region comprising an D265A substitution, according to the Kabat numbering system. In some embodiments, an antibody comprises an IgG1 Fc region comprising an S228P substitution, according to the Kabat numbering system. In some embodiments, an antibody comprises an IgG1 Fc region comprising an L235A substitution, according to the Kabat numbering system. In some embodiments, an antibody comprises an IgG1 Fc region comprising an L237A substitution, according to the Kabat numbering system. In some embodiments, an antibody comprises an IgG1 Fc region comprising an L234A substitution, according to the Kabat numbering system. In some embodiments, an antibody comprises an IgG1 Fc region comprising an E233P substitution, according to the Kabat numbering system. In some embodiments, an antibody comprises an IgG1 Fc region comprising an L234V substitution, according to the Kabat numbering system. In some embodiments, an antibody comprises an IgG1 Fc region comprising an C236 deletion, according to the Kabat numbering system. In some embodiments, an antibody comprises an IgG1 Fc region comprising a P238A substitution, according to the Kabat numbering system. In some embodiments, an antibody comprises an IgG1 Fc region comprising an A327Q substitution, according to the Kabat numbering system. In some embodiments, an antibody comprises an IgG1 Fc region comprising a P329A substitution, according to the Kabat numbering system. In some embodiments, an antibody comprises an IgG1 Fc region comprising an P329G substitution, according to the Kabat numbering system. In some embodiments, an antibody comprises an IgG1 Fc region comprising an L235E substitution, according to the Kabat numbering system. In some embodiments, an antibody comprises an IgG1 Fc region comprising an P331S substitution, according to the Kabat numbering system. In some embodiments, an antibody comprises an IgG1 Fc region comprising an L234F substitution, according to the Kabat numbering system. In some embodiments, an antibody comprises an IgG1 Fc region comprising a 235G substitution, according to the Kabat numbering system. In some embodiments, an antibody comprises an IgG1 Fc region comprising an 235Q substitution, according to the Kabat numbering system. In some embodiments, an antibody comprises an IgG1 Fc region comprising an 235R substitution, according to the Kabat numbering system. In some embodiments, an antibody comprises an IgG1 Fc region comprising an 235S substitution, according to the Kabat numbering system. In some embodiments, an antibody comprises an IgG1 Fc region comprising an 236F substitution, according to the Kabat numbering system. In some embodiments, an antibody comprises an IgG1 Fc region comprising an 236R substitution, according to the Kabat numbering system. In some embodiments, an antibody comprises an IgG1 Fc region comprising an 237E substitution, according to the Kabat numbering system. In some embodiments, an antibody comprises an IgG1 Fc region comprising an 237K substitution, according to the Kabat numbering system. In some embodiments, an antibody comprises an IgG1 Fc region comprising an 237N substitution, according to the Kabat numbering system. In some embodiments, an antibody comprises an IgG1 Fc region comprising an 237R substitution, according to the Kabat numbering system. In some embodiments, an antibody comprises an IgG1 Fc region comprising an 238A substitution, according to the Kabat numbering system. In some embodiments, an antibody comprises an IgG1 Fc region comprising an 238E substitution, according to the Kabat numbering system. In some embodiments, an antibody comprises an IgG1 Fc region comprising an 238G substitution, according to the Kabat numbering system. In some embodiments, an antibody comprises an IgG1 Fc region comprising an 238H substitution, according to the Kabat numbering system. In some embodiments, an antibody comprises an IgG1 Fc region comprising an 238I substitution, according to the Kabat numbering system. In some embodiments, an antibody comprises an IgG1 Fc region comprising an 238V substitution, according to the Kabat numbering system. In some embodiments, an antibody comprises an IgG1 Fc region comprising an 238W substitution, according to the Kabat numbering system. In some embodiments, an antibody comprises an IgG1 Fc region comprising an 238Y substitution, according to the Kabat numbering system. In some embodiments, an antibody comprises an IgG1 Fc region comprising an 248A substitution, according to the Kabat numbering system. In some embodiments, an antibody comprises an IgG1 Fc region comprising an 254D substitution, according to the Kabat numbering system. In some embodiments, an antibody comprises an IgG1 Fc region comprising an 254E substitution, according to the Kabat numbering system. In some embodiments, an antibody comprises an IgG1 Fc region comprising an 254G substitution, according to the Kabat numbering system. In some embodiments, an antibody comprises an IgG1 Fc region comprising an 254H substitution, according to the Kabat numbering system. In some embodiments, an antibody comprises an IgG1 Fc region comprising an 254I substitution, according to the Kabat numbering system. In some embodiments, an antibody comprises an IgG1 Fc region comprising an 254N substitution, according to the Kabat numbering system. In some embodiments, an antibody comprises an IgG1 Fc region comprising an 254P substitution, according to the Kabat numbering system. In some embodiments, an antibody comprises an IgG1 Fc region comprising an 254Q substitution, according to the Kabat numbering system. In some embodiments, an antibody comprises an IgG1 Fc region comprising an 254T substitution, according to the Kabat numbering system. In some embodiments, an antibody comprises an IgG1 Fc region comprising an 254V substitution, according to the Kabat numbering system. In some embodiments, an antibody comprises an IgG1 Fc region comprising an 255N substitution, according to the Kabat numbering system. In some embodiments, an antibody comprises an IgG1 Fc region comprising an 256H substitution, according to the Kabat numbering system. In some embodiments, an antibody comprises an IgG1 Fc region comprising an 256K substitution, according to the Kabat numbering system. In some embodiments, an antibody comprises an IgG1 Fc region comprising an 256R substitution, according to the Kabat numbering system. In some embodiments, an antibody comprises an IgG1 Fc region comprising an 256V substitution, according to the Kabat numbering system. In some embodiments, an antibody comprises an IgG1 Fc region comprising an 264S substitution, according to the Kabat numbering system. In some embodiments, an antibody comprises an IgG1 Fc region comprising an 265H substitution, according to the Kabat numbering system. In some embodiments, an antibody comprises an IgG1 Fc region comprising an 265K substitution, according to the Kabat numbering system. In some embodiments, an antibody comprises an IgG1 Fc region comprising an 265S substitution, according to the Kabat numbering system. In some embodiments, an antibody comprises an IgG1 Fc region comprising an 265Y substitution, according to the Kabat numbering system. In some embodiments, an antibody comprises an IgG1 Fc region comprising an 267G substitution, according to the Kabat numbering system. In some embodiments, an antibody comprises an IgG1 Fc region comprising an 267H substitution, according to the Kabat numbering system. In some embodiments, an antibody comprises an IgG1 Fc region comprising an 267I substitution, according to the Kabat numbering system. In some embodiments, an antibody comprises an IgG1 Fc region comprising an 267K substitution, according to the Kabat numbering system. In some embodiments, an antibody comprises an IgG1 Fc region comprising an 268K substitution, according to the Kabat numbering system. In some embodiments, an antibody comprises an IgG1 Fc region comprising an 269N substitution, according to the Kabat numbering system. In some embodiments, an antibody comprises an IgG1 Fc region comprising an 269Q substitution, according to the Kabat numbering system. In some embodiments, an antibody comprises an IgG1 Fc region comprising an 270A substitution, according to the Kabat numbering system. In some embodiments, an antibody comprises an IgG1 Fc region comprising an 270G substitution, according to the Kabat numbering system. In some embodiments, an antibody comprises an IgG1 Fc region comprising an 270M substitution, according to the Kabat numbering system. In some embodiments, an antibody comprises an IgG1 Fc region comprising an 270N substitution, according to the Kabat numbering system. In some embodiments, an antibody comprises an IgG1 Fc region comprising an 271T substitution, according to the Kabat numbering system. In some embodiments, an antibody comprises an IgG1 Fc region comprising an 272N substitution, according to the Kabat numbering system. In some embodiments, an antibody comprises an IgG1 Fc region comprising an 279F substitution, according to the Kabat numbering system. In some embodiments, an antibody comprises an IgG1 Fc region comprising an 279K substitution, according to the Kabat numbering system. In some embodiments, an antibody comprises an IgG1 Fc region comprising an 279L substitution, according to the Kabat numbering system. In some embodiments, an antibody comprises an IgG1 Fc region comprising an 292E substitution, according to the Kabat numbering system. In some embodiments, an antibody comprises an IgG1 Fc region comprising an 292F substitution, according to the Kabat numbering system. In some embodiments, an antibody comprises an IgG1 Fc region comprising an 292G substitution, according to the Kabat numbering system. In some embodiments, an antibody comprises an IgG1 Fc region comprising an 292I substitution, according to the Kabat numbering system. In some embodiments, an antibody comprises an IgG1 Fc region comprising an 293 S substitution, according to the Kabat numbering system. In some embodiments, an antibody comprises an IgG1 Fc region comprising an 301W substitution, according to the Kabat numbering system. In some embodiments, an antibody comprises an IgG1 Fc region comprising an 304E substitution, according to the Kabat numbering system. In some embodiments, an antibody comprises an IgG1 Fc region comprising an 311E substitution, according to the Kabat numbering system. In some embodiments, an antibody comprises an IgG1 Fc region comprising an 311G substitution, according to the Kabat numbering system. In some embodiments, an antibody comprises an IgG1 Fc region comprising an 311S substitution, according to the Kabat numbering system. In some embodiments, an antibody comprises an IgG1 Fc region comprising an 316F substitution, according to the Kabat numbering system. In some embodiments, an antibody comprises an IgG1 Fc region comprising an 327T substitution, according to the Kabat numbering system. In some embodiments, an antibody comprises an IgG1 Fc region comprising an 328V substitution, according to the Kabat numbering system. In some embodiments, an antibody comprises an IgG1 Fc region comprising an 329Y substitution, according to the Kabat numbering system. In some embodiments, an antibody comprises an IgG1 Fc region comprising an 330R substitution, according to the Kabat numbering system. In some embodiments, an antibody comprises an IgG1 Fc region comprising an 339E substitution, according to the Kabat numbering system. In some embodiments, an antibody comprises an IgG1 Fc region comprising an 339L substitution, according to the Kabat numbering system. In some embodiments, an antibody comprises an IgG1 Fc region comprising an 343I substitution, according to the Kabat numbering system. In some embodiments, an antibody comprises an IgG1 Fc region comprising an 343V substitution, according to the Kabat numbering system. In some embodiments, an antibody comprises an IgG1 Fc region comprising an 373A substitution, according to the Kabat numbering system. In some embodiments, an antibody comprises an IgG1 Fc region comprising an 373G substitution, according to the Kabat numbering system. In some embodiments, an antibody comprises an IgG1 Fc region comprising an 373S substitution, according to the Kabat numbering system. In some embodiments, an antibody comprises an IgG1 Fc region comprising an 376E substitution, according to the Kabat numbering system. In some embodiments, an antibody comprises an IgG1 Fc region comprising an 376W substitution, according to the Kabat numbering system. In some embodiments, an antibody comprises an IgG1 Fc region comprising an 376Y substitution, according to the Kabat numbering system. In some embodiments, an antibody comprises an IgG1 Fc region comprising an 380D substitution, according to the Kabat numbering system. In some embodiments, an antibody comprises an IgG1 Fc region comprising an 382D substitution, according to the Kabat numbering system. In some embodiments, an antibody comprises an IgG1 Fc region comprising an 382P substitution, according to the Kabat numbering system. In some embodiments, an antibody comprises an IgG1 Fc region comprising an 385P substitution, according to the Kabat numbering system. In some embodiments, an antibody comprises an IgG1 Fc region comprising an 424H substitution, according to the Kabat numbering system. In some embodiments, an antibody comprises an IgG1 Fc region comprising an 424M substitution, according to the Kabat numbering system. In some embodiments, an antibody comprises an IgG1 Fc region comprising an 424V substitution, according to the Kabat numbering system. In some embodiments, an antibody comprises an IgG1 Fc region comprising an 434I substitution, according to the Kabat numbering system. In some embodiments, an antibody comprises an IgG1 Fc region comprising an 438G substitution, according to the Kabat numbering system. In some embodiments, an antibody comprises an IgG1 Fc region comprising an 439E substitution, according to the Kabat numbering system. In some embodiments, an antibody comprises an IgG1 Fc region comprising an 439H substitution, according to the Kabat numbering system. In some embodiments, an antibody comprises an IgG1 Fc region comprising an 439Q substitution, according to the Kabat numbering system. In some embodiments, an antibody comprises an IgG1 Fc region comprising an 440A substitution, according to the Kabat numbering system. In some embodiments, an antibody comprises an IgG1 Fc region comprising an 440D substitution, according to the Kabat numbering system. In some embodiments, an antibody comprises an IgG1 Fc region comprising an 440E substitution, according to the Kabat numbering system. In some embodiments, an antibody comprises an IgG1 Fc region comprising an 440F substitution, according to the Kabat numbering system. In some embodiments, an antibody comprises an IgG1 Fc region comprising an 440M substitution, according to the Kabat numbering system. In some embodiments, an antibody comprises an IgG1 Fc region comprising an 440T Fc region substitution, according to the Kabat numbering system. In some embodiments, an antibody comprises an IgG1 Fc region comprising an 440V substitution, according to the Kabat numbering system.

In some embodiments, an antibody comprises a Fc region selected from the representative sequences disclosed in Table 3. In some embodiments, an antibody comprises an IgG1 Fc region comprising E233P, according to the Kabat numbering system. In some embodiments, an antibody comprises an IgG4 Fc region comprising S228P and L235E. In some embodiments, an antibody comprises an IgG1 Fc region comprising L235E, according to the Kabat numbering system. In some embodiments, an antibody comprises an IgG1 Fc region comprising L234A and L235A, according to the Kabat numbering system. In some embodiments, an antibody comprises an IgG1 Fc region comprising L234A, L235A, and G237A, according to the Kabat numbering system. In some embodiments, an antibody comprises an IgG1 Fc region comprising L234A, L235A, P329G, according to the Kabat numbering system. In some embodiments, an antibody comprises an IgG1 Fc region comprising L234F, L235E, and P331S, according to the Kabat numbering system. In some embodiments, an antibody comprises an IgG1 Fc region comprising L234A, L235E, and G237A, according to the Kabat numbering system. In some embodiments, an antibody comprises an IgG1 Fc region comprising L234A, L235E, G237A, and P331S, according to the Kabat numbering system. In some embodiments, an antibody comprises an IgG1 Fc region comprising L234A, L235A, G237A, P238S, H268A, A330S, and P331S (IgG1σ), according to the Kabat numbering system. In some embodiments, an antibody comprises an IgG1 Fc region comprising L234A, L235A, and P329A, according to the Kabat numbering system. In some embodiments, an antibody comprises an IgG1 Fc region comprising G236R and L328R, according to the Kabat numbering system. In some embodiments, an antibody comprises an IgG1 Fc region comprising G237A, according to the Kabat numbering system. In some embodiments, an antibody comprises an IgG1 Fc region comprising F241A, according to the Kabat numbering system. In some embodiments, an antibody comprises an IgG1 Fc region comprising V264A, according to the Kabat numbering system. In some embodiments, an antibody comprises an IgG1 Fc region comprising D265A, according to the Kabat numbering system. In some embodiments, an antibody comprises an IgG1 Fc region comprising D265A and N297A, according to the Kabat numbering system. In some embodiments, an antibody comprises an IgG1 Fc region comprising D265A and N297G, according to the Kabat numbering system. In some embodiments, an antibody comprises an IgG1 Fc region comprising D270A, according to the Kabat numbering system. In some embodiments, an antibody comprises an IgG1 Fc region comprising N297A, according to the Kabat numbering system. In some embodiments, an antibody comprises an IgG1 Fc region comprising N297G, according to the Kabat numbering system. In some embodiments, an antibody comprises an IgG1 Fc region comprising N297D, according to the Kabat numbering system. In some embodiments, an antibody comprises an IgG1 Fc region comprising N297Q, according to the Kabat numbering system. In some embodiments, an antibody comprises an IgG1 Fc region comprising P329A, according to the Kabat numbering system. In some embodiments, an antibody comprises an IgG1 Fc region comprising P329G, according to the Kabat numbering system. In some embodiments, an antibody comprises an IgG1 Fc region comprising P329R, according to the Kabat numbering system. In some embodiments, an antibody comprises an IgG1 Fc region comprising A330L, according to the Kabat numbering system. In some embodiments, an antibody comprises an IgG1 Fc region comprising P331A, according to the Kabat numbering system. In some embodiments, an antibody comprises an IgG1 Fc region comprising P331S, according to the Kabat numbering system. In some embodiments, an antibody comprises an IgG2 Fc region. In some embodiments, an antibody comprises an IgG4 Fc region. In some embodiments, an antibody comprises an IgG4 Fc region comprising S228P, according to the Kabat numbering system. In some embodiments, an antibody comprises an IgG4 Fc region comprising S228P, F234A, and L235A, according to the Kabat numbering system. In some embodiments, an antibody comprises an IgG2-IgG4 cross-subclass (IgG2/G4) Fc region. In some embodiments, an antibody comprises an IgG2-IgG3 cross-subclass Fc region. In some embodiments, an antibody comprises an IgG2 Fc region comprising H268Q, V309L, A330S, and P331S, according to the Kabat numbering system. In some embodiments, an antibody comprises an IgG2 Fc region comprising V234A, G237A, P238S, H268A, V309L, A330S, and P331S, according to the Kabat numbering system. In some embodiments, an antibody comprises a Fc region comprising high mannose glycosylation.

In some embodiments, an antibody comprises an IgG4 Fc region comprising a S228P substitution, according to the Kabat numbering system. In some embodiments, an antibody comprises an IgG4 Fc region comprising an A330S substitution, according to the Kabat numbering system. In some embodiments, an antibody comprises an IgG4 Fc region comprising a P331S substitution, according to the Kabat numbering system.

In some embodiments, an antibody comprises an IgG2 Fc region comprising an A330S substitution, according to the Kabat numbering system. In some embodiments, an antibody comprises an IgG2 Fc region comprising an P331S substitution, according to the Kabat numbering system. In some embodiments, an antibody comprises an IgG2 Fc region comprising an 234A substitution, according to the Kabat numbering system. In some embodiments, an antibody comprises an IgG2 Fc region comprising an 237A substitution, according to the Kabat numbering system.

In certain embodiments, an anti-TL1A antibody described herein comprises a Fc region comprising a sequence from Table 9B. In certain embodiments, an anti-TL1A described herein comprises a Fc region as shown in Table 14.

TABLE 14

Exemplary Fc Mutations

| Mutations | Constant Region (SEQ ID NO) | | |
|---|---|---|---|
| | K_DL | R_EM | K_EM |
| Wild-type IgG1 | 320 | 321 | 322 |
| L235E | 323 | 324 | 325 |
| L234A, L235A | 326 | 327 | 328 |
| L234A, L235A, G237A | 329 | 330 | 331 |
| L234A, L235A, P329G | 332 | 333 | 334 |
| L234F, L235E, P331S | 335 | 336 | 337 |
| L234A, L235E, G237A | 338 | 339 | 340 |
| L234A, L235E, G237A, P331S | 341 | 342 | 343 |
| L234A, L235A, P329A | 344 | 345 | 346 |
| D265A | 347 | 348 | 349 |
| N297G | 350 | 351 | 352 |
| D265A, N297A | 353 | 354 | 355 |
| D265A, N297G | 356 | 357 | 358 |
| L235A, G237A | 359 | 360 | 361 |
| Wild-type IgG4 | 362 | | |

In certain embodiments, an anti-TL1A antibody described herein comprises a Fc region comprising SEQ ID NO: 320 or a sequence at least about 90%, 91%, 92%, 93%, 94%, 95%, 96%, 97%, 98%, or 99% identical to SEQ ID NO: 320. In certain embodiments, an anti-TL1A antibody described herein comprises a Fc region comprising SEQ ID NO: 321 or a sequence at least about 90%, 91%, 92%, 93%, 94%, 95%, 96%, 97%, 98%, or 99% identical to SEQ ID NO: 321. In certain embodiments, an anti-TL1A antibody described herein comprises a Fc region comprising SEQ ID NO: 322 or a sequence at least about 90%, 91%, 92%, 93%, 94%, 95%, 96%, 97%, 98%, or 99% identical to SEQ ID NO: 322. In certain embodiments, an anti-TL1A antibody described herein comprises a Fc region comprising SEQ ID NO: 323 or a sequence at least about 90%, 91%, 92%, 93%, 94%, 95%, 96%, 97%, 98%, or 99% identical to SEQ ID NO: 323. In certain embodiments, an anti-TL1A antibody described herein comprises a Fc region comprising SEQ ID NO: 324 or a sequence at least about 90%, 91%, 92%, 93%, 94%, 95%, 96%, 97%, 98%, or 99% identical to SEQ ID NO: 324. In certain embodiments, an anti-TL1A antibody described herein comprises a Fc region comprising SEQ ID NO: 325 or a sequence at least about 90%, 91%, 92%, 93%, 94%, 95%, 96%, 97%, 98%, or 99% identical to SEQ ID NO: 325. In certain embodiments, an anti-TL1A antibody described herein comprises a Fc region comprising SEQ ID NO: 326 or a sequence at least about 90%, 91%, 92%, 93%, 94%, 95%, 96%, 97%, 98%, or 99% identical to SEQ ID NO: 326. In certain embodiments, an anti-TL1A antibody described herein comprises a Fc region comprising SEQ ID NO: 327 or a sequence at least about 90%, 91%, 92%, 93%, 94%, 95%, 96%, 97%, 98%, or 99% identical to SEQ ID NO: 327. In certain embodiments, an anti-TL1A antibody described herein comprises a Fc region comprising SEQ ID NO: 328 or a sequence at least about 90%, 91%, 92%, 93%, 94%, 95%, 96%, 97%, 98%, or 99% identical to SEQ ID NO: 328.

In certain embodiments, an anti-TL1A antibody described herein comprises a Fc region comprising SEQ ID NO: 329 or a sequence at least about 90%, 91%, 92%, 93%, 94%, 95%, 96%, 97%, 98%, or 99% identical to SEQ ID NO: 329. In certain embodiments, an anti-TL1A antibody described herein comprises a Fc region comprising SEQ ID NO: 330 or a sequence at least about 90%, 91%, 92%, 93%, 94%, 95%, 96%, 97%, 98%, or 99% identical to SEQ ID NO: 330. In certain embodiments, an anti-TL1A antibody described herein comprises a Fc region comprising SEQ ID NO: 331 or a sequence at least about 90%, 91%, 92%, 93%, 94%, 95%, 96%, 97%, 98%, or 99% identical to SEQ ID NO: 331. In certain embodiments, an anti-TL1A antibody described herein comprises a Fc region comprising SEQ ID NO: 332 or a sequence at least about 90%, 91%, 92%, 93%, 94%, 95%, 96%, 97%, 98%, or 99% identical to SEQ ID NO: 332. In certain embodiments, an anti-TL1A antibody described herein comprises a Fc region comprising SEQ ID NO: 333 or a sequence at least about 90%, 91%, 92%, 93%, 94%, 95%, 96%, 97%, 98%, or 99% identical to SEQ ID NO: 333. In certain embodiments, an anti-TL1A antibody described herein comprises a Fc region comprising SEQ ID NO: 334 or a sequence at least about 90%, 91%, 92%, 93%, 94%, 95%, 96%, 97%, 98%, or 99% identical to SEQ ID NO: 334. In certain embodiments, an anti-TL1A antibody described herein comprises a Fc region comprising SEQ ID NO: 335 or a sequence at least about 90%, 91%, 92%, 93%, 94%, 95%, 96%, 97%, 98%, or 99% identical to SEQ ID NO: 335. In certain embodiments, an anti-TL1A antibody described herein comprises a Fc region comprising SEQ ID NO: 336 or a sequence at least about 90%, 91%, 92%, 93%, 94%, 95%, 96%, 97%, 98%, or 99% identical to SEQ ID NO: 336. In certain embodiments, an anti-TL1A antibody described herein comprises a Fc region comprising SEQ ID NO: 337 or a sequence at least about 90%, 91%, 92%, 93%, 94%, 95%, 96%, 97%, 98%, or 99% identical to SEQ ID NO: 337. In certain embodiments, an anti-TL1A antibody described herein comprises a Fc region comprising SEQ ID NO: 338 or a sequence at least about 90%, 91%, 92%, 93%, 94%, 95%, 96%, 97%, 98%, or 99% identical to SEQ ID NO: 338. In certain embodiments, an anti-TL1A antibody described herein comprises a Fc region comprising SEQ ID NO: 339 or a sequence at least about 90%, 91%, 92%, 93%, 94%, 95%, 96%, 97%, 98%, or 99% identical to SEQ ID NO: 339. In certain embodiments, an anti-TL1A antibody described herein comprises a Fc region comprising SEQ ID NO: 340 or a sequence at least about 90%, 91%, 92%, 93%, 94%, 95%, 96%, 97%, 98%, or 99% identical to SEQ ID NO: 340. In certain embodiments, an anti-TL1A antibody described herein comprises a Fc region comprising SEQ ID NO: 341 or a sequence at least about 90%, 91%, 92%, 93%, 94%, 95%, 96%, 97%, 98%, or 99% identical to SEQ ID NO: 341. In certain embodiments, an anti-TL1A antibody described herein comprises a Fc region comprising SEQ ID NO: 342 or a sequence at least about 90%, 91%, 92%, 93%, 94%, 95%, 96%, 97%, 98%, or 99% identical to SEQ ID NO: 342. In certain embodiments, an anti-TL1A antibody described herein comprises a Fc region comprising SEQ ID NO: 343 or a sequence at least about 90%, 91%, 92%, 93%, 94%, 95%, 96%, 97%, 98%, or 99% identical to SEQ ID NO: 343. In certain embodiments, an anti-TL1A antibody described herein comprises a Fc region comprising SEQ ID NO: 344 or a sequence at least about 90%, 91%, 92%, 93%, 94%, 95%, 96%, 97%, 98%, or 99% identical to SEQ ID NO: 344. In certain embodiments, an anti-TL1A antibody described herein comprises a Fc region comprising SEQ ID NO: 345 or a sequence at least about 90%, 91%, 92%, 93%, 94%, 95%, 96%, 97%, 98%, or 99% identical to SEQ ID NO: 345. In certain embodiments, an anti-TL1A antibody described herein comprises a Fc region comprising SEQ ID NO: 346 or a sequence at least about 90%, 91%, 92%, 93%, 94%, 95%, 96%, 97%, 98%, or 99% identical to SEQ ID NO: 346. In certain embodiments, an anti-TL1A antibody described herein comprises a Fc region comprising SEQ ID NO: 347 or a sequence at least about 90%, 91%, 92%, 93%, 94%, 95%, 96%, 97%, 98%, or 99% identical to SEQ ID NO: 347. In certain embodiments, an anti-TL1A antibody described herein comprises a Fc region comprising SEQ ID NO: 348 or a sequence at least about 90%, 91%, 92%, 93%, 94%, 95%, 96%, 97%, 98%, or 99% identical to SEQ ID NO: 348. In certain embodiments, an anti-TL1A antibody described herein comprises a Fc region comprising SEQ ID NO: 349 or a sequence at least about 90%, 91%, 92%, 93%, 94%, 95%, 96%, 97%, 98%, or 99% identical to SEQ ID NO: 349. In certain embodiments, an anti-TL1A antibody described herein comprises a Fc region comprising SEQ ID NO: 350 or a sequence at least about 90%, 91%, 92%, 93%, 94%, 95%, 96%, 97%, 98%, or 99% identical to SEQ ID NO: 350. In certain embodiments, an anti-TL1A antibody described herein comprises a Fc region comprising SEQ ID NO: 351 or a sequence at least about 90%, 91%, 92%, 93%, 94%, 95%, 96%, 97%, 98%, or 99% identical to SEQ ID NO: 351. In certain embodiments, an anti-TL1A antibody described herein comprises a Fc region comprising SEQ ID NO: 352 or a sequence at least about 90%, 91%, 92%, 93%, 94%, 95%, 96%, 97%, 98%, or 99% identical to SEQ ID NO: 352. In certain embodiments, an anti-TL1A antibody described herein comprises a Fc region comprising SEQ ID NO: 353 or a sequence at least about 90%, 91%, 92%, 93%, 94%, 95%, 96%, 97%, 98%, or 99% identical to SEQ ID NO: 353. In certain embodiments, an anti-TL1A antibody described herein comprises a Fc region comprising SEQ ID NO: 354 or a sequence at least about 90%, 91%, 92%, 93%, 94%, 95%, 96%, 97%, 98%, or 99% identical to SEQ ID NO: 354. In certain embodiments, an anti-TL1A antibody described herein comprises a Fc region comprising SEQ ID NO: 355 or a sequence at least about 90%, 91%, 92%, 93%, 94%, 95%, 96%, 97%, 98%, or 99% identical to SEQ ID NO: 355. In certain embodiments, an anti-TL1A antibody described herein comprises a Fc region comprising SEQ ID NO: 356 or a sequence at least about 90%, 91%, 92%, 93%, 94%, 95%, 96%, 97%, 98%, or 99% identical to SEQ ID NO: 356. In certain embodiments, an anti-TL1A antibody described herein comprises a Fc region comprising SEQ ID NO: 357 or a sequence at least about 90%, 91%, 92%, 93%, 94%, 95%, 96%, 97%, 98%, or 99% identical to SEQ ID NO: 357. In certain embodiments, an anti-TL1A antibody described herein comprises a Fc region comprising SEQ ID NO: 358 or a sequence at least about 90%, 91%, 92%, 93%, 94%, 95%, 96%, 97%, 98%, or 99% identical to SEQ ID NO: 358. In certain embodiments, an anti-TL1A antibody described herein comprises a Fc region comprising SEQ ID NO: 359 or a sequence at least about 90%, 91%, 92%, 93%, 94%, 95%, 96%, 97%, 98%, or 99% identical to SEQ ID NO: 359. In certain embodiments, an anti-TL1A antibody described herein comprises a Fc region comprising SEQ ID NO: 360 or a sequence at least about 90%, 91%, 92%, 93%, 94%, 95%, 96%, 97%, 98%, or 99% identical to SEQ ID NO: 360. In certain embodiments, an anti-TL1A antibody described herein comprises a Fc region comprising SEQ ID NO: 361 or a sequence at least about 90%, 91%, 92%, 93%, 94%, 95%, 96%, 97%, 98%, or 99% identical to SEQ ID NO: 361. In certain embodiments, an anti-TL1A antibody described herein comprises a Fc region comprising SEQ ID NO: 362 or a sequence at least about 90%, 91%, 92%, 93%, 94%, 95%, 96%, 97%, 98%, or 99% identical to SEQ ID NO: 362.

In some embodiments, the antibodies of this disclosure are variants that possess some but not all effector functions, which make it a desirable candidate for applications in which the half-life of the antibody in vivo is important yet certain effector functions (such as complement and ADCC) are unnecessary or deleterious.

In vitro and/or in vivo cytotoxicity assays can be conducted to confirm the reduction/depletion of CDC and/or ADCC activities. For example, Fc receptor (FCR) binding assays can be conducted to ensure that the antibody lacks FcγR binding (hence likely lacking ADCC activity) but retains FcRn binding ability. Measurement of effector function may be performed as described in Example 3.

In some embodiments, antibodies are tested for binding to Fcγ receptors and complement C1q by ELISA. In some embodiments, antibodies are tested for the ability to activate primary human immune cells in vitro, for example, by assessing their ability to induce expression of activation markers.

In some embodiments, assessment of ADCC activity of an anti-TL1A antibody comprises adding the antibody to target cells in combination with immune effector cells, which may be activated by the antigen antibody complexes resulting in cytolysis of the target cell. Cytolysis may be detected by the release of label (e.g. radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985 79:277-282; Bruggemann et al., 1987, J Exp Med 166:1351-1361; Wilkinson et al., 2001, J Immunol Methods 258:183-191; Patel et al., 1995 J Immunol Methods 184:29-38. Alternatively, or additionally, ADCC activity of the antibody of interest may be assessed in vivo, e.g., in an animal model such as that disclosed in Clynes et al., 1998, PNAS USA 95:652-656.

In some embodiments, antibodies comprising a Fc region herein exhibit decreased ADCC activities as compared to an unmodified antibody (e.g., an antibody with human IgG1). In some embodiments, the antibodies herein exhibit ADCC activities that are at least 2-fold, or at least 3-fold, or at least 5-fold or at least 10-fold or at least 50-fold or at least 100-fold less than that of an unmodified antibody. In some embodiments, antibodies herein exhibit ADCC activities that are reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to an unmodified antibody. In certain embodiments, antibodies herein have no detectable ADCC activity. In certain embodiments, the reduction and/or ablatement of ADCC activity may be attributed to the reduced affinity antibodies of the invention exhibit for Fc ligands and/or receptors.

In some embodiments, an assessment of complement activation, a CDC assay, may be performed as described in Gazzano-Santoro et al., 1996, J. Immunol. Methods, 202: 163.

In some embodiments, antibodies comprising Fc regions described herein exhibit decreased affinities to C1q relative to an unmodified antibody (e.g., human IgG1). In some embodiments, antibodies herein exhibit affinities for C1q receptor that are at least 2 fold, or at least 3 fold, or at least 5 fold, or at least 7 fold, or at least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than an unmodified antibody. In some embodiments, antibodies herein exhibit affinities for C1q that are at least 90%, at least 80%, at least 70%, at least 60%, at least 50%, at least 40%, at least 30%, at least 20%, at least 10%, or at least 5% less than an unmodified antibody. In some embodiments, antibodies herein exhibit affinities for C1q that are between about 100 nM to about 100 μM, or about 100 nM to about 10 μM, or about 100 nM to about 1 μM, or about 1 nM to about 100 μM, or about 10 nM to about 100 μM, or about 1 μM to about 100 μM, or about 10 μM to about 100 μM. In certain embodiments, antibodies herein exhibit affinities for C1q that are greater than 1 μM, greater than 5 μM, greater than 10 μM, greater than 25 μM, greater than 50 μM, or greater than 100 μM.

In some embodiments, antibodies comprising Fc regions described herein exhibit decreased CDC activities as compared to an unmodified antibody (e.g., human IgG1). In some embodiments, antibodies herein exhibit CDC activities that are at least 2-fold, or at least 3-fold, or at least 5-fold or at least 10-fold or at least 50-fold or at least 100-fold less than that of an unmodified antibody. In some embodiments, antibodies herein exhibit CDC activities that are reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to an unmodified antibody. In certain embodiments, antibodies herein exhibit no detectable CDC activities. In some embodiments, the reduction and/or ablatement of CDC activity may be attributed to the reduced affinity antibodies of the invention exhibit for Fc ligands and/or receptors.

Accordingly, further provided and described herein are anti-TL1A antibodies comprising a variant (e.g. harboring mutations) Fc region that reduce the cytotoxic response (e.g. ADCC or CDC) elicited by an anti-TL1A antibody. In some embodiments, an anti-TL1A antibody described herein comprises a Fc region comprising SEQ ID NO: 401 or a sequence at least about 90%, 91%, 92%, 93%, 94%, 95%, 96%, 97%, 98%, or 99% identical to SEQ ID NO: 401. In some embodiments, an anti-TL1A antibody described herein comprises a Fc region comprising SEQ ID NO: 402 or a sequence at least about 90%, 91%, 92%, 93%, 94%, 95%, 96%, 97%, 98%, or 99% identical to SEQ ID NO: 402. In some embodiments, an anti-TL1A antibody described herein comprises a Fc region comprising SEQ ID NO: 403 or a sequence at least about 90%, 91%, 92%, 93%, 94%, 95%, 96%, 97%, 98%, or 99% identical to SEQ ID NO: 403. In some embodiments, an anti-TL1A antibody described herein comprises a Fc region comprising SEQ ID NO: 404 or a sequence at least about 90%, 91%, 92%, 93%, 94%, 95%, 96%, 97%, 98%, or 99% identical to SEQ ID NO: 404. In some embodiments, an anti-TL1A antibody described herein comprises a Fc region comprising SEQ ID NO: 405 or a sequence at least about 90%, 91%, 92%, 93%, 94%, 95%, 96%, 97%, 98%, or 99% identical to SEQ ID NO: 405. In some embodiments, an anti-TL1A antibody described herein comprises a Fc region comprising SEQ ID NO: 406 or a sequence at least about 90%, 91%, 92%, 93%, 94%, 95%, 96%, 97%, 98%, or 99% identical to SEQ ID NO: 406. In some embodiments, an anti-TL1A antibody described herein comprises a Fc region comprising SEQ ID NO: 407 or a sequence at least about 90%, 91%, 92%, 93%, 94%, 95%, 96%, 97%, 98%, or 99% identical to SEQ ID NO: 407. In some embodiments, an anti-TL1A antibody described herein comprises a Fc region comprising SEQ ID NO: 408 or a sequence at least about 90%, 91%, 92%, 93%, 94%, 95%, 96%, 97%, 98%, or 99% identical to SEQ ID NO: 408. In some embodiments, an anti-TL1A antibody described herein comprises a Fc region comprising SEQ ID NO: 409 or a sequence at least about 90%, 91%, 92%, 93%, 94%, 95%, 96%, 97%, 98%, or 99% identical to SEQ ID NO: 409. In some embodiments, an anti-TL1A antibody described herein comprises a Fc region comprising SEQ ID NO: 410 or a sequence at least about 90%, 91%, 92%, 93%, 94%, 95%, 96%, 97%, 98%, or 99% identical to SEQ ID NO: 410. In some embodiments, an anti-TL1A antibody described herein comprises a Fc region comprising SEQ ID NO: 411 or a sequence at least about 90%, 91%, 92%, 93%, 94%, 95%, 96%, 97%, 98%, or 99% identical to SEQ ID NO: 411. In some embodiments, an anti-TL1A antibody described herein comprises a Fc region comprising SEQ ID NO: 412 or a sequence at least about 90%, 91%, 92%, 93%, 94%, 95%, 96%, 97%, 98%, or 99% identical to SEQ ID NO: 412. In some embodiments, an anti-TL1A antibody described herein comprises a Fc region comprising SEQ ID NO: 413 or a sequence at least about 90%, 91%, 92%, 93%, 94%, 95%, 96%, 97%, 98%, or 99% identical to SEQ ID NO: 413.

By way of further example, in certain embodiments, an anti-TL1A antibody described herein comprises a heavy chain comprising SEQ ID NO: 501 or a sequence at least about 90%, 91%, 92%, 93%, 94%, 95%, 96%, 97%, 98%, or 99% identical to SEQ ID NO: 501. In certain embodiments, an anti-TL1A antibody described herein comprises a heavy chain comprising SEQ ID NO: 502 or a sequence at least about 90%, 91%, 92%, 93%, 94%, 95%, 96%, 97%, 98%, or 99% identical to SEQ ID NO: 502. In certain embodiments, an anti-TL1A antibody described herein comprises a heavy chain comprising SEQ ID NO: 503 or a sequence at least about 90%, 91%, 92%, 93%, 94%, 95%, 96%, 97%, 98%, or 99% identical to SEQ ID NO: 503. In certain embodiments, an anti-TL1A antibody described herein comprises a heavy chain comprising SEQ ID NO: 504 or a sequence at least about 90%, 91%, 92%, 93%, 94%, 95%, 96%, 97%, 98%, or 99% identical to SEQ ID NO: 504. In certain embodiments, an anti-TL1A antibody described herein comprises a heavy chain comprising SEQ ID NO: 505 or a sequence at least about 90%, 91%, 92%, 93%, 94%, 95%, 96%, 97%, 98%, or 99% identical to SEQ ID NO: 505. In certain embodiments, an anti-TL1A antibody described herein comprises a heavy chain comprising SEQ ID NO: 506 or a sequence at least about 90%, 91%, 92%, 93%, 94%, 95%, 96%, 97%, 98%, or 99% identical to SEQ ID NO: 506. In certain embodiments, an anti-TL1A antibody described herein comprises a heavy chain comprising SEQ ID NO: 507 or a sequence at least about 90%, 91%, 92%, 93%, 94%, 95%, 96%, 97%, 98%, or 99% identical to SEQ ID NO: 507. In certain embodiments, an anti-TL1A antibody described herein comprises a heavy chain comprising SEQ ID NO: 508 or a sequence at least about 90%, 91%, 92%, 93%, 94%, 95%, 96%, 97%, 98%, or 99% identical to SEQ ID NO: 508. In certain embodiments, an anti-TL1A antibody described herein comprises a heavy chain comprising SEQ ID NO: 509 or a sequence at least about 90%, 91%, 92%, 93%, 94%, 95%, 96%, 97%, 98%, or 99% identical to SEQ ID NO: 509. In certain embodiments, an anti-TL1A antibody described herein comprises a heavy chain comprising SEQ ID NO: 510 or a sequence at least about 90%, 91%, 92%, 93%, 94%, 95%, 96%, 97%, 98%, or 99% identical to SEQ ID NO: 510. In certain embodiments, an anti-TL1A antibody described herein comprises a heavy chain comprising SEQ ID NO: 511 or a sequence at least about 90%, 91%, 92%, 93%, 94%, 95%, 96%, 97%, 98%, or 99% identical to SEQ ID NO: 511. In certain embodiments, an anti-TL1A antibody described herein comprises a heavy chain comprising SEQ ID NO: 512 or a sequence at least about 90%, 91%, 92%, 93%, 94%, 95%, 96%, 97%, 98%, or 99% identical to SEQ ID NO: 512. In certain embodiments, an anti-TL1A antibody described herein comprises a heavy chain comprising SEQ ID NO: 513 or a sequence at least about 90%, 91%, 92%, 93%, 94%, 95%, 96%, 97%, 98%, or 99% identical to SEQ ID NO: 513. In certain embodiments, the heavy chain is paired with a light chain comprising SEQ ID NO: 514 or a sequence at least about 90%, 91%, 92%, 93%, 94%, 95%, 96%, 97%, 98%, or 99% identical to SEQ ID NO: 514. In certain embodiments, the heavy chain is paired with the light chain variable region of SEQ ID NO: 514 or a sequence at least about 90%, 91%, 92%, 93%, 94%, 95%, 96%, 97%, 98%, or 99% identical to the light chain variable region of SEQ ID NO: 514.

In some embodiments, anti-TL1A described herein comprise a light chain constant region comprising SEQ ID NO: 319 or a sequence at least about 90%, 91%, 92%, 93%, 94%, 95%, 96%, 97%, 98%, or 99% identical to SEQ ID NO: 319.

Further Non-Limiting Exemplary Anti-TL1A Antibodies

In one aspect, provided herein is a first embodiment of an anti-TL1A antibody comprising a heavy chain comprising a HCDR1, a HCDR2, and a HCDR3, and a light chain comprising a LCDR1, a LCDR2, and a LCDR3. Non-limiting additional embodiments include: (Embodiment 2) The anti-TL1A antibody of embodiment 1, comprising a HCDR1 comprising SEQ ID NO: 1. (Embodiment 3) The anti-TL1A antibody of embodiment 1 or embodiment 2, comprising a HCDR2 comprising SEQ ID NO: 2. (Embodiment 4) The anti-TL1A antibody of embodiment 1 or embodiment 2, comprising a HCDR2 comprising SEQ ID NO: 3. (Embodiment 5) The anti-TL1A antibody of embodiment 1 or embodiment 2, comprising a HCDR2 comprising SEQ ID NO: 4. (Embodiment 6) The anti-TL1A antibody of embodiment 1 or embodiment 2, comprising a HCDR2 comprising SEQ ID NO: 5. (Embodiment 7) The anti-TL1A antibody of any one of embodiments 1-6, comprising a HCDR3 comprising SEQ ID NO: 6. (Embodiment 8) The anti-TL1A antibody of any one of embodiments 1-6, comprising a HCDR3 comprising SEQ ID NO: 7. (Embodiment 9) The anti-TL1A antibody of any one of embodiments 1-6, comprising a HCDR3 comprising SEQ ID NO: 8. (Embodiment 10) The anti-TL1A antibody of any one of embodiments 1-6, comprising a HCDR3 comprising SEQ ID NO: 9. (Embodiment 11) The anti-TL1A antibody of any one of embodiments 1-10, comprising a LCDR1 comprising SEQ ID NO: 10. (Embodiment 12) The anti-TL1A antibody of any one of embodiments 1-11, comprising a LCDR2 comprising SEQ ID NO: 11. (Embodiment 13) The anti-TL1A antibody of any one of embodiments 1-12, comprising a LCDR3 comprising SEQ ID NO: 12. (Embodiment 14) The anti-TL1A antibody of any one of embodiments 1-12, comprising a LCDR3 comprising SEQ ID NO: 13. (Embodiment 15) The anti-TL1A antibody of any one of embodiments 1-12, comprising a LCDR3 comprising SEQ ID NO: 14 or 15.

(Embodiment 16) The anti-TL1A antibody of any one of embodiments 1-15, comprising a heavy chain framework comprising IGHV1-46*02. (Embodiment 17) The anti-TL1A antibody of any one of embodiments 1-15, comprising a heavy chain framework comprising a variant of IGHV1-46*02 comprising between about 1 and about 20 amino acid substitutions from SEQ ID NO: 316. (Embodiment 18) The anti-TL1A antibody of any one of embodiments 1-15, comprising a heavy chain framework comprising a variant of IGHV1-46*02 comprising between about 1 and about 9 amino acid substitutions from SEQ ID NO: 316. (Embodiment 19) The anti-TL1A antibody of any one of embodiments 1-15, comprising a heavy chain framework comprising a variant of IGHV1-46*02 comprising about 1, 2, 3, 4, 5, 6, 7, 8, 9, 10, 11, 12, 13, 14, 15, 16, 17, 18, 19, or 20 amino acid substitutions from SEQ ID NO: 316 in the framework. (Embodiment 20) The anti-TL1A antibody of any one of embodiments 17-19, wherein the heavy chain framework substitution comprises Q1E, as determined by Aho numbering. (Embodiment 21) The anti-TL1A antibody of any one of embodiments 17-20, wherein the heavy chain framework substitution comprises R45K, as determined by Aho numbering. (Embodiment 22) The anti-TL1A antibody of any one of embodiments 17-21, wherein the heavy chain framework substitution comprises A47R, as determined by Aho numbering. (Embodiment 23) The anti-TL1A antibody of any one of embodiments 17-22, wherein the heavy chain framework substitution comprises M55I, as determined by Aho numbering. (Embodiment 24) The anti-TL1A antibody of any one of embodiments 17-23, wherein the heavy chain framework substitution comprises V78A, as determined by Aho numbering. (Embodiment 25) The anti-TL1A antibody of any one of embodiments 17-24, wherein the heavy chain framework substitution comprises M80I, as determined by Aho numbering. (Embodiment 26) The anti-TL1A antibody of any one of embodiments 17-25, wherein the heavy chain framework substitution comprises R82T, as determined by Aho numbering. (Embodiment 27) The anti-TL1A antibody of any one of embodiments 17-26, wherein the heavy chain framework substitution comprises V89A, as determined by Aho numbering. (Embodiment 28) The anti-TL1A antibody of any one of embodiments 17-27, wherein the heavy chain framework substitution comprises M91L, as determined by Aho numbering.

(Embodiment 29) The anti-TL1A antibody of any one of embodiments 1-15, comprising a heavy chain framework comprising SEQ ID NO: 301. (Embodiment 30) The anti-TL1A antibody of embodiment 29, wherein X1 is Q. (Embodiment 31) The anti-TL1A of embodiment 29, wherein X1=E. (Embodiment 32) The anti-TL1A of any one of embodiments 29-31, wherein X2=R. (Embodiment 33) The anti-TL1A of any one of embodiments 29-31, wherein X2=K. (Embodiment 34) The anti-TL1A of any one of embodiments 29-33, wherein X3=A. (Embodiment 35) The anti-TL1A of any one of embodiments 29-33, wherein X3=R. (Embodiment 36) The anti-TL1A of any one of embodiments 29-35, wherein X4=M. (Embodiment 37) The anti-TL1A of any one of embodiments 29-35, wherein X4=I. (Embodiment 38) The anti-TL1A of any one of embodiments 29-37, wherein X5=V. (Embodiment 39) The anti-TL1A of any one of embodiments 29-37, wherein X5=A. (Embodiment 40) The anti-TL1A of any one of embodiments 29-39, wherein X6=M. (Embodiment 41) The anti-TL1A of any one of embodiments 29-39, wherein X6=I. (Embodiment 42) The anti-TL1A of any one of embodiments 29-41, wherein X7=R. (Embodiment 43) The anti-TL1A of any one of embodiments 29-41, wherein X7=T. (Embodiment 44) The anti-TL1A of any one of embodiments 29-43, wherein X8=V. (Embodiment 45) The anti-TL1A of any one of embodiments 29-43, wherein X8=A. (Embodiment 46) The anti-TL1A of any one of embodiments 29-45, wherein X9=M. (Embodiment 47) The anti-TL1A of any one of embodiments 29-45, wherein X9=L.

(Embodiment 48) The anti-TL1A antibody of any one of embodiments 1-15, comprising a heavy chain framework comprising SEQ ID NO: 302. (Embodiment 49) The anti-TL1A antibody of embodiment 48, wherein X1 is Q. (Embodiment 50) The anti-TL1A of embodiment 48, wherein X1=E. (Embodiment 51) The anti-TL1A of any one of embodiments 48-50, wherein X2=R. (Embodiment 52) The anti-TL1A of any one of embodiments 48-50, wherein X2=K. (Embodiment 53) The anti-TL1A of any one of embodiments 48-52, wherein X3=A. (Embodiment 54) The anti-TL1A of any one of embodiments 48-52, wherein X3=R. (Embodiment 55) The anti-TL1A of any one of embodiments 48-54, wherein X4=M. (Embodiment 56) The anti-TL1A of any one of embodiments 48-54, wherein X4=I. (Embodiment 57) The anti-TL1A of any one of embodiments 48-56, wherein X5=V. (Embodiment 58) The anti-TL1A of any one of embodiments 48-56, wherein X5=A. (Embodiment 59) The anti-TL1A of any one of embodiments 48-58, wherein X6=M. (Embodiment 60) The anti-TL1A of any one of embodiments 48-58, wherein X6=I. (Embodiment 61) The anti-TL1A of any one of embodiments 48-60, wherein X7=R. (Embodiment 62) The anti-TL1A of any one of embodiments 48-60, wherein X7=T. (Embodiment 63) The anti-TL1A of any one of embodiments 48-62, wherein X8=V. (Embodiment 64) The anti-TL1A of any one of embodiments 48-62, wherein X8=A. (Embodiment 65) The anti-TL1A of any one of embodiments 48-64, wherein X9=M. (Embodiment 66) The anti-TL1A of any one of embodiments 48-64, wherein X9=L.

(Embodiment 67) The anti-TL1A antibody of any one of embodiments 1-66, comprising a light chain framework comprising IGKV3-20*01. (Embodiment 68) The anti-TL1A antibody of any one of embodiments 1-66, comprising a light chain framework comprising a variant of IGKV3-20*01 comprising between about 1 and about 20 amino acid substitutions from SEQ ID NO: 317. (Embodiment 69) The anti-TL1A antibody of any one of embodiments 1-66, comprising a light chain framework comprising a variant of IGKV3-20*01 comprising about 1 amino acid substitution from SEQ ID NO: 317. (Embodiment 70) The anti-TL1A antibody of any one of embodiments 1-66, comprising a light chain framework comprising a variant of IGKV3-20*01 comprising about 2 amino acid substitutions from SEQ ID NO: 317. (Embodiment 71) The anti-TL1A antibody of any one of embodiments 1-66, comprising a light chain framework comprising a variant of IGKV3-20*01 comprising about 1, 2, 3, 4, 5, 6, 7, 8, 9, 10, 11, 12, 13, 14, 15, 16, 17, 18, 19, or 20 amino acid substitutions from SEQ ID NO: 317 in the framework. (Embodiment 72) The anti-TL1A antibody of any one of embodiments 69-71, wherein the light chain framework substitution comprises Q1E, as determined by Aho numbering. (Embodiment 73) The anti-TL1A antibody of any one of embodiments 69-72, wherein the light chain framework substitution comprises R45K, as determined by Aho numbering.

(Embodiment 74) The anti-TL1A antibody of any one of embodiments 1-66, comprising a light chain comprising a light chain framework comprising SEQ ID NO: 303. (Embodiment 75) The anti-TL1A antibody of embodiment 74, wherein X10 is L. (Embodiment 76) The anti-TL1A antibody of embodiment 74, wherein X10 is P. (Embodiment 77) The anti-TL1A antibody of any one of embodiments 74-76, wherein X11 is L. (Embodiment 78) The anti-TL1A antibody of any one of embodiments 74-76, wherein X11 is W.

(Embodiment 79) The anti-TL1A of any one of embodiments 1-78, comprising a human IgG1 Fc region comprising (a) 297A, 297Q, 297G, or 297D, (b) 279F, 279K, or 279L, (c) 228P, (d) 235A, 235E, 235G, 235Q, 235R, or 235S, (e)

237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 3431 or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. (Embodiment 80) The anti-TL1A of any one of embodiments 1-78, comprising a (i) human IgG4 Fc region or (ii) a human IgG4 Fc region comprising (a) S228P and L235E, or (b) S228P, F234A, and L235A, per Kabat numbering. (Embodiment 81) The anti-TL1A of any one of embodiments 1-78, comprising a human IgG2 Fc region; IgG2-IgG4 cross-subclass Fc region; IgG2-IgG3 cross-subclass Fc region; IgG2 comprising H268Q, V309L, A330S, P331S (IgG2m4); or IgG2 comprising V234A, G237A, P238S, H268A, V309L, A330S, P331S (IgG2a). (Embodiment 82) The anti-TL1A of any one of embodiments 1-81, comprising a heavy chain Fc region comprising any one of SEQ ID NOS: 320-362. (Embodiment 83) The anti-TL1A antibody of any one of embodiments 1-82, comprising a light chain constant region comprising SEQ ID NO: 319.

(Embodiment 84) The anti-TL1A antibody of any one of embodiments 1-83, comprising at least about 80% monomeric fraction as determined by the size exclusion chromatography method described herein. (Embodiment 85) The anti-TL1A antibody of any one of embodiments 1-84, comprising at least about 81%, at least about 82%, at least about 83%, or at least about 84% monomeric fraction as determined by the size exclusion chromatography method described herein. (Embodiment 86) The anti-TL1A antibody of any one of embodiments 1-85, comprising at least about 85% monomeric fraction as determined by the size exclusion chromatography method described herein. (Embodiment 87) The anti-TL1A antibody of any one of embodiments 1-86, comprising at least about 86%, at least about 87%, at least about 88%, or at least about 89% monomeric fraction as determined by the size exclusion chromatography method described herein. (Embodiment 88) The anti-TL1A antibody of any one of embodiments 1-87, comprising at least about 90% monomeric fraction as determined by the size exclusion chromatography method described herein. (Embodiment 89) The anti-TL1A antibody of any one of embodiments 1-88, comprising at least about 91%, at least about 92%, at least about 93%, or at least about 94% monomeric fraction as determined by the size exclusion chromatography method described herein. (Embodiment 90) The anti-TL1A antibody of any one of embodiments 1-89, comprising at least about 95% monomeric fraction as determined by the size exclusion chromatography method described herein. (Embodiment 91) The anti-TL1A antibody of any one of embodiments 1-90, comprising at least about 96%, at least about 97%, at least about 98%, or at least about 99% monomeric fraction as determined by the size exclusion chromatography method described herein.

(Embodiment 92) The anti-TL1A antibody of any one of embodiments 1-91, comprising at least about 2 µg/mL expression as determined by the method disclosed herein. (Embodiment 93) The anti-TL1A antibody of any one of embodiments 1-92, comprising between about 2 µg/mL and about 60 µg/mL expression as determined by the method disclosed herein. (Embodiment 94) The anti-TL1A antibody of any one of embodiments 1-93, comprising between about 5 µg/mL and about 60 µg/mL expression as determined by the method disclosed herein. (Embodiment 95) The anti-TL1A antibody of any one of embodiments 1-94, comprising between about 10 µg/mL and about 60 µg/mL expression as determined by the method disclosed herein. (Embodiment 96) The anti-TL1A antibody of any one of embodiments 1-95, comprising at least about 5 µg/mL expression as determined by the method disclosed herein. (Embodiment 97) The anti-TL1A antibody of any one of embodiments 1-96, comprising at least about 10 µg/mL expression as determined by the method disclosed herein. (Embodiment 98) The anti-TL1A antibody of any one of embodiments 1-97, comprising at least about 15 µg/mL expression as determined by the method disclosed herein. (Embodiment 99) The anti-TL1A antibody of any one of embodiments 1-98, comprising at least about 20 µg/mL expression as determined by the method disclosed herein. (Embodiment 100) The anti-TL1A antibody of any one of embodiments 1-91, comprising between about 2 µg/mL and about 50 µg/mL, between about 2 µg/mL and about 40 µg/mL, between about 2 µg/mL and about 30 µg/mL expression, between about 2 µg/mL and about 20 µg/mL, between about 5 µg/mL and about 50 µg/mL, between about 5 µg/mL and about 40 µg/mL, between about 5 µg/mL and about 30 µg/mL, between about 10 µg/mL and about 50 µg/mL, between about 10 µg/mL and about 40 µg/mL, or between about 10 µg/mL and about 30 µg/mL as determined by the method disclosed herein. (Embodiment 101) The anti-TL1A antibody of any one of embodiments 1-91, comprising about 2, 3, 4, 5, 6, 7, 8, 9, 10, 11, 12, 13, 14, 15, 16, 17, 18, 19, 20, 21, 22, 23, 24, 25, 26, 27, 28, 29, 30 µg/mL expression as determined by the method disclosed herein.

In some embodiments, an anti-TL1A antibody comprises antibody A. As used herein, antibody A comprises the CDRs of antibody A in Table 10. In some cases, antibody A comprises a heavy chain framework comprising SEQ ID NO: 301 (Embodiment X1VQLVQSGAEVKKPGASVKVSCKAS[HCDR1] WVX2QX3PGQGLEWX4G[HCDR2] RX5TX6TX7DTSTSTX8YX9ELSSLRSEDTAVYYCAR [HCDR3]WGQGTTVTVSS), wherein X1=Q or E, X2=R or K, X3=A or R, X4=M or I, X5=V or A, X6=M or I, X7=R or T, X8=V or A, and X9=M or L. In some cases, antibody A comprises a light chain framework comprising SEQ ID NO: 303 (Embodiment EIVLTQSPGTLSLSPGERATLSC [LCDR1]WYQQKPGQAPRX10X11IY[LCDR2]GIPDR FSGSGSGTDFTLTISRLEPEDFAVYYC[LCDR3] FGGGTKLEIK), wherein X10=L or P and X11=L or W. In some cases, antibody A comprises a heavy chain variable region comprising human IGHV1-46*02 framework or a modified human IGHV1-46*02 framework, wherein the modified human IGHV1-46*02 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody A comprises a light chain variable region comprising human IGKV3-20 framework or a modified human IGKV3-20 framework, wherein the modified human IGKV3-20 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody A comprises a constant region comprising reduced ADCC and/or CDC as compared to IgG1. For instance, antibody A comprises a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 320. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 321. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 322. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 323. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 324. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 325. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 326. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 327. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 328. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 329. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 330. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 331. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 332. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 333. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 334. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 335. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 336. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 337. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 338. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 339. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 340. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 341. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 342. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 343. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 344. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 345. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 346. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 347. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 348. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 349. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 350. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 351. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 352. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 353. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 354. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 355. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 356. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 357. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 358. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 359. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 360. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 361. In some cases, antibody A comprises a constant region comprising at least about 85%, 87%, 88%, 89%, 90%, 91%, 92%, 93%, 94%, 95%, 96%, 97%, 98%, 99%, or 100% identity to SEQ ID NO: 362. In some cases, antibody A comprises at least about 80%, 81%, 82%, 83%, 84%, 85%, 85%, 87%, 88%, 89%, 90%, 91%, 92%, 93%, 94%, 95%, 96%, 97%, 98%, 99%, or 100% monomeric fraction as measured by the size exclusion method described in Example 2. In some cases, antibody A is expressed from FreeStyle 293-F (e.g., ThermoFisher Scientific #R79007) cells at an expression level of about or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 5, 57, 58, 59 or 60 µg/mL as determined by the method described in Example 2. In some cases, antibody A is expressed from FreeStyle 293-F cells at an expression level of between about 2 µg/mL to about 60 µg/mL. In some cases, antibody A is expressed from FreeStyle 293-F cells at an expression level of between about 10 µg/mL to about 60 µg/mL. In some cases, antibody A comprises a viscosity less than about 30 mPa-s. In some cases, antibody A comprises a viscosity from about 4 mPa-s to about 30 mPa-s, or about 4, 5, 6, 7, 8, 9, 10. 11, 12, 13, 14, 15, 16, 17, 18, 19, 20, 21, 22, 23, 24, 25, 26, 27, 28, 29, 30 mPa-s. In some cases, antibody A is formulated in a solution having a concentration of about 10 mg/ml to about 170 mg/ml, with a viscosity less than about 30 mPa-s. In some cases, the formulation has a pH of about 5 to about 7.5.

In some embodiments, an anti-TL1A antibody comprises antibody B. As used herein, antibody B comprises the CDRs of antibody B in Table 10. In some cases, antibody B comprises a heavy chain framework comprising SEQ ID NO: 301 (X1VQLVQSGAEVKKPGASVKVSCKAS[HCDR1]WVX2QX3PGQGLEWX4G[HCDR2] RX5TX6TX7DTSTSTX8YX9ELSSLRSEDTAVYYCAR[HCDR3]WGQGTTVTVSS), wherein X1=Q or E, X2=R or K, X3=A or R, X4=M or I, X5=V or A, X6=M or I, X7=R or T, X8=V or A, and X9=M or L. In some cases, antibody B comprises a light chain framework comprising SEQ ID NO: 303 (EIVLTQSPGTLSLSPGERATLSC[LCDR1] WYQQKPGQAPRX10X11IY[LCDR2]GIPDR FSGSGSGTDFTLTISRLEPEDFAVYYC[LCDR3] FGGGTKLEIK), wherein X10=L or P and X11=L or W. In some cases, antibody B comprises a heavy chain variable region comprising human IGHV1-46*02 framework or a modified human IGHV1-46*02 framework, wherein the modified human IGHV1-46*02 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody B comprises a light chain variable region comprising human IGKV3-20 framework or a modified human IGKV3-20 framework, wherein the modified human IGKV3-20 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody B comprises a constant region comprising reduced ADCC and/or CDC as compared to IgG1. For instance, antibody B comprises a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii)

D265A and N297A, (jjj) D265A and N297G, (kkk) D270A, (lll) A330L, (mmm) P331A or P331S, or (nnn) any combination of (a)-(uu), per Kabat numbering. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 320. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 321. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 322. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 323. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 324. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 325. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 326. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 327. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 328. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 329. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 330. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 331. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 332. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 333. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 334. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 335. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 336. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 337. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 338. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 339. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 340. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 341. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 342. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 343. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 344. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 345. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 346. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 347. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 348. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 349. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 350. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 351. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 352. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 353. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 354. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 355. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 356. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 357. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 358. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 359. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 360. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 361. In some cases, antibody B comprises a constant region comprising at least about 85%, 87%, 88%, 89%, 90%, 91%, 92%, 93%, 94%, 95%, 96%, 97%, 98%, 99%, or 100% identity to SEQ ID NO: 362. In some cases, antibody B comprises at least about 80%, 81%, 82%, 83%, 84%, 85%, 85%, 87%, 88%, 89%, 90%, 91%, 92%, 93%, 94%, 95%, 96%, 97%, 98%, 99%, or 100% monomeric fraction as measured by the size exclusion method described in Example 2. In some cases, antibody B is expressed from FreeStyle 293-F cells at an expression level of about or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 5, 57, 58, 59 or 60 µg/mL as determined by the method described in Example 2. In some cases, antibody B is expressed from FreeStyle 293-F cells at an expression level of between about 2 µg/mL to about 60 µg/mL. In some cases, antibody B is expressed from FreeStyle 293-F cells at an expression level of between about 10 µg/mL to about 60 µg/mL.

In some embodiments, an anti-TL1A antibody comprises antibody C. As used herein, antibody C comprises the CDRs of antibody C in Table 10. In some cases, antibody C comprises a heavy chain framework comprising SEQ ID NO: 301 (X1VQLVQSGAEVKKPGASVKVSCKAS[HCDR1]WVX2QX3PGQGLEWX4G[HCDR2]RX5TX6TX7DTSTSTX8YX9ELSSLRSEDTAVYYCAR[HCDR3]WGQGTTVTVSS), wherein X1=Q or E, X2=R or K, X3=A or R, X4=M or I, X5=V or A, X6=M or I, X7=R or T, X8=V or A, and X9=M or L. In some cases, antibody C comprises a light chain framework comprising SEQ ID NO: 303 (EIVLTQSPGTLSLSPGERATLSC[LCDR1]WYQQKPGQAPRX10X11IY[LCDR2]GIPDRFSGSGSGTDFTLTISRLEPEDFAVYYC[LCDR3]FGGGTKLEIK), wherein X10=L or P and X11=L or W. In some cases, antibody C comprises a heavy chain variable region comprising human IGHV1-46*02 framework or a modified human IGHV1-46*02 framework, wherein the modified human IGHV1-46*02 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody C comprises a light chain variable region comprising human IGKV3-20 framework or a modified human IGKV3-20 framework, wherein the modified human IGKV3-20 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody C comprises a constant region comprising reduced ADCC and/or CDC as compared to IgG1. For instance, antibody C comprises a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 3431 or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 320. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 321. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 322. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 323. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 324. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 325. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 326. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 327. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 328. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 329. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 330. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 331. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 332. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 333. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 334. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 335. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 336. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 337. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 338. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 339. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 340. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 341. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 342. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 343. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 344. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 345. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 346. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 347. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 348. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 349. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 350. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 351. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 352. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 353. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 354. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 355. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 356. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 357. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 358. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 359. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 360. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 361. In some cases, antibody C comprises a constant region comprising at least about 85%, 87%, 88%, 89%, 90%, 91%, 92%, 93%, 94%, 95%, 96%, 97%, 98%, 99%, or 100% identity to SEQ ID NO: 362. In some cases, antibody C comprises at least about 80%, 81%, 82%, 83%, 84%, 85%, 85%, 87%, 88%, 89%, 90%, 91%, 92%, 93%, 94%, 95%, 96%, 97%, 98%, 99%, or 100% monomeric fraction as measured by the size exclusion method described in Example 2. In some cases, antibody C is expressed from FreeStyle 293-F cells at an expression level of about or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 5, 57, 58, 59 or 60 µg/mL as determined by the method described in Example 2. In some cases, antibody C is expressed from FreeStyle 293-F cells at an expression level of between about 2 µg/mL to about 60 µg/mL. In some cases, antibody C is expressed from FreeStyle 293-F cells at an expression level of between about 10 µg/mL to about 60 µg/mL.

In some embodiments, an anti-TL1A antibody comprises antibody D. As used herein, antibody D comprises the CDRs of antibody D in Table 10. In some cases, antibody D comprises a heavy chain framework comprising SEQ ID NO: 301 (X1VQLVQSGAEVKKPGASVKVSCKAS[HCDR1]WVX2QX3PGQGLEWX4G[HCDR2]RX5TX6TX7DTSTSTX8YX9ELSSLRSEDTAVYYCAR[HCDR3]WGQGTTVTVSS), wherein X1=Q or E, X2=R or K, X3=A or R, X4=M or I, X5=V or A, X6=M or I, X7=R or T, X8=V or A, and X9=M or L. In some cases, antibody D comprises a light chain framework comprising SEQ ID NO: 303 (EIVLTQSPGTLSLSPGERATLSC[LCDR1]WYQQKPGQAPRX10X11IY[LCDR2]GIPDR FSGSGSGTDFTLTISRLEPEDFAVYYC[LCDR3] FGGGTKLEIK), wherein X10=L or P and X11=L or W. In some cases, antibody D comprises a heavy chain variable region comprising human IGHV1-46*02 framework or a modified human IGHV1-46*02 framework, wherein the modified human IGHV1-46*02 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody D comprises a light chain variable region comprising human IGKV3-20 framework or a modified human IGKV3-20 framework, wherein the modified human IGKV3-20 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody D comprises a constant region comprising reduced ADCC and/or CDC as compared to IgG1. For instance, antibody D comprises a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329S, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 320. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 321. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 322. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 323. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 324. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 325. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 326. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 327. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 328. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 329. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 330. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 331. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 332. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 333. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 334. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 335. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 336. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 337. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 338. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 339. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 340. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 341. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 342. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 343. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 344. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 345. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 346. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 347. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 348. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 349. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 350. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 351. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 352. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 353. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 354. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 355. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 356. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 357. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 358. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 359. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 360. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 361. In some cases, antibody D comprises a constant region comprising at least about 85%, 87%, 88%, 89%, 90%, 91%, 92%, 93%, 94%, 95%, 96%, 97%, 98%, 99%, or 100% identity to SEQ ID NO: 362. In some cases, antibody D comprises at least about 80%, 81%, 82%, 83%, 84%, 85%, 85%, 87%, 88%, 89%, 90%, 91%, 92%, 93%, 94%, 95%, 96%, 97%, 98%, 99%, or 100% monomeric fraction as measured by the size exclusion method described in Example 2. In some cases, antibody D is expressed from FreeStyle 293-F cells at an expression level of about or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 5, 57, 58, 59 or 60 µg/mL as determined by the method described in Example 2. In some cases, antibody D is expressed from FreeStyle 293-F cells at an expression level of between about 2 µg/mL to about 60 µg/mL. In some cases, antibody D is expressed from FreeStyle 293-F cells at an expression level of between about 10 µg/mL to about 60 µg/mL.

In some embodiments, an anti-TL1A antibody comprises antibody E. As used herein, antibody E comprises the CDRs of antibody E in Table 10. In some cases, antibody E comprises a heavy chain framework comprising SEQ ID NO: 301 (X1VQLVQSGAEVKKPGASVKVSCKAS[HCDR1]WVX2QX3PGQGLEWX4G[HCDR2]RX5TX6TX7DTSTSTX8YX9ELSSLRSEDTAVYYCAR[HCDR3]WGQGTTVTVSS), wherein X1=Q or E, X2=R or K, X3=A or R, X4=M or I, X5=V or A, X6=M or I, X7=R or T, X8=V or A, and X9=M or L. In some cases, antibody E comprises a light chain framework comprising SEQ ID NO: 303 (EIVLTQSPGTLSLSPGERATLSC[LCDR1]WYQQKPGQAPRX10X11IY[LCDR2]GIPDR FSGSGSGTDFTLTISRLEPEDFAVYYC[LCDR3] FGGGTKLEIK), wherein X10=L or P and X11=L or W. In some cases, antibody E comprises a heavy chain variable region comprising human IGHV1-46*02 framework or a modified human IGHV1-46*02 framework, wherein the modified human IGHV1-46*02 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody E comprises a light chain variable region comprising human IGKV3-20 framework or a modified human IGKV3-20 framework, wherein the modified human IGKV3-20 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody E comprises a constant region comprising reduced ADCC and/or CDC as compared to IgG1. For instance, antibody E comprises a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc)

L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 320. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 321. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 322. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 323. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 324. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 325. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 326. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 327. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 328. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 329. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 330. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 331. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 332. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 333. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 334. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 335. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 336. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 337. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 338. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 339. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 340. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 341. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 342. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 343. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 344. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 345. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 346. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 347. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 348. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 349. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 350. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 351. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 352. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 353. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 354. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 355. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 356. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 357. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 358. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 359. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 360. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 361. In some cases, antibody E comprises a constant region comprising at least about 85%, 87%, 88%, 89%, 90%, 91%, 92%, 93%, 94%, 95%, 96%, 97%, 98%, 99%, or 100% identity to SEQ ID NO: 362. In some cases, antibody E comprises at least about 80%, 81%, 82%, 83%, 84%, 85%, 85%, 87%, 88%, 89%, 90%, 91%, 92%, 93%, 94%, 95%, 96%, 97%, 98%, 99%, or 100% monomeric fraction as measured by the size exclusion method described in Example 2. In some cases, antibody E is expressed from FreeStyle 293-F cells at an expression level of about or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 5, 57, 58, 59 or 60 µg/mL as determined by the method described in Example 2. In some cases, antibody E is expressed from FreeStyle 293-F cells at an expression level of between about 2 µg/mL to about 60 µg/mL. In some cases, antibody E is expressed from FreeStyle 293-F cells at an expression level of between about 10 µg/mL to about 60 µg/mL.

In some embodiments, an anti-TL1A antibody comprises antibody F. As used herein, antibody F comprises the CDRs of antibody F in Table 10. In some cases, antibody F comprises a heavy chain framework comprising SEQ ID NO: 301 (X1VQLVQSGAEVKKPGASVKVSCKAS[HCDR1]WVX2QX3PGQGLEWX4G[HCDR2]RX5TX6TX7DTSTSTX8YX9ELSSLRSEDTAVYYCAR[HCDR3]WGQGTTVTVSS), wherein X1=Q or E, X2=R or K, X3=A or R, X4=M or I, X5=V or A, X6=M or I, X7=R or T, X8=V or A, and X9=M or L. In some cases, antibody F comprises a light chain framework comprising SEQ ID NO: 303 (EIVLTQSPGTLSLSPGERATLSC[LCDR1]WYQQKPGQAPRX10X11IY[LCDR2]GIPDR FSGSGSGTDFTLTISRLEPEDFAVYYC[LCDR3]FGGGTKLEIK), wherein X10=L or P and X11=L or W. In some cases, antibody F comprises a heavy chain variable region comprising human IGHV1-46*02 framework or a modified human IGHV1-46*02 framework, wherein the modified human IGHV1-46*02 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody F comprises a light chain variable region comprising human IGKV3-20 framework or a modified human IGKV3-20 framework, wherein the modified human IGKV3-20 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody F comprises a constant region comprising reduced ADCC and/or CDC as compared to IgG1. For instance, antibody F comprises a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 320. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 321. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 322. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 323. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 324. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 325. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 326. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 327. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 328. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 329. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 330. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 331. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 332. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 333. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 334. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 335. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 336. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 337. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 338. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 339. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 340. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 341. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 342. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 343. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 344. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 345. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 346. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 347. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 348. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 349. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 350. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 351. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 352. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 353. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 354. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 355. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 356. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 357. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 358. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 359. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 360. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 361. In some cases, antibody F comprises a constant region comprising at least about 85%, 87%, 88%, 89%, 90%, 91%, 92%, 93%, 94%, 95%, 96%, 97%, 98%, 99%, or 100% identity to SEQ ID NO: 362. In some cases, antibody F comprises at least about 80%, 81%, 82%, 83%, 84%, 85%, 85%, 87%, 88%, 89%, 90%, 91%, 92%, 93%, 94%, 95%, 96%, 97%, 98%, 99%, or 100% monomeric fraction as measured by the size exclusion method described in Example 2. In some cases, antibody F is expressed from FreeStyle 293-F cells at an expression level of about or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 5, 57, 58, 59 or 60 µg/mL as determined by the method described in Example 2. In some cases, antibody F is expressed from FreeStyle 293-F cells at an expression level of between about 2 µg/mL to about 60 µg/mL. In some cases, antibody F is expressed from FreeStyle 293-F cells at an expression level of between about 10 µg/mL to about 60 µg/mL.

In some embodiments, an anti-TL1A antibody comprises antibody G. As used herein, antibody G comprises the CDRs of antibody G in Table 10. In some cases, antibody G comprises a heavy chain framework comprising SEQ ID NO: 301 (X1VQLVQSGAEVKKPGASVKVSCKAS [HCDR1]WVX2QX3PGQGLEWX4G[HCDR2] RX5TX6TX7DTSTSTX8YX9ELSSLRSEDTAVYYCAR

[HCDR3]WGQGTTVTVSS), wherein X1=Q or E, X2=R or K, X3=A or R, X4=M or I, X5=V or A, X6=M or I, X7=R or T, X8=V or A, and X9=M or L. In some cases, antibody G comprises a light chain framework comprising SEQ ID NO: 303 (EIVLTQSPGTLSLSPGERATLSC [LCDR1] WYQQKPGQAPRX10X11IY[LCDR2]GIPDR FSGSGSGTDFTLTISRLEPEDFAVYYC[LCDR3] FGGGTKLEIK), wherein X10=L or P and X11=L or W. In some cases, antibody G comprises a heavy chain variable region comprising human IGHV1-46*02 framework or a modified human IGHV1-46*02 framework, wherein the modified human IGHV1-46*02 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody G comprises a light chain variable region comprising human IGKV3-20 framework or a modified human IGKV3-20 framework, wherein the modified human IGKV3-20 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody G comprises a constant region comprising reduced ADCC and/or CDC as compared to IgG1. For instance, antibody G comprises a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 320. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 321. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 322. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 323. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 324. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 325. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 326. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 327. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 328. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 329. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 330. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 331. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 332. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 333. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 334. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 335. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 336. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 337. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 338. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 339. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 340. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 341. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 342. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 343. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 344. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 345. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 346. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 347. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 348. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 349. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 350. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 351. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 352. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 353. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 354. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 355. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 356. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 357. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 358. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 359. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 360. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 361. In some cases, antibody G comprises a constant region comprising at least about 85%, 87%, 88%, 89%, 90%, 91%, 92%, 93%, 94%, 95%, 96%, 97%, 98%, 99%, or 100% identity to SEQ ID NO: 362. In some cases, antibody G comprises at least about 80%, 81%, 82%, 83%, 84%, 85%, 85%, 87%, 88%, 89%, 90%, 91%, 92%, 93%, 94%, 95%, 96%, 97%, 98%, 99%, or 100% monomeric fraction as measured by the size exclusion method described in Example 2. In some cases, antibody G is expressed from FreeStyle 293-F cells at an expression level of about or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 5, 57, 58, 59 or 60 µg/mL as determined by the method described in Example 2. In some cases, antibody G is expressed from FreeStyle 293-F cells at an expression level of between about 2 µg/mL to about 60 µg/mL. In some cases, antibody G is expressed from FreeStyle 293-F cells at an expression level of between about 10 µg/mL to about 60 µg/mL.

In some embodiments, an anti-TL1A antibody comprises antibody H. As used herein, antibody H comprises the CDRs of antibody H in Table 10. In some cases, antibody H comprises a heavy chain framework comprising SEQ ID NO: 301 (X1VQLVQSGAEVKKPGASVKVSCKAS[HCDR1]WVX2QX3PGQGLEWX4G[HCDR2]RX5TX6TX7DTSTSTX8YX9ELSSLRSEDTAVYYCAR[HCDR3]WGQGTTVTVSS), wherein X1=Q or E, X2=R or K, X3=A or R, X4=M or I, X5=V or A, X6=M or I, X7=R or T, X8=V or A, and X9=M or L. In some cases, antibody H comprises a light chain framework comprising SEQ ID NO: 303 (EIVLTQSPGTLSLSPGERATLSC[LCDR1]WYQQKPGQAPRX10X11IY[LCDR2]GIPDR FSGSGSGTDFTLTISRLEPEDFAVYYC[LCDR3] FGGGTKLEIK), wherein X10=L or P and X11=L or W. In some cases, antibody H comprises a heavy chain variable region comprising human IGHV1-46*02 framework or a modified human IGHV1-46*02 framework, wherein the modified human IGHV1-46*02 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody H comprises a light chain variable region comprising human IGKV3-20 framework or a modified human IGKV3-20 framework, wherein the modified human IGKV3-20 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody H comprises a constant region comprising reduced ADCC and/or CDC as compared to IgG1. For instance, antibody H comprises a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 320. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 321. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 322. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 323. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 324. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 325. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 326. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 327. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 328. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 329. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 330. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 331. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 332. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 333. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 334. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 335. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 336. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 337. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 338. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 339. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 340. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 341. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 342. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 343. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 344. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 345. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 346. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 347. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 348. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 349. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 350. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 351. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 352. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 353. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 354. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 355. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 356. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 357. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 358. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 359. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 360. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 361. In some cases, antibody H comprises a constant region comprising at least about 85%, 87%, 88%, 89%, 90%, 91%, 92%, 93%, 94%, 95%, 96%, 97%, 98%, 99%, or 100% identity to SEQ ID NO: 362. In some cases, antibody H comprises at least about 80%, 81%, 82%, 83%, 84%, 85%, 85%, 87%, 88%, 89%, 90%, 91%, 92%, 93%, 94%, 95%, 96%, 97%, 98%, 99%, or 100% monomeric fraction as measured by the size exclusion method described in Example 2. In some cases, antibody H is expressed from FreeStyle 293-F cells at an expression level of about or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 5, 57, 58, 59 or 60 µg/mL as determined by the method described in Example 2. In some cases, antibody H is expressed from FreeStyle 293-F cells at an expression level of between about 2 µg/mL to about 60 µg/mL. In some cases, antibody H is expressed from FreeStyle 293-F cells at an expression level of between about 10 µg/mL to about 60 µg/mL.

In some embodiments, an anti-TL1A antibody comprises antibody I. As used herein, antibody I comprises the CDRs of antibody I in Table 10. In some cases, antibody I comprises a heavy chain framework comprising SEQ ID NO: 301 (X1VQLVQSGAEVKKPGASVKVSCKAS[HCDR1]WVX2QX3PGQGLEWX4G[HCDR2]RX5TX6TX7DTSTSTX8YX9ELSSLRSEDTAVYYCAR[HCDR3]WGQGTTVTVSS), wherein X1=Q or E, X2=R or K, X3=A or R, X4=M or I, X5=V or A, X6=M or I, X7=R or T, X8=V or A, and X9=M or L. In some cases, antibody I comprises a light chain framework comprising SEQ ID NO: 303 (EIVLTQSPGTLSLSPGERATLSC[LCDR1]WYQQKPGQAPRX10X11IY[LCDR2]GIPDRFSGSGSGTDFTLTISRLEPEDFAVYYC[LCDR3]FGGGTKLEIK), wherein X10=L or P and X11=L or W. In some cases, antibody I comprises a heavy chain variable region comprising human IGHV1-46*02 framework or a modified human IGHV1-46*02 framework, wherein the modified human IGHV1-46*02 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody I comprises a light chain variable region comprising human IGKV3-20 framework or a modified human IGKV3-20 framework, wherein the modified human IGKV3-20 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody I comprises a constant region comprising reduced ADCC and/or CDC as compared to IgG1. For instance, antibody I comprises a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 320. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 321. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 322. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 323. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 324. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 325. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 326. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 327. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 328. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 329. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 330. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 331. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 332. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 333. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 334. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 335. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 336. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 337. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 338. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 339. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 340. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 341. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 342. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 343. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 344. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 345. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 346. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 347. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 348. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 349. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 350. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 351. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 352. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 353. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 354. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 355. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 356. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 357. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 358. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 359. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 360. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 361. In some cases, antibody I comprises a constant region comprising at least about 85%, 87%, 88%, 89%, 90%, 91%, 92%, 93%, 94%, 95%, 96%, 97%, 98%, 99%, or 100% identity to SEQ ID NO: 362. In some cases, antibody I comprises at least about 80%, 81%, 82%, 83%, 84%, 85%, 85%, 87%, 88%, 89%, 90%, 91%, 92%, 93%, 94%, 95%, 96%, 97%, 98%, 99%, or 100% monomeric fraction as measured by the size exclusion method described in Example 2. In some cases, antibody I is expressed from FreeStyle 293-F cells at an expression level of about or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 5, 57, 58, 59 or 60 µg/mL as determined by the method described in Example 2. In some cases, antibody I is expressed from FreeStyle 293-F cells at an expression level of between about 2 µg/mL to about 60 µg/mL. In some cases, antibody I is expressed from FreeStyle 293-F cells at an expression level of between about 10 µg/mL to about 60 µg/mL.

In some embodiments, an anti-TL1A antibody comprises antibody A2. As used herein, antibody A2 comprises the CDRs of antibody A2 in Table 10. In some cases, antibody A2 comprises a heavy chain framework comprising SEQ ID NO: 302 (X1VQLVQSGAEVKKPGASVKVSCKAS

[HCDR1]WVX2QX3PGQGLEWX4G[HCDR2]
RX5TX6TX7DTSTSTX8YX9ELSSLRSEDTAVYYC
[HCDR3]WGQGTTVTVSS), wherein X1=Q or E, X2=R or K, X3=A or R, X4=M or I, X5=V or A, X6=M or I, X7=R or T, X8=V or A, and X9=M or L. In some cases, antibody A2 comprises a light chain framework comprising SEQ ID NO: 303 (EIVLTQSPGTLSLSPGERATLSC[LCDR1] WYQQKPGQAPRX10X11IY[LCDR2]GIPDR FSGSGSGTDFTLTISRLEPEDFAVYYC[LCDR3] FGGGTKLEIK), wherein X10=L or P and X11=L or W. In some cases, antibody A2 comprises a heavy chain variable region comprising human IGHV1-46*02 framework or a modified human IGHV1-46*02 framework, wherein the modified human IGHV1-46*02 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody A2 comprises a light chain variable region comprising human IGKV3-20 framework or a modified human IGKV3-20 framework, wherein the modified human IGKV3-20 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody A2 comprises a constant region comprising reduced ADCC and/or CDC as compared to IgG1. For instance, antibody A2 comprises a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa) L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 320. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 321. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 322. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 323. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 324. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 325. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 326. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 327. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 328. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 329. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 330. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 331. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 332. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 333. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 334. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 335. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 336. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 337. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 338. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 339. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 340. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 341. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 342. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 343. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 344. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 345. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 346. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 347. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 348. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 349. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 350. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 351. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 352. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 353. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 354. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 355. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 356. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 357. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 358. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 359. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 360. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 361. In some cases, antibody A2 comprises a constant region comprising at least about 85%, 87%, 88%, 89%, 90%, 91%, 92%, 93%, 94%, 95%, 96%, 97%, 98%, 99%, or 100% identity to SEQ ID NO: 362. In some cases, antibody A2 comprises at least about 80%, 81%, 82%, 83%, 84%, 85%, 85%, 87%, 88%, 89%, 90%, 91%, 92%, 93%, 94%, 95%, 96%, 97%, 98%, 99%, or 100% monomeric fraction as measured by the size exclusion method described in Example 2. In some cases, antibody A2 is expressed from FreeStyle 293-F cells at an expression level of about or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 5, 57, 58, 59 or 60 µg/mL as determined by the method described in Example 2. In some cases, antibody A2 is expressed from FreeStyle 293-F cells at an expression level of between about 2 µg/mL to about 60 µg/mL. In some cases, antibody A2 is expressed from FreeStyle 293-F cells at an expression level of between about 10 µg/mL to about 60 µg/mL.

In some embodiments, an anti-TL1A antibody comprises antibody B2. As used herein, antibody B2 comprises the CDRs of antibody B2 in Table 10. In some cases, antibody B2 comprises a heavy chain framework comprising SEQ ID NO: 302 (X1VQLVQSGAEVKKPGASVKVSCKAS[HCDR1]WVX2QX3PGQGLEWX4G[HCDR2] RX5TX6TX7DTSTSTX8YX9ELSSLRSEDTAVYYC[HCDR3]WGQGTTVTVSS), wherein X1=Q or E, X2=R or K, X3=A or R, X4=M or I, X5=V or A, X6=M or I, X7=R or T, X8=V or A, and X9=M or L. In some cases, antibody B2 comprises a light chain framework comprising SEQ ID NO: 303 (EIVLTQSPGTLSLSPGERATLSC[LCDR1]WYQQKPGQAPRX10X11IY[LCDR2]GIPDR FSGSGSGTDFTLTISRLEPEDFAVYYC[LCDR3] FGGGTKLEIK), wherein X10=L or P and X11=L or W. In some cases, antibody B2 comprises a heavy chain variable region comprising human IGHV1-46*02 framework or a modified human IGHV1-46*02 framework, wherein the modified human IGHV1-46*02 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody B2 comprises a light chain variable region comprising human IGKV3-20 framework or a modified human IGKV3-20 framework, wherein the modified human IGKV3-20 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody B2 comprises a constant region comprising reduced ADCC and/or CDC as compared to IgG1. For instance, antibody B2 comprises a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 320. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 321. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 322. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 323. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 324. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 325. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 326. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 327. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 328. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 329. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 330. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 331. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 332. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 333. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 334. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 335. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 336. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 337. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 338. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 339. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 340. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 341. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 342. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 343. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 344. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 345. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 346. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 347. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 348. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 349. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 350. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 351. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 352. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 353. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 354. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 355. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 356. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 357. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 358. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 359. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 360. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 361. In some cases, antibody B2 comprises a constant region comprising at least about 85%, 87%, 88%, 89%, 90%, 91%, 92%, 93%, 94%, 95%, 96%, 97%, 98%, 99%, or 100% identity to SEQ ID NO: 362. In some cases, antibody B2 comprises at least about 80%, 81%, 82%, 83%, 84%, 85%, 85%, 87%, 88%, 89%, 90%, 91%, 92%, 93%, 94%, 95%, 96%, 97%, 98%, 99%, or 100% monomeric fraction as measured by the size exclusion method described in Example 2. In some cases, antibody B2 is expressed from FreeStyle 293-F cells at an expression level of about or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 5, 57, 58, 59 or 60 µg/mL as determined by the method described in Example 2. In some cases, antibody B2 is expressed from FreeStyle 293-F cells at an expression level of between about 2 µg/mL to about 60 µg/mL. In some cases, antibody B2 is expressed from FreeStyle 293-F cells at an expression level of between about 10 µg/mL to about 60 µg/mL.

In some embodiments, an anti-TL1A antibody comprises antibody C2. As used herein, antibody C2 comprises the CDRs of antibody C2 in Table 10. In some cases, antibody C2 comprises a heavy chain framework comprising SEQ ID NO: 302 (X1VQLVQSGAEVKKPGASVKVSCKAS[HCDR1]WVX2QX3PGQGLEWX4G[HCDR2]RX5TX6TX7DTSTSTX8YX9ELSSLRSEDTAVYYC[HCDR3]WGQGTTVTVSS), wherein X1=Q or E, X2=R or K, X3=A or R, X4=M or I, X5=V or A, X6=M or I, X7=R or T, X8=V or A, and X9=M or L. In some cases, antibody C2 comprises a light chain framework comprising SEQ ID NO: 303 (EIVLTQSPGTLSLSPGERATLSC[LCDR1]WYQQKPGQAPRX10X11IY[LCDR2]GIPDRFSGSGSGTDFTLTISRLEPEDFAVYYC[LCDR3]FGGGTKLEIK), wherein X10=L or P and X11=L or W. In some cases, antibody C2 comprises a heavy chain variable region comprising human IGHV1-46*02 framework or a modified human IGHV1-46*02 framework, wherein the modified human IGHV1-46*02 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody C2 comprises a light chain variable region comprising human IGKV3-20 framework or a modified human IGKV3-20 framework, wherein the modified human IGKV3-20 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody C2 comprises a constant region comprising reduced ADCC and/or CDC as compared to IgG1. For instance, antibody C2 comprises a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 320. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 321. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 322. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 323. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 324. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 325. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 326. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 327. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 328. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 329. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 330. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 331. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 332. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 333. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 334. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 335. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 336. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 337. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 338. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 339. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 340. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 341. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 342. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 343. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 344. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 345. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 346. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 347. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 348. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 349. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 350. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 351. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 352. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 353. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 354. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 355. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 356. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 357. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 358. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 359. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 360. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 361. In some cases, antibody C2 comprises a constant region comprising at least about 85%, 87%, 88%, 89%, 90%, 91%, 92%, 93%, 94%, 95%, 96%, 97%, 98%, 99%, or 100% identity to SEQ ID NO: 362. In some cases, antibody C2 comprises at least about 80%, 81%, 82%, 83%, 84%, 85%, 85%, 87%, 88%, 89%, 90%, 91%, 92%, 93%, 94%, 95%, 96%, 97%, 98%, 99%, or 100% monomeric fraction as measured by the size exclusion method described in Example 2. In some cases, antibody C2 is expressed from FreeStyle 293-F cells at an expression level of about or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 5, 57, 58, 59 or 60 µg/mL as determined by the method described in Example 2. In some cases, antibody C2 is expressed from FreeStyle 293-F cells at an expression level of between about 2 µg/mL to about 60 µg/mL. In some cases, antibody C2 is expressed from FreeStyle 293-F cells at an expression level of between about 10 µg/mL to about 60 µg/mL.

In some embodiments, an anti-TL1A antibody comprises antibody D2. As used herein, antibody D2 comprises the CDRs of antibody D2 in Table 10. In some cases, antibody D2 comprises a heavy chain framework comprising SEQ ID NO: 302 (X1VQLVQSGAEVKKPGASVKVSCKAS[HCDR1]WVX2QX3PGQGLEWX4G[HCDR2]RX5TX6TX7DTSTSTX8YX9ELSSLRSEDTAVYYC[HCDR3]WGQGTTVTVSS), wherein X1=Q or E, X2=R or K, X3=A or R, X4=M or I, X5=V or A, X6=M or I, X7=R or T, X8=V or A, and X9=M or L. In some cases, antibody D2 comprises a light chain framework comprising SEQ ID NO: 303 (EIVLTQSPGTLSLSPGERATLSC[LCDR1]WYQQKPGQAPRX10X11IY[LCDR2]GIPDRFSGSGSGTDFTLTISRLEPEDFAVYYC[LCDR3]FGGGTKLEIK), wherein X10=L or P and X11=L or W. In some cases, antibody D2 comprises a heavy chain variable region comprising human IGHV1-46*02 framework or a modified human IGHV1-46*02 framework, wherein the modified human IGHV1-46*02 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody D2 comprises a light chain variable region comprising human IGKV3-20 framework or a modified human IGKV3-20 framework, wherein the modified human IGKV3-20 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody D2 comprises a constant region comprising reduced ADCC and/or CDC as compared to IgG1. For instance, antibody D2 comprises a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 320. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 321. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 322. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 323. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 324. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 325. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 326. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 327. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 328. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 329. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 330. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 331. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 332. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 333. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 334. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 335. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 336. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 337. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 338. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 339. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 340. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 341. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 342. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 343. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 344. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 345. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 346. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 347. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 348. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 349. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 350. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 351. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 352. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 353. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 354. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 355. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 356. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 357. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 358. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 359. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 360. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 361. In some cases, antibody D2 comprises a constant region comprising at least about 85%, 87%, 88%, 89%, 90%, 91%, 92%, 93%, 94%, 95%, 96%, 97%, 98%, 99%, or 100% identity to SEQ ID NO: 362. In some cases, antibody D2 comprises at least about 80%, 81%, 82%, 83%, 84%, 85%, 85%, 87%, 88%, 89%, 90%, 91%, 92%, 93%, 94%, 95%, 96%, 97%, 98%, 99%, or 100% monomeric fraction as measured by the size exclusion method described in Example 2. In some cases, antibody D2 is expressed from FreeStyle 293-F cells at an expression level of about or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 5, 57, 58, 59 or 60 µg/mL as determined by the method described in Example 2. In some cases, antibody D2 is expressed from FreeStyle 293-F cells at an expression level of between about 2 µg/mL to about 60 µg/mL. In some cases, antibody D2 is expressed from FreeStyle 293-F cells at an expression level of between about 10 µg/mL to about 60 µg/mL.

In some embodiments, an anti-TL1A antibody comprises antibody E2. As used herein, antibody E2 comprises the CDRs of antibody E2 in Table 10. In some cases, antibody E2 comprises a heavy chain framework comprising SEQ ID NO: 302 (X1VQLVQSGAEVKKPGASVKVSCKAS[HCDR1]WVX2QX3PGQGLEWX4G[HCDR2]RX5TX6TX7DTSTSTX8YX9ELSSLRSEDTAVYYC[HCDR3]WGQGTTVTVSS), wherein X1=Q or E, X2=R or K, X3=A or R, X4=M or I, X5=V or A, X6=M or I, X7=R or T, X8=V or A, and X9=M or L. In some cases, antibody E2 comprises a light chain framework comprising SEQ ID NO: 303 (EIVLTQSPGTLSLSPGERATLSC[LCDR1]WYQQKPGQAPRX10X11IY[LCDR2]GIPDRFSGSGSGTDFTLTISRLEPEDFAVYYC[LCDR3]FGGGTKLEIK), wherein X10=L or P and X11=L or W. In some cases, antibody E2 comprises a heavy chain variable region comprising human IGHV1-46*02 framework or a modified human IGHV1-46*02 framework, wherein the modified human IGHV1-46*02 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody E2 comprises a light chain variable region comprising human IGKV3-20 framework or a modified human IGKV3-20 framework, wherein the modified human IGKV3-20 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody E2 comprises a constant region comprising reduced ADCC and/or CDC as compared to IgG1. For instance, antibody E2 comprises a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 320. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 321. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 322. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 323. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 324. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 325. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 326. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 327. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 328. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 329. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 330. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 331. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 332. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 333. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 334. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 335. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 336. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 337. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 338. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 339. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 340. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 341. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 342. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 343. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 344. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 345. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 346. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 347. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 348. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 349. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 350. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 351. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 352. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 353. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 354. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 355. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 356. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 357. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 358. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 359. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 360. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 361. In some cases, antibody E2 comprises a constant region comprising at least about 85%, 87%, 88%, 89%, 90%, 91%, 92%, 93%, 94%, 95%, 96%, 97%, 98%, 99%, or 100% identity to SEQ ID NO: 362. In some cases, antibody E2 comprises at least about 80%, 81%, 82%, 83%, 84%, 85%, 85%, 87%, 88%, 89%, 90%, 91%, 92%, 93%, 94%, 95%, 96%, 97%, 98%, 99%, or 100% monomeric fraction as measured by the size exclusion method described in Example 2. In some cases, antibody E2 is expressed from FreeStyle 293-F cells at an expression level of about or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 5, 57, 58, 59 or 60 µg/mL as determined by the method described in Example 2. In some cases, antibody E2 is expressed from FreeStyle 293-F cells at an expression level of between about 2 µg/mL to about 60 µg/mL. In some cases, antibody E2 is expressed from FreeStyle 293-F cells at an expression level of between about 10 µg/mL to about 60 µg/mL.

In some embodiments, an anti-TL1A antibody comprises antibody F2. As used herein, antibody F2 comprises the CDRs of antibody F2 in Table 10. In some cases, antibody F2 comprises a heavy chain framework comprising SEQ ID NO: 302 (X1VQLVQSGAEVKKPGASVKVSCKAS[HCDR1]WVX2QX3PGQGLEWX4G[HCDR2]RX5TX6TX7DTSTSTX8YX9ELSSLRSEDTAVYYC[HCDR3]WGQGTTVTVSS), wherein X1=Q or E, X2=R or K, X3=A or R, X4=M or I, X5=V or A, X6=M or I, X7=R or T, X8=V or A, and X9=M or L. In some cases, antibody F2 comprises a light chain framework comprising SEQ ID NO: 303 (EIVLTQSPGTLSLSPGERATLSC[LCDR1]WYQQKPGQAPRX10X11IY[LCDR2]GIPDRFSGSGSGTDFTLTISRLEPEDFAVYYC[LCDR3]FGGGTKLEIK), wherein X10=L or P and X11=L or W. In some cases, antibody F2 comprises a heavy chain variable region comprising human IGHV1-46*02 framework or a modified human IGHV1-46*02 framework, wherein the modified human IGHV1-46*02 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody F2 comprises a light chain variable region comprising human IGKV3-20 framework or a modified human IGKV3-20 framework, wherein the modified human IGKV3-20 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody F2 comprises a constant region comprising reduced ADCC and/or CDC as compared to IgG1. For instance, antibody F2 comprises a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 320. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 321. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 322. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 323. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 324. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 325. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 326. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 327. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 328. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 329. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 330. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 331. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 332. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 333. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 334. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 335. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 336. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 337. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 338. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 339. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 340. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 341. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 342. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 343. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 344. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 345. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 346. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 347. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 348. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 349. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 350. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 351. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 352. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 353. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 354. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 355. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 356. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 357. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 358. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 359. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 360. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 361. In some cases, antibody F2 comprises a constant region comprising at least about 85%, 87%, 88%, 89%, 90%, 91%, 92%, 93%, 94%, 95%, 96%, 97%, 98%, 99%, or 100% identity to SEQ ID NO: 362. In some cases, antibody F2 comprises at least about 80%, 81%, 82%, 83%, 84%, 85%, 85%, 87%, 88%, 89%, 90%, 91%, 92%, 93%, 94%, 95%, 96%, 97%, 98%, 99%, or 100% monomeric fraction as measured by the size exclusion method described in Example 2. In some cases, antibody F2 is expressed from FreeStyle 293-F cells at an expression level of about or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 5, 57, 58, 59 or 60 µg/mL as determined by the method described in Example 2. In some cases, antibody F2 is expressed from FreeStyle 293-F cells at an expression level of between about 2 µg/mL to about 60 µg/mL. In some cases, antibody F2 is expressed from FreeStyle 293-F cells at an expression level of between about 10 µg/mL to about 60 µg/mL.

In some embodiments, an anti-TL1A antibody comprises antibody G2. As used herein, antibody G2 comprises the CDRs of antibody G2 in Table 10. In some cases, antibody G2 comprises a heavy chain framework comprising SEQ ID NO: 302 (X1VQLVQSGAEVKKPGASVKVSCKAS[HCDR1]WVX2QX3PGQGLEWX4G[HCDR2]RX5TX6TX7DTSTSTX8YX9ELSSLRSEDTAVYYC[HCDR3]WGQGTTVTVSS), wherein X1=Q or E, X2=R or K, X3=A or R, X4=M or I, X5=V or A, X6=M or I, X7=R or T, X8=V or A, and X9=M or L. In some cases, antibody G2 comprises a light chain framework comprising SEQ ID NO: 303 (EIVLTQSPGTLSLSPGERATLSC[LCDR1]WYQQKPGQAPRX10X11IY[LCDR2]GIPDRFSGSGSGTDFTLTISRLEPEDFAVYYC[LCDR3]FGGGTKLEIK), wherein X10=L or P and X11=L or W. In some cases, antibody G2 comprises a heavy chain variable region comprising human IGHV1-46*02 framework or a modified human IGHV1-46*02 framework, wherein the modified human IGHV1-46*02 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody G2 comprises a light chain variable region comprising human IGKV3-20 framework or a modified human IGKV3-20 framework, wherein the modified human IGKV3-20 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody G2 comprises a constant region comprising reduced ADCC and/or CDC as compared to IgG1. For instance, antibody G2 comprises a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 320. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 321. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 322. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 323. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 324. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 325. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 326. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 327. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 328. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 329. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 330. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 331. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 332. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 333. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 334. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 335. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 336. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 337. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 338. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 339. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 340. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 341. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 342. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 343. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 344. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 345. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 346. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 347. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 348. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 349. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 350. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 351. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 352. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 353. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 354. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 355. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 356. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 357. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 358. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 359. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 360. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 361. In some cases, antibody G2 comprises a constant region comprising at least about 85%, 87%, 88%, 89%, 90%, 91%, 92%, 93%, 94%, 95%, 96%, 97%, 98%, 99%, or 100% identity to SEQ ID NO: 362. In some cases, antibody G2 comprises at least about 80%, 81%, 82%, 83%, 84%, 85%, 85%, 87%, 88%, 89%, 90%, 91%, 92%, 93%, 94%, 95%, 96%, 97%, 98%, 99%, or 100% monomeric fraction as measured by the size exclusion method described in Example 2. In some cases, antibody G2 is expressed from FreeStyle 293-F cells at an expression level of about or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 5, 57, 58, 59 or 60 µg/mL as determined by the method described in Example 2. In some cases, antibody G2 is expressed from FreeStyle 293-F cells at an expression level of between about 2 µg/mL to about 60 µg/mL. In some cases, antibody G2 is expressed from FreeStyle 293-F cells at an expression level of between about 10 µg/mL to about 60 µg/mL.

In some embodiments, an anti-TL1A antibody comprises antibody H2. As used herein, antibody H2 comprises the CDRs of antibody H2 in Table 10. In some cases, antibody H2 comprises a heavy chain framework comprising SEQ ID NO: 302 (X1VQLVQSGAEVKKPGASVKVSCKAS[HCDR1]WVX2QX3PGQGLEWX4G[HCDR2]RX5TX6TX7DTSTSTX8YX9ELSSLRSEDTAVYYC[HCDR3]WGQGTTVTVSS), wherein X1=Q or E, X2=R or K, X3=A or R, X4=M or I, X5=V or A, X6=M or I, X7=R or T, X8=V or A, and X9=M or L. In some cases, antibody H2 comprises a light chain framework comprising SEQ ID NO: 303 (EIVLTQSPGTLSLSPGERATLSC[LCDR1]WYQQKPGQAPRX10X11IY[LCDR2]GIPDR FSGSGSGTDFTLTISRLEPEDFAVYYC[LCDR3] FGGGTKLEIK), wherein X10=L or P and X11=L or W. In some cases, antibody H2 comprises a heavy chain variable region comprising human IGHV1-46*02 framework or a modified human IGHV1-46*02 framework, wherein the modified human IGHV1-46*02 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody H2 comprises a light chain variable region comprising human IGKV3-20 framework or a modified human IGKV3-20 framework, wherein the modified human IGKV3-20 framework has less than or equal to about 1, 2, 3, 4, 5, 6, 7, 8, 9, 10, 11, 12, 13, 14, 15, 16, 17, 18, 19, or 20 amino acid substitutions in the framework. In some cases, antibody H2 comprises a constant region comprising reduced ADCC and/or CDC as compared to IgG1. For instance, antibody H2 comprises a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 3431 or 343V, (jj)

373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 320. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 321. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 322. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 323. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 324. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 325. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 326. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 327. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 328. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 329. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 330. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 331. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 332. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 333. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 334. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 335. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 336. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 337. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 338. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 339. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 340. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 341. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 342. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 343. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 344. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 345. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 346. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 347. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 348. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 349. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 350. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 351. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 352. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 353. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 354. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 355. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 356. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 357. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 358. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 359. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 360. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 361. In some cases, antibody H2 comprises a constant region comprising at least about 85%, 87%, 88%, 89%, 90%, 91%, 92%, 93%, 94%, 95%, 96%, 97%, 98%, 99%, or 100% identity to SEQ ID NO: 362. In some cases, antibody H2 comprises at least about 80%, 81%, 82%, 83%, 84%, 85%, 85%, 87%, 88%, 89%, 90%, 91%, 92%, 93%, 94%, 95%, 96%, 97%, 98%, 99%, or 100% monomeric fraction as measured by the size exclusion method described in Example 2. In some cases, antibody H2 is expressed from FreeStyle 293-F cells at an expression level of about or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 5, 57, 58, 59 or 60 µg/mL as determined by the method described in Example 2. In some cases, antibody H2 is expressed from FreeStyle 293-F cells at an expression level of between about 2 µg/mL to about 60 µg/mL. In some cases, antibody H2 is expressed from FreeStyle 293-F cells at an expression level of between about 10 µg/mL to about 60 µg/mL.

The TL1A antibodies described herein bind to specific regions or epitopes of human TL1A demonstrated herein as useful to inhibit interferon gamma secretion from T lymphocytes. Various embodiments provide for an anti-TL1A antibody that binds to the same region of a TL1A protein or portion thereof as a reference antibody such as the anti-TL1A antibodies described herein. In some embodiments, the reference antibody comprises antibody A, B, C, D, E, F, G, H, A2, B2, C2, D2, E2, F2, G2, or H2, or a combination thereof. In some embodiments, provided herein is an anti-TL1A antibody that binds specifically to the same region of TL1A as a reference antibody comprising a heavy chain sequence at least about 90%, 92%, 93%, 94%, 95%, 96%, 97%, 98%, 99% or 100% identical to SEQ ID NO: 104, and a light chain comprising a sequence at least about 90%, 92%, 93%, 94%, 95%, 96%, 97%, 98%, 99% or 100% identical to SEQ ID NO: 201. In some embodiments, provided herein is an anti-TL1A antibody that binds specifically to the same region of TL1A as a reference antibody comprising a heavy chain sequence at least about 90%, 92%, 93%, 94%, 95%, 96%, 97%, 98%, 99% or 100% identical to SEQ ID NO: 107, and a light chain comprising a sequence at least about 90%, 92%, 93%, 94%, 95%, 96%, 97%, 98%, 99% or 100% identical to SEQ ID NO: 201.

Non-limiting methods for determining whether an anti-TL1A antibody (i.e. test antibody) binds to the same region of a TL1A protein or portion thereof as an antibody described herein are provided. An exemplary embodiment comprises a competition assay. For instance, the method comprises determining whether the test antibody can compete with binding between the reference antibody and the TL1A protein or portion thereof, or determining whether the reference antibody can compete with binding between the test antibody and the TL1A protein or portion thereof. Exemplary methods include use of surface plasmon resonance to evaluate whether an anti-TL1A antibody can compete with the binding between TL1A and another anti-TL1A antibody. In some cases, surface plasmon resonance is utilized in the competition assay. Non-limiting methods are described in the examples.

In certain embodiments, disclosed herein are antibodies that compete for binding TL1A with the antibodies described herein. In certain embodiments, disclosed herein are antibodies that bind a discrete epitope that overlaps with an epitope of TL1A bound by an antibody described herein. In certain embodiments, disclosed herein are antibodies that bind the same epitope of TL1A, overlap with the an epitope of TL1A by one or more amino acid residues, or that compete for binding to an epitope of TL1A with an antibody or fragment thereof that comprises a heavy chain variable region comprising the amino acid sequence of SEQ ID NO: 104; and a light chain variable region comprising the amino acid of SEQ ID NO: 201. In certain embodiments, disclosed herein are antibodies that bind the same epitope of TL1A, overlap with the an epitope of TL1A by one or more amino acid residues, or that compete for binding to an epitope of TL1A with an antibody or fragment thereof that comprises a heavy chain variable region comprising the amino acid sequence of SEQ ID NO: 107; and a light chain variable region comprising the amino acid of SEQ ID NO: 201.

ADDITIONAL ANTIBODY EMBODIMENTS (Embodiment 1) Further provided herein is an embodiment of an antibody or antigen binding fragment thereof that binds to TL1A, comprising a heavy chain variable framework region comprising a modified human IGHV1-46*02 framework, and a light chain variable framework region comprising a human IGKV3-20 framework or a modified human IGKV3-20 framework; wherein the heavy chain variable framework region and the light chain variable framework region collectively comprise between one and about 14 amino acid modifications from the human IGHV1-46*02 framework and the human IGKV3-20 framework, and wherein the amino acid modifications comprise A47R in the modified human IGHV1-46*02 framework. (Embodiment 2) The antibody or antigen binding fragment of embodiment 1, wherein the heavy chain variable framework region and the light chain variable framework region collectively comprise 13, 12, 11, 10, 9, 8, 7, 6, 5, 4, 3, 2, or 1 amino acid modifications from the human IGHV1-46*02 framework and the human IGKV3-20 framework. (Embodiment 3) The antibody or antigen binding fragment of embodiment 1 or embodiment 2, wherein the amino acid modification comprises a modification at amino acid position 1 in the heavy chain variable region, per Kabat numbering. (Embodiment 4) The antibody or antigen binding fragment of embodiment 3, wherein the amino acid at position 1 comprises A, R, N, D, C, E, G, H, I, L, K, M, F, P, S, T, W, Y, or V. (Embodiment 5) The antibody or antigen binding fragment of embodiment 3, wherein the amino acid at position 1 comprises a hydrophobic amino acid, a hydrophilic amino acid, or an amphipathic amino acid. (Embodiment 6) The antibody or antigen binding fragment of embodiment 3, wherein the amino acid at position 1 comprises an aliphatic amino acid, an aromatic amino acid, an acidic amino acid, a basic amino acid, a hydroxylic amino acid, a sulfur-containing amino acid, or an amidic amino acid. (Embodiment 7) The antibody or antigen binding fragment of embodiment 3, wherein the amino acid at position 1 comprises E. (Embodiment 8) The antibody or antigen binding fragment of any one of embodiments 1-7, wherein the amino acid modification comprises a modification at amino acid position 45 in the heavy chain variable region, per Kabat numbering. (Embodiment 9) The antibody or antigen binding fragment of embodiment 8, wherein the amino acid at position 45 comprises A, N, D, C, Q, E, G, H, I, L, K, M, F, P, S, T, W, Y, or V. (Embodiment 10) The antibody or antigen binding fragment of embodiment 8, wherein the amino acid at position 45 comprises a hydrophobic amino acid, a hydrophilic amino acid, or an amphipathic amino acid. (Embodiment 11) The antibody or antigen binding fragment of embodiment 8, wherein the amino acid at position 45 comprises an aliphatic amino acid, an aromatic amino acid, an acidic amino acid, a basic amino acid, a hydroxylic amino acid, a sulfur-containing amino acid, or an amidic amino acid. (Embodiment 12) The antibody or antigen binding fragment of embodiment 8, wherein the amino acid at position 45 comprises K. (Embodiment 13) The antibody or antigen binding fragment of any one of embodiments 1-12, wherein the amino acid modification comprises a modification at amino acid position 55 in the heavy chain variable region, per Kabat numbering. (Embodiment 14) The antibody or antigen binding fragment of embodiment 13, wherein the amino acid at position 55 comprises A, R, N, D, C, Q, E, G, H, I, L, K, F, P, S, T, W, Y, or V. (Embodiment 15) The antibody or antigen binding fragment of embodiment 13, wherein the amino acid at position 55 comprises a hydrophobic amino acid, a hydrophilic amino acid, or an amphipathic amino acid. (Embodiment 16) The antibody or antigen binding fragment of embodiment 13, wherein the amino acid at position 55 comprises an aliphatic amino acid, an aromatic amino acid, an acidic amino acid, a basic amino acid, a hydroxylic amino acid, a sulfur-containing amino acid, or an amidic amino acid. (Embodiment 17) The antibody or antigen binding fragment of embodiment 13, wherein the amino acid at position 55 comprises I. (Embodiment 18) The antibody or antigen binding fragment of any one of embodiments 1-17, wherein the amino acid modification comprises a modification at amino acid position 78 in the heavy chain variable region, per Kabat numbering. (Embodiment 19) The antibody or antigen binding fragment of embodiment 18, wherein the amino acid at position 78 comprises A, R, N, D, C, Q, E, G, H, I, L, K, M, F, P, S, T, W, or Y. (Embodiment 20) The antibody or antigen binding fragment of embodiment 18, wherein the amino acid at position 78 comprises a hydrophobic amino acid, a hydrophilic amino acid, or an amphipathic amino acid. (Embodiment 21) The antibody or antigen binding fragment of embodiment 18, wherein the amino acid at position 78 comprises an aliphatic amino acid, an aromatic amino acid, an acidic amino acid, a basic amino acid, a hydroxylic amino acid, a sulfur-containing amino acid, or an amidic amino acid. (Embodiment 22) The antibody or antigen binding fragment of embodiment 18, wherein the amino acid at position 78 comprises A. (Embodiment 23) The antibody or antigen binding fragment of any one of embodiments 1-22, wherein the amino acid modification comprises a modification at amino acid position 80 in the heavy chain variable region, per Kabat numbering. (Embodiment 24) The antibody or antigen binding fragment of embodiment 23, wherein the amino acid at position 80 comprises A, R, N, D, C, Q, E, G, H, I, L, K, F, P, S, T, W, Y, or V. (Embodiment 25) The antibody or antigen binding fragment of embodiment 23, wherein the amino acid at position 80 comprises a hydrophobic amino acid, a hydrophilic amino acid, or an amphipathic amino acid.

(Embodiment 26) The antibody or antigen binding fragment of embodiment 23, wherein the amino acid at position 80 comprises an aliphatic amino acid, an aromatic amino acid, an acidic amino acid, a basic amino acid, a hydroxylic amino acid, a sulfur-containing amino acid, or an amidic amino acid. (Embodiment 27) The antibody or antigen binding fragment of embodiment 23, wherein the amino acid at position 80 comprises I. (Embodiment 28) The antibody or antigen binding fragment of any one of embodiments 1-27, wherein the amino acid modification comprises a modification at amino acid position 82 in the heavy chain variable region, per Kabat numbering. (Embodiment 29) The antibody or antigen binding fragment of embodiment 28, wherein the amino acid at position 82 comprises A, N, D, C, Q, E, G, H, I, L, K, M, F, P, S, T, W, Y, or V. (Embodiment 30) The antibody or antigen binding fragment of embodiment 28, wherein the amino acid at position 82 comprises a hydrophobic amino acid, a hydrophilic amino acid, or an amphipathic amino acid. (Embodiment 31) The antibody or antigen binding fragment of embodiment 28, wherein the amino acid at position 82 comprises an aliphatic amino acid, an aromatic amino acid, an acidic amino acid, a basic amino acid, a hydroxylic amino acid, a sulfur-containing amino acid, or an amidic amino acid. (Embodiment 32) The antibody or antigen binding fragment of embodiment 28, wherein the amino acid at position 82 comprises T. (Embodiment 33) The antibody or antigen binding fragment of any one of embodiments 1-32, wherein the amino acid modification comprises a modification at amino acid position 89 in the heavy chain variable region, per Kabat numbering. (Embodiment 34) The antibody or antigen binding fragment of embodiment 33, wherein the amino acid at position 89 comprises A, R, N, D, C, Q, E, G, H, I, L, K, M, F, P, S, T, W, or Y. (Embodiment 35) The antibody or antigen binding fragment of embodiment 33, wherein the amino acid at position 89 comprises a hydrophobic amino acid, a hydrophilic amino acid, or an amphipathic amino acid. (Embodiment 36) The antibody or antigen binding fragment of embodiment 33, wherein the amino acid at position 89 comprises an aliphatic amino acid, an aromatic amino acid, an acidic amino acid, a basic amino acid, a hydroxylic amino acid, a sulfur-containing amino acid, or an amidic amino acid. (Embodiment 37) The antibody or antigen binding fragment of embodiment 33, wherein the amino acid at position 89 comprises A. (Embodiment 38) The antibody or antigen binding fragment of any one of embodiments 1-37, wherein the amino acid modification comprises a modification at amino acid position 91 in the heavy chain variable region, per Kabat numbering. (Embodiment 39) The antibody or antigen binding fragment of embodiment 38, wherein the amino acid at position 91 comprises A, R, N, D, C, Q, E, G, H, I, L, K, F, P, S, T, W, Y, or V. (Embodiment 40) The antibody or antigen binding fragment of embodiment 38, wherein the amino acid at position 91 comprises a hydrophobic amino acid, a hydrophilic amino acid, or an amphipathic amino acid. (Embodiment 41) The antibody or antigen binding fragment of embodiment 38, wherein the amino acid at position 91 comprises an aliphatic amino acid, an aromatic amino acid, an acidic amino acid, a basic amino acid, a hydroxylic amino acid, a sulfur-containing amino acid, or an amidic amino acid. (Embodiment 42) The antibody or antigen binding fragment of embodiment 38, wherein the amino acid at position 91 comprises L. (Embodiment 43) The antibody or antigen binding fragment of embodiment 1 or embodiment 2, wherein the amino acid modifications comprise one or more of: Q1E, R45K, M55I, V78A, M80I, R82T, V89A, M91L in the heavy chain variable region, per Aho numbering. (Embodiment 44) The antibody or antigen binding fragment of embodiment 43, wherein the amino acid modifications comprise Q1E. (Embodiment 45) The antibody or antigen binding fragment of embodiment 43 or embodiment 44, wherein the amino acid modifications comprise R45K. (Embodiment 46) The antibody or antigen binding fragment of any one of embodiments 43-45, wherein the amino acid modifications comprise M55I. (Embodiment 47) The antibody or antigen binding fragment of any one of embodiments 43-46, wherein the amino acid modifications comprise V78A. (Embodiment 48) The antibody or antigen binding fragment of any one of embodiments 43-47, wherein the amino acid modifications comprise M80I. (Embodiment 49) The antibody or antigen binding fragment of any one of embodiments 43-48, wherein the amino acid modifications comprise R82T. (Embodiment 50) The antibody or antigen binding fragment of any one of embodiments 43-49, wherein the amino acid modifications comprise V89A. (Embodiment 51) The antibody or antigen binding fragment of any one of embodiments 43-50, wherein the amino acid modifications comprise M91L. (Embodiment 52) The antibody or antigen binding fragment of any one of embodiments 1-51, wherein the amino acid modification comprises a modification at amino acid position 54 in the light chain variable region, per Kabat numbering. (Embodiment 53) The antibody or antigen binding fragment of embodiment 52, wherein the amino acid at position 54 comprises A, R, N, D, C, Q, E, G, H, I, K, M, F, P, S, T, W, Y, or V. (Embodiment 54) The antibody or antigen binding fragment of embodiment 52, wherein the amino acid at position 54 comprises a hydrophobic amino acid, a hydrophilic amino acid, or an amphipathic amino acid. (Embodiment 55) The antibody or antigen binding fragment of embodiment 52, wherein the amino acid at position 54 comprises an aliphatic amino acid, an aromatic amino acid, an acidic amino acid, a basic amino acid, a hydroxylic amino acid, a sulfur-containing amino acid, or an amidic amino acid. (Embodiment 56) The antibody or antigen binding fragment of embodiment 52, wherein the amino acid at position 54 comprises P. (Embodiment 57) The antibody or antigen binding fragment of any one of embodiments 1-56, wherein the amino acid modification comprises a modification at amino acid position 55 in the light chain variable region, per Kabat numbering. (Embodiment 58) The antibody or antigen binding fragment of embodiment 57, wherein the amino acid at position 55 comprises A, R, N, D, C, Q, E, G, H, I, K, M, F, P, S, T, W, Y, or V. (Embodiment 59) The antibody or antigen binding fragment of embodiment 57, wherein the amino acid at position 55 comprises a hydrophobic amino acid, a hydrophilic amino acid, or an amphipathic amino acid. (Embodiment 60) The antibody or antigen binding fragment of embodiment 57, wherein the amino acid at position 55 comprises an aliphatic amino acid, an aromatic amino acid, an acidic amino acid, a basic amino acid, a hydroxylic amino acid, a sulfur-containing amino acid, or an amidic amino acid. (Embodiment 61) The antibody or antigen binding fragment of embodiment 57, wherein the amino acid at position 55 comprises W. (Embodiment 62) The antibody or antigen binding fragment of any one of embodiments 1-51, wherein the amino acid modifications comprise L54P and/or L55W in the light chain variable region, per Aho numbering. (Embodiment 63) The antibody or antigen binding fragment of embodiment 62, wherein the amino acid modifications comprise L54P. (Embodiment 64) The antibody or antigen binding fragment of embodiment 62 or embodiment 63, wherein the amino acid modifications comprise L55W.

(Embodiment 65) The antibody or antigen binding fragment of any one of embodiments 1-64, comprising a heavy chain CDR1 as set forth by SEQ ID NO: 1. (Embodiment 66) The antibody or antigen binding fragment of any one of embodiments 1-65, comprising a heavy chain CDR2 as set forth by SEQ ID NO: 2. (Embodiment 67) The antibody or antigen binding fragment of any one of embodiments 1-65, comprising a heavy chain CDR2 as set forth by SEQ ID NO: 3. (Embodiment 68) The antibody or antigen binding fragment of any one of embodiments 1-65, comprising a heavy chain CDR2 as set forth by SEQ ID NO: 4. (Embodiment 69) The antibody or antigen binding fragment of any one of embodiments 1-65, comprising a heavy chain CDR2 as set forth by SEQ ID NO: 5. (Embodiment 70) The antibody or antigen binding fragment of any one of embodiments 1-69, comprising a heavy chain CDR3 as set forth by SEQ ID NO: 6. (Embodiment 71) The antibody or antigen binding fragment of any one of embodiments 1-69, comprising a heavy chain CDR3 as set forth by SEQ ID NO: 7. (Embodiment 72) The antibody or antigen binding fragment of any one of embodiments 1-69, comprising a heavy chain CDR3 as set forth by SEQ ID NO: 8. (Embodiment 73) The antibody or antigen binding fragment of any one of embodiments 1-69, comprising a heavy chain CDR3 as set forth by SEQ ID NO: 9. (Embodiment 74) The antibody or antigen binding fragment of any one of embodiments 1-73, comprising a light chain CDR1 as set forth by SEQ ID NO: 10. (Embodiment 75) The antibody or antigen binding fragment of any one of embodiments 1-74, comprising a light chain CDR2 as set forth by SEQ ID NO: 11. (Embodiment 76) The antibody or antigen binding fragment of any one of embodiments 1-75, comprising a light chain CDR3 as set forth by SEQ ID NO: 12. (Embodiment 77) The antibody or antigen binding fragment of any one of embodiments 1-75, comprising a light chain CDR3 as set forth by SEQ ID NO: 13. (Embodiment 78) The antibody or antigen binding fragment of any one of embodiments 1-75, comprising a light chain CDR3 as set forth by SEQ ID NO: 14 or 15. (Embodiment 79) The antibody or antigen binding fragment of any one of embodiments 1-78, comprising a heavy chain FR1 as set forth by SEQ ID NO: 304. (Embodiment 80) The antibody or antigen binding fragment of any one of embodiments 1-79, comprising a heavy chain FR2 as set forth by SEQ ID NO: 305. (Embodiment 81) The antibody or antigen binding fragment of any one of embodiments 1-79, comprising a heavy chain FR2 as set forth by SEQ ID NO: 313. (Embodiment 82) The antibody or antigen binding fragment of any one of embodiments 1-81, comprising a heavy chain FR3 as set forth by SEQ ID NO: 306. (Embodiment 83) The antibody or antigen binding fragment of any one of embodiments 1-81, comprising a heavy chain FR3 as set forth by SEQ ID NO: 307. (Embodiment 84) The antibody or antigen binding fragment of any one of embodiments 1-81, comprising a heavy chain FR3 as set forth by SEQ ID NO: 314. (Embodiment 85) The antibody or antigen binding fragment of any one of embodiments 1-81, comprising a heavy chain FR3 as set forth by SEQ ID NO: 315. (Embodiment 86) The antibody or antigen binding fragment of any one of embodiments 1-85, comprising a heavy chain FR4 as set forth by SEQ ID NO: 308. (Embodiment 87) The antibody or antigen binding fragment of any one of embodiments 1-86, comprising a light chain FR1 as set forth by SEQ ID NO: 309. (Embodiment 88) The antibody or antigen binding fragment of any one of embodiments 1-87, comprising a light chain FR2 as set forth by SEQ ID NO: 310. (Embodiment 89) The antibody or antigen binding fragment of any one of embodiments 1-88, comprising a light chain FR3 as set forth by SEQ ID NO: 311. (Embodiment 90) The antibody or antigen binding fragment of any one of embodiments 1-89, comprising a light chain FR4 as set forth by SEQ ID NO: 312. (Embodiment 91) The antibody or antigen binding fragment of any one of embodiments 1-90, comprising a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. (Embodiment 92) The antibody or antigen binding fragment of any one of embodiments 1-90, comprising a human IgG4 Fc region. (Embodiment 93) The antibody or antigen binding fragment of any one of embodiments 1-90, comprising a Fc region comprising a sequence at least about 90%, 91%, 92%, 93%, 94%, 95%, 96%, 97%, 98%, 99%, or 100% identical to any one of SEQ ID NOS: 320-362. (Embodiment 94) The antibody or antigen binding fragment of any one of embodiments 1-93, comprising at least about 80% monomeric fraction as determined by size exclusion chromatography. (Embodiment 95) The antibody or antigen binding fragment of embodiment 94, comprising at least about 85%, 90%, 91%, 92%, 93%, 94%, 95%, 96%, 97%, 98%, or 99% monomeric fraction. (Embodiment 96) The antibody or antigen binding fragment of embodiment 94 or embodiment 95, wherein the size exclusion chromatography comprises injecting purified antibody or antigen binding fragment onto a size exclusion column, wherein the antibody or antigen binding fragment is purified by protein A. (Embodiment 97) The antibody or antigen binding fragment of embodiment 96, wherein the antibody or antigen binding fragment is purified as described in Example 2. (Embodiment 98) The antibody or antigen binding fragment of embodiment 96 or embodiment 97, wherein the antibody or antigen binding fragment is expressed under conditions described in Example 2. (Embodiment 99) The antibody or antigen binding fragment of any one of embodiments 96-98, wherein the size exclusion chromatography column has an inner diameter of 4.6 mm. (Embodiment 100) The antibody or antigen binding fragment of any one of embodiments 96-99, wherein the size exclusion chromatography column has a length of 150 mm. (Embodiment 101) The antibody or antigen binding fragment of any one of embodiments 96-100, wherein the size exclusion chromatography column has a pore size of 200 Å. (Embodiment 102) The antibody or antigen binding fragment of any one of embodiments 96-101, wherein the size exclusion chromatography column has a particle size of 1.7 micrometer. (Embodiment 103) The antibody or antigen binding fragment of any one of embodiments 96-102, wherein the size exclusion chromatography column is ACQUITY UPLC BEH200 SEC column. (Embodiment 104) The antibody or antigen binding fragment of any one of embodiments 96-103, wherein the antibody or antigen binding fragment is injected at a total volume of 15 μL. (Embodiment 105) The antibody or antigen binding fragment of any one of embodiments 96-104, wherein the antibody or antigen binding fragment is injected at a concentration of about 0.1 μg/μL to about 1.0 μg/μL. (Embodiment 106) The antibody or antigen binding fragment of any one of embodiments 96-105, wherein the size exclusion chromatography is performed on a Shimadzu UPLC instrument. (Embodiment 107) The antibody or antigen binding fragment of any one of embodiments 96-106, wherein the size exclusion chromatography is performed at a flow rate of 0.2 mL/min. (Embodiment 108) The antibody or antigen binding fragment of any one of embodiments 96-107, wherein the size exclusion chromatography is performed at a column oven temperature of 30° C. (Embodiment 109) The antibody or antigen binding fragment of any one of embodiments 96-108, wherein the percentage of monomer is calculated using Shimadzu software. (Embodiment 110) The antibody or antigen binding fragment of any one of embodiments 96-109, wherein the size exclusion chromatography is performed as described in Example 2. (Embodiment 111) The antibody or antigen binding fragment of any one of embodiments 1-110, expressing at least about 20 ug/ml total antibody. (Embodiment 112) The antibody or antigen binding fragment of any one of embodiments 1-110, expressing between about 20 ug/ml and 70 ug/mL total antibody. (Embodiment 113) The antibody or antigen binding fragment of embodiment 111 or embodiment 112, wherein the antibody or antigen binding fragment is expressed in FreeStyle 293-F cells. (Embodiment 114) The antibody or antigen binding fragment of any one of embodiments 111-113, wherein the antibody or antigen binding fragment is expressed as described in Example 2. (Embodiment 115) The antibody or antigen binding fragment of any one of embodiments 111-114, wherein the antibody or antigen binding fragment expression level is quantified using Enzyme-Linked Immunosorbent assay (ELISA). (Embodiment 116) The antibody or antigen binding fragment of embodiment 115, wherein the ELISA comprises coating a surface of a substrate with a capture antibody that binds to a human or humanized antibody, applying the antibody or antigen binding fragment to the substrate, and applying to the substrate a second antibody that binds to a human or humanized antibody. (Embodiment 117) The antibody or antigen binding fragment of embodiment 116, where the capture antibody comprises an anti-kappa antibody. (Embodiment 118) The antibody or antigen binding fragment of embodiment 116 or embodiment 117, where the second antibody comprises an anti-Fc antibody. (Embodiment 119) The antibody or antigen binding fragment of any one of embodiments 115-118, where the ELISA is performed as described in Example 2.

(Embodiment 120) An antibody or antigen binding fragment thereof that binds to TL1A, comprising: a) a heavy chain variable region comprising SEQ ID NO: 1301 b) X1VQLVQSGAEVKKPGASVKVSCKAS[HCDR1]WVX2QRPGQGLEWX4G[HCDR2]R X5TX6TX7DTSTSTX8YX9ELSSLRSEDTAVYYCAR[HCDR3]WGQGTTVTVSS, and c) a light chain variable region comprising SEQ ID NO: 303 d) EIVLTQSPGTLSLSPGERATLSC[LCDR1]WYQQKPGQAPRX10X11IY[LCDR2]GIPDR FSGSGSGTDFTLTISRLEPEDFAVYYC[LCDR3]FGGGTKLEIK, e) wherein each of X1, X2, X4, X5, X6, X7, X8, X9, X10, and X11 is independently selected from A, R, N, D, C, Q, E, G, H, I, L, K, M, F, P, S, T, W, Y, or V. (Embodiment 121) The antibody or antigen binding fragment of embodiment 120, wherein X1 comprises a hydrophobic amino acid, a hydrophilic amino acid, or an amphipathic amino acid. (Embodiment 122) The antibody or antigen binding fragment of embodiment 120, wherein X1 comprises an aliphatic amino acid, an aromatic amino acid, an acidic amino acid, a basic amino acid, a hydroxylic amino acid, a sulfur-containing amino acid, or an amidic amino acid. (Embodiment 123) The antibody or antigen binding fragment of any one of embodiments 120-122, wherein X2 comprises a hydrophobic amino acid, a hydrophilic amino acid, or an amphipathic amino acid. (Embodiment 124) The antibody or antigen binding fragment of any one of embodiments 120-122, wherein X2 comprises an aliphatic amino acid, an aromatic amino acid, an acidic amino acid, a basic amino acid, a hydroxylic amino acid, a sulfur-containing amino acid, or an amidic amino acid. (Embodiment 125) The antibody or antigen binding fragment of any one of embodiments 120-124, wherein X4 comprises a hydrophobic amino acid, a hydrophilic amino acid, or an amphipathic amino acid. (Embodiment 126) The antibody or antigen binding fragment of any one of embodiments 120-124, wherein X4 comprises an aliphatic amino acid, an aromatic amino acid, an acidic amino acid, a basic amino acid, a hydroxylic amino acid, a sulfur-containing amino acid, or an amidic amino acid. (Embodiment 127) The antibody or antigen binding fragment of any one of embodiments 120-126, wherein X5 comprises a hydrophobic amino acid, a hydrophilic amino acid, or an amphipathic amino acid. (Embodiment 128) The antibody or antigen binding fragment of any one of embodiments 120-126, wherein X5 comprises an aliphatic amino acid, an aromatic amino acid, an acidic amino acid, a basic amino acid, a hydroxylic amino acid, a sulfur-containing amino acid, or an amidic amino acid. (Embodiment 129) The antibody or antigen binding fragment of any one of embodiments 120-128, wherein X6 comprises a hydrophobic amino acid, a hydrophilic amino acid, or an amphipathic amino acid. (Embodiment 130) The antibody or antigen binding fragment of any one of embodiments 120-128, wherein X6 comprises an aliphatic amino acid, an aromatic amino acid, an acidic amino acid, a basic amino acid, a hydroxylic amino acid, a sulfur-containing amino acid, or an amidic amino acid. (Embodiment 131) The antibody or antigen binding fragment of any one of embodiments 120-130, wherein X7 comprises a hydrophobic amino acid, a hydrophilic amino acid, or an amphipathic amino acid. (Embodiment 132) The antibody or antigen binding fragment of any one of embodiments 120-130, wherein X7 comprises an aliphatic amino acid, an aromatic amino acid, an acidic amino acid, a basic amino acid, a hydroxylic amino acid, a sulfur-containing amino acid, or an amidic amino acid. (Embodiment 133) The antibody or antigen binding fragment of any one of embodiments 120-132, wherein X8 comprises a hydrophobic amino acid, a hydrophilic amino acid, or an amphipathic amino acid. (Embodiment 134) The antibody or antigen binding fragment of any one of embodiments 120-132, wherein X8 comprises an aliphatic amino acid, an aromatic amino acid, an acidic amino acid, a basic amino acid, a hydroxylic amino acid, a sulfur-containing amino acid, or an amidic amino acid. (Embodiment 135) The antibody or antigen binding fragment of any one of embodiments 120-134, wherein X9 comprises a hydrophobic amino acid, a hydrophilic amino acid, or an amphipathic amino acid. (Embodiment 136) The antibody or antigen binding fragment of any one of embodiments 120-134, wherein X9 comprises an aliphatic amino acid, an aromatic amino acid, an acidic amino acid, a basic amino acid, a hydroxylic amino acid, a sulfur-containing amino acid, or an amidic amino acid. (Embodiment 137) The antibody or antigen binding fragment of any one of embodiments 120-136, wherein X10 comprises a hydrophobic amino acid, a hydrophilic amino acid, or an amphipathic amino acid. (Embodiment 138) The antibody or antigen binding fragment of any one of embodiments 120-136, wherein X10 comprises an aliphatic amino acid, an aromatic amino acid, an acidic amino acid, a basic amino acid, a hydroxylic amino acid, a sulfur-containing amino acid, or an amidic amino acid. (Embodiment 139) The antibody or antigen binding fragment of any one of embodiments 120-138, wherein X11 comprises a hydrophobic amino acid, a hydrophilic amino acid, or an amphipathic amino acid. (Embodiment 140) The antibody or antigen binding fragment of any one of embodiments 120-138, wherein X11 comprises an aliphatic amino acid, an aromatic amino acid, an acidic amino acid, a basic amino acid, a hydroxylic amino acid, a sulfur-containing amino acid, or an amidic amino acid. (Embodiment 141) The antibody or antigen binding fragment of embodiment 120, wherein X1=Q or E, X2=R or K, X4=M or I, X5=V or A, X6=M or I, X7=R or T, X8=V or A, X9=M or L, X10=L or P, and X11=L or W. (Embodiment 142) The antibody or antigen binding fragment of any one of embodiments 120-141, wherein X1=Q. (Embodiment 143) The antibody or antigen binding fragment of any one of embodiments 120-141, wherein X1=E. (Embodiment 144) The antibody or antigen binding fragment of any one of embodiments 120-143, wherein X2=R. (Embodiment 145) The antibody or antigen binding fragment of any one of embodiments 120-143, wherein X2=K. (Embodiment 146) The antibody or antigen binding fragment of any one of embodiments 120-145, wherein X4=M. (Embodiment 147) The antibody or antigen binding fragment of any one of embodiments 120-145, wherein X4=I. (Embodiment 148) The antibody or antigen binding fragment of any one of embodiments 120-147, wherein X5=V. (Embodiment 149) The antibody or antigen binding fragment of any one of embodiments 120-147, wherein X5=A. (Embodiment 150) The antibody or antigen binding fragment of any one of embodiments 120-149, wherein X6=M. (Embodiment 151) The antibody or antigen binding fragment of any one of embodiments 120-149, wherein X6=I. (Embodiment 152) The antibody or antigen binding fragment of any one of embodiments 120-151, wherein X7=R. (Embodiment 153) The antibody or antigen binding fragment of any one of embodiments 120-151, wherein X7=T. (Embodiment 154) The antibody or antigen binding fragment of any one of embodiments 120-153, wherein X8=V. (Embodiment 155) The antibody or antigen binding fragment of any one of embodiments 120-153, wherein X8=A. (Embodiment 156) The antibody or antigen binding fragment of any one of embodiments 120-155, wherein X9=M. (Embodiment 157) The antibody or antigen binding fragment of any one of embodiments 120-155, wherein X9=L. (Embodiment 158) The antibody or antigen binding fragment of any one of embodiments 120-157, wherein X10=L. (Embodiment 159) The antibody or antigen binding fragment of any one of embodiments 120-157, wherein X10=P. (Embodiment 160) The antibody or antigen binding fragment of any one of embodiments 120-159, wherein X11=L. (Embodiment 161) The antibody or antigen binding fragment of any one of embodiments 120-159, wherein X11=W. (Embodiment 162) An antibody or antigen binding fragment thereof that binds to TL1A, comprising: a) a heavy chain variable region comprising SEQ ID NO: 1302 b) X1VQLVQSGAEVKKPGASVKVSCKAS[HCDR1]WVX2QRPGQGLEWX4G[HCDR2]R X5TX6TX7DTSTSTX8YX9ELSSLRSEDTAVYYC [HCDR3]WGQGTTVTVSS, and c) a light chain variable region comprising SEQ ID NO: 303 d) EIVLTQSPGTLSLSPGERATLSC[LCDR1]WYQQKPGQAPRX10X11IY [LCDR2]GIPDR FSGSGSGTDFTLTISRLEPEDFAVYYC [LCDR3]FGGGTKLEIK, e) wherein each of X1, X2, X4, X5, X6, X7, X8, X9, X10 and X11 is independently selected from A, R, N, D, C, Q, E, G, H, I, L, K, M, F, P, S, T, W, Y, or V. (Embodiment 163) The antibody or antigen binding fragment of embodiment 162, wherein X1 comprises a hydrophobic amino acid, a hydrophilic amino acid, or an amphipathic amino acid. (Embodiment 164) The antibody or antigen binding fragment of embodiment 162, wherein X1 comprises an aliphatic amino acid, an aromatic amino acid, an acidic amino acid, a basic amino acid, a hydroxylic amino acid, a sulfur-containing amino acid, or an amidic amino acid. (Embodiment 165) The antibody or antigen binding fragment of any one of embodiments 162-164, wherein X2 comprises a hydrophobic amino acid, a hydrophilic amino acid, or an amphipathic amino acid. (Embodiment 166) The antibody or antigen binding fragment of any one of embodiments 162-164, wherein X2 comprises an aliphatic amino acid, an aromatic amino acid, an acidic amino acid, a basic amino acid, a hydroxylic amino acid, a sulfur-containing amino acid, or an amidic amino acid. (Embodiment 167) The antibody or antigen binding fragment of any one of embodiments 162-166, wherein X4 comprises a hydrophobic amino acid, a hydrophilic amino acid, or an amphipathic amino acid. (Embodiment 168) The antibody or antigen binding fragment of any one of embodiments 162-166, wherein X4 comprises an aliphatic amino acid, an aromatic amino acid, an acidic amino acid, a basic amino acid, a hydroxylic amino acid, a sulfur-containing amino acid, or an amidic amino acid. (Embodiment 169) The antibody or antigen binding fragment of any one of embodiments 162-168, wherein X5 comprises a hydrophobic amino acid, a hydrophilic amino acid, or an amphipathic amino acid. (Embodiment 170) The antibody or antigen binding fragment of any one of embodiments 162-168, wherein X5 comprises an aliphatic amino acid, an aromatic amino acid, an acidic amino acid, a basic amino acid, a hydroxylic amino acid, a sulfur-containing amino acid, or an amidic amino acid. (Embodiment 171) The antibody or antigen binding fragment of any one of embodiments 162-170, wherein X6 comprises a hydrophobic amino acid, a hydrophilic amino acid, or an amphipathic amino acid. (Embodiment 172) The antibody or antigen binding fragment of any one of embodiments 162-170, wherein X6 comprises an aliphatic amino acid, an aromatic amino acid, an acidic amino acid, a basic amino acid, a hydroxylic amino acid, a sulfur-containing amino acid, or an amidic amino acid. (Embodiment 173) The antibody or antigen binding fragment of any one of embodiments 162-172, wherein X7 comprises a hydrophobic amino acid, a hydrophilic amino acid, or an amphipathic amino acid. (Embodiment 174) The antibody or antigen binding fragment of any one of embodiments 162-172, wherein X7 comprises an aliphatic amino acid, an aromatic amino acid, an acidic amino acid, a basic amino acid, a hydroxylic amino acid, a sulfur-containing amino acid, or an amidic amino acid. (Embodiment 175) The antibody or antigen binding fragment of any one of embodiments 162-174, wherein X8 comprises a hydrophobic amino acid, a hydrophilic amino acid, or an amphipathic amino acid. (Embodiment 176) The antibody or antigen binding fragment of any one of embodiments 162-174, wherein X8 comprises an aliphatic amino acid, an aromatic amino acid, an acidic amino acid, a basic amino acid, a hydroxylic amino acid, a sulfur-containing amino acid, or an amidic amino acid. (Embodiment 177) The antibody or antigen binding fragment of any one of embodiments 162-176, wherein X9 comprises a hydrophobic amino acid, a hydrophilic amino acid, or an amphipathic amino acid. (Embodiment 178) The antibody or antigen binding fragment of any one of embodiments 162-176, wherein X9 comprises an aliphatic amino acid, an aromatic amino acid, an acidic amino acid, a basic amino acid, a hydroxylic amino acid, a sulfur-containing amino acid, or an amidic amino acid. (Embodiment 179) The antibody or antigen binding fragment of any one of embodiments 162-178, wherein X10 comprises a hydrophobic amino acid, a hydrophilic amino acid, or an amphipathic amino acid. (Embodiment 180) The antibody or antigen binding fragment of any one of embodiments 162-178, wherein X10 comprises an aliphatic amino acid, an aromatic amino acid, an acidic amino acid, a basic amino acid, a hydroxylic amino acid, a sulfur-containing amino acid, or an amidic amino acid. (Embodiment 181) The antibody or antigen binding fragment of any one of embodiments 162-180, wherein X11 comprises a hydrophobic amino acid, a hydrophilic amino acid, or an amphipathic amino acid. (Embodiment 182) The antibody or antigen binding fragment of any one of embodiments 162-180, wherein X11 comprises an aliphatic amino acid, an aromatic amino acid, an acidic amino acid, a basic amino acid, a hydroxylic amino acid, a sulfur-containing amino acid, or an amidic amino acid. (Embodiment 183) The antibody or antigen binding fragment of embodiment 162, wherein X1=Q or E, X2=R or K, X4=M or I, X5=V or A, X6=M or I, X7=R or T, X8=V or A, X9=M or L, X10=L or P, and X11=L or W. (Embodiment 184) The antibody or antigen binding fragment of any one of embodiments 162-183, wherein X1=Q. (Embodiment 185) The antibody or antigen binding fragment of any one of embodiments 162-183, wherein X1=E. (Embodiment 186) The antibody or antigen binding fragment of any one of embodiments 162-185, wherein X2=R. (Embodiment 187) The antibody or antigen binding fragment of any one of embodiments 162-185, wherein X2=K. (Embodiment 188) The antibody or antigen binding fragment of any one of embodiments 162-187, wherein X4=M. (Embodiment 189) The antibody or antigen binding fragment of any one of embodiments 162-187, wherein X4=I. (Embodiment 190) The antibody or antigen binding fragment of any one of embodiments 162-189, wherein X5=V. (Embodiment 191) The antibody or antigen binding fragment of any one of embodiments 162-189, wherein X5=A. (Embodiment 192) The antibody or antigen binding fragment of any one of embodiments 162-191, wherein X6=M. (Embodiment 193)

The antibody or antigen binding fragment of any one of embodiments 162-191, wherein X6=I. (Embodiment 194) The antibody or antigen binding fragment of any one of embodiments 162-193, wherein X7=R. (Embodiment 195) The antibody or antigen binding fragment of any one of embodiments 162-193, wherein X7=T. (Embodiment 196) The antibody or antigen binding fragment of any one of embodiments 162-195, wherein X8=V. (Embodiment 197) The antibody or antigen binding fragment of any one of embodiments 162-195, wherein X8=A. (Embodiment 198) The antibody or antigen binding fragment of any one of embodiments 162-197, wherein X9=M. (Embodiment 199) The antibody or antigen binding fragment of any one of embodiments 162-197, wherein X9=L. (Embodiment 200) The antibody or antigen binding fragment of any one of embodiments 162-199, wherein X10=L. (Embodiment 201) The antibody or antigen binding fragment of any one of embodiments 162-199, wherein X10=P. (Embodiment 202) The antibody or antigen binding fragment of any one of embodiments 162-201, wherein X11=L. (Embodiment 203) The antibody or antigen binding fragment of any one of embodiments 162-201, wherein X11=W. (Embodiment 204) The antibody or antigen binding fragment of any one of embodiments 120-203, wherein HCDR1 comprises SEQ ID NO: 1. (Embodiment 205) The antibody or antigen binding fragment of any one of embodiments 126-204, wherein HCDR2 comprises SEQ ID NO: 2. (Embodiment 206) The antibody or antigen binding fragment of any one of embodiments 126-204, wherein HCDR2 comprises SEQ ID NO: 3. (Embodiment 207) The antibody or antigen binding fragment of any one of embodiments 126-204, wherein HCDR2 comprises SEQ ID NO: 4. (Embodiment 208) The antibody or antigen binding fragment of any one of embodiments 126-204, wherein HCDR2 comprises SEQ ID NO: 5. (Embodiment 209) The antibody or antigen binding fragment of any one of embodiments 126-208, wherein HCDR3 comprises SEQ ID NO: 6. (Embodiment 210) The antibody or antigen binding fragment of any one of embodiments 126-208, wherein HCDR3 comprises SEQ ID NO: 7. (Embodiment 211) The antibody or antigen binding fragment of any one of embodiments 126-208, wherein HCDR3 comprises SEQ ID NO: 8. (Embodiment 212) The antibody or antigen binding fragment of any one of embodiments 126-208, wherein HCDR3 comprises SEQ ID NO: 9. (Embodiment 213) The antibody or antigen binding fragment of any one of embodiments 126-212, wherein LCDR1 comprises SEQ ID NO: 10. (Embodiment 214) The antibody or antigen binding fragment of any one of embodiments 126-213, wherein LCDR2 comprises SEQ ID NO: 11. (Embodiment 215) The antibody or antigen binding fragment of any one of embodiments 126-214, wherein LCDR3 comprises SEQ ID NO: 12. (Embodiment 216) The antibody or antigen binding fragment of any one of embodiments 126-214, wherein LCDR3 comprises SEQ ID NO: 13. (Embodiment 217) The antibody or antigen binding fragment of any one of embodiments 126-214, wherein LCDR3 comprises SEQ ID NO: 14 or 15. (Embodiment 218) The antibody or antigen binding fragment of embodiment 120 or embodiment 162, wherein the heavy chain variable region comprises SEQ ID NO: 101. (Embodiment 219) The antibody or antigen binding fragment of embodiment 120 or embodiment 162, wherein the heavy chain variable region comprises SEQ ID NO: 102. (Embodiment 220) The antibody or antigen binding fragment of embodiment 120 or embodiment 162, wherein the heavy chain variable region comprises SEQ ID NO: 103. (Embodiment 221) The antibody or antigen binding fragment of embodiment 120 or embodiment 162, wherein the heavy chain variable region comprises SEQ ID NO: 104. (Embodiment 222) The antibody or antigen binding fragment of embodiment 120 or embodiment 162, wherein the heavy chain variable region comprises SEQ ID NO: 105. (Embodiment 223) The antibody or antigen binding fragment of embodiment 120 or embodiment 162, wherein the heavy chain variable region comprises SEQ ID NO: 106. (Embodiment 224) The antibody or antigen binding fragment of embodiment 120 or embodiment 162, wherein the heavy chain variable region comprises SEQ ID NO: 107. (Embodiment 225) The antibody or antigen binding fragment of embodiment 120 or embodiment 162, wherein the heavy chain variable region comprises SEQ ID NO: 108. (Embodiment 226) The antibody or antigen binding fragment of embodiment 120 or embodiment 162, wherein the heavy chain variable region comprises SEQ ID NO: 109. (Embodiment 227) The antibody or antigen binding fragment of embodiment 120 or embodiment 162, wherein the heavy chain variable region comprises SEQ ID NO: 110. (Embodiment 228) The antibody or antigen binding fragment of embodiment 120 or embodiment 162, wherein the heavy chain variable region comprises SEQ ID NO: 111. (Embodiment 229) The antibody or antigen binding fragment of embodiment 120 or embodiment 162, wherein the heavy chain variable region comprises SEQ ID NO: 112. (Embodiment 230) The antibody or antigen binding fragment of embodiment 120 or embodiment 162, wherein the heavy chain variable region comprises SEQ ID NO: 113. (Embodiment 231) The antibody or antigen binding fragment of embodiment 120 or embodiment 162, wherein the heavy chain variable region comprises SEQ ID NO: 114. (Embodiment 232) The antibody or antigen binding fragment of embodiment 120 or embodiment 162, wherein the heavy chain variable region comprises SEQ ID NO: 115. (Embodiment 233) The antibody or antigen binding fragment of embodiment 120 or embodiment 162, wherein the heavy chain variable region comprises SEQ ID NO: 116. (Embodiment 234) The antibody or antigen binding fragment of embodiment 120 or embodiment 162, wherein the heavy chain variable region comprises SEQ ID NO: 117. (Embodiment 235) The antibody or antigen binding fragment of embodiment 120 or embodiment 162, wherein the heavy chain variable region comprises SEQ ID NO: 118. (Embodiment 236) The antibody or antigen binding fragment of embodiment 120 or embodiment 162, wherein the heavy chain variable region comprises SEQ ID NO: 119. (Embodiment 237) The antibody or antigen binding fragment of embodiment 120 or embodiment 162, wherein the heavy chain variable region comprises SEQ ID NO: 120. (Embodiment 238) The antibody or antigen binding fragment of embodiment 120 or embodiment 162, wherein the heavy chain variable region comprises SEQ ID NO: 121. (Embodiment 239) The antibody or antigen binding fragment of embodiment 120 or embodiment 162, wherein the heavy chain variable region comprises SEQ ID NO: 122. (Embodiment 240) The antibody or antigen binding fragment of embodiment 120 or embodiment 162, wherein the heavy chain variable region comprises SEQ ID NO: 123. (Embodiment 241) The antibody or antigen binding fragment of embodiment 120 or embodiment 162, wherein the heavy chain variable region comprises SEQ ID NO: 124. (Embodiment 242) The antibody or antigen binding fragment of embodiment 120 or embodiment 162, wherein the heavy chain variable region comprises SEQ ID NO: 125. (Embodiment 243) The antibody or antigen binding fragment of embodiment 120 or embodiment 162, wherein the heavy chain variable region comprises SEQ ID NO: 126. (Embodiment 244) The antibody or antigen binding fragment of embodiment 120 or embodiment 162, wherein the heavy chain variable region comprises SEQ ID NO: 127. (Embodiment 245) The antibody or antigen binding fragment of embodiment 120 or embodiment 162, wherein the heavy chain variable region comprises SEQ ID NO: 128. (Embodiment 246) The antibody or antigen binding fragment of embodiment 120 or embodiment 162, wherein the heavy chain variable region comprises SEQ ID NO: 129. (Embodiment 247) The antibody or antigen binding fragment of embodiment 120 or embodiment 162, wherein the heavy chain variable region comprises SEQ ID NO: 130. (Embodiment 248) The antibody or antigen binding fragment of embodiment 120 or embodiment 162, wherein the heavy chain variable region comprises SEQ ID NO: 131. (Embodiment 249) The antibody or antigen binding fragment of embodiment 120 or embodiment 162, wherein the heavy chain variable region comprises SEQ ID NO: 132. (Embodiment 250) The antibody or antigen binding fragment of embodiment 120 or embodiment 162, wherein the heavy chain variable region comprises SEQ ID NO: 133. (Embodiment 251) The antibody or antigen binding fragment of embodiment 120 or embodiment 162, wherein the heavy chain variable region comprises SEQ ID NO: 134. (Embodiment 252) The antibody or antigen binding fragment of embodiment 120 or embodiment 162, wherein the heavy chain variable region comprises SEQ ID NO: 135. (Embodiment 253) The antibody or antigen binding fragment of any one of embodiments 120, 162, or 218-252, wherein the light chain variable region comprises SEQ ID NO: 201. (Embodiment 254) The antibody or antigen binding fragment of any one of embodiments 120, 162, or 218-252, wherein the light chain variable region comprises SEQ ID NO: 202. (Embodiment 255) The antibody or antigen binding fragment of any one of embodiments 120, 162, or 218-252, wherein the light chain variable region comprises SEQ ID NO: 203. (Embodiment 256) The antibody or antigen binding fragment of any one of embodiments 120, 162, or 218-252, wherein the light chain variable region comprises SEQ ID NO: 204. (Embodiment 257) The antibody or antigen binding fragment of any one of embodiments 120, 162, or 218-252, wherein the light chain variable region comprises SEQ ID NO: 205. (Embodiment 258) The antibody or antigen binding fragment of any one of embodiments 120, 162, or 218-252, wherein the light chain variable region comprises SEQ ID NO: 206.

(Embodiment 259) The antibody or antigen binding fragment of any one of embodiments 120-258, comprising a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. (Embodiment 260) The antibody or antigen binding fragment of any one of embodiments 120-258, comprising a light chain comprising SEQ ID NO: 319. (Embodiment 261) The antibody or antigen binding fragment of any one of embodiments 120-258, comprising a Fc region comprising a sequence at least about 90%, 91%, 92%, 93%, 94%, 95%, 96%, 97%, 98%, 99%, or 100% identical to any one of SEQ ID NOS: 320-362. (Embodiment 262) The antibody or antigen binding fragment of any one of embodiments 120-261, comprising at least about 80% monomeric fraction as determined by size exclusion chromatography. (Embodiment 263) The antibody or antigen binding fragment of embodiment 262, comprising at least about 85%, 90%, 91%, 92%, 93%, 94%, 95%, 96%, 97%, 98%, or 99% monomeric fraction.

(Embodiment 264) The antibody or antigen binding fragment of embodiment 262 or embodiment 263, wherein the size exclusion chromatography comprises injecting purified antibody or antigen binding fragment onto a size exclusion column, wherein the antibody or antigen binding fragment is purified by protein A. (Embodiment 265) The antibody or antigen binding fragment of embodiment 264 wherein the antibody or antigen binding fragment is purified as described in Example 2. (Embodiment 266) The antibody or antigen binding fragment of embodiment 264 or embodiment 265, wherein the antibody or antigen binding fragment is expressed under conditions described in Example 2. (Embodiment 267) The antibody or antigen binding fragment of any one of embodiments 264-266, wherein the size exclusion chromatography column has an inner diameter of 4.6 mm. (Embodiment 268) The antibody or antigen binding fragment of any one of embodiments 264-267, wherein the size exclusion chromatography column has a length of 150 mm. (Embodiment 269) The antibody or antigen binding fragment of any one of embodiments 264-268, wherein the size exclusion chromatography column has a pore size of 200 Å. (Embodiment 270) The antibody or antigen binding fragment of any one of embodiments 264-269, wherein the size exclusion chromatography column has a particle size of 1.7 micrometer. (Embodiment 271) The antibody or antigen binding fragment of any one of embodiments 264-270, wherein the size exclusion chromatography column is ACQUITY UPLC BEH200 SEC column. (Embodiment 272) The antibody or antigen binding fragment of any one of embodiments 264-271, wherein the antibody or antigen binding fragment is injected at a total volume of 15 µL. (Embodiment 273) The antibody or antigen binding fragment of any one of embodiments 264-272, wherein the antibody or antigen binding fragment is injected at a concentration of about 0.1 µg/µL to about 1.0 µg/µL. (Embodiment 274) The antibody or antigen binding fragment of any one of embodiments 264-273, wherein the size exclusion chromatography is performed on a Shimadzu UPLC instrument. (Embodiment 275) The antibody or antigen binding fragment of any one of embodiments 264-274, wherein the size exclusion chromatography is performed at a flow rate of 0.2 mL/min. (Embodiment 276) The antibody or antigen binding fragment of any one of embodiments 264-275, wherein the size exclusion chromatography is performed at a column oven temperature of 30° C. (Embodiment 277) The antibody or antigen binding fragment of any one of embodiments 264-276, wherein the percentage of monomer is calculated using Shimadzu software. (Embodiment 278) The antibody or antigen binding fragment of any one of embodiments 262-277, wherein the size exclusion chromatography is performed as described in Example 2. (Embodiment 279) The antibody or antigen binding fragment of any one of embodiments 120-278, expressing at least about 20 ug/ml total antibody. (Embodiment 280) The antibody or antigen binding fragment of any one of embodiments 120-278, expressing between about 20 ug/ml and 70 ug/mL total antibody. (Embodiment 281) The antibody or antigen binding fragment of embodiment 279 or embodiment 280, wherein the antibody or antigen binding fragment is expressed in FreeStyle 293-F cells. (Embodiment 282) The antibody or antigen binding fragment of any one of embodiments 279-281, wherein the antibody or antigen binding fragment is expressed as described in Example 2. (Embodiment 283) The antibody or antigen binding fragment of any one of embodiments 279-282, wherein the antibody or antigen binding fragment expression level is quantified using Enzyme-Linked Immunosorbent assay (ELISA). (Embodiment 284) The antibody or antigen binding fragment of embodiment 283, wherein the ELISA comprises coating a surface of a substrate with a capture antibody that binds to a human or humanized antibody, applying the antibody or antigen binding fragment to the substrate, and applying to the substrate a second antibody that binds to a human or humanized antibody. (Embodiment 285) The antibody or antigen binding fragment of embodiment 284, where the capture antibody comprises an anti-kappa antibody. (Embodiment 286) The antibody or antigen binding fragment of embodiment 284 or embodiment 285, where the second antibody comprises an anti-Fc antibody. (Embodiment 287) The antibody or antigen binding fragment of any one of embodiments 284-286, where the ELISA is performed as described in Example 2.

(Embodiment 288) An antibody or antigen binding fragment thereof that binds to tumor necrosis factor-like protein 1A (TL1A), comprising a heavy chain variable domain comprising an amino acid sequence at least about 97% identical to SEQ ID NO: 104, and a light chain variable domain comprising an amino acid sequence at least about 97% identical to SEQ ID NO: 201.

(Embodiment 289) The antibody or antigen binding fragment of embodiment 288, wherein the heavy chain variable domain comprises an amino acid sequence at least about 98% identical to SEQ ID NO: 104. (Embodiment 290) The antibody or antigen binding fragment of embodiment 289, wherein the heavy chain variable domain comprises an amino acid sequence at least about 99% identical to SEQ ID NO: 104. (Embodiment 291) The antibody or antigen binding fragment of embodiment 290, wherein the heavy chain variable domain comprises SEQ ID NO: 104. (Embodiment 292) The antibody or antigen binding fragment of any one of embodiments 288-291, wherein the light chain variable domain comprises an amino acid sequence at least about 98% identical to SEQ ID NO: 201. (Embodiment 293) The antibody or antigen binding fragment of any one of embodiments 288-291, wherein the light chain variable domain comprises an amino acid sequence at least about 99% identical to SEQ ID NO: 201. (Embodiment 294) The antibody or antigen binding fragment of any one of embodiments 288-291, wherein the light chain variable domain comprises SEQ ID NO: 201. (Embodiment 295) An antibody or antigen binding fragment thereof that binds to tumor necrosis factor-like protein 1A (TL1A), comprising a heavy chain variable domain comprising an amino acid sequence at least about 99% identical to SEQ ID NO: 107, and a light chain variable domain comprising an amino acid sequence at least about 99% identical to SEQ ID NO: 201. (Embodiment 296) The antibody or antigen binding fragment of embodiment 295, wherein the heavy chain variable domain comprises SEQ ID NO: 107. (Embodiment 297) The antibody or antigen binding fragment of embodiment 295 or embodiment 296, wherein the light chain variable domain comprises SEQ ID NO: 201.

(Embodiment 298) An antibody or antigen binding fragment thereof that binds to tumor necrosis factor-like protein 1A (TL1A), comprising a heavy chain variable domain comprising an amino acid sequence at least about 95%, 96%, 97%, 98%, 99%, or 100% identical to any one of SEQ ID NOS: 101-135, and a light chain variable domain comprising an amino acid sequence at least about 95%, 96%, 97%, 98%, 99%, or 100% identical to any one of SEQ ID NOS: 201-206. (Embodiment 299) The antibody or antigen binding fragment of embodiment 298, wherein the heavy chain variable domain comprises a sequence at least about 95%, 96%, 97%, 98%, 99%, or 100% identical to SEQ ID NO: 101. (Embodiment 300) The antibody or antigen binding fragment of embodiment 298, wherein the heavy chain variable domain comprises a sequence at least about 95%, 96%, 97%, 98%, 99%, or 100% identical to SEQ ID NO: 102. (Embodiment 301) The antibody or antigen binding fragment of embodiment 298, wherein the heavy chain variable domain comprises a sequence at least about 95%, 96%, 97%, 98%, 99%, or 100% identical to SEQ ID NO: 103. (Embodiment 302) The antibody or antigen binding fragment of embodiment 298, wherein the heavy chain variable domain comprises a sequence at least about 95%, 96%, 97%, 98%, 99%, or 100% identical to SEQ ID NO: 104. (Embodiment 303) The antibody or antigen binding fragment of embodiment 298, wherein the heavy chain variable domain comprises a sequence at least about 95%, 96%, 97%, 98%, 99%, or 100% identical to SEQ ID NO: 105. (Embodiment 304) The antibody or antigen binding fragment of embodiment 298, wherein the heavy chain variable domain comprises a sequence at least about 95%, 96%, 97%, 98%, 99%, or 100% identical to SEQ ID NO: 106. (Embodiment 305) The antibody or antigen binding fragment of embodiment 298, wherein the heavy chain variable domain comprises a sequence at least about 95%, 96%, 97%, 98%, 99%, or 100% identical to SEQ ID NO: 107. (Embodiment 306) The antibody or antigen binding fragment of embodiment 298, wherein the heavy chain variable domain comprises a sequence at least about 95%, 96%, 97%, 98%, 99%, or 100% identical to SEQ ID NO: 108. (Embodiment 307) The antibody or antigen binding fragment of embodiment 298, wherein the heavy chain variable domain comprises a sequence at least about 95%, 96%, 97%, 98%, 99%, or 100% identical to SEQ ID NO: 109. (Embodiment 308) The antibody or antigen binding fragment of embodiment 298, wherein the heavy chain variable domain comprises a sequence at least about 95%, 96%, 97%, 98%, 99%, or 100% identical to SEQ ID NO: 110. (Embodiment 309) The antibody or antigen binding fragment of embodiment 298, wherein the heavy chain variable domain comprises a sequence at least about 95%, 96%, 97%, 98%, 99%, or 100% identical to SEQ ID NO: 111. (Embodiment 310) The antibody or antigen binding fragment of embodiment 298, wherein the heavy chain variable domain comprises a sequence at least about 95%, 96%, 97%, 98%, 99%, or 100% identical to SEQ ID NO:

112. (Embodiment 311) The antibody or antigen binding fragment of embodiment 298, wherein the heavy chain variable domain comprises a sequence at least about 95%, 96%, 97%, 98%, 99%, or 100% identical to SEQ ID NO: 113. (Embodiment 312) The antibody or antigen binding fragment of embodiment 298, wherein the heavy chain variable domain comprises a sequence at least about 95%, 96%, 97%, 98%, 99%, or 100% identical to SEQ ID NO: 114. (Embodiment 313) The antibody or antigen binding fragment of embodiment 298, wherein the heavy chain variable domain comprises a sequence at least about 95%, 96%, 97%, 98%, 99%, or 100% identical to SEQ ID NO: 115. (Embodiment 314) The antibody or antigen binding fragment of embodiment 298, wherein the heavy chain variable domain comprises a sequence at least about 95%, 96%, 97%, 98%, 99%, or 100% identical to SEQ ID NO: 116. (Embodiment 315) The antibody or antigen binding fragment of embodiment 298, wherein the heavy chain variable domain comprises a sequence at least about 95%, 96%, 97%, 98%, 99%, or 100% identical to SEQ ID NO: 117. (Embodiment 316) The antibody or antigen binding fragment of embodiment 298, wherein the heavy chain variable domain comprises a sequence at least about 95%, 96%, 97%, 98%, 99%, or 100% identical to SEQ ID NO: 118. (Embodiment 317) The antibody or antigen binding fragment of embodiment 298, wherein the heavy chain variable domain comprises a sequence at least about 95%, 96%, 97%, 98%, 99%, or 100% identical to SEQ ID NO: 119. (Embodiment 318) The antibody or antigen binding fragment of embodiment 298, wherein the heavy chain variable domain comprises a sequence at least about 95%, 96%, 97%, 98%, 99%, or 100% identical to SEQ ID NO: 120. (Embodiment 319) The antibody or antigen binding fragment of embodiment 298, wherein the heavy chain variable domain comprises a sequence at least about 95%, 96%, 97%, 98%, 99%, or 100% identical to SEQ ID NO: 121. (Embodiment 320) The antibody or antigen binding fragment of embodiment 298, wherein the heavy chain variable domain comprises a sequence at least about 95%, 96%, 97%, 98%, 99%, or 100% identical to SEQ ID NO: 122. (Embodiment 321) The antibody or antigen binding fragment of embodiment 298, wherein the heavy chain variable domain comprises a sequence at least about 95%, 96%, 97%, 98%, 99%, or 100% identical to SEQ ID NO: 123. (Embodiment 322) The antibody or antigen binding fragment of embodiment 298, wherein the heavy chain variable domain comprises a sequence at least about 95%, 96%, 97%, 98%, 99%, or 100% identical to SEQ ID NO: 124. (Embodiment 323) The antibody or antigen binding fragment of embodiment 298, wherein the heavy chain variable domain comprises a sequence at least about 95%, 96%, 97%, 98%, 99%, or 100% identical to SEQ ID NO: 125. (Embodiment 324) The antibody or antigen binding fragment of embodiment 298, wherein the heavy chain variable domain comprises a sequence at least about 95%, 96%, 97%, 98%, 99%, or 100% identical to SEQ ID NO: 126. (Embodiment 325) The antibody or antigen binding fragment of embodiment 298, wherein the heavy chain variable domain comprises a sequence at least about 95%, 96%, 97%, 98%, 99%, or 100% identical to SEQ ID NO: 127. (Embodiment 326) The antibody or antigen binding fragment of embodiment 298, wherein the heavy chain variable domain comprises a sequence at least about 95%, 96%, 97%, 98%, 99%, or 100% identical to SEQ ID NO: 128. (Embodiment 327) The antibody or antigen binding fragment of embodiment 298, wherein the heavy chain variable domain comprises a sequence at least about 95%, 96%, 97%, 98%, 99%, or 100% identical to SEQ ID NO: 129. (Embodiment 328) The antibody or antigen binding fragment of embodiment 298, wherein the heavy chain variable domain comprises a sequence at least about 95%, 96%, 97%, 98%, 99%, or 100% identical to SEQ ID NO: 130. (Embodiment 329) The antibody or antigen binding fragment of embodiment 298, wherein the heavy chain variable domain comprises a sequence at least about 95%, 96%, 97%, 98%, 99%, or 100% identical to SEQ ID NO: 131. (Embodiment 330) The antibody or antigen binding fragment of embodiment 298, wherein the heavy chain variable domain comprises a sequence at least about 95%, 96%, 97%, 98%, 99%, or 100% identical to SEQ ID NO: 132. (Embodiment 331) The antibody or antigen binding fragment of embodiment 298, wherein the heavy chain variable domain comprises a sequence at least about 95%, 96%, 97%, 98%, 99%, or 100% identical to SEQ ID NO: 133. (Embodiment 332) The antibody or antigen binding fragment of embodiment 298, wherein the heavy chain variable domain comprises a sequence at least about 95%, 96%, 97%, 98%, 99%, or 100% identical to SEQ ID NO: 134. (Embodiment 333) The antibody or antigen binding fragment of embodiment 298, wherein the heavy chain variable domain comprises a sequence at least about 95%, 96%, 97%, 98%, 99%, or 100% identical to SEQ ID NO: 135. (Embodiment 334) The antibody or antigen binding fragment of any one of embodiments 298-333, wherein the light chain variable domain comprises a sequence at least about 95%, 96%, 97%, 98%, 99%, or 100% identical to SEQ ID NO: 201. (Embodiment 335) The antibody or antigen binding fragment of any one of embodiments 298-333, wherein the light chain variable domain comprises a sequence at least about 95%, 96%, 97%, 98%, 99%, or 100% identical to SEQ ID NO: 202. (Embodiment 336) The antibody or antigen binding fragment of any one of embodiments 298-333, wherein the light chain variable domain comprises a sequence at least about 95%, 96%, 97%, 98%, 99%, or 100% identical to SEQ ID NO: 203. (Embodiment 337) The antibody or antigen binding fragment of any one of embodiments 298-333, wherein the light chain variable domain comprises a sequence at least about 95%, 96%, 97%, 98%, 99%, or 100% identical to SEQ ID NO: 204. (Embodiment 338) The antibody or antigen binding fragment of any one of embodiments 298-333, wherein the light chain variable domain comprises a sequence at least about 95%, 96%, 97%, 98%, 99%, or 100% identical to SEQ ID NO: 205. (Embodiment 339) The antibody or antigen binding fragment of any one of embodiments 298-333, wherein the light chain variable domain comprises a sequence at least about 95%, 96%, 97%, 98%, 99%, or 100% identical to SEQ ID NO: 206.

(Embodiment 340) An antibody or antigen binding fragment thereof that binds to tumor necrosis factor-like protein 1A (TL1A), comprising a heavy chain variable domain comprising SEQ ID NO: 101, and a light chain variable domain comprising SEQ ID NOS: 201. (Embodiment 341) An antibody or antigen binding fragment thereof that binds to tumor necrosis factor-like protein 1A (TL1A), comprising a heavy chain variable domain comprising SEQ ID NO: 102, and a light chain variable domain comprising SEQ ID NOS: 201. (Embodiment 342) An antibody or antigen binding fragment thereof that binds to tumor necrosis factor-like protein 1A (TL1A), comprising a heavy chain variable domain comprising SEQ ID NO: 103, and a light chain variable domain comprising SEQ ID NOS: 202. (Embodiment 343) An antibody or antigen binding fragment thereof that binds to tumor necrosis factor-like protein 1A (TL1A), comprising a heavy chain variable domain comprising SEQ ID NO: 104, and a light chain variable domain comprising SEQ ID NOS: 201. (Embodiment 344) An antibody or antigen binding fragment thereof that binds to tumor necrosis factor-like protein 1A (TL1A), comprising a heavy chain variable domain comprising SEQ ID NO: 105, and a light chain variable domain comprising SEQ ID NOS: 201. (Embodiment 345) An antibody or antigen binding fragment thereof that binds to tumor necrosis factor-like protein 1A (TL1A), comprising a heavy chain variable domain comprising SEQ ID NO: 103, and a light chain variable domain comprising SEQ ID NOS: 201. (Embodiment 346) An antibody or antigen binding fragment thereof that binds to tumor necrosis factor-like protein 1A (TL1A), comprising a heavy chain variable domain comprising SEQ ID NO: 106, and a light chain variable domain comprising SEQ ID NOS: 201. (Embodiment 347) An antibody or antigen binding fragment thereof that binds to tumor necrosis factor-like protein 1A (TL1A), comprising a heavy chain variable domain comprising SEQ ID NO: 107, and a light chain variable domain comprising SEQ ID NOS: 201. (Embodiment 348) An antibody or antigen binding fragment thereof that binds to tumor necrosis factor-like protein 1A (TL1A), comprising a heavy chain variable domain comprising SEQ ID NO: 108, and a light chain variable domain comprising SEQ ID NOS: 202. (Embodiment 349) An antibody or antigen binding fragment thereof that binds to tumor necrosis factor-like protein 1A (TL1A), comprising a heavy chain variable domain comprising SEQ ID NO: 109, and a light chain variable domain comprising SEQ ID NOS: 202. (Embodiment 350) An antibody or antigen binding fragment thereof that binds to tumor necrosis factor-like protein 1A (TL1A), comprising a heavy chain variable domain comprising SEQ ID NO: 108, and a light chain variable domain comprising SEQ ID NOS: 201. (Embodiment 351) An antibody or antigen binding fragment thereof that binds to tumor necrosis factor-like protein 1A (TL1A), comprising a heavy chain variable domain comprising SEQ ID NO: 109, and a light chain variable domain comprising SEQ ID NOS: 201. (Embodiment 352) An antibody or antigen binding fragment thereof that binds to tumor necrosis factor-like protein 1A (TL1A), comprising a heavy chain variable domain comprising SEQ ID NO: 108, and a light chain variable domain comprising SEQ ID NOS: 203. (Embodiment 353) An antibody or antigen binding fragment thereof that binds to tumor necrosis factor-like protein 1A (TL1A), comprising a heavy chain variable domain comprising SEQ ID NO: 108, and a light chain variable domain comprising SEQ ID NOS: 204. (Embodiment 354) An antibody or antigen binding fragment thereof that binds to tumor necrosis factor-like protein 1A (TL1A), comprising a heavy chain variable domain comprising SEQ ID NO: 107, and a light chain variable domain comprising SEQ ID NOS: 204. (Embodiment 355) An antibody or antigen binding fragment thereof that binds to tumor necrosis factor-like protein 1A (TL1A), comprising a heavy chain variable domain comprising SEQ ID NO: 107, and a light chain variable domain comprising SEQ ID NOS: 202. (Embodiment 356) An antibody or antigen binding fragment thereof that binds to tumor necrosis factor-like protein 1A (TL1A), comprising a heavy chain variable domain comprising SEQ ID NO: 110, and a light chain variable domain comprising SEQ ID NOS: 204. (Embodiment 357) An antibody or antigen binding fragment thereof that binds to tumor necrosis factor-like protein 1A (TL1A), comprising a heavy chain variable domain comprising SEQ ID NO: 111, and a light chain variable domain comprising SEQ ID NOS: 201. (Embodiment 358) An antibody or antigen binding fragment thereof that binds to tumor necrosis factor-like protein 1A (TL1A), comprising a heavy chain variable domain comprising SEQ ID NO: 112, and a light chain variable domain comprising SEQ ID NOS: 201. (Embodiment 359) An antibody or antigen binding fragment thereof that binds to tumor necrosis factor-like protein 1A (TL1A), comprising a heavy chain variable domain comprising SEQ ID NO: 113, and a light chain variable domain comprising SEQ ID NOS: 204. (Embodiment 360) An antibody or antigen binding fragment thereof that binds to tumor necrosis factor-like protein 1A (TL1A), comprising a heavy chain variable domain comprising SEQ ID NO: 114, and a light chain variable domain comprising SEQ ID NOS: 201. (Embodiment 361) An antibody or antigen binding fragment thereof that binds to tumor necrosis factor-like protein 1A (TL1A), comprising a heavy chain variable domain comprising SEQ ID NO: 115, and a light chain variable domain comprising SEQ ID NOS: 202. (Embodiment 362) An antibody or antigen binding fragment thereof that binds to tumor necrosis factor-like protein 1A (TL1A), comprising a heavy chain variable domain comprising SEQ ID NO: 116, and a light chain variable domain comprising SEQ ID NOS: 201. (Embodiment 363) An antibody or antigen binding fragment thereof that binds to tumor necrosis factor-like protein 1A (TL1A), comprising a heavy chain variable domain comprising SEQ ID NO: 117, and a light chain variable domain comprising SEQ ID NOS: 201. (Embodiment 364) An antibody or antigen binding fragment thereof that binds to tumor necrosis factor-like protein 1A (TL1A), comprising a heavy chain variable domain comprising SEQ ID NO: 118, and a light chain variable domain comprising SEQ ID NOS: 204. (Embodiment 365) An antibody or antigen binding fragment thereof that binds to tumor necrosis factor-like protein 1A (TL1A), comprising a heavy chain variable domain comprising SEQ ID NO: 114, and a light chain variable domain comprising SEQ ID NOS: 204. (Embodiment 366) An antibody or antigen binding fragment thereof that binds to tumor necrosis factor-like protein 1A (TL1A), comprising a heavy chain variable domain comprising SEQ ID NO: 102, and a light chain variable domain comprising SEQ ID NOS: 204. (Embodiment 367) An antibody or antigen binding fragment thereof that binds to tumor necrosis factor-like protein 1A (TL1A), comprising a heavy chain variable domain comprising SEQ ID NO: 104, and a light chain variable domain comprising SEQ ID NOS: 204. (Embodiment 368) An antibody or antigen binding fragment thereof that binds to tumor necrosis factor-like protein 1A (TL1A), comprising a heavy chain variable domain comprising SEQ ID NO: 119, and a light chain variable domain comprising SEQ ID NOS: 204. (Embodiment 369) An antibody or antigen binding fragment thereof that binds to tumor necrosis factor-like protein 1A (TL1A), comprising a heavy chain variable domain comprising SEQ ID NO: 119, and a light chain variable domain comprising SEQ ID NOS: 201. (Embodiment 370) An antibody or antigen binding fragment thereof that binds to tumor necrosis factor-like protein 1A (TL1A), comprising a heavy chain variable domain comprising SEQ ID NO: 101, and a light chain variable domain comprising SEQ ID NOS: 204. (Embodiment 371) An antibody or antigen binding fragment thereof that binds to tumor necrosis factor-like protein 1A (TL1A), comprising a heavy chain variable domain comprising SEQ ID NO: 105, and a light chain variable domain comprising SEQ ID NOS: 204. (Embodiment 372) An antibody or antigen binding fragment thereof that binds to tumor necrosis factor-like protein 1A (TL1A), comprising a heavy chain variable domain comprising SEQ ID NO: 120, and a light chain variable domain comprising SEQ ID NOS: 204. (Embodiment 373) An antibody or antigen binding fragment thereof that binds to tumor necrosis factor-like protein 1A (TL1A), comprising a heavy chain variable domain comprising SEQ ID NO: 121, and a light chain variable domain comprising SEQ ID NOS: 202. (Embodiment 374) An antibody or antigen binding fragment thereof that binds to tumor necrosis factor-like protein 1A (TL1A), comprising a heavy chain variable domain comprising SEQ ID NO: 122, and a light chain variable domain comprising SEQ ID NOS: 202. (Embodiment 375) An antibody or antigen binding fragment thereof that binds to tumor necrosis factor-like protein 1A (TL1A), comprising a heavy chain variable domain comprising SEQ ID NO: 122, and a light chain variable domain comprising SEQ ID NOS: 204. (Embodiment 376) An antibody or antigen binding fragment thereof that binds to tumor necrosis factor-like protein 1A (TL1A), comprising a heavy chain variable domain comprising SEQ ID NO: 123, and a light chain variable domain comprising SEQ ID NOS: 202. (Embodiment 377) An antibody or antigen binding fragment thereof that binds to tumor necrosis factor-like protein 1A (TL1A), comprising a heavy chain variable domain comprising SEQ ID NO: 124, and a light chain variable domain comprising SEQ ID NOS: 202. (Embodiment 378) An antibody or antigen binding fragment thereof that binds to tumor necrosis factor-like protein 1A (TL1A), comprising a heavy chain variable domain comprising SEQ ID NO: 125, and a light chain variable domain comprising SEQ ID NOS: 205. (Embodiment 379) An antibody or antigen binding fragment thereof that binds to tumor necrosis factor-like protein 1A (TL1A), comprising a heavy chain variable domain comprising SEQ ID NO: 116, and a light chain variable domain comprising SEQ ID NOS: 205. (Embodiment 380) An antibody or antigen binding fragment thereof that binds to tumor necrosis factor-like protein 1A (TL1A), comprising a heavy chain variable domain comprising SEQ ID NO: 117, and a light chain variable domain comprising SEQ ID NOS: 205. (Embodiment 381) An antibody or antigen binding fragment thereof that binds to tumor necrosis factor-like protein 1A (TL1A), comprising a heavy chain variable domain comprising SEQ ID NO: 126, and a light chain variable domain comprising SEQ ID NOS: 205. (Embodiment 382) An antibody or antigen binding fragment thereof that binds to tumor necrosis factor-like protein 1A (TL1A), comprising a heavy chain variable domain comprising SEQ ID NO: 127, and a light chain variable domain comprising SEQ ID NOS: 205. (Embodiment 383) An antibody or antigen binding fragment thereof that binds to tumor necrosis factor-like protein 1A (TL1A), comprising a heavy chain variable domain comprising SEQ ID NO: 127, and a light chain variable domain comprising SEQ ID NOS: 201. (Embodiment 384) An antibody or antigen binding fragment thereof that binds to tumor necrosis factor-like protein 1A (TL1A), comprising a heavy chain variable domain comprising SEQ ID NO: 121, and a light chain variable domain comprising SEQ ID NOS: 201. (Embodiment 385) An antibody or antigen binding fragment thereof that binds to tumor necrosis factor-like protein 1A (TL1A), comprising a heavy chain variable domain comprising SEQ ID NO: 122, and a light chain variable domain comprising SEQ ID NOS: 205. (Embodiment 386) An antibody or antigen binding fragment thereof that binds to tumor necrosis factor-like protein 1A (TL1A), comprising a heavy chain variable domain comprising SEQ ID NO: 122, and a light chain variable domain comprising SEQ ID NOS: 201. (Embodiment 387) An antibody or antigen binding fragment thereof that binds to tumor necrosis factor-like protein 1A (TL1A), comprising a heavy chain variable domain comprising SEQ ID NO: 122, and a light chain variable domain comprising SEQ ID NOS: 206. (Embodiment 388) An antibody or antigen binding fragment thereof that binds to tumor necrosis factor-like protein 1A (TL1A), comprising a heavy chain variable domain comprising SEQ ID NO: 124, and a light chain variable domain comprising SEQ ID NOS: 205. (Embodiment 389) An antibody or antigen binding fragment thereof that binds to tumor necrosis factor-like protein 1A (TL1A), comprising a heavy chain variable domain comprising SEQ ID NO: 124, and a light chain variable domain comprising SEQ ID NOS: 201. (Embodiment 390) An antibody or antigen binding fragment thereof that binds to tumor necrosis factor-like protein 1A (TL1A), comprising a heavy chain variable domain comprising SEQ ID NO: 128, and a light chain variable domain comprising SEQ ID NOS: 205. (Embodiment 391) An antibody or antigen binding fragment thereof that binds to tumor necrosis factor-like protein 1A (TL1A), comprising a heavy chain variable domain comprising SEQ ID NO: 128, and a light chain variable domain comprising SEQ ID NOS: 206. (Embodiment 392) An antibody or antigen binding fragment thereof that binds to tumor necrosis factor-like protein 1A (TL1A), comprising a heavy chain variable domain comprising SEQ ID NO: 129, and a light chain variable domain comprising SEQ ID NOS: 205. (Embodiment 393) An antibody or antigen binding fragment thereof that binds to tumor necrosis factor-like protein 1A (TL1A), comprising a heavy chain variable domain comprising SEQ ID NO: 130, and a light chain variable domain comprising SEQ ID NOS: 205. (Embodiment 394) An antibody or antigen binding fragment thereof that binds to tumor necrosis factor-like protein 1A (TL1A), comprising a heavy chain variable domain comprising SEQ ID NO: 131, and a light chain variable domain comprising SEQ ID NOS: 205. (Embodiment 395) An antibody or antigen binding fragment thereof that binds to tumor necrosis factor-like protein 1A (TL1A), comprising a heavy chain variable domain comprising SEQ ID NO: 132, and a light chain variable domain comprising SEQ ID NOS: 205. (Embodiment 396) An antibody or antigen binding fragment thereof that binds to tumor necrosis factor-like protein 1A (TL1A), comprising a heavy chain variable domain comprising SEQ ID NO: 133, and a light chain variable domain comprising SEQ ID NOS: 205. (Embodiment 397) An antibody or antigen binding fragment thereof that binds to tumor necrosis factor-like protein 1A (TL1A), comprising a heavy chain variable domain comprising SEQ ID NO: 134, and a light chain variable domain comprising SEQ ID NOS: 205. (Embodiment 398) An antibody or antigen binding fragment thereof that binds to tumor necrosis factor-like protein 1A (TL1A), comprising a heavy chain variable domain comprising SEQ ID NO: 135, and a light chain variable domain comprising SEQ ID NOS: 205. (Embodiment 399) An antibody or antigen binding fragment thereof that binds to tumor necrosis factor-like protein 1A (TL1A), comprising a heavy chain variable domain comprising SEQ ID NO: 132, and a light chain variable domain comprising SEQ ID NOS: 201. (Embodiment 400) An antibody or antigen binding fragment thereof that binds to tumor necrosis factor-like protein 1A (TL1A), comprising a heavy chain variable domain comprising SEQ ID NO: 126, and a light chain variable domain comprising SEQ ID NOS: 201. (Embodiment 401) An antibody or antigen binding fragment thereof that binds to tumor necrosis factor-like protein 1A (TL1A), comprising a heavy chain variable domain comprising SEQ ID NO: 130, and a light chain variable domain comprising SEQ ID NOS: 201.

(Embodiment 402) The antibody or antigen binding fragment of any one of embodiments 288-401, comprising a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa) L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. (Embodiment 403) The antibody or antigen binding fragment of any one of embodiments 288-401, comprising a human IgG4 Fc region. (Embodiment 404) The antibody or antigen binding fragment of any one of embodiments 288-401, comprising a Fc region comprising a sequence at least about 90%, 91%, 92%, 93%, 94%, 95%, 96%, 97%, 98%, 99%, or 100% identical to any one of SEQ ID NOS: 320-362. (Embodiment 405) The antibody or antigen binding fragment of any one of embodiments 288-404, comprising at least about 80% monomeric fraction as determined by size exclusion chromatography. (Embodiment 406) The antibody or antigen binding fragment of embodiment 405, comprising at least about 85%, 90%, 91%, 92%, 93%, 94%, 95%, 96%, 97%, 98%, or 99% monomeric fraction. (Embodiment 407) The antibody or antigen binding fragment of embodiment 405 or embodiment 406, wherein the size exclusion chromatography comprises injecting purified antibody or antigen binding fragment onto a size exclusion column, wherein the antibody or antigen binding fragment is purified by protein A. (Embodiment 408) The antibody or antigen binding fragment of embodiment 407 wherein the antibody or antigen binding fragment is purified as described in Example 2. (Embodiment 409) The antibody or antigen binding fragment of embodiment 47 or embodiment 408, wherein the antibody or antigen binding fragment is expressed under conditions described in Example 2. (Embodiment 410) The antibody or antigen binding fragment of any one of embodiments 407-409, wherein the size exclusion chromatography column has an inner diameter of 4.6 mm. (Embodiment 411) The antibody or antigen binding fragment of any one of embodiments 407-410, wherein the size exclusion chromatography column has a length of 150 mm. (Embodiment 412) The antibody or antigen binding fragment of any one of embodiments 407-411, wherein the size exclusion chromatography column has a pore size of 200 Å. (Embodiment 413) The antibody or antigen binding fragment of any one of embodiments 407-412, wherein the size exclusion chromatography column has a particle size of 1.7 micrometer. (Embodiment 414) The antibody or antigen binding fragment of any one of embodiments 407-413, wherein the size exclusion chromatography column is ACQUITY UPLC BEH200 SEC column. (Embodiment 415) The antibody or antigen binding fragment of any one of embodiments 407-414, wherein the antibody or antigen binding fragment is injected at a total volume of 15 µL. (Embodiment 416) The antibody or antigen binding fragment of any one of embodiments 407-415, wherein the antibody or antigen binding fragment is injected at a concentration of about 0.1 µg/µL to about 1.0 µg/µL. (Embodiment 417) The antibody or antigen binding fragment of any one of embodiments 407-416, wherein the size exclusion chromatography is performed on a Shimadzu UPLC instrument. (Embodiment 418) The antibody or antigen binding fragment of any one of embodiments 407-417, wherein the size exclusion chromatography is performed at a flow rate of 0.2 mL/min. (Embodiment 419) The antibody or antigen binding fragment of any one of embodiments 407-418, wherein the size exclusion chromatography is performed at a column oven temperature of 30° C. (Embodiment 420) The antibody or antigen binding fragment of any one of embodiments 407-419, wherein the percentage of monomer is calculated using Shimadzu software. (Embodiment 421) The antibody or antigen binding fragment of any one of embodiments 405-420, wherein the size exclusion chromatography is performed as described in Example 2. (Embodiment 422) The antibody or antigen binding fragment of any one of embodiments 288-421, expressing at least about 20 ug/ml total antibody. (Embodiment 423) The antibody or antigen binding fragment of any one of embodiments 288-421, expressing between about 20 ug/ml and 70 ug/mL total antibody. (Embodiment 424) The antibody or antigen binding fragment of embodiment 422 or embodiment 423, wherein the antibody or antigen binding fragment is expressed in FreeStyle 293-F cells. (Embodiment 425) The antibody or antigen binding fragment of any one of embodiments 422-424, wherein the antibody or antigen binding fragment is expressed as described in Example 2. (Embodiment 426) The antibody or antigen binding fragment of any one of embodiments 422-425, wherein the antibody or antigen binding fragment expression level is quantified using Enzyme-Linked Immunosorbent assay (ELISA). (Embodiment 427) The antibody or antigen binding fragment of embodiment 426, wherein the ELISA comprises coating a surface of a substrate with a capture antibody that binds to a human or humanized antibody, applying the antibody or antigen binding fragment to the substrate, and applying to the substrate a second antibody that binds to a human or humanized antibody. (Embodiment 428) The antibody or antigen binding fragment of embodiment 427, where the capture antibody comprises an anti-kappa antibody. (Embodiment 429) The antibody or antigen binding fragment of embodiment 427 or embodiment 428, where the second antibody comprises an anti-Fc antibody. (Embodiment 430) The antibody or antigen binding fragment of any one of embodiments 426-429, where the ELISA is performed as described in Example 2. (Embodiment 431) An antibody or antigen binding fragment thereof that binds to TL1A, comprising a heavy chain variable region comprising: (a) an HCDR1 comprising an amino acid sequence set forth by SEQ ID NO: 1; (b) an HCDR2 comprising an amino acid sequence set forth by any one of SEQ ID NOS: 2-5; and (c) an HCDR3 comprising an amino acid sequence set forth by any one of SEQ ID NOS: 6-9; and the light chain variable region comprises: (d) an LCDR1 comprising an amino acid sequence set forth by SEQ ID NO: 10; (e) an LCDR2 comprising an amino acid sequence set forth by SEQ ID NO: 11; (f) an LCDR3 comprising an amino acid sequence set forth by any one of SEQ ID NOS: 12-15; and a fragment crystallizable (Fc) region comprising reduced antibody-dependent cell-mediated cytotoxicity (ADCC) function as compared to human IgG1 and/or reduced complement-dependent cytotoxicity (CDC) as compared to human IgG1. (Embodiment 432) The antibody of antigen binding fragment of embodiment 431, wherein the human IgG1 comprises SEQ ID NO: 320. (Embodiment 433) The antibody of antigen binding fragment of embodiment 431 or embodiment 432, wherein the ADCC function of the Fc region comprising reduced ADCC is at least about 50% reduced as compared to human IgG1. (Embodiment 434) The antibody of antigen binding fragment of any one of embodiments 431-433, wherein the CDC function of the Fc region comprising reduced ADCC is at least about 50% reduced as compared to human IgG1. (Embodiment 435) The antibody of antigen binding fragment of any one of embodiments 431-434, wherein the Fc region comprises a human IgG1 comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. (Embodiment 436) The antibody of antigen binding fragment of any one of embodiments 431-434, comprising (i) a human IgG4 Fc region or (ii) a human IgG4 Fc region comprising (a) S228P, (b) S228P and L235E, or (c) S228P, F234A, and L235A, per Kabat numbering. (Embodiment 437) The antibody of antigen binding fragment of any one of embodiments 431-434, comprising a human IgG2 Fc region; IgG2-IgG4 cross-subclass Fc region; IgG2-IgG3 cross-subclass Fc region; IgG2 comprising H268Q, V309L, A330S, P331S (IgG2m4); or IgG2 comprising V234A, G237A, P238S, H268A, V309L, A330S, P331S (IgG2a). (Embodiment 438) The antibody of antigen binding fragment of any one of embodiments 431-435, wherein the Fc region comprises a human IgG1 with a substitution selected from 329A, 329G, 329Y, 331S, 236F, 236R, 238A, 238E, 238G, 238H, 238I, 238V, 238W, 238Y, 248A, 254D, 254E, 254G, 254H, 254I, 254N, 254P, 254Q, 254T, 254V, 264S, 265H, 265K, 265S, 265Y, 265A, 267G, 267H, 267I, 267K, 434I, 438G, 439E, 439H, 439Q, 440A, 440D, 440E, 440F, 440M, 440T, and 440V, per Kabat numbering. (Embodiment 439) The antibody or antigen binding fragment of any one of embodiments 431-437, comprising a sequence at least about 90%, 91%, 92%, 93%, 94%, 95%, 96%, 97%, 98%, 99%, or 100% identical to any one of SEQ ID NOS: 320-362. (Embodiment 440) The antibody or antigen binding fragment of any one of embodiments 431-439, wherein HCDR1 comprises SEQ ID NO: 1. (Embodiment 441) The antibody or antigen binding fragment of any one of embodiments 431-440, wherein HCDR2 comprises SEQ ID NO: 2. (Embodiment 442) The antibody or antigen binding fragment of any one of embodiments 431-440, wherein HCDR2 comprises SEQ ID NO: 3. (Embodiment 443) The antibody or antigen binding fragment of any one of embodiments 431-440, wherein HCDR2 comprises SEQ ID NO: 4. (Embodiment 444) The antibody or antigen binding fragment of any one of embodiments 431-440, wherein HCDR2 comprises SEQ ID NO: 5. (Embodiment 445) The antibody or antigen binding fragment of any one of embodiments 431-444, wherein HCDR3 comprises SEQ ID NO: 6. (Embodiment 446) The antibody or antigen binding fragment of any one of embodiments 431-444, wherein HCDR3 comprises SEQ ID NO: 7. (Embodiment 447) The antibody or antigen binding fragment of any one of embodiments 431-444, wherein HCDR3 comprises SEQ ID NO: 8. (Embodiment 448) The antibody or antigen binding fragment of any one of embodiments 431-444, wherein HCDR3 comprises SEQ ID NO: 9. (Embodiment 449) The antibody or antigen binding fragment of any one of embodiments 431-448, wherein LCDR1 comprises SEQ ID NO: 10. (Embodiment 450) The antibody or antigen binding fragment of any one of embodiments 431-449, wherein LCDR2 comprises SEQ ID NO: 11. (Embodiment 451) The antibody or antigen binding fragment of any one of embodiments 431-450, wherein LCDR3 comprises SEQ ID NO: 12. (Embodiment 452) The antibody or antigen binding fragment of any one of embodiments 431-450, wherein LCDR3 comprises SEQ ID NO: 13. (Embodiment 453) The antibody or antigen binding fragment of any one of embodiments 431-450, wherein LCDR3 comprises SEQ ID NO: 14 or 15. (Embodiment 454) The antibody or antigen binding fragment of any one of embodiments 431-453, comprising at least about 80% monomeric fraction as determined by size exclusion chromatography. (Embodiment 455) The antibody or antigen binding fragment of embodiment 454, comprising at least about 85%, 90%, 91%, 92%, 93%, 94%, 95%, 96%, 97%, 98%, or 99% monomeric fraction. (Embodiment 456) The antibody or antigen binding fragment of embodiment 454 or embodiment 455, wherein the size exclusion chromatography comprises injecting purified antibody or antigen binding fragment onto a size exclusion column, wherein the antibody or antigen binding fragment is purified by protein A. (Embodiment 457) The antibody or antigen binding fragment of embodiment 456, wherein the antibody or antigen binding fragment is purified as described in Example 2. (Embodiment 458) The antibody or antigen binding fragment of embodiment 456 or embodiment 457, wherein the antibody or antigen binding fragment is expressed under conditions described in Example 2. (Embodiment 459) The antibody or antigen binding fragment of any one of embodiments 456-458, wherein the size exclusion chromatography column has an inner diameter of 4.6 mm. (Embodiment 460) The antibody or antigen binding fragment of any one of embodiments 456-459, wherein the size exclusion chromatography column has a length of 150 mm. (Embodiment 461) The antibody or antigen binding fragment of any one of embodiments 456-460, wherein the size exclusion chromatography column has a pore size of 200 Å. (Embodiment 462) The antibody or antigen binding fragment of any one of embodiments 456-461, wherein the size exclusion chromatography column has a particle size of 1.7 micrometer. (Embodiment 463) The antibody or antigen binding fragment of any one of embodiments 456-462, wherein the size exclusion chromatography column is ACQUITY UPLC BEH200 SEC column. (Embodiment 464) The antibody or antigen binding fragment of any one of embodiments 456-463, wherein the antibody or antigen binding fragment is injected at a total volume of 15 µL. (Embodiment 465) The antibody or antigen binding fragment of any one of embodiments 456-464, wherein the antibody or antigen binding fragment is injected at a concentration of about 0.1 µg/µL to about 1.0 µg/µL. (Embodiment 466) The antibody or antigen binding fragment of any one of embodiments 456-465, wherein the size exclusion chromatography is performed on a Shimadzu UPLC instrument. (Embodiment 467) The antibody or antigen binding fragment of any one of embodiments 456-466, wherein the size exclusion chromatography is performed at a flow rate of 0.2 mL/min. (Embodiment 468) The antibody or antigen binding fragment of any one of embodiments 456-467, wherein the size exclusion chromatography is performed at a column oven temperature of 30° C. (Embodiment 469) The antibody or antigen binding fragment of any one of embodiments 456-468, wherein the percentage of monomer is calculated using Shimadzu software. (Embodiment 470) The antibody or antigen binding fragment of any one of embodiments 454-469, wherein the size exclusion chromatography is performed as described in Example 2. (Embodiment 471) The antibody or antigen binding fragment of any one of embodiments 431-470, expressing at least about 20 ug/ml total antibody. (Embodiment 472) The antibody or antigen binding fragment of any one of embodiments 431-470, expressing between about 20 ug/ml and 70 ug/mL total antibody. (Embodiment 473) The antibody or antigen binding fragment of embodiment 471 or embodiment 472, wherein the antibody or antigen binding fragment is expressed in FreeStyle 293-F cells. (Embodiment 474) The antibody or antigen binding fragment of any one of embodiments 471-473, wherein the antibody or antigen binding fragment is expressed as described in Example 2. (Embodiment 475) The antibody or antigen binding fragment of any one of embodiments 471-474, wherein the antibody or antigen binding fragment expression level is quantified using Enzyme-Linked Immunosorbent assay (ELISA). (Embodiment 476) The antibody or antigen binding fragment of embodiment 475, wherein the ELISA comprises coating a surface of a substrate with a capture antibody that binds to a human or humanized antibody, applying the antibody or antigen binding fragment to the substrate, and applying to the substrate a second antibody that binds to a human or humanized antibody. (Embodiment 477) The antibody or antigen binding fragment of embodiment 476, where the capture antibody comprises an anti-kappa antibody. (Embodiment 478) The antibody or antigen binding fragment of embodiment 476 or embodiment 477, where the second antibody comprises an anti-Fc antibody. (Embodiment 479) The antibody or antigen binding fragment of any one of embodiments 475-478, where the ELISA is performed as described in Example 2. (Embodiment 480) A An antibody or antigen binding fragment thereof that binds to TL1A, comprising a heavy chain variable region comprising: (a) an HCDR1 comprising an amino acid sequence set forth by SEQ ID NO: 1; (b) an HCDR2 comprising an amino acid sequence set forth by any one of SEQ ID NOS: 2-5; and (c) an HCDR3 comprising an amino acid sequence set forth by any one of SEQ ID NOS: 6-9; and the light chain variable region comprises: (d) an LCDR1 comprising an amino acid sequence set forth by SEQ ID NO: 10; (e) an LCDR2 comprising an amino acid sequence set forth by SEQ ID NO: 11; and (f) an LCDR3 comprising an amino acid sequence set forth by any one of SEQ ID NOS: 12-15, wherein the heavy chain variable region comprises 47R. (Embodiment 481) The antibody or antigen binding fragment of embodiment 480, wherein the heavy chain variable region comprises human IGHV1-46*02 framework or a modified human IGHV1-46*02 framework. (Embodiment 482) The antibody or antigen binding fragment of embodiment 480 or embodiment 481, wherein the light chain variable framework region comprising a human IGKV3-20 framework or a modified human IGKV3-20 framework. (Embodiment 483) The antibody or antigen binding fragment of any one of embodiments 480-482, wherein the heavy chain variable region comprises one of more of the following amino acids: 1E, 45K, 55I, 78A, 80I, 82T, 89A, 91L, per Kabat numbering. (Embodiment 484) The antibody or antigen binding fragment of embodiment 483, wherein the heavy chain variable region comprises 1E. (Embodiment 485) The antibody or antigen binding fragment of embodiment 483 or embodiment 484, wherein the heavy chain variable region comprises 45K. (Embodiment 486) The antibody or antigen binding fragment of any one of embodiments 483-485, wherein the heavy chain variable region comprises 55I. (Embodiment 487) The antibody or antigen binding fragment of any one of embodiments 483-486, wherein the heavy chain variable region comprises 78A. (Embodiment 488) The antibody or antigen binding fragment of any one of embodiments 483-487, wherein the heavy chain variable region comprises 80I. (Embodiment 489) The antibody or antigen binding fragment of any one of embodiments 483-488, wherein the heavy chain variable region comprises 82T. (Embodiment 490) The antibody or antigen binding fragment of any one of embodiments 483-489, wherein the heavy chain variable region comprises 89A. (Embodiment 491) The antibody or antigen binding fragment of any one of embodiments 483-490, wherein the heavy chain variable region comprises 91L. (Embodiment 492) The antibody or antigen binding fragment of any one of embodiments 480-491, wherein the light chain variable region comprises one or more of the following amino acids: 54P and 55W, per Kabat numbering. (Embodiment 493) The antibody or antigen binding fragment of embodiment 492, wherein the light chain variable region comprises 54P. (Embodiment 494) The antibody or antigen binding fragment of embodiment 492 or embodiment 493, wherein the light chain variable region comprises 55W. (Embodiment 495) The antibody of antigen binding fragment of any one of embodiments 480-494, wherein the HCDR2 comprises SEQ ID NO: 2. (Embodiment 496) The antibody of antigen binding fragment of any one of embodiments 480-494, wherein the HCDR2 comprises SEQ ID NO: 3. (Embodiment 497) The antibody of antigen binding fragment of any one of embodiments 480-494, wherein the HCDR2 comprises SEQ ID NO: 4. (Embodiment 498) The antibody of antigen binding fragment of any one of embodiments 480-494, wherein the HCDR2 comprises SEQ ID NO: 5. (Embodiment 499) The antibody of antigen binding fragment of any one of embodiments 480-498, wherein the HCDR3 comprises SEQ ID NO: 6. (Embodiment 500) The antibody of antigen binding fragment of any one of embodiments 480-498, wherein the HCDR3 comprises SEQ ID NO: 7. (Embodiment 501) The antibody of antigen binding fragment of any one of embodiments 480-498, wherein the HCDR3 comprises SEQ ID NO: 8. (Embodiment 502) The antibody of antigen binding fragment of any one of embodiments 480-498, wherein the HCDR3 comprises SEQ ID NO: 9. (Embodiment 503) The antibody of antigen binding fragment of any one of embodiments 480-502, wherein the LCDR3 comprises SEQ ID NO: 12. (Embodiment 504) The antibody of antigen binding fragment of any one of embodiments 480-502, wherein the LCDR3 comprises SEQ ID NO: 13. (Embodiment 505) The antibody of antigen binding fragment of any one of embodiments 480-502, wherein the LCDR3 comprises SEQ ID NO: 14 or 15.

(Embodiment 506) The antibody of antigen binding fragment of any one of embodiments 480-505, comprising a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. (Embodiment 507) The antibody of antigen binding fragment of any one of embodiments 480-505, comprising a (i) human IgG4 Fc region or (ii) a human IgG4 Fc region comprising (a) S228P, (b) S228P and L235E, or (c) S228P, F234A, and L235A, per Kabat numbering. (Embodiment 508) The antibody of antigen binding fragment of any one of embodiments 480-505, comprising a human IgG2 Fc region; IgG2-IgG4 cross-subclass Fc region; IgG2-IgG3 cross-subclass Fc region; IgG2 comprising H268Q, V309L, A330S, P331S (IgG2m4); or IgG2 comprising V234A, G237A, P238S, H268A, V309L, A330S, P331S (IgG2a). (Embodiment 509) The antibody of antigen binding fragment of any one of embodiments 480-506, comprising a human IgG1 comprising a substitution selected from 329A, 329G, 329Y, 331S, 236F, 236R, 238A, 238E, 238G, 238H, 238I, 238V, 238W, 238Y, 248A, 254D, 254E, 254G, 254H, 254I, 254N, 254P, 254Q, 254T, 254V, 264S, 265H, 265K, 265S, 265Y, 265A, 267G, 267H, 267I, 267K, 434I, 438G, 439E, 439H, 439Q, 440A, 440D, 440E, 440F, 440M, 440T, and 440V, per Kabat numbering. (Embodiment 510) The antibody or antigen binding fragment of any one of embodiments 480-505, comprising a sequence at least about 90%, 91%, 92%, 93%, 94%, 95%, 96%, 97%, 98%, 99%, or 100% identical to any one of SEQ ID NOS: 320-362. (Embodiment 511) The antibody or antigen binding fragment of any one of embodiments 480-510, comprising at least about 80% monomeric fraction as determined by size exclusion chromatography. (Embodiment 512) The antibody or antigen binding fragment of embodiment 511, comprising at least about 85%, 90%, 91%, 92%, 93%, 94%, 95%, 96%, 97%, 98%, or 99% monomeric fraction. (Embodiment 513) The antibody or antigen binding fragment of embodiment 511 or embodiment 512, wherein the size exclusion chromatography comprises injecting purified antibody or antigen binding fragment onto a size exclusion column, wherein the antibody or antigen binding fragment is purified by protein A. (Embodiment 514) The antibody or antigen binding fragment of embodiment 513, wherein the antibody or antigen binding fragment is purified as described in Example 2. (Embodiment 515) The antibody or antigen binding fragment of embodiment 513 or embodiment 514, wherein the antibody or antigen binding fragment is expressed under conditions described in Example 2. (Embodiment 516) The antibody or antigen binding fragment of any one of embodiments 513-514, wherein the size exclusion chromatography column has an inner diameter of 4.6 mm. (Embodiment 517) The antibody or antigen binding fragment of any one of embodiments 513-514, wherein the size exclusion chromatography column has a length of 150 mm. (Embodiment 518) The antibody or antigen binding fragment of any one of embodiments 513-515, wherein the size exclusion chromatography column has a pore size of 200 Å. (Embodiment 519) The antibody or antigen binding fragment of any one of embodiments 513-516, wherein the size exclusion chromatography column has a particle size of 1.7 micrometer. (Embodiment 520) The antibody or antigen binding fragment of any one of embodiments 513-517, wherein the size exclusion chromatography column is ACQUITY UPLC BEH200 SEC column. (Embodiment 521) The antibody or antigen binding fragment of any one of embodiments 513-520, wherein the antibody or antigen binding fragment is injected at a total volume of 15 µL. (Embodiment 522) The antibody or antigen binding fragment of any one of embodiments 513-521, wherein the antibody or antigen binding fragment is injected at a concentration of about 0.1 µg/µL to about 1.0 µg/µL. (Embodiment 523) The antibody or antigen binding fragment of any one of embodiments 513-522, wherein the size exclusion chromatography is performed on a Shimadzu UPLC instrument. (Embodiment 524) The antibody or antigen binding fragment of any one of embodiments 513-523, wherein the size exclusion chromatography is performed at a flow rate of 0.2 mL/min. (Embodiment 525) The antibody or antigen binding fragment of any one of embodiments 513-524, wherein the size exclusion chromatography is performed at a column oven temperature of 30° C. (Embodiment 526) The antibody or antigen binding fragment of any one of embodiments 513-525, wherein the percentage of monomer is calculated using Shimadzu software. (Embodiment 527) The antibody or antigen binding fragment of any one of embodiments 511-526, wherein the size exclusion chromatography is performed as described in Example 2. (Embodiment 528) The antibody or antigen binding fragment of any one of embodiments 480-527, expressing at least about 20 ug/ml total antibody. (Embodiment 529) The antibody or antigen binding fragment of any one of embodiments 480-527, expressing between about 20 ug/ml and 70 ug/mL total antibody. (Embodiment 530) The antibody or antigen binding fragment of embodiment 528 or embodiment 529, wherein the antibody or antigen binding fragment is expressed in FreeStyle 293-F cells. (Embodiment 531)

The antibody or antigen binding fragment of any one of embodiments 528-530, wherein the antibody or antigen binding fragment is expressed as described in Example 2. (Embodiment 532) The antibody or antigen binding fragment of any one of embodiments 528-531, wherein the antibody or antigen binding fragment expression level is quantified using Enzyme-Linked Immunosorbent assay (ELISA). (Embodiment 533) The antibody or antigen binding fragment of embodiment 532, wherein the ELISA comprises coating a surface of a substrate with a capture antibody that binds to a human or humanized antibody, applying the antibody or antigen binding fragment to the substrate, and applying to the substrate a second antibody that binds to a human or humanized antibody. (Embodiment 534) The antibody or antigen binding fragment of embodiment 533, where the capture antibody comprises an anti-kappa antibody. (Embodiment 535) The antibody or antigen binding fragment of embodiment 533 or embodiment 534, where the second antibody comprises an anti-Fc antibody. (Embodiment 536) The antibody or antigen binding fragment of any one of embodiments 532-535, where the ELISA is performed as described in Example 2. (Embodiment 537) A method of treating inflammatory bowel disease (IBD) in a subject in need thereof, the method comprising administering to the subject an antibody or antigen binding fragment of any one of embodiments 1-536. (Embodiment 538) The method of embodiment 537, wherein the IBD comprises Crohn's Disease. (Embodiment 539) The method of embodiment 537, wherein the IBD comprises ulcerative colitis.

Also provided are antibodies or antigen binding fragments thereof that bind to tumor necrosis factor-like protein 1A (TL1A), comprising a heavy chain variable domain comprising an amino acid sequence at least 96% identical to SEQ ID NO: 104, and a light chain variable domain comprising an amino acid sequence at least 97% identical to SEQ ID NO: 201. In some embodiments, the heavy chain variable domain comprises an amino acid sequence at least 97% identical to SEQ ID NO: 104. In some embodiments, the heavy chain variable domain comprises an amino acid sequence at least 98% identical to SEQ ID NO: 104. In some embodiments, the heavy chain variable domain comprises an amino acid sequence at least 99% identical to SEQ ID NO: 104. In some embodiments, the heavy chain variable domain comprises SEQ ID NO: 104. In some embodiments, the light chain variable domain comprises an amino acid sequence at least 98% identical to SEQ ID NO: 201. In some embodiments, the light chain variable domain comprises an amino acid sequence at least about 99% identical to SEQ ID NO: 201. In some embodiments, the light chain variable domain comprises SEQ ID NO: 201.

Further provided are antibodies or antigen binding fragments thereof that bind to tumor necrosis factor-like protein 1A (TL1A), comprising a heavy chain variable domain comprising an amino acid sequence at least about 99% identical to any one of SEQ ID NOS: 101-135, and a light chain variable domain comprising an amino acid sequence at least about 99% identical to any one of SEQ ID NOS: 201-206. Table 7 and Table 8 set forth exemplary variable region amino acid sequences of anti-TL1A antibodies.

Provided are also antibodies or antigen binding fragments, as described herein, further comprising a human IgG1 Fc region comprising (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S (IgG1σ), (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(uu), per Kabat numbering. In some embodiments, the antibodies comprise a human IgG4 Fc region. In some embodiments, the antibodies a Fc region comprising a sequence at least about 90%, 91%, 92%, 93%, 94%, 95%, 96%, 97%, 98%, 99%, or 100% identical to any one of SEQ ID NOS: 320-362. In some embodiments, the antibodies comprise at least about 80% monomeric fraction as determined by size exclusion chromatography. In some embodiments, the antibodies are expressed in an amount at least about 20 ug/ml total antibody, optionally about 20 ug/ml and 70 ug/mL total antibody.

Antibody Properties

In various embodiments, the anti-TL1A antibody is an antagonist of a TL1A receptor, such as, but not limited to, DR3 and TR6/DcR3. In certain embodiments, the antibody inhibits at least about 10%, at least about 20%, at least about 30%, at least about 50%, at least about 75%, at least about 90%, or about 100% of one or more activity of the bound TL1A receptor. In certain embodiments, the antibodies inhibit TL1A activation as measured by interferon gamma release in human blood. In certain embodiments, the antibody inhibits interferon gamma release in human blood at an $IC_{50}$ of between about 1 nanomolar and about 30 picomolar. In certain embodiments, the antibody inhibits interferon gamma release in human blood at an $IC_{50}$ of between about 500 picomolar and about 30 picomolar. In certain embodiments, the antibody inhibits interferon gamma release in human blood at an $IC_{50}$ of between about 200 picomolar and about 30 picomolar. In certain embodiments, the antibody inhibits interferon gamma release in human blood at an $IC_{50}$ of less than or equal to about 200 picomolar. In certain embodiments, the antibody inhibits interferon gamma release in human blood at an $IC_{50}$ of less than or equal to about 100 picomolar.

In various embodiments, an anti-TL1A antibody provided herein has a binding affinity to human TL1A of less than about $1E^{-7}$, $1E^{-8}$, $1E^{-9}$, or $1E^{-10}$ Kd. In some cases, the binding affinity is from about $1E^{-9}$ to about $1E^{-10}$ Kd. In some embodiments, an anti-TL1A antibody provided herein has a binding affinity to murine TL1A and/or rat TL1A of less than about $1E^{-7}$, $1E^{-8}$, $1E^{-9}$, $1E^{-10}$, or $1E^{-11}$ Kd. Methods for determining binding affinity are exemplified herein, including in Example 2.

In various embodiments, an anti-TL1A antibody provided herein comprises at least about 80% monomeric fraction after expression and purification as described in Example 2 or elsewhere herein. In various embodiments, an anti-TL1A antibody provided herein comprises at least about 85% monomeric fraction after expression and purification as described in Example 2 or elsewhere herein. In various embodiments, an anti-TL1A antibody provided herein comprises at least about 90% monomeric fraction after expression and purification as described in Example 2 or elsewhere herein. In various embodiments, an anti-TL1A antibody provided herein comprises at least about 91%, 92%, 93%, 94%, 95%, 96%, 97%, 98%, 99%, or 100% monomeric fraction after expression and purification as described in Example 2 or elsewhere herein.

In various embodiments, an anti-TL1A antibody provided herein has at least about 2 µg/mL expression as determined by the method disclosed herein. In some embodiments, the anti-TL1A antibody has about 2 µg/mL to about 60 µg/mL expression as determined by the method disclosed herein. In some embodiments, the anti-TL1A antibody has about 5 µg/mL to about 60 µg/mL expression as determined by the method disclosed herein. In some embodiments, the anti-TL1A antibody has about 10 µg/mL to about 60 µg/mL expression as determined by the method disclosed herein. In some embodiments, the anti-TL1A antibody has at least about 5 µg/mL expression as determined by the method disclosed herein. In some embodiments, the anti-TL1A antibody has at least about 10 µg/mL expression as determined by the method disclosed herein. In some embodiments, the anti-TL1A antibody has at least about 15 µg/mL expression as determined by the method disclosed herein. In some embodiments, the anti-TL1A antibody has at least about 20 µg/mL expression as determined by the method disclosed herein. In some embodiments, the anti-TL1A antibody expresses between about 2 µg/mL and about 50 µg/mL, between about 2 µg/mL and about 40 µg/mL, between about 2 µg/mL and about 30 µg/mL expression, between about 2 µg/mL and about 20 µg/mL, between about 5 µg/mL and about 50 µg/mL, between about 5 µg/mL and about 40 µg/mL, between about 5 µg/mL and about 30 µg/mL, between about 10 µg/mL and about 50 µg/mL, between about 10 µg/mL and about 40 µg/mL, or between about 10 µg/mL and about 30 µg/mL as determined by the method disclosed herein. In some embodiments, the anti-TL1A antibody has about 2, 3, 4, 5, 6, 7, 8, 9, 10, 11, 12, 13, 14, 15, 16, 17, 18, 19, 20, 21, 22, 23, 24, 25, 26, 27, 28, 29, 30 µg/mL expression as determined by the method disclosed herein. Methods disclosed herein include those described in Example 2.

In various embodiments, an anti-TL1A antibody provided herein is humanized and has less than about 20% non-human sequence in the framework region of each of the heavy chain and light chain variable regions. For instance, the humanized antibody comprises less than about 20%, 19%, 18%, 17%, 16%, 15%, 14%, 13%, 12%, 11%, 10%, 9%, 8%, 7%, 6%, 5%, 4%, 3%, 2%, or 1% non-human sequence in the framework region of each of the heavy chain and light chain variable regions. As another example, the humanized antibody comprises about or less than about 15, 14, 13, 12, 11, 10, 9, 8, 7, 6, 5, 4, 3, 2, or 1 non-human sequences in the framework region of each of the heavy chain and light chain variable regions. The humanized heavy chain variable domain may comprise IGHV1-46*02 framework with no or fewer than about 10, 9, 8, 7, 6, 5, 4, 3, 2, or 1 non-human mutations. The humanized light chain variable domain may comprise IGKV3-20 framework with no or fewer than about 10, 9, 8, 7, 6, 5, 4, 3, 2, or 1 non-human mutations.

Assays

An exemplary screening paradigm for identification of antibody variants that express well in mammalian cells and preserve TL1A binding activity while minimizing the propensity of the antibody to aggregate comprises a five-step process. This screen was performed as detailed in the examples. Briefly, (1) variants were cloned and transiently expressed as intact Ig in 293 cells using small-scale (3 mL, 6-well culture plates) transfections, (2) the expression level of the antibody was assessed in the culture supernatant 96-120 hours after transfection using an antibody quantitation ELISA, (3) the binding of the supernatant antibody variants to human TL1A was assessed by ELISA, (4) the antibody was purified in a single step using Protein A and (5) the material was analyzed by analytical SEC to assess monomer/aggregate content. This approach enabled identification of variants that expressed well, preserved binding to TL1A, and displayed high monomer content.

Further provided herein are methods for analyzing antibody solubility based on percentage of monomeric fraction. For example, as described in Example 2.

Further provided herein are assays for quantifying antibody expression. For example, as described in Example 2.

Further provided herein are assays for quantifying immunogenicity of an antibody.

The antibodies described herein can be assayed for specific binding by any method known in the art. The immunoassays which can be used include, but are not limited to, competitive and non-competitive assay systems using techniques such as BIAcore analysis, FACS analysis, immunofluorescence, immunocytochemistry, Western blots, radioimmunoassays, ELISA, "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, and protein A immunoassays. Such assays are provided in for e.g., Ausubel et al., eds, 1994, Current Protocols in Molecular Biology, Vol. 1, John Wiley & Sons, Inc., New York.

Methods of Generating Antibodies

In various embodiments, monoclonal antibodies are prepared using methods known in the art, such as, but not limited to the hybridoma method, where a host animal is immunized to elicit the production by lymphocytes of antibodies that will specifically bind to an immunizing antigen (Kohler and Milstein (1975) Nature 256:495). Hybridomas produce monoclonal antibodies directed specifically against a chosen antigen. The monoclonal antibodies are purified from the culture medium or ascites fluid by techniques known in the art, when propagated either in vitro or in vivo.

In some embodiments, monoclonal antibodies are made using recombinant DNA methods. The polynucleotides encoding a monoclonal antibody are isolated from mature B-cells or hybridoma cells. The isolated polynucleotides encoding the heavy and light chains are then cloned into suitable expression vectors, which when transfected into host cells (e.g., E. coli cells, simian COS cells, Chinese hamster ovary (CHO) cells, or myeloma cells) generate monoclonal antibodies. The polynucleotide(s) encoding a monoclonal antibody can further be modified in a number of different manners using recombinant DNA technology to generate alternative antibodies.

In various embodiments, a chimeric antibody, a molecule in which different portions are derived from different animal species, such as those having a variable region derived from a murine monoclonal antibody and a human immunoglobulin constant region (e.g., humanized antibodies) can be generated.

In some embodiments, the anti-TL1A monoclonal antibody is a humanized antibody, to reduce antigenicity and HAMA (human anti-mouse antibody) responses when administered to a human subject. Humanized antibodies can be produced using various techniques known in the art. For example, an antibody is humanized by (1) determining the nucleotide and predicted amino acid sequence of the starting antibody light and heavy variable domains; (2) designing the humanized antibody, e.g., deciding which antibody framework region to use during the humanizing process; (3) the actual humanizing methodologies/techniques; and (4) the transfection and expression of the humanized antibody. In various embodiments, a humanized antibody can be further optimized to decrease potential immunogenicity, while maintaining functional activity, for therapy in humans.

Humanized antibodies can also be made in transgenic mice containing human immunoglobulin loci that are capable, upon immunization, of producing the full repertoire of human antibodies in the absence of endogenous immunoglobulin production. A humanized antibody may also be obtained by a genetic engineering approach that enables production of affinity-matured human-like polyclonal antibodies in large animals.

A fully humanized antibody may be created by first designing a variable region amino acid sequence that contains non-human, e.g., rodent-derived CDRs, embedded in human-derived framework sequences. The non-human CDRs provide the desired specificity. Accordingly, in some cases these residues are included in the design of the reshaped variable region essentially unchanged. In some cases, modifications should therefore be restricted to a minimum and closely watched for changes in the specificity and affinity of the antibody. On the other hand, framework residues in theory can be derived from any human variable region. A human framework sequences should be chosen, which is equally suitable for creating a reshaped variable region and for retaining antibody affinity, in order to create a reshaped antibody which shows an acceptable or an even improved affinity. The human framework may be of germline origin, or may be derived from non-germline (e.g., mutated or affinity matured) sequences. Genetic engineering techniques well known to those in the art, for example, but not limited to, phage display of libraries of human antibodies, transgenic mice, human-human hybridoma, hybrid hybridoma, B cell immortalization and cloning, single-cell RT-PCR or HuRAb Technology, may be used to generate a humanized antibody with a hybrid DNA sequence containing a human framework and a non-human CDR.

In certain embodiments, the anti-TL1A antibody is a human antibody. Human antibodies can be directly prepared using various techniques known in the art. Immortalized human B lymphocytes immunized in vitro or isolated from an immunized individual that produce an antibody directed against a target antigen can be generated.

Chimeric, humanized and human antibodies may be produced by recombinant expression. Recombinant polynucleotide constructs typically include an expression control sequence operably linked to the coding sequences of antibody chains, including naturally associated or heterologous promoter regions. In certain embodiments, it may be desirable to generate amino acid sequence variants of these humanized antibodies, particularly where these improve the binding affinity or other biological properties of the antibody.

In certain embodiments, an antibody fragment is used to treat and/or ameliorate IBD. Various techniques are known for the production of antibody fragments. Generally, these fragments are derived via proteolytic digestion of intact antibodies (for example Morimoto et al., 1993, Journal of Biochemical and Biophysical Methods 24:107-117; Brennan et al., 1985, Science, 229:81). Fab, Fv, and scFv antibody fragments can all be expressed in and secreted from E. coli or other host cells, thus allowing the production of large amounts of these fragments. Other techniques for the production of antibody fragments will be apparent to the skilled practitioner.

According to the present disclosure, techniques can be adapted for the production of single-chain antibodies specific to TL1A. In addition, methods can be adapted for the construction of Fab expression libraries to allow rapid and effective identification of monoclonal Fab fragments with the desired specificity for TL1A, or derivatives, fragments, analogs or homologs thereof. Antibody fragments may be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

Also provided herein are modified antibodies comprising any type of variable region that provides for the association of the antibody with TL1A. Those skilled in the art will appreciate that the modified antibodies may comprise antibodies (e.g., full-length antibodies or immunoreactive fragments thereof) in which at least a fraction of one or more of the constant region domains has been deleted or otherwise altered so as to provide desired biochemical characteristics such as decreasing TL1A. In certain embodiments, the variable regions in both the heavy and light chains are altered by at least partial replacement of one or more CDRs and, if necessary, by partial framework region replacement and sequence changing. In some embodiments, the replaced CDRs may be derived from an antibody of the same class, subclass, from an antibody of a different class, for instance, from an antibody from a different species and/or a combination thereof. In some embodiments, the constant region of the modified antibodies will comprise a human constant region. Modifications to the constant region compatible with this disclosure comprise additions, deletions or substitutions of one or more amino acids in one or more domains.

In various embodiments, the expression of an antibody or antigen-binding fragment thereof as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. In other embodiments, the antibody or antigen-fragment thereof as described herein may be transfected into the host.

In some embodiments, the expression vectors are transfected into the recipient cell line for the production of the chimeric, humanized, or composite human antibodies described herein. In various embodiments, mammalian cells can be useful as hosts for the production of antibody proteins, which can include, but are not limited to cells of fibroblast origin, such as Vero (ATCC CRL 81) or CHO-K1 (ATCC CRL 61) cells, HeLa cells and L cells. Exemplary eukaryotic cells that can be used to express polypeptides include, but are not limited to, COS cells, including COS 7 cells; 293 cells, including 293-6E cells; CHO cells, including CHO—S and DG44 cells; PER.C6™ cells (Crucell); and NSO cells. In some embodiments, a particular eukaryotic host cell is selected based on its ability to make desired post-translational modifications to the heavy chains and/or light chains.

A number of suitable host cell lines capable of secreting intact heterologous proteins have been developed in the art, and include, but are not limited to CHO cell lines, various COS cell lines, HeLa cells, L cells and multiple myeloma cell lines.

An expression vector carrying a chimeric, humanized, or composite human antibody construct, antibody or antigen-binding fragment thereof as described herein can be introduced into an appropriate host cell by any of a variety of suitable means, depending on the type of cellular host including, but not limited to transformation, transfection, lipofection, conjugation, electroporation, direct microinjection, and microprojectile bombardment, as known to one of ordinary skill in the art. Expression vectors for these cells can include expression control sequences, such as an origin of replication sites, a promoter, an enhancer and necessary processing information sites, such as ribosome binding sites, RNA splice sites, polyadenylation sites, and transcriptional terminator sequences.

In various embodiments, yeast can also be utilized as hosts for the production of the antibody molecules or peptides described herein. In various other embodiments, bacterial strains can also be utilized as hosts for the production of the antibody molecules or peptides described herein. Examples of bacterial strains include, but are not limited to *E. coli*, *Bacillus* species, enterobacteria, and various *Pseudomonas* species.

In some embodiments, one or more antibodies or antigen-binding fragments thereof as described herein can be produced in vivo in an animal that has been engineered (transgenic) or transfected with one or more nucleic acid molecules encoding the polypeptides, according to any suitable method. For production of transgenic animals, transgenes can be microinjected into fertilized oocytes, or can be incorporated into the genome of embryonic stem cells, and the nuclei of such cells transferred into enucleated oocytes. Once expressed, antibodies can be purified according to standard procedures of the art, including HPLC purification, column chromatography, gel electrophoresis and the like (see generally, Scopes, Protein Purification (Springer-Verlag, NY, 1982)).

Once expressed in the host, the whole antibodies, antibody-fragments (e.g., individual light and heavy chains), or other immunoglobulin forms of the present disclosure can be recovered and purified by known techniques, e.g., immunoabsorption or immunoaffinity chromatography, chromatographic methods such as HPLC (high performance liquid chromatography), ammonium sulfate precipitation, gel electrophoresis, or any combination of these. See generally, Scopes, PROTEIN PURIF. (Springer-Verlag, N Y, 1982). Substantially pure immunoglobulins of at least about 90% to 95% homogeneity are advantageous, as are those with 98% to 99% or more homogeneity, particularly for pharmaceutical uses. Once purified, partially or to homogeneity as desired, a humanized or composite human antibody can then be used therapeutically or in developing and performing assay procedures, immunofluorescent stainings, etc. See generally, Vols. I & II Immunol. Meth. (Lefkovits & Pernis, eds., Acad. Press, N Y, 1979 and 1981).

Various embodiments provide for a genetic construct comprising a nucleic acid encoding an anti-TL1A antibody or fragment provided herein. Genetic constructs of the antibody can be in the form of expression cassettes, which can be suitable for expression of the encoded anti-TL1A antibody or fragment. The genetic construct may be introduced into a host cell with or without being incorporated in a vector. For example, the genetic construct can be incorporated within a liposome or a virus particle. Alternatively, a purified nucleic acid molecule can be inserted directly into a host cell by methods known in the art. The genetic construct can be introduced directly into cells of a host subject by transfection, infection, electroporation, cell fusion, protoplast fusion, microinjection or ballistic bombardment.

Various embodiments provide a recombinant vector comprising the genetic construct of an antibody provided herein. The recombinant vector can be a plasmid, cosmid or phage. The recombinant vectors can include other functional elements; for example, a suitable promoter to initiate gene expression.

Various embodiments provide a host cell comprising a genetic construct and/or recombinant vector described herein.

Various host systems are also advantageously employed to express recombinant protein. Examples of suitable mammalian host cell lines include the COS-7 lines of monkey kidney cells, and other cell lines capable of expressing an appropriate vector including, for example, L cells, C127, 3T3, Chinese hamster ovary (CHO), HeLa and BHK cell lines. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine (SEQ ID NO: 1303), maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography. Recombinant protein produced in bacterial culture can be isolated.

One of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retain the ability to specifically bind the target antigen. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as He, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. antigen-binding activity and specificity of a native or reference polypeptide is retained.

Particular conservative substitutions include, for example; Ala into Gly or into Ser; Arg into Lys; Asn into Gin or into H is; Asp into Glu; Cys into Ser; Gin into Asn; Glu into Asp; Gly into Ala or into Pro; His into Asn or into Gin; lie into Leu or into Val; Leu into lie or into Val; Lys into Arg, into Gin or into Glu; Met into Leu, into Tyr or into lie; Phe into Met, into Leu or into Tyr; Ser into Thr; Thr into Ser; Trp into Tyr; Tyr into Trp; and/or Phe into Val, into lie or into Leu.

In some embodiments, the antibody and/or antigen-binding fragment thereof described herein can be a variant of a sequence described herein, e.g., a conservative substitution variant of an antibody polypeptide. In some embodiments, the variant is a conservatively modified variant. A variant may refer to a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity, e.g., antigen-specific binding activity for the relevant target polypeptide.

Alterations of the native amino acid sequence can be accomplished by any of a number of techniques known to one of skill in the art. Mutations can be introduced at particular loci or by oligonucleotide-directed site-specific mutagenesis procedures. Techniques for making such alterations are very well established and include, for example, those disclosed by Walder et al. (Gene 42: 133, 1986); Bauer et al. (Gene 37:73, 1985); Craik (BioTechniques, Jan. 1985, 12-19); Smith et al. (Genetic Engineering: Principles and Methods, Plenum Press, 1981).

Nucleic acid molecules encoding amino acid sequence variants of antibodies are prepared by a variety of methods known in the art. These methods include, but are not limited to, preparation by oligonucleotide-mediated (or site-directed) mutagenesis, PCR mutagenesis, and cassette mutagenesis of an earlier prepared variant or a non-variant version of the antibody. A nucleic acid sequence encoding at least one antibody, portion or polypeptide as described herein can be recombined with vector DNA in accordance with conventional techniques, including but not limited to, blunt-ended or staggered-ended termini for ligation and restriction enzyme digestion. Techniques for such manipulations are disclosed, e.g., by Maniatis et al., Molecular Cloning, Lab. Manual (Cold Spring Harbor Lab. Press, N Y, 1982 and 1989), and can be used to construct nucleic acid sequences which encode a monoclonal antibody molecule or antigen-binding region.

In some embodiments, a nucleic acid encoding an antibody or antigen-binding fragment thereof as described herein is comprised by a vector. In some of the aspects described herein, a nucleic acid sequence encoding an antibody or antigen-binding fragment thereof as described herein, or any module thereof, is operably linked to a vector. The term "vector," as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g., 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding an antibody or antigen-binding portion thereof as described herein in place of non-essential viral genes. The vector and/or particle may be utilized for the purpose of transferring any nucleic acids into cells either in vitro or in vivo. Numerous forms of viral vectors are known in the art.

By "recombinant vector," it is meant that the vector includes a heterologous nucleic acid sequence, or "transgene" that is capable of expression in vivo.

Pharmaceutical Compositions, Administration and Dosage

The anti-TL1A antibodies provided are useful in a variety of applications including, but not limited to, therapeutic treatment methods, such as the treatment of IBD. The methods of use may be in vitro, ex vivo, or in vivo methods. In certain embodiments, the anti-TL1A antibody is an antagonist for TL1A receptors.

In certain embodiments, the disease treated with anti-TL1A antibody or TL1A receptor antagonist is IBD, CD, UC and/or MR-UC.

In various embodiments, the pharmaceutical compositions are formulated for delivery via any route of administration. "Route of administration" may refer to any administration pathway known in the art, including but not limited to aerosol, nasal, oral, transmucosal, transdermal or parenteral.

The pharmaceutical compositions can also contain any pharmaceutically acceptable carrier. "Pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

In various embodiments, provided are pharmaceutical compositions including a pharmaceutically acceptable excipient along with a therapeutically effective amount of an anti-TL1A antibody. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. The active ingredient can be mixed with excipients which are pharmaceutically acceptable and compatible with the active ingredient and in amounts suitable for use in therapeutic methods described herein. Such excipients may be solid, liquid, semisolid, or, in the case of an aerosol composition, gaseous. Suitable excipients are, for example, starch, glucose, lactose, sucrose, gelatin, malt, rice, flour, chalk, silica gel, sodium stearate, glycerol monostearate, talc, sodium chloride, dried skim milk, water, saline, dextrose, propylene glycol, glycerol, ethanol, mannitol, polysorbate or the like and combinations thereof. In addition, if desired, the composition can contain minor amounts of auxiliary substances such as wetting or emulsifying agents, pH buffering agents and the like which enhance or maintain the effectiveness of the active ingredient. Therapeutic compositions as described herein can include pharmaceutically acceptable salts. Pharmaceutically acceptable salts include the acid addition salts formed with inorganic acids such as, for example, hydrochloric or phosphoric acids, organic acids, for example, acetic, tartaric or mandelic, salts formed from inorganic bases such as, for example, sodium, potassium, ammonium, calcium or ferric hydroxides, and salts formed from organic bases such as isopropylamine, trimethylamine, 2-ethylamino ethanol, histidine, procaine and the like. Liquid compositions can contain liquid phases in addition to and in the exclusion of water, for example, glycerin, vegetable oils such as cottonseed oil, and water-oil emulsions. Physiologically tolerable carriers are well known in the art. The amount of an active agent (i.e. antibody or fragment thereof) used that will be effective in the treatment of a particular disorder or condition will depend on the nature of the disorder or condition and can be determined by one of skill in the art with standard clinical techniques.

The pharmaceutical compositions may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

For the treatment of the disease, the appropriate dosage of an antibody depends on the type of disease to be treated, the severity and course of the disease, the responsiveness of the disease, whether the antibody is administered for therapeutic or preventative purposes, previous therapy, and patient's clinical history. The dosage can also be adjusted by the individual physician in the event of any complication and at the discretion of the treating physician. The administering physician can determine optimum dosages, dosing methodologies and repetition rates. The TL1A antibody can be administered one time or over a series of treatments lasting from several days to several months, or until a cure is effected or a diminution of the disease state is achieved (e.g., treatment or amelioration of IBD). The duration of treatment depends upon the subject's clinical progress and responsiveness to therapy. In certain embodiments, dosage is from 0.01 µg to 100 mg per kg of body weight, and can be given once or more daily, weekly, monthly or yearly.

Figure 3A:
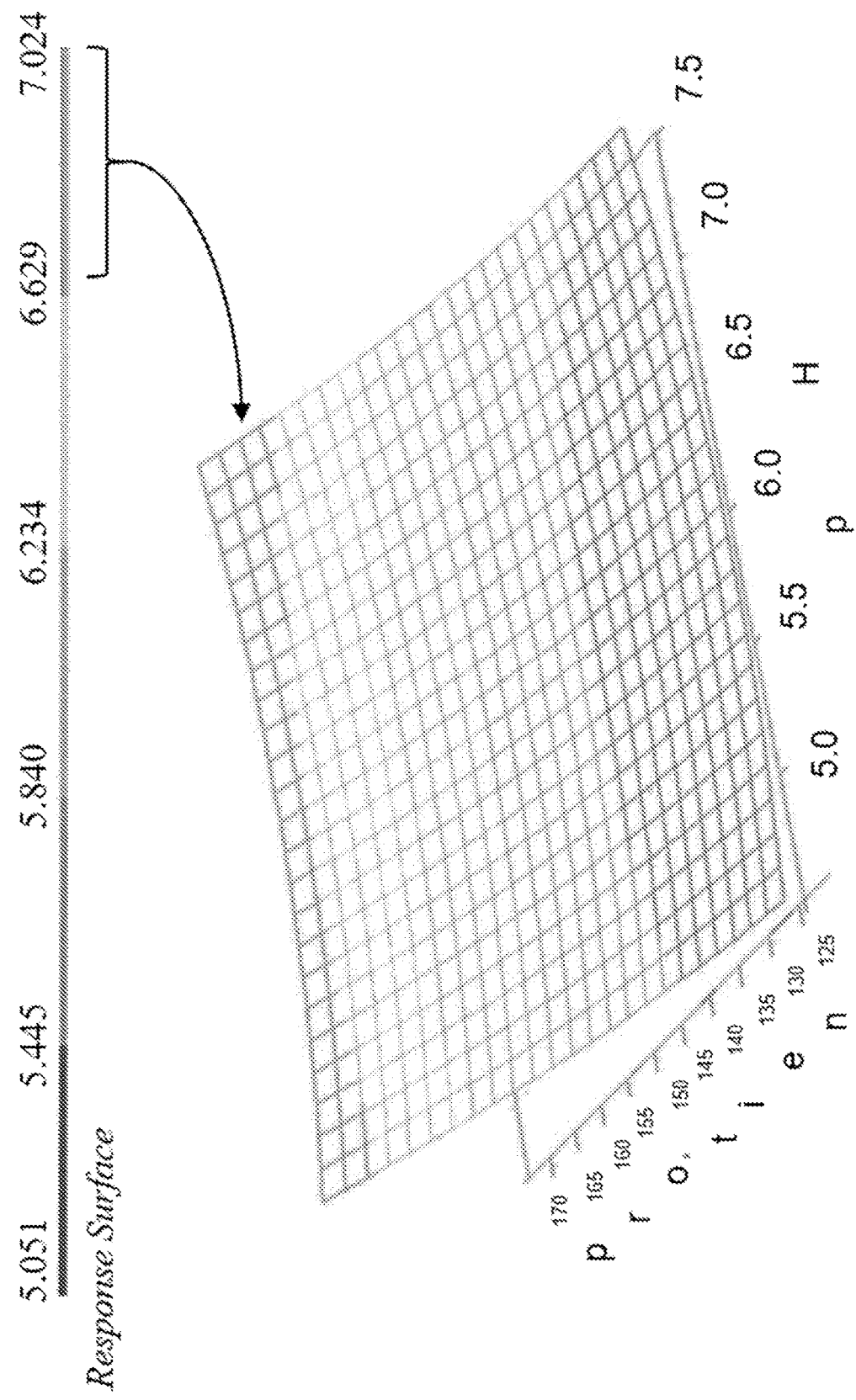
FIGS. 3A-3C depict a PLS model demonstrating effect of pH and protein concentration on viscosity.
Figure 3B:
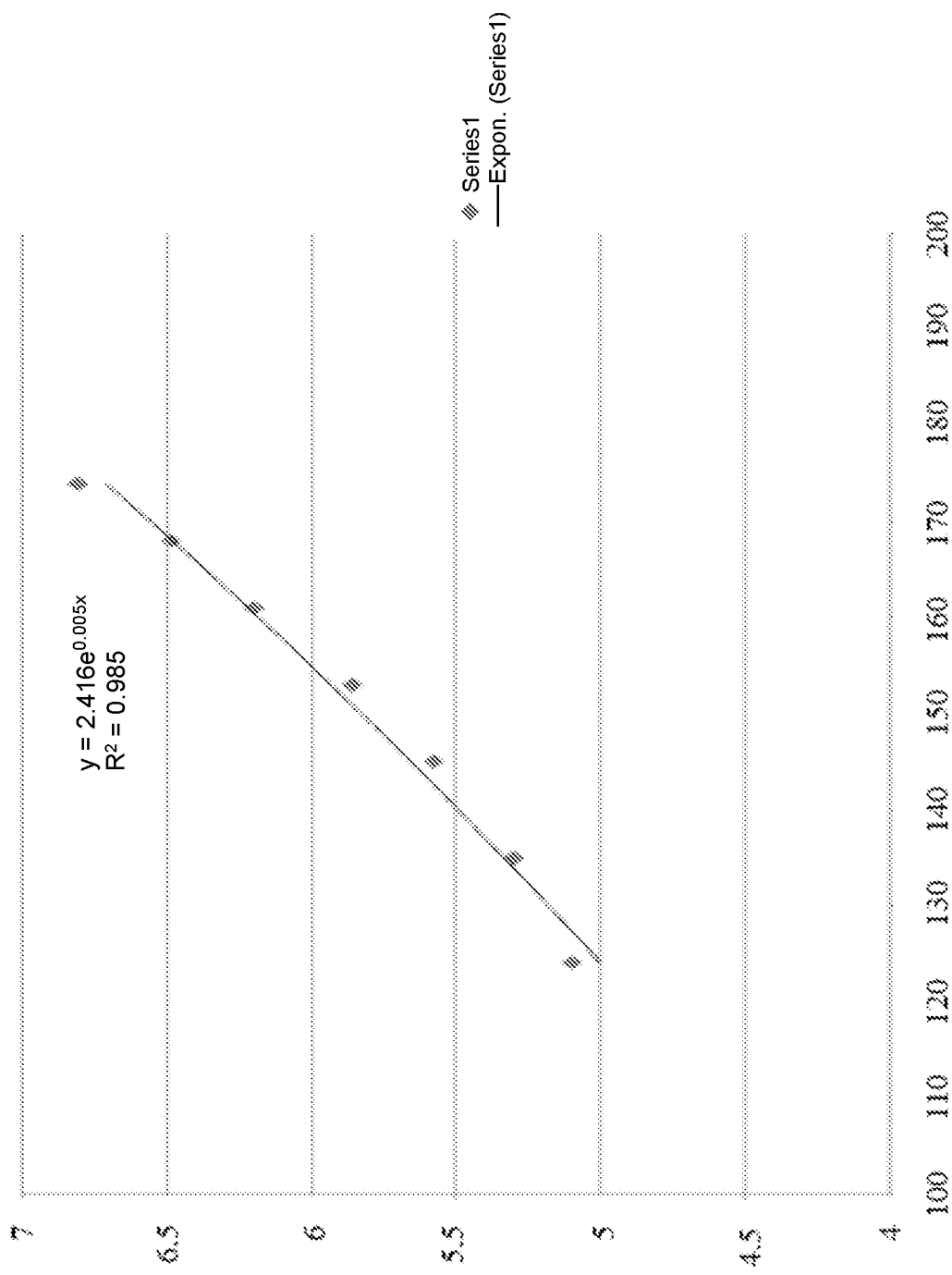
Figure 3C:
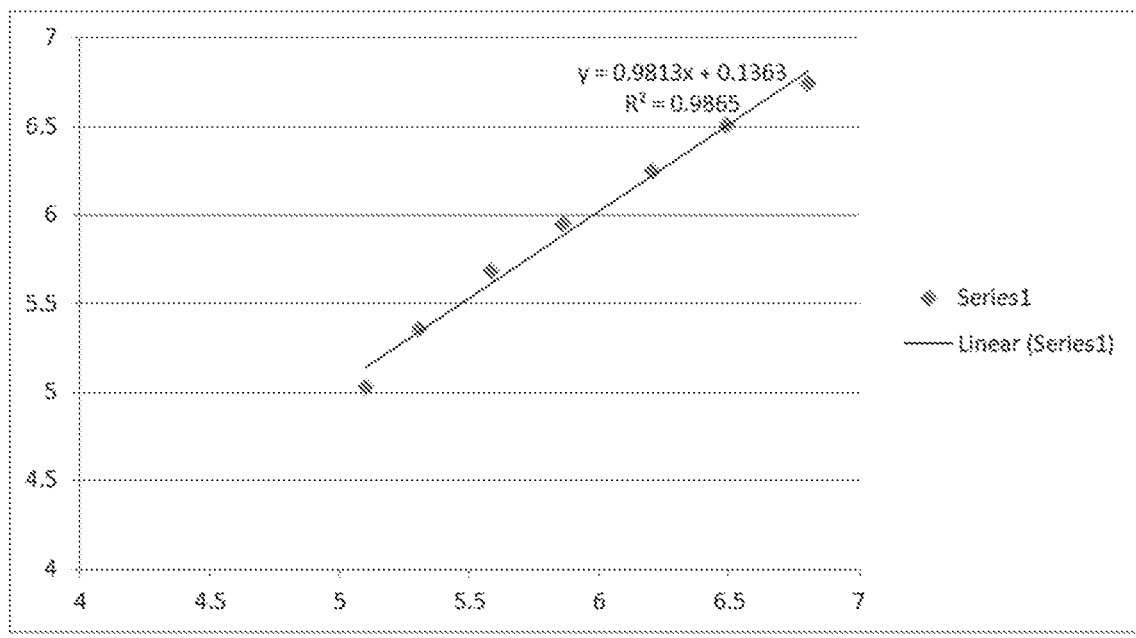

Antibody therapeutics suitable for injection and/or administration are important to realizing the full therapeutic potential of mAbs (monoclonal antibodies, e.g. an anti-TL1A monoclonal antibody). However, administration is generally restricted by volume. This, in turn, elucidates the importance developing of high concentration mAb formulations of greater than, for example in some cases, 100 mg/ml. Problems associated with mAb development include high solution viscosity and opalescence, which are commonly encountered during the development of high-concentration (e.g. greater than 100 mg/ml). Both viscosity and opalescence impact mAb developability broadly, affecting manufacturability, stability, and delivery. High solution viscosities (e.g. greater than 30 mPa-s) cause limiting back-pressures in ultrafiltration/diafiltration during the mAb concentration unit operation. Similarly, viscous mAb solutions also result in forbidding or incompatible injection forces when administering via injection, including via patient friendly autoinjectors. In effect, solution viscosity can be a determining factor for the maximum mAb dose possible via injection. Solution opalescence in therapeutic mAbs can be equally problematic as opalescence can indicate predisposition for liquid-liquid phase separation, precipitation, or aggregation The anti-TL1A antibodies provided herein demonstrate advantageous viscosity and aggregation properties at high antibody concentrations (e.g. greater than 100 mg/mL or greater than 150 mg/mL). Notably, anti-TL1A antibodies provided herein are characterized by low viscosity (e.g. less than 10 mPa-s) and low aggregation (e.g. less than 5% high molecular weight species) at high concentrations (FIGS. 3A-3C).

For example, for an antibody or antigen binding fragment wherein HCDR1 comprises SEQ ID NO: 1, HCDR2 comprises SEQ ID NO: 2, HCDR3 comprises SEQ ID NO: 6, LCDR1 comprises SEQ ID NO: 10, LCDR2 comprises SEQ ID NO: 11, and LCDR3 comprises SEQ ID NO: 12 or an antibody or antigen binding fragment wherein the heavy chain variable region comprises SEQ ID NO: 104 and the light chain variable region comprises SEQ ID NO: 201, in some embodiments, the anti-T1LA antibody is characterized by a viscosity less than about 30, 20, 15, or 10 mPa-s at a concentration greater than about 100 mg/mL, e.g., up to about 170 mg/mL. In some embodiments, the anti-T1LA antibody is characterized by a viscosity less than about 30, 20, 15, or 10 mPa-s at a concentration greater than at least about 100 mg/mL. In some embodiments, the anti-T1LA antibody is characterized by a viscosity less than about 30, 20, 15, or 10 mPa-s at a concentration up to about 170 mg/mL. In some embodiments, the anti-T1LA antibody is characterized by a viscosity less than about 30, 20, 15, or 10 mPa-s at a concentration from about 100 mg/mL to about 125 mg/mL, about 100 mg/mL to about 150 mg/mL, about 100 mg/mL to about 160 mg/mL, about 100 mg/mL to about 170 mg/mL, about 125 mg/mL to about 150 mg/mL, about 125 mg/mL to about 160 mg/mL, about 125 mg/mL to about 170 mg/mL, about 150 mg/mL to about 160 mg/mL, about 150 mg/mL to about 170 mg/mL, or about 160 mg/mL to about 170 mg/mL. In some embodiments, the anti-T1LA antibodies is characterized by a viscosity less than about 30, 20, 15, or 10 mPa-s at a concentration about or greater than about 100 mg/mL, about 125 mg/mL, about 150 mg/mL, about 160 mg/mL, or about 170 mg/mL. In some embodiments, less than about 10 mPa-s includes from about 4 to about 10 mPa-s, from about 4 to about 9 mPa-s, from about 4 to about 8 mPa-s, from about 4 to about 7 mPa-s, from about 4 to about 6 mPa-s, from about 4 to about 5 mPa-s, from about 5 to about 10 mPa-s, from about 5 to about 9 mPa-s, from about 5 to about 8 mPa-s, from about 5 to about 7 mPa-s, from about 5 to about 6 mPa-s, from about 6 to about 10 mPa-s, from about 6 to about 9 mPa-s, from about 6 to about 8 mPa-s, or from about 6 to about 7 mPa-s. In some embodiments, greater than about 100, 125, 150, or 160 mg/ml is up to about 170 mg/ml.

Additionally, for example, for an antibody or antigen binding fragment wherein HCDR1 comprises SEQ ID NO: 1, HCDR2 comprises SEQ ID NO: 2, HCDR3 comprises SEQ ID NO: 6, LCDR1 comprises SEQ ID NO: 10, LCDR2 comprises SEQ ID NO: 11, and LCDR3 comprises SEQ ID NO: 12 or an antibody or antigen binding fragment wherein the heavy chain variable region comprises SEQ ID NO: 104 and the light chain variable region comprises SEQ ID NO: 201, in some embodiments, the anti-TL1A antibody is characterized by a turbidity less than 12 Nephelometric Turbidity Units (NTU) when at a concentration greater than about 100 mg/mL to about 170 mg/mL. In some embodiments, the anti-TL1A antibody is characterized by a turbidity less than 12 Nephelometric Turbidity Units (NTU) when at a concentration greater than at least about 100 mg/mL. In some embodiments, the anti-TL1A antibody is characterized by a turbidity less than 12 Nephelometric Turbidity Units (NTU) when at a concentration up to about 170 mg/mL. In some embodiments, the anti-TL1A antibody is characterized by a turbidity less than 12 Nephelometric Turbidity Units (NTU) when at a concentration from about 100 mg/mL to about 125 mg/mL, about 100 mg/mL to about 150 mg/mL, about 100 mg/mL to about 160 mg/mL, about 100 mg/mL to about 170 mg/mL, about 125 mg/mL to about 150 mg/mL, about 125 mg/mL to about 160 mg/mL, about 125 mg/mL to about 170 mg/mL, about 150 mg/mL to about 160 mg/mL, about 150 mg/mL to about 170 mg/mL, or about 160 mg/mL to about 170 mg/mL. In some embodiments, the anti-TL1A antibody is characterized by a turbidity less than 12 Nephelometric Turbidity Units (NTU) when at a concentration at or greater than about 100 mg/mL, about 125 mg/mL, about 150 mg/mL, about 160 mg/mL, or about 170 mg/mL.

By way of further example, for an antibody or antigen binding fragment wherein HCDR1 comprises SEQ ID NO: 1, HCDR2 comprises SEQ ID NO: 2, HCDR3 comprises SEQ ID NO: 6, LCDR1 comprises SEQ ID NO: 10, LCDR2 comprises SEQ ID NO: 11, and LCDR3 comprises SEQ ID NO: 12 or an antibody or antigen binding fragment wherein the heavy chain variable region comprises SEQ ID NO: 104 and the light chain variable region comprises SEQ ID NO: 201, in some embodiments, the anti-T1LA antibody at a concentration from about 150 mg/mL to about or greater than about 170 mg/mL is characterized by a viscosity less than about 10 mPa-s to about 30 mPa-s. In some embodiments, the anti-T1LA antibody at a concentration from about 150 mg/mL to about or greater than about 170 mg/mL is characterized by a viscosity less than about 30 mPa-s. In some embodiments, the anti-T1LA antibody at a concentration from about 150 mg/mL to about or greater than about 170 mg/mL is characterized by a viscosity less than about 5 mPa-s to about 10 mPa-s, about 5 mPa-s to about 15 mPa-s, about 5 mPa-s to about 20 mPa-s, about 5 mPa-s to about 30 mPa-s, about 10 mPa-s to about 15 mPa-s, about 10 mPa-s to about 20 mPa-s, about 10 mPa-s to about 30 mPa-s, about 15 mPa-s to about 20 mPa-s, about 15 mPa-s to about 30 mPa-s, about 20 mPa-s to about 30 mPa-s, about 5 mPa-s to about 9 mPa-s, about 4 to about 10 mPa-s, about 4 to about 9 mPa-s, about 4 to about 8 mPa-s, about 4 to about 7 mPa-s, about 4 to about 6 mPa-s, about 4 to about 5 mPa-s, about 5 to about 10 mPa-s, about 5 to about 9 mPa-s, about 5 to about 8 mPa-s, about 5 to about 7 mPa-s, about 5 to about 6 mPa-s, about 6 to about 10 mPa-s, about 6 to about 9 mPa-s, about 6 to about 8 mPa-s, or about 6 to about 7 mPa-s. In some embodiments, the anti-T1LA antibody at a concentration of about 150 mg/mL to about or greater than about 170 mg/mL is characterized by a viscosity less than about 5 mPa-s, about 10 mPa-s, about 15 mPa-s, about 20 mPa-s, or about 30 mPa-s. In some embodiments, less than about 5, 10, 15, 20, or 30 mPa-s is at least about 1 mPa-s.

Additionally, for example, for an antibody or antigen binding fragment wherein HCDR1 comprises SEQ ID NO: 1, HCDR2 comprises SEQ ID NO: 2, HCDR3 comprises SEQ ID NO: 6, LCDR1 comprises SEQ ID NO: 10, LCDR2 comprises SEQ ID NO: 11, and LCDR3 comprises SEQ ID NO: 12 or an antibody or antigen binding fragment wherein the heavy chain variable region comprises SEQ ID NO: 104 and the light chain variable region comprises SEQ ID NO: 201, in some embodiments, the anti-TL1A antibody having a concentration greater than 150 mg/mL is characterized by a turbidity less than about 5 Nephelometric Turbidity Units (NTU) to about 15 Nephelometric Turbidity Units (NTU). In some embodiments, the anti-TL1A antibody having a concentration greater than 150 mg/mL is characterized by a turbidity less than at least about 5 Nephelometric Turbidity Units (NTU). In some embodiments, the anti-TL1A antibody having a concentration greater than 150 mg/mL is characterized by a turbidity less than at most about 15 Nephelometric Turbidity Units (NTU). In some embodiments, the anti-TL1A antibody having a concentration greater than 150 mg/mL is characterized by a turbidity less than about 5 Nephelometric Turbidity Units (NTU) to about 7.5 Nephelometric Turbidity Units (NTU), about 5 Nephelometric Turbidity Units (NTU) to about 10 Nephelometric Turbidity Units (NTU), about 5 Nephelometric Turbidity Units (NTU) to about 12.5 Nephelometric Turbidity Units (NTU), about 5 Nephelometric Turbidity Units (NTU) to about 15 Nephelometric Turbidity Units (NTU), about 7.5 Nephelometric Turbidity Units (NTU) to about 10 Nephelometric Turbidity Units (NTU), about 7.5 Nephelometric Turbidity Units (NTU) to about 12.5 Nephelometric Turbidity Units (NTU), about 7.5 Nephelometric Turbidity Units (NTU) to about 15 Nephelometric Turbidity Units (NTU), about 10 Nephelometric Turbidity Units (NTU) to about 12.5 Nephelometric Turbidity Units (NTU), about 10 Nephelometric Turbidity Units (NTU) to about 15 Nephelometric Turbidity Units (NTU), or about 12.5 Nephelometric Turbidity Units (NTU) to about 15 Nephelometric Turbidity Units (NTU). In some embodiments, the anti-TL1A antibody having a concentration greater than 150 mg/mL is characterized by a turbidity less than about 5 Nephelometric Turbidity Units (NTU), about 7.5 Nephelometric Turbidity Units (NTU), about 10 Nephelometric Turbidity Units (NTU), about 12.5 Nephelometric Turbidity Units (NTU), or about 15 Nephelometric Turbidity Units (NTU).

The anti-TL1A antibodies described herein also demonstrate advantageous aggregation properties. For an antibody or antigen binding fragment wherein HCDR1 comprises SEQ ID NO: 1, HCDR2 comprises SEQ ID NO: 2, HCDR3 comprises SEQ ID NO: 6, LCDR1 comprises SEQ ID NO: 10, LCDR2 comprises SEQ ID NO: 11, and LCDR3 comprises SEQ ID NO: 12 or an antibody or antigen binding fragment wherein the heavy chain variable region comprises SEQ ID NO: 104 and the light chain variable region comprises SEQ ID NO: 201, in some embodiments, the anti-TL1A antibody composition is characterized by percent high molecular weight species (e.g. a species having a molecular weight greater than the molecular weight of the monomer)) less than 10% when at a concentration greater than about 100 mg/mL to about greater than 170 mg/mL. In some embodiments, the anti-TL1A antibody composition is characterized by percent high molecular weight species less than 10% when at a concentration greater than at least about 100 mg/mL. In some embodiments, the anti-TL1A antibody composition is characterized by percent high molecular weight species less than 10% when at a concentration up to about 170 mg/mL. In some embodiments, the anti-TL1A antibody composition is characterized by percent high molecular weight species less than 10% when at a concentration from about 100 mg/mL to about 125 mg/mL, about 100 mg/mL to about 150 mg/mL, about 100 mg/mL to about 160 mg/mL, about 100 mg/mL to about 170 mg/mL, about 125 mg/mL to about 150 mg/mL, about 125 mg/mL to about 160 mg/mL, about 125 mg/mL to about 170 mg/mL, about 150 mg/mL to about 160 mg/mL, about 150 mg/mL to about 170 mg/mL, or about 160 mg/mL to about 170 mg/mL. In some embodiments, the anti-TL1A antibody composition is characterized by percent high molecular weight species less than 10% when at a concentration about or greater than about 100 mg/mL, about 125 mg/mL, about 150 mg/mL, about 160 mg/mL, or about 170 mg/mL. In some embodiments, the anti-TL1A antibody composition having an antibody concentration greater than 150 mg/mL is characterized by a high molecular weight species less than about 5% to about 15%. In some embodiments, the anti-TL1A antibody composition having an antibody concentration greater than 150 mg/mL is characterized by a high molecular weight species less than at most about 15%. In some embodiments, the anti-TL1A antibody composition having an antibody concentration greater than 150 mg/mL is characterized by a high molecular weight species less than about 5% to about 7.5%, about 5% to about 10%, about 5% to about 15%, about 5% to about 17.5%, about 5% to about 20%, about 5% to about 25%, about 7.5% to about 10%, about 7.5% to about 15%, about 7.5% to about 17.5%, about 7.5% to about 20%, about 7.5% to about 25%, about 10% to about 15%, about 10% to about 17.5%, about 10% to about 20%, about 10% to about 25%, about 15% to about 17.5%, about 15% to about 20%, about 15% to about 25%, about 17.5% to about 20%, about 17.5% to about 25%, or about 20% to about 25%. In some embodiments, the anti-TL1A antibody composition having an antibody concentration greater than 150 mg/mL is characterized by a high molecular weight species less than about 5%, about 7.5%, about 10%, about 15%, about 17.5%, about 20%, or about 25%.

By way of further example, for an antibody or antigen binding fragment comprising a heavy chain variable framework region comprising a human IGHV1-46*02 framework or a modified human IGHV1-46*02 framework, and a light chain variable framework region comprising a human IGKV3-20 framework or a modified human IGKV3-20 framework; wherein the heavy chain variable framework region and the light chain variable framework region collectively comprise less than 9 amino acid modifications from the human IGHV1-46*02 framework and the human IGKV3-20 framework, in some embodiments, the anti-T1LA antibodies is characterized by a viscosity less than 10 mPa-s at a concentration greater than about 100 mg/mL to about greater than 170 mg/mL. In some embodiments, the anti-T1LA antibodies is characterized by a viscosity less than 10 mPa-s at a concentration greater than at least about 100 mg/mL. In some embodiments, the anti-T1LA antibodies is characterized by a viscosity less than 10 mPa-s at a concentration greater than at most about 170 mg/mL. In some embodiments, the anti-T1LA antibodies is characterized by a viscosity less than 10 mPa-s at a concentration greater than about 100 mg/mL to about 125 mg/mL, about 100 mg/mL to about 150 mg/mL, about 100 mg/mL to about 160 mg/mL, about 100 mg/mL to about 170 mg/mL, about 125 mg/mL to about 150 mg/mL, about 125 mg/mL to about 160 mg/mL, about 125 mg/mL to about 170 mg/mL, about 150 mg/mL to about 160 mg/mL, about 150 mg/mL to about 170 mg/mL, or about 160 mg/mL to about 170 mg/mL. In some embodiments, the anti-T1LA antibodies is characterized by a viscosity less than 10 mPa-s at a concentration greater than about 100 mg/mL, about 125 mg/mL, about 150 mg/mL, about 160 mg/mL, or about 170 mg/mL.

Additionally, for example, for an antibody or antigen binding fragment comprising a heavy chain variable framework region comprising a human IGHV1-46*02 framework or a modified human IGHV1-46*02 framework, and a light chain variable framework region comprising a human IGKV3-20 framework or a modified human IGKV3-20 framework; wherein the heavy chain variable framework region and the light chain variable framework region collectively comprise less than 9 amino acid modifications from the human IGHV1-46*02 framework and the human IGKV3-20 framework, in some embodiments, the anti-TL1A antibody is characterized by a turbidity less than 12 Nephelometric Turbidity Units (NTU) when at a concentration greater than about 100 mg/mL to about greater than 170 mg/mL. In some embodiments, the anti-TL1A antibody is characterized by a turbidity less than 12 Nephelometric Turbidity Units (NTU) when at a concentration greater than at least about 100 mg/mL. In some embodiments, the anti-TL1A antibody is characterized by a turbidity less than 12 Nephelometric Turbidity Units (NTU) when at a concentration greater than at most about 170 mg/mL. In some embodiments, the anti-TL1A antibody is characterized by a turbidity less than 12 Nephelometric Turbidity Units (NTU) when at a concentration greater than about 100 mg/mL to about 125 mg/mL, about 100 mg/mL to about 150 mg/mL, about 100 mg/mL to about 160 mg/mL, about 100 mg/mL to about 170 mg/mL, about 125 mg/mL to about 150 mg/mL, about 125 mg/mL to about 160 mg/mL, about 125 mg/mL to about 170 mg/mL, about 150 mg/mL to about 160 mg/mL, about 150 mg/mL to about 170 mg/mL, or about 160 mg/mL to about 170 mg/mL. In some embodiments, the anti-TL1A antibody is characterized by a turbidity less than 12 Nephelometric Turbidity Units (NTU) when at a concentration greater than about 100 mg/mL, about 125 mg/mL, about 150 mg/mL, about 160 mg/mL, or about 170 mg/mL.

Additionally, for an antibody or antigen binding fragment comprising a heavy chain variable framework region comprising a human IGHV1-46*02 framework or a modified human IGHV1-46*02 framework, and a light chain variable framework region comprising a human IGKV3-20 framework or a modified human IGKV3-20 framework; wherein the heavy chain variable framework region and the light chain variable framework region collectively comprise less than 9 amino acid modifications from the human IGHV1-46*02 framework and the human IGKV3-20 framework, in some embodiments, the anti-T1LA antibody at a concentration greater than 150 mg/mL to greater than about 170 mg/mL is characterized by a viscosity less than about 10 mPa-s to about 30 mPa-s. In some embodiments, the anti-T1LA antibody at a concentration greater than 150 mg/mL to greater than about 170 mg/mL is characterized by a viscosity less than at most about 30 mPa-s. In some embodiments, the anti-T1LA antibody at a concentration greater than 150 mg/mL to greater than about 170 mg/mL is characterized by a viscosity less than about 5 mPa-s to about 10 mPa-s, about 5 mPa-s to about 15 mPa-s, about 5 mPa-s to about 20 mPa-s, about 5 mPa-s to about 30 mPa-s, about 10 mPa-s to about 15 mPa-s, about 10 mPa-s to about 20 mPa-s, about 10 mPa-s to about 30 mPa-s, about 15 mPa-s to about 20 mPa-s, about 15 mPa-s to about 30 mPa-s, or about 20 mPa-s to about 30 mPa-s. In some embodiments, the anti-T1LA antibody at a concentration greater than 150 mg/mL to greater than about 170 mg/mL is characterized by a viscosity less than about 5 mPa-s, about 10 mPa-s, about 15 mPa-s, about 20 mPa-s, or about 30 mPa-s.

Additionally, for example, for an antibody or antigen binding fragment comprising a heavy chain variable framework region comprising a human IGHV1-46*02 framework or a modified human IGHV1-46*02 framework, and a light chain variable framework region comprising a human IGKV3-20 framework or a modified human IGKV3-20 framework; wherein the heavy chain variable framework region and the light chain variable framework region collectively comprise less than 9 amino acid modifications from the human IGHV1-46*02 framework and the human IGKV3-20 framework, in some embodiments, the anti-TL1A antibody having a concentration greater than 150 mg/mL is characterized by a turbidity less than about 5 Nephelometric Turbidity Units (NTU) to about 15 Nephelometric Turbidity Units (NTU). In some embodiments, the anti-TL1A antibody having a concentration greater than 150 mg/mL is characterized by a turbidity less than at least about 5 Nephelometric Turbidity Units (NTU). In some embodiments, the anti-TL1A antibody having a concentration greater than 150 mg/mL is characterized by a turbidity less than at most about 15 Nephelometric Turbidity Units (NTU). In some embodiments, the anti-TL1A antibody having a concentration greater than 150 mg/mL is characterized by a turbidity less than about 5 Nephelometric Turbidity Units (NTU) to about 7.5 Nephelometric Turbidity Units (NTU), about 5 Nephelometric Turbidity Units (NTU) to about 10 Nephelometric Turbidity Units (NTU), about 5 Nephelometric Turbidity Units (NTU) to about 12.5 Nephelometric Turbidity Units (NTU), about 5 Nephelometric Turbidity Units (NTU) to about 15 Nephelometric Turbidity Units (NTU), about 7.5 Nephelometric Turbidity Units (NTU) to about 10 Nephelometric Turbidity Units (NTU), about 7.5 Nephelometric Turbidity Units (NTU) to about 12.5 Nephelometric Turbidity Units (NTU), about 7.5 Nephelometric Turbidity Units (NTU) to about 15 Nephelometric Turbidity Units (NTU), about 10 Nephelometric Turbidity Units (NTU) to about 12.5 Nephelometric Turbidity Units (NTU), about 10 Nephelometric Turbidity Units (NTU) to about 15 Nephelometric Turbidity Units (NTU), or about 12.5 Nephelometric Turbidity Units (NTU) to about 15 Nephelometric Turbidity Units (NTU). In some embodiments, the anti-TL1A antibody having a concentration greater than 150 mg/mL is characterized by a turbidity less than about 5 Nephelometric Turbidity Units (NTU), about 7.5 Nephelometric Turbidity Units (NTU), about 10 Nephelometric Turbidity Units (NTU), about 12.5 Nephelometric Turbidity Units (NTU), or about 15 Nephelometric Turbidity Units (NTU).

The anti-TL1A antibodies described herein also demonstrate advantageous aggregation properties. For an antibody or antigen binding fragment comprising a heavy chain variable framework region comprising a human IGHV1-46*02 framework or a modified human IGHV1-46*02 framework, and a light chain variable framework region comprising a human IGKV3-20 framework or a modified human IGKV3-20 framework; wherein the heavy chain variable framework region and the light chain variable framework region collectively comprise less than 9 amino acid modifications from the human IGHV1-46*02 framework and the human IGKV3-20 framework, in some embodiments, the anti-TL1A antibody composition is characterized by percent high molecular weight species (e.g. a species having a molecular weight greater than the molecular weight of the monomer)) less than 10% when at a concentration greater than about 100 mg/mL to about greater than 170 mg/mL. In some embodiments, the anti-TL1A antibody composition is characterized by percent high molecular weight species less than 10% when at a concentration greater than at least about 100 mg/mL. In some embodiments, the anti-TL1A antibody composition is characterized by percent high molecular weight species less than 10% when at a concentration greater than at most about 170 mg/mL. In some embodiments, the anti-TL1A antibody composition is characterized by percent high molecular weight species less than 10% when at a concentration greater than about 100 mg/mL to about 125 mg/mL, about 100 mg/mL to about 150 mg/mL, about 100 mg/mL to about 160 mg/mL, about 100 mg/mL to about 170 mg/mL, about 125 mg/mL to about 150 mg/mL, about 125 mg/mL to about 160 mg/mL, about 125 mg/mL to about 170 mg/mL, about 150 mg/mL to about 160 mg/mL, about 150 mg/mL to about 170 mg/mL, or about 160 mg/mL to about 170 mg/mL. In some embodiments, the anti-TL1A antibody composition is characterized by percent high molecular weight species less than 10% when at a concentration greater than about 100 mg/mL, about 125 mg/mL, about 150 mg/mL, about 160 mg/mL, or about 170 mg/mL. In some embodiments, the anti-TL1A antibody composition having an antibody concentration greater than 150 mg/mL is characterized by a high molecular weight species less than about 5% to about 15%. In some embodiments, the anti-TL1A antibody composition having an antibody concentration greater than 150 mg/mL is characterized by a high molecular weight species less than at most about 15%. In some embodiments, the anti-TL1A antibody composition having an antibody concentration greater than 150 mg/mL is characterized by a high molecular weight species less than about 5% to about 7.5%, about 5% to about 10%, about 5% to about 15%, about 5% to about 17.5%, about 5% to about 20%, about 5% to about 25%, about 7.5% to about 10%, about 7.5% to about 15%, about 7.5% to about 17.5%, about 7.5% to about 20%, about 7.5% to about 25%, about 10% to about 15%, about 10% to about 17.5%, about 10% to about 20%, about 10% to about 25%, about 15% to about 17.5%, about 15% to about 20%, about 15% to about 25%, about 17.5% to about 20%, about 17.5% to about 25%, or about 20% to about 25%. In some embodiments, the anti-TL1A antibody composition having an antibody concentration greater than 150 mg/mL is characterized by a high molecular weight species less than about 5%, about 7.5%, about 10%, about 15%, about 17.5%, about 20%, or about 25%.

Methods of Treatment

Various embodiments provide for methods of treating inflammatory bowel disease (IBD), comprising administering an anti-TL1A antibody described herein to a subject in need thereof. In some embodiments, the subject comprises one or more risk genotypes. In some embodiments, the IBD is a severe form of IBD.

In some embodiments, the terms "individual" or "subject" are used interchangeably and refer to any animal, including, but not limited to, humans, non-human primates, rodents, and domestic and game animals, which is to be the recipient of a particular treatment. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In various embodiments, a subject can be one who has been previously diagnosed with or identified as suffering from or having a condition in need of treatment. In certain embodiments, the subject is a human. In various other embodiments, the subject previously diagnosed with or identified as suffering from or having a condition may or may not have undergone treatment for a condition. In yet other embodiments, a subject can also be one who has not been previously diagnosed as having a condition (i.e., a subject who exhibits one or more risk factors for a condition). A "subject in need" of treatment for a particular condition can be a subject having that condition, diagnosed as having that condition, or at risk of developing that condition. In some embodiments, the subject is a "patient," that has been diagnosed with a disease or condition described herein.

In some embodiments, the term "therapeutically effective amount" refers to an amount of an antibody, polypeptide, polynucleotide, small organic molecule, or other drug effective to "treat" a disease or disorder in a subject or mammal. In some cases, therapeutically effective amount of the drug reduces the severity of symptoms of the disease or disorder. In some instances, the disease or disorder comprises inflammatory bowel disease (IBD), Crohn's disease (CD), or ulcerative colitis (UC). In some instances, the IBD, CD, and/or UC are severe or medically refractory forms of the IBD, CD, and/or UC. Non-limiting examples of symptoms of IBD, CD, and/or UC include, but are not limited to, diarrhea, fever, fatigue, abdominal pain, abdominal cramping, inflammation, ulceration, nausea, vomiting, bleeding, blood in stool, reduced appetite, and weight loss.

In some embodiments, the terms, "treat" or "treating" as used herein refer to both therapeutic treatment and prophylactic or preventative measures (e.g., disease progression), wherein the object is to prevent or slow down (lessen) the targeted pathologic condition. In some aspects provided herein, subjects in need of treatment include those already with a disease or condition, as well as those susceptible to develop the disease or condition. The disease or condition may comprise an inflammatory disease or condition.

In various embodiments, provided herein is a method of treating inflammatory bowel disease (IBD) in a subject in need thereof, comprising: administering to the subject a therapeutically effective amount of an antibody or an antigen-binding fragment that specifically binds TL1A. In some embodiments, the anti-TL1A antibody comprises antibody A. In some embodiments, the anti-TL1A antibody comprises antibody B. In some embodiments, the anti-TL1A antibody comprises antibody C. In some embodiments, the anti-TL1A antibody comprises antibody D. In some embodiments, the anti-TL1A antibody comprises antibody E. In some embodiments, the anti-TL1A antibody comprises antibody F. In some embodiments, the anti-TL1A antibody comprises antibody G. In some embodiments, the anti-TL1A antibody comprises antibody I. In some embodiments, the anti-TL1A antibody comprises antibody H. In some embodiments, the anti-TL1A antibody comprises antibody A2. In some embodiments, the anti-TL1A antibody comprises antibody B2. In some embodiments, the anti-TL1A antibody comprises antibody C2. In some embodiments, the anti-TL1A antibody comprises antibody D2. In some embodiments, the anti-TL1A antibody comprises antibody E2. In some embodiments, the anti-TL1A antibody comprises antibody F2. In some embodiments, the anti-TL1A antibody comprises antibody G2. In some embodiments, the anti-TL1A antibody comprises antibody 12. In some embodiments, the anti-TL1A antibody comprises antibody H2. In certain embodiments, the anti-TL1A antibody comprises any one of the antibodies of Table 1. In some embodiments, the anti-TL1A antibody comprises antibody A217. In some embodiments, the anti-TL1A antibody comprises antibody A220. In some embodiments, the anti-TL1A antibody comprises antibody A223. In some embodiments, the anti-TL1A antibody comprises antibody A219. In some embodiments, the anti-TL1A antibody comprises antibody A221. In some embodiments, the anti-TL1A antibody comprises antibody A200. In some embodiments, the anti-TL1A antibody comprises antibody A213. In some embodiments, the anti-TL1A antibody comprises antibody A212. In some embodiments, the anti-TL1A antibody comprises antibody A107. In some embodiments, the anti-TL1A antibody comprises antibody A205. In some embodiments, the anti-TL1A antibody comprises antibody A211. In some embodiments, the anti-TL1A antibody comprises antibody A199. In some embodiments, the anti-TL1A antibody comprises antibody A15. In some embodiments, the anti-TL1A antibody comprises antibody A30. In some embodiments, the anti-TL1A antibody comprises antibody A100. In some embodiments, the anti-TL1A antibody comprises antibody A181. In some embodiments, the anti-TL1A antibody comprises antibody A129. In some embodiments, the anti-TL1A antibody comprises antibody A214. In some embodiments, the anti-TL1A antibody comprises antibody A216. In some embodiments, the anti-TL1A antibody comprises antibody A122. In some embodiments, the anti-TL1A antibody comprises antibody A222. In some embodiments, the anti-TL1A antibody comprises antibody A188. In some embodiments, the anti-TL1A antibody comprises antibody A203. In some embodiments, the anti-TL1A antibody comprises antibody A147. In some embodiments, the anti-TL1A antibody comprises antibody A127. In some embodiments, the anti-TL1A antibody comprises antibody A126. In some embodiments, the anti-TL1A antibody comprises antibody A160. In some embodiments, the anti-TL1A antibody comprises antibody A157. In some embodiments, the anti-TL1A antibody comprises antibody A159. In some embodiments, the anti-TL1A antibody comprises antibody A218. In some embodiments, the anti-TL1A antibody comprises antibody A158. In some embodiments, the anti-TL1A antibody comprises antibody A125. In some embodiments, the anti-TL1A antibody comprises antibody A103. In some embodiments, the anti-TL1A antibody comprises antibody A64. In some embodiments, the anti-TL1A antibody comprises antibody A67. In some embodiments, the anti-TL1A antibody comprises antibody A138. In some embodiments, the anti-TL1A antibody comprises antibody A68. In some embodiments, the anti-TL1A antibody comprises antibody A94. In some embodiments, the anti-TL1A antibody comprises antibody A110. In some embodiments, the anti-TL1A antibody comprises antibody A197. In some embodiments, the anti-TL1A antibody comprises antibody A112. In some embodiments, the anti-TL1A antibody comprises antibody A169. In some embodiments, the anti-TL1A antibody comprises antibody A173. In some embodiments, the anti-TL1A antibody comprises antibody A179. In some embodiments, the anti-TL1A antibody comprises antibody A148. In some embodiments, the anti-TL1A antibody comprises antibody A115. In some embodiments, the anti-TL1A antibody comprises antibody A149. In some embodiments, the anti-TL1A antibody comprises antibody A134. In some embodiments, the anti-TL1A antibody comprises antibody A113. In some embodiments, the anti-TL1A antibody comprises antibody A151. In some embodiments, the anti-TL1A antibody comprises antibody A96. In some embodiments, the anti-TL1A antibody comprises antibody A132. In some embodiments, the anti-TL1A antibody comprises antibody A196. In some embodiments, the anti-TL1A antibody comprises antibody A172. In some embodiments, the anti-TL1A antibody comprises antibody A75. In some embodiments, the anti-TL1A antibody comprises antibody A174. In some embodiments, the anti-TL1A antibody comprises antibody A109. In some embodiments, the anti-TL1A antibody comprises antibody A198. In some embodiments, the anti-TL1A antibody comprises antibody A170.

The subject disclosed herein can be a mammal, such as for example a mouse, rat, guinea pig, rabbit, non-human primate, or farm animal. In some instances, the subject is human. In some instances, the subject is a patient who is diagnosed with IBD. In some instances, the subject is not diagnosed with the IBD. In some instances, the subject is suffering from a symptom related to a disease or condition disclosed herein (e.g., abdominal pain, cramping, diarrhea, rectal bleeding, fever, weight loss, fatigue, loss of appetite, dehydration, and malnutrition, anemia, or ulcers).

In various other embodiments, the subject is determined to have an increased TL1A expression. In some embodiments, the administration of a therapeutically effective amount of an anti-TL1A antibody causes a decrease in TL1A in the subject treated.

Methods disclosed herein provide methods of treating an inflammatory bowel disease (IBD) in a subject by administering an anti-TL1A antibody described herein to the subject. In various embodiments, IBD is Crohn's Disease (CD) or ulcerative colitis (UC). In some embodiments, the IBD is a severe form of IBD. In some embodiments, the IBD is a moderate to severe form of IBD. In some embodiments, the IBD is a moderate form of IBD.

Kits

Further provided is a kit to treat IBD (e.g., CD, UC and/or mrUC). The kit comprises of the antibodies described herein, which can be used to perform the methods described herein. The kit is useful for practicing the inventive method of providing treatment to an IBD, CD, UC and/or mrUC patient by administering an anti-TL1A antibody. The kit is an assemblage of materials or components, including at least one of the inventive compositions. Thus, in some embodiments, the kit contains a composition including anti-TL1A antibodies, for the treatment of IBD, CD, UC and/or MR-UC, as described above. In other embodiments, the kits contain all of the components necessary and/or sufficient to perform a detection assay for TL1A, including all controls, directions for performing assays, and any necessary software for analysis and presentation of results.

The exact nature of the components configured in the inventive kit depends on its intended purpose. For example, some embodiments are configured for the purpose of treating IBD, CD, UC and/or MR-UC. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat or alleviate IBD, CD, UC and/or MR-UC. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in gene expression assays and in the administration of treatments. As used herein, the term "package" refers to a suitable solid matrix or material such as glass, plastic, paper, foil, and the like, capable of holding the individual kit components. Thus, for example, a package can be a glass vial or prefilled syringes used to contain suitable quantities of an inventive composition containing anti-TL1A antibodies and/or primers and probes for TL1A. The packaging material generally has an external label which indicates the contents and/or purpose of the kit and/or its components.

EXAMPLES

The following examples are illustrative of the embodiments described herein and are not to be interpreted as limiting the scope of this disclosure. To the extent that specific materials are mentioned, it is merely for purposes of illustration and is not intended to be limiting. One skilled in the art may develop equivalent means or reactants without the exercise of inventive capacity and without departing from the scope of this disclosure.

Example 1: Design of Humanized Anti-TL1A Antibodies

Two different strategies were employed to identify humanized variants that express well in mammalian cells, preserve TL1A binding, and display high monomeric content.

The first strategy utilized a previously humanized variant, termed ASX, that displays high monomeric content (98%) and expresses well (30 µg/mL in small-scale transient cultures) as a template for additional mutagenesis. However, ASX contains a significant number of murine framework residues, eight heavy chain residues and 7 light chain residues, that may pose an immunogenicity risk. The ASX heavy and light chain templates were used to systematically mutate murine framework residues to human residues corresponding to the most closely related human germline framework. The goal of this strategy was to reduce the total number of murine framework residues while preserving the favorable expression and solubility characteristics of ASX. Because ASX contained 15 murine framework residues there were 2^15 (32,768) distinct variants (restricting each position to either the murine or the human residue) that could be made and tested.

The second strategy utilized a previously humanized variant, termed c34, that expresses well (17 μg/mL in small-scale transient cultures) and contains CDRs optimized for binding within a fully human germline framework, as a template for additional mutagenesis. Large-scale expression of c34 unexpectedly resulted in a sub-optimal monomeric content (55-60%). The c34 heavy and light chain templates were used to systematically mutate certain framework residues to murine residues corresponding to the original murine antibody framework. The goal of this strategy was to improve the solubility of c34 (monomeric content) through the introduction of as few murine framework residues as possible (minimizing potential immunogenicity risks) while preserving the favorable expression characteristics of c34.

For both strategies, the initial approach was to scan differing framework residues, one at a time, and express and characterize the variants. Thus, human framework residues were introduced into variant ASX where it differed from c34 and conversely, murine framework mutations were introduced into variant c34 where it differed from ASX. The initial scan identified certain framework and CDR residues that had minimal impact on the characteristics displayed by the template antibody while other mutations had a more dramatic impact, favorable in some cases and unfavorable in others. The information gained from the positional scan was subsequently used in an iterative and combinatorial fashion, to identify multiple variants with favorable characteristics. Importantly, by applying a stepwise, iterative and combinatorial approach the beneficial variants were identified without necessitating the expression and characterization of 32,768 distinct variants.

In certain cases, mutation of the first residue of the heavy chain from glutamine to aspartic acid or glutamic acid was evaluated, alone or in combination with other mutations.

In addition, for both strategies certain CDR residues were also mutated to determine the impact on expression and solubility. For example, a limited number of mutations in HCDR2, HCDR3 and LCDR3 were examined. Similar to the approach used with frameworks, the mutations were predominantly restricted to the original murine CDR residue or mutations that were previously identified as enhancing binding affinity.

Finally, for both strategies "shuffling" of heavy and light chains was used. Specifically, certain human light chains containing few murine framework residues and having a favorable impact on expression of antibody with higher monomeric content were identified early in the process and these were paired with various engineered heavy chains in order to accelerate the process of identifying suitable variants.

TABLE 1

Sequences of Certain Designed anti-TL1A Antibodies

| Antibody | Heavy Chain Variable Region SEQ ID NO | Light Chain Variable Region SEQ ID NOS |
|---|---|---|
| A15 | 108 | 203 |
| A29 | 108 | 205 |
| A30 | 108 | 204 |
| A31 | 136 | 205 |
| A32 | 137 | 205 |
| A33 | 137 | 202 |
| A34 | 107 | 208 |
| A35 | 138 | 208 |
| A36 | 139 | 208 |
| A37 | 140 | 208 |
| A38 | 141 | 208 |
| A39 | 142 | 208 |
| A40 | 143 | 208 |
| A41 | 115 | 208 |
| A42 | 144 | 208 |
| A43 | 145 | 208 |
| A44 | 146 | 208 |
| A45 | 120 | 208 |
| A46 | 147 | 208 |
| A47 | 148 | 208 |
| A48 | 108 | 210 |
| A49 | 108 | 211 |
| A50 | 108 | 212 |
| A51 | 108 | 213 |
| A52 | 108 | 214 |
| A53 | 146 | 208 |
| A54 | 149 | 208 |
| A55 | 109 | 208 |
| A56 | 108 | 215 |
| A57 | 150 | 202 |
| A58 | 125 | 202 |
| A59 | 117 | 202 |
| A60 | 151 | 202 |
| A61 | 152 | 202 |
| A62 | 153 | 202 |
| A63 | 154 | 202 |
| A64 | 121 | 202 |
| A65 | 128 | 202 |
| A66 | 155 | 202 |
| A67 | 122 | 202 |
| A68 | 123 | 202 |
| A69 | 156 | 202 |
| A70 | 157 | 202 |
| A71 | 158 | 202 |
| A72 | 131 | 202 |
| A73 | 157 | 205 |
| A74 | 158 | 205 |
| A75 | 131 | 205 |
| A76 | 159 | 202 |
| A77 | 160 | 202 |
| A78 | 124 | 202 |
| A79 | 107 | 208 |
| A81 | 139 | 208 |
| A82 | 140 | 208 |
| A83 | 144 | 208 |
| A85 | 136 | 209 |
| A86 | 136 | 216 |
| A87 | 136 | 217 |
| A88 | 136 | 218 |
| A89 | 136 | 219 |
| A90 | 136 | 220 |
| A91 | 133 | 202 |
| A92 | 161 | 202 |
| A93 | 162 | 202 |
| A94 | 124 | 202 |
| A95 | 131 | 205 |
| A96 | 128 | 205 |
| A97 | 121 | 202 |
| A98 | 122 | 202 |
| A99 | 123 | 202 |
| A100 | 107 | 204 |
| A101 | 140 | 204 |
| A102 | 115 | 204 |
| A103 | 120 | 204 |

TABLE 1-continued

Sequences of Certain Designed anti-TL1A Antibodies

| Antibody | Heavy Chain Variable Region SEQ ID NO | Light Chain Variable Region SEQ ID NOS |
|---|---|---|
| A104 | 139 | 204 |
| A105 | 143 | 204 |
| A107 | 108 | 202 |
| A108 | 156 | 205 |
| A109 | 133 | 205 |
| A110 | 125 | 205 |
| A111 | 150 | 205 |
| A112 | 117 | 205 |
| A113 | 124 | 205 |
| A114 | 121 | 205 |
| A115 | 122 | 205 |
| A116 | 123 | 205 |
| A117 | 151 | 205 |
| A118 | 153 | 205 |
| A119 | 159 | 205 |
| A120 | 154 | 205 |
| A121 | 163 | 204 |
| A122 | 113 | 204 |
| A123 | 112 | 204 |
| A124 | 164 | 204 |
| A125 | 105 | 204 |
| A126 | 114 | 204 |
| A127 | 118 | 204 |
| A128 | 111 | 204 |
| A129 | 110 | 204 |
| A130 | 121 | 205 |
| A132 | 128 | 206 |
| A133 | 121 | 206 |
| A134 | 122 | 206 |
| A135 | 133 | 206 |
| A136 | 125 | 206 |
| A137 | 121 | 207 |
| A138 | 122 | 207 |
| A139 | 110 | 207 |
| A140 | 110 | 202 |
| A141 | 111 | 207 |
| A142 | 111 | 202 |
| A143 | 136 | 202 |
| A144 | 111 | 204 |
| A145 | 133 | 201 |
| A146 | 125 | 201 |
| A147 | 117 | 201 |
| A148 | 121 | 201 |
| A149 | 122 | 201 |
| A150 | 128 | 201 |
| A151 | 124 | 201 |
| A152 | 131 | 201 |
| A153 | 133 | 205 |
| A154 | 125 | 205 |
| A155 | 121 | 205 |
| A156 | 122 | 205 |
| A157 | 104 | 204 |
| A158 | 101 | 204 |
| A159 | 119 | 204 |
| A160 | 102 | 204 |
| A161 | 165 | 204 |
| A162 | 106 | 204 |
| A163 | 166 | 204 |
| A164 | 167 | 204 |
| A165 | 139 | 205 |
| A166 | 146 | 205 |
| A167 | 120 | 205 |
| A168 | 147 | 205 |
| A169 | 126 | 205 |
| A170 | 135 | 205 |
| A171 | 168 | 205 |
| A172 | 130 | 205 |
| A173 | 127 | 205 |
| A174 | 132 | 205 |
| A175 | 126 | 201 |
| A176 | 135 | 201 |
| A177 | 168 | 201 |
| A178 | 130 | 201 |
| A179 | 127 | 201 |
| A180 | 132 | 201 |
| A181 | 107 | 202 |
| A182 | 138 | 202 |
| A183 | 140 | 202 |
| A184 | 145 | 202 |
| A185 | 147 | 202 |
| A186 | 144 | 202 |
| A187 | 120 | 202 |
| A188 | 115 | 202 |
| A189 | 146 | 202 |
| A190 | 141 | 202 |
| A191 | 142 | 202 |
| A192 | 143 | 202 |
| A193 | 109 | 205 |
| A194 | 103 | 205 |
| A195 | 169 | 205 |
| A196 | 129 | 205 |
| A197 | 116 | 205 |
| A198 | 134 | 205 |
| A199 | 109 | 201 |
| A200 | 103 | 201 |
| A201 | 169 | 201 |
| A202 | 129 | 201 |
| A203 | 116 | 201 |
| A204 | 134 | 201 |
| A205 | 109 | 202 |
| A206 | 103 | 202 |
| A207 | 169 | 202 |
| A208 | 129 | 202 |
| A209 | 116 | 202 |
| A210 | 134 | 202 |
| A211 | 108 | 201 |
| A212 | 107 | 201 |
| A213 | 106 | 201 |
| A214 | 111 | 201 |
| A215 | 110 | 201 |
| A216 | 112 | 201 |
| A217 | 101 | 201 |
| A218 | 119 | 201 |
| A219 | 104 | 201 |
| A220 | 102 | 205 |
| A221 | 105 | 201 |
| A222 | 114 | 201 |
| A223 | 103 | 202 |
| A224 | 116 | 201 |
| A500 | 301 | 303 |
| A501 | 302 | 303 |

As used herein, reference to A (number), refers to an antibody of this table. For instance, A15 used herein refers to A15 in Table 1.

Example 2: Generation and Characterization of Humanized Anti-TL1A Antibodies

Humanized anti-TL1A antibodies designed in Example 1 were prepared and characterized.

Cloning of Humanized Antibodies

DNA encoding leader sequence and the heavy and light chain variable regions of humanized variants of interest was cloned into pFuse1-hIgG1-Fc1 (InvivoGen) and pFuse2-CLig-hk (InvivoGen), respectively. Two distinct humanized heavy chain templates, termed ASX-HC and c34-HC, and four distinct humanized light chain templates, termed ASX-LC, cH3-1, c34-LC, cXL3-13-LC and cXL3-15-LC were all cloned.

In order to introduce mutations into the templates, the QuickChange Site Directed Mutagenesis Kit (Agilent, cat. #200518) was used per manufacturer's directions. Briefly, mutagenesis was performed using miniprep double-stranded plasmid DNA, two synthetic oligonucleotides primers containing the desired mutation, PfuTurbo® DNA polymerase and a temperature cycler. Following temperature cycling, the product was treated with Dpn I. The nicked vector DNA containing the mutation(s) of interest was used to transform bacteria. Subsequently, colonies were picked, the DNA was sequenced to confirm mutagenesis and was subsequently used for transfection of mammalian FreeStyle 293-F cells.

Antibody Expression

Small-scale (3 mL, 6-well) expression of variants in FreeStyle 293-F cells was performed in the following manner. One or two days prior to transfection cells were passaged so that the density would be >1×10$^6$ cells/mL on the day of the transfection. Typically, this meant passaging at 6-7×10$^5$ cells/mL one day prior or 4×10$^5$ cells/mL two days prior. Transfections were only performed with cell viability >90%. On the day of the transfection Opti-MEM media was warmed to 37° C. and cells were resuspended to 1.1×10$^6$ cells/mL, using 3.3×10$^6$ cells per 3 mL transfection. A total of 3 µg DNA was used for each transfection. Briefly, the transfections used heavy and light chain plasmid at a heavy chain:light chain ratio of 1:3. For 3 mL transfections, 4 µL 293fectin was added to 96 µL Opti-MEM, combined with 100 µL DNA mixture, and incubated at 25° C. for 20-30 minutes. Subsequently, this mixture was added dropwise to 2.8 mL cells and the plate was transferred to an incubator and placed on a rotating platform at 175 rpm for up to 120 hours. After 96-120 hours, transfection supernatants were collected by centrifuging the transfected cells and supernatant at 1200 rpm for 5 min. The supernatant was transferred to a clean tube and centrifuged again at 3900 rpm for 10 min to remove any remaining cell debris. The supernatant was filtered through a 0.45 mm PES syringe filter and stored at 4° C. until the next step.

Quantitation of Antibody Expression

Antibody expression was quantitated by ELISA. Briefly, a Corning Costar 3366 96-well round bottom high bind plate was coated with 50 mL anti-kappa (2 µg/mL) in PBS overnight at 4° C. The plate was washed 3× with PBS-0.05% Tween 20 (PBS-T) and was blocked with 100 µL 1% BSA/PBS for 1 h at 25° C. The block was removed, and culture supernatant diluted 5-fold was added and serially diluted 2-fold across the plate. Every plate also contained an IgG standard diluted serially 3-fold beginning at 1 µg/mL. Samples were incubated for 1 h at 25° C., the plate was washed three times with PBS-T, and 50 µL anti-Fc HRP secondary (Southern Biotech #2048-05), diluted 1:4000 in BSA/PBS was added for 1 h at 25° C. The plate was washed three times with PBS-T and developed for up to 15 min following the addition of 50 µL Ultra TMB ELISA substrate (Thermo #34028). The reaction was terminated by the addition of 50 µL 2 N $H_2SO_4$ and the A450 nm was measured. Antibody expression levels obtained from 3 mL scale transfections are shown in Table 2.

TABLE 2

Expression, Binding, and Analytical SEC Characterization of anti-TL1A Antibodies (ND, not determined)

| Variant | Expression (µg/mL) | KD (pM) | % Monomer | Murine FR | HC Template | LC Template |
|---|---|---|---|---|---|---|
| 15 | 21 | ND | 87 | 8 | ASX | cH3-1 |
| 29 | 18 | 65 | 65 | 10 | ASX | c34 |
| 30 | 29 | 77 | 90 | 8 | ASX | cXL3-13 |
| 31 | 11 | 92 | 73 | 2 | c34 | c34 |
| 32 | 10 | 111 | 78 | 2 + D | c34 | c34 |
| 33 | 21 | 81 | 54 | 0 + D | c34 | c34 |
| 34 | 35 | <50 | 97 | 14 | ASX | ASX |
| 35 | 36 | 72 | 91 | 14 | ASX | ASX |
| 36 | 40 | <50 | 87 | 13 | ASX | ASX |
| 37 | 40 | 34 | 95 | 14 | ASX | ASX |
| 38 | 28 | 103 | 75 | 14 | ASX | ASX |
| 39 | 15 | 125 | 83 | 14 | ASX | ASX |
| 40 | 30 | <50 | 87 | 13 | ASX | ASX |
| 41 | 20 | 16 | 96 | 14 | ASX | ASX |
| 42 | 30 | <50 | 88 | 14 | ASX | ASX |
| 43 | 18 | 51 | 90 | 14 | ASX | ASX |
| 44 | ND | ND | ND | 13 | ASX | ASX |
| 45 | 15 | 85 | 90 | 13 | ASX | ASX |
| 46 | 27 | 63 | 72 | 13 | ASX | ASX |
| 47 | 18 | 82 | 78 | 12 | ASX | ASX |
| 48 | 22 | 76 | 92 | 14 | ASX | ASX |
| 49 | 26 | 92 | 65 | 13 | ASX | ASX |
| 50 | 33 | 19 | 94 | 14 | ASX | ASX |
| 51 | 16 | <50 | 93 | 14 | ASX | ASX |
| 52 | 29 | 27 | 91 | 13 | ASX | ASX |
| 53 | 26 | 126 | 84 | 13 | ASX | ASX |
| 54 | 25 | 83 | 94 | 15 + D | ASX | ASX |
| 55 | 22 | 91 | 99 | 15 + E | ASX | ASX |
| 56 | 15 | 116 | 71 | 14 | ASX | ASX |
| 57 | 20 | 191 | 59 | 1 | c34 | c34 |
| 58 | 9 | 112 | 67 | 1 | c34 | c34 |
| 59 | 11 | 136 | 78 | 2 | c34 | c34 |
| 60 | 19 | 168 | 57 | 0 | c34 | c34 |
| 61 | 15 | 127 | 44 | 1 | c34 | c34 |
| 62 | 21 | 150 | 58 | 1 | c34 | c34 |
| 63 | 20 | 132 | 52 | 0 | c34 | c34 |
| 64 | 2 | 90 | 97 | 0 | c34 | c34 |
| 65 | 7 | 97 | 69 | 1 | c34 | c34 |
| 66 | 19 | 150 | 49 | 1 | c34 | c34 |
| 67 | 4 | 89 | 97 | 1 | c34 | c34 |
| 68 | 2 | 74 | 92 | 1 | c34 | c34 |
| 69 | 12 | 136 | 64 | 0 + E | c34 | c34 |
| 70 | 15 | 149 | 54 | 1 | c34 | c34 |
| 71 | 18 | 150 | 55 | 2 | c34 | c34 |
| 72 | 13 | 159 | 61 | 3 | c34 | c34 |
| 73 | 8 | 128 | 71 | 3 | c34 | c34 |
| 74 | 10 | 141 | 70 | 4 | c34 | c34 |
| 75 | 8 | 259 | 95 | 5 | c34 | c34 |
| 76 | 19 | ND | 50 | 0 | c34 | c34 |
| 77 | 12 | ND | 50 | 2 | c34 | c34 |
| 78 | 3 | ND | 86 | 2 | c34 | c34 |
| 79 | 42 | ND | 98 | 14 | ASX | ASX |
| 81 | 31 | ND | 88 | 13 | ASX | ASX |
| 82 | 26 | ND | 92 | 14 | ASX | ASX |
| 83 | 29 | ND | 74 | 14 | ASX | ASX |
| 85 | 25 | 130 | 49 | 1 | c34 | c34 |
| 86 | 26 | 129 | 55 | 1 | c34 | c34 |
| 87 | 26 | 121 | 52 | 1 | c34 | c34 |
| 88 | 9 | 81 | 63 | 2 | c34 | c34 |
| 89 | 31 | 117 | 55 | 1 | c34 | c34 |
| 90 | 19 | 107 | 53 | 1 | c34 | c34 |
| 91 | 14 | 132 | 63 | 1 | c34 | c34 |
| 92 | 20 | 121 | 49 | 1 | c34 | c34 |
| 93 | 12 | 117 | 63 | 2 | c34 | c34 |
| 94 | 5 | 81 | 91 | 2 | c34 | c34 |
| 95 | 13 | 105 | 92 | 5 | c34 | c34 |
| 96 | 7 | 95 | 99 | 3 | c34 | c34 |
| 97 | 2 | 71 | 97 | 0 | c34 | c34 |
| 98 | 7 | 140 | 98 | 1 | c34 | c34 |
| 99 | 3 | 102 | 95 | 1 | c34 | c34 |
| 100 | 39 | 84 | 84 | 7 | ASX | cXL3-13 |
| 101 | 23 | 96 | 81 | 7 | ASX | cXL3-13 |
| 102 | 19 | 104 | 75 | 7 | ASX | cXL3-13 |
| 103 | 11 | 107 | 90 | 6 | ASX | cXL3-13 |
| 104 | 26 | 108 | 70 | 6 | ASX | cXL3-13 |
| 105 | 23 | 110 | 58 | 6 | ASX | cXL3-13 |
| 107 | 55 | 71 | 85 | 8 | ASX | c34 |
| 108 | 9 | 55 | 83 | 2 + E | c34 | c34 |
| 109 | 9 | 50 | 96 | 3 | c34 | c34 |
| 110 | 7 | 56 | 95 | 3 | c34 | c34 |

TABLE 2-continued

Expression, Binding, and Analytical SEC Characterization of anti-TL1A Antibodies (ND, not determined)

| Variant | Expression (µg/mL) | KD (pM) | % Monomer | Murine FR | HC Template | LC Template |
|---|---|---|---|---|---|---|
| 111 | 17 | 68 | 61 | 3 | c34 | c34 |
| 112 | 6 | 54 | 93 | 4 | c34 | c34 |
| 113 | 2 | 50 | 99 | 4 | c34 | c34 |
| 114 | 1 | 51 | 99 | 2 | c34 | c34 |
| 115 | 3 | 58 | 99 | 3 | c34 | c34 |
| 116 | 1 | 53 | 99 | 3 | c34 | c34 |
| 117 | 16 | 94 | 80 | 2 | c34 | c34 |
| 118 | 21 | 83 | 70 | 3 | c34 | c34 |
| 119 | 15 | 87 | 77 | 2 | c34 | c34 |
| 120 | 12 | 85 | 64 | 2 | c34 | c34 |
| 121 | 24 | 106 | 77 | 6 | ASX | cXL3-13 |
| 122 | 22 | 112 | 85 | 6 | ASX | cXL3-13 |
| 123 | 18 | 104 | 76 | 5 | ASX | cXL3-13 |
| 124 | 21 | 91 | 83 | 6 | ASX | cXL3-13 |
| 125 | 10 | 116 | 98 | 6 | ASX | cXL3-13 |
| 126 | 4 | 123 | 99 | 5 | ASX | cXL3-13 |
| 127 | 8 | 70 | 94 | 6 | ASX | cXL3-13 |
| 128 | 17 | 111 | 84 | 4 | ASX | cXL3-13 |
| 129 | 17 | 99 | 92 | 5 | ASX | cXL3-13 |
| 130 | 1 | 75 | 99 | 2 | c34 | c34 |
| 132 | 6 | 62 | 99 | 2 | c34 | cXL3-13 |
| 133 | 1 | 58 | 99 | 1 | c34 | cXL3-13 |
| 134 | 3 | 55 | 99 | 2 | c34 | cXL3-13 |
| 135 | 7 | 56 | 74 | 2 | c34 | cXL3-13 |
| 136 | 6 | 53 | 84 | 2 | c34 | cXL3-13 |
| 137 | 2 | 50 | 96 | 0 | c34 | cXL3-15 |
| 138 | 5 | 69 | 99 | 1 | c34 | cXL3-15 |
| 139 | 35 | 74 | 78 | 5 | ASX | cXL3-15 |
| 140 | 26 | 73 | 75 | 5 | ASX | c34 |
| 141 | 27 | 108 | 81 | 4 | ASX | cXL3-15 |
| 142 | 25 | 126 | 68 | 4 | ASX | c34 |
| 143 | 16 | 85 | 57 | 0 | c34 | c34 |
| 144 | ND | ND | ND | 4 | ASX | cXL3-13 |
| 145 | 20 | 70 | 78 | 2 | c34 | c34 |
| 146 | 25 | 65 | 84 | 2 | c34 | c34 |
| 147 | 26 | 63 | 87 | 3 | c34 | c34 |
| 148 | 2 | 46 | 98 | 1 | c34 | c34 |
| 149 | 7 | 48 | 99 | 2 | c34 | c34 |
| 150 | 15 | 59 | 83 | 2 | c34 | c34 |
| 151 | 5 | 57 | 96 | 3 | c34 | c34 |
| 152 | 36 | 58 | 73 | 4 | c34 | c34 |
| 153 | 9 | 49 | 97 | 3 | c34 | c34 |
| 154 | 8 | 66 | 92 | 3 | c34 | c34 |
| 155 | 1 | 67 | 99 | 2 | c34 | c34 |
| 156 | 2 | 94 | 99 | 3 | c34 | c34 |
| 157 | 6 | 69 | 93 | 4 | ASX | cXL3-13 |
| 158 | 6 | 66 | 91 | 3 | ASX | cXL3-13 |
| 159 | 4 | 69 | 99 | 4 | ASX | cXL3-13 |
| 160 | 7 | 94 | 99 | 4 | ASX | cXL3-13 |
| 161 | 11 | 72 | 59 | 4 | ASX | cXL3-13 |
| 162 | 9 | 75 | 79 | 3 | ASX | cXL3-13 |
| 163 | 22 | 51 | 60 | 4 | ASX | cXL3-13 |
| 164 | 23 | 58 | 61 | 4 | ASX | cXL3-13 |
| 165 | 19 | 59 | 53 | 8 | ASX | c34 |
| 166 | 13 | 57 | 76 | 8 | ASX | c34 |
| 167 | 9 | 42 | 96 | 8 | ASX | c34 |
| 168 | 16 | 62 | 85 | 8 | ASX | c34 |
| 169 | 8 | 47 | 90 | 3 | c34 | c34 |
| 170 | 9 | 49 | 93 | 3 | c34 | c34 |
| 171 | 13 | 50 | 80 | 5 | c34 | c34 |
| 172 | 7 | 40 | 96 | 3 | c34 | c34 |
| 173 | 4 | 40 | 99 | 4 | c34 | c34 |
| 174 | 4 | 43 | 98 | 4 | c34 | c34 |
| 175 | 31 | 45 | 86 | 2 | c34 | c34 |
| 176 | 18 | 48 | 80 | 2 | c34 | c34 |
| 177 | 35 | 52 | 67 | 4 | c34 | c34 |
| 178 | 18 | 43 | 85 | 2 | c34 | c34 |
| 179 | 16 | 79 | 93 | 3 | c34 | c34 |
| 180 | 17 | 58 | 94 | 3 | c34 | c34 |
| 181 | 46 | 60 | 87 | 7 | ASX | c34 |
| 182 | 39 | 67 | 74 | 7 | ASX | c34 |
| 183 | 38 | 65 | 82 | 7 | ASX | c34 |
| 184 | 30 | 61 | 73 | 7 | ASX | c34 |
| 185 | 30 | 56 | 66 | 6 | ASX | c34 |
| 186 | 38 | 67 | 66 | 7 | ASX | c34 |
| 187 | 27 | 56 | 72 | 6 | ASX | c34 |
| 188 | 31 | 63 | 87 | 7 | ASX | c34 |
| 189 | 44 | 76 | 71 | 6 | ASX | c34 |
| 190 | 32 | 57 | 69 | 7 | ASX | c34 |
| 191 | 21 | 57 | 80 | 7 | ASX | c34 |
| 192 | 27 | 55 | 70 | 6 | ASX | c34 |
| 193 | 16 | 55 | 68 | 10 + E | ASX | c34 |
| 194 | 16 | 51 | 87 | 9 + E | ASX | c34 |
| 195 | 12 | 56 | 82 | 5 + E | c34 | c34 |
| 196 | 7 | 54 | 97 | 3 + E | c34 | c34 |
| 197 | 7 | 54 | 97 | 3 + E | c34 | c34 |
| 198 | 9 | 53 | 95 | 3 + E | c34 | c34 |
| 199 | 28 | 50 | 93 | 9 + E | ASX | c34 |
| 200 | 24 | 52 | 99 | 8 + E | ASX | c34 |
| 201 | 25 | 58 | 82 | 4 + E | c34 | c34 |
| 202 | 13 | 59 | 87 | 2 + E | c34 | c34 |
| 203 | 18 | 62 | 89 | 2 + E | c34 | c34 |
| 204 | 11 | 53 | 84 | 2 + E | c34 | c34 |
| 205 | 27 | 55 | 86 | 8 + E | ASX | c34 |
| 206 | 20 | 50 | 98 | 7 + E | ASX | c34 |
| 207 | ND | ND | ND | 3 + E | c34 | c34 |
| 208 | ND | ND | ND | 1 + E | c34 | c34 |
| 209 | 14 | 58 | 66 | 1 + E | c34 | c34 |
| 210 | 15 | 70 | 61 | 1 + E | c34 | c34 |
| 211 | 42 | 58 | 96 | 9 | ASX | c34 |
| 212 | 33 | 50 | 99 | 8 | ASX | c34 |
| 213 | 29 | 49 | 99 | 4 | ASX | c34 |
| 214 | 27 | 51 | 97 | 5 | ASX | c34 |
| 215 | 20 | 48 | 77 | 6 | ASX | c34 |
| 216 | 24 | 49 | 97 | 6 | ASX | c34 |
| 217 | 15 | 43 | 99 | 4 | ASX | c34 |
| 218 | 13 | 51 | 96 | 5 | ASX | c34 |
| 219 | 21 | 50 | 99 | 5 | ASX | c34 |
| 220 | 18 | 50 | 99 | 6 | ASX | c34 |
| 221 | 23 | 51 | 98 | 7 | ASX | c34 |
| 222 | 29 | 60 | 96 | 6 | ASX | c34 |
| 223 | 19 | 62 | 98 | 7 + E | ASX | c34 |
| 224 | 15 | 76 | 92 | 2 + E | c34 | c34 |

Antibody Binding to Human TL1A

Antibody binding to human TL1A (Fitzgerald #30R-AT070) was quantitated by ELISA. Briefly, a Corning Costar 3366 96-well round bottom high bind plate was coated with 50 µL TL1A (1 µg/mL) in PBS overnight at 4° C. The plate was washed 3× with PBS-0.05% Tween 20 (PBS-T) and was blocked with 100 µL 1% BSA/PBS for 1 h at 25° C. The block was removed, and culture supernatant diluted 5-fold was added and serially diluted 2-fold across the plate. Samples were incubated for 1 h at 25° C., the plate was washed three times with PBS-T, and 50 µL anti-Fc HRP secondary, diluted 1:4000 in BSA/PBS was added for 1 h at 25° C. The plate was washed three times with PBS-T and developed for up to 15 min following the addition of 50 µL Ultra TMB ELISA substrate. The reaction was terminated by the addition of 50 µL 2 N $H_2SO_4$ and the A450 nm was measured. The antibody affinities, as determined by ELISA titration against human TL1A using unpurified culture supernatants, is shown in Table 2.

Purification of Antibodies

Antibodies were purified from culture supernatants in a single step using Dynabeads Protein A (ThermoFisher Scientific, cat. #10002D). First, culture supernatants were concentrated per manufacturer's instructions using an Amicon Ultra-4 Centrifugal Filter Unit (30,000 MWCO; MilliporeSigma, cat. #C7719). The Dynabeads were resuspended by gentle vortexing and 100 µL were transferred to an Eppendorf tube. Using a magnet to retain the beads, the storage buffer was removed, and the beads were washed with 0.5 mL of 20 mM sodium phosphate, 150 mM NaCl, pH 7.4 (EB, Equilibration Buffer). A total of up to 24 µg of IgG from culture supernatant was added to the beads and mixed gently until the beads were resuspended. When necessary, antibody supernatants were diluted with EB. The tubes were placed sideways on a shaking platform and mixed for 10 min at 25° C. at 500 rpm. Subsequently, the beads were collected at the bottom of the tube using a microfuge at 10,000 rpm for 30 sec. Using a magnet to retain the beads, the supernatant was removed. The beads were washed once with 0.5 mL of 20 mM sodium phosphate, 500 mM NaCl, pH 7.4 followed by another wash with 50 mM sodium phosphate, pH 6.0. The beads were collected at the bottom of the tube using a microfuge at 10,000 rpm for 30 sec. Purified antibody was eluted from the beads using 20 µL 50 mM sodium acetate, pH 3.5 with gentle mixing for 2 min at 25° C. Using a magnet to retain the beads, the eluate was transferred to a fresh tube containing 1.1 µL 1 M Tris, pH 8.5 to neutralize the pH of the sample. This sample was then centrifuged at 10,000 rpm for 2 min and transferred to a fresh tube to ensure removal of residual Dynabeads. The concentration of the purified sample was determined using a DeNovix DS-11 Spectrophotometer/Fluorometer, buffer blank, and a mass extinction coefficient of 13.70 at 280 nm for a 1% IgG solution.

Size Exclusion Chromatography

Figure 1B:
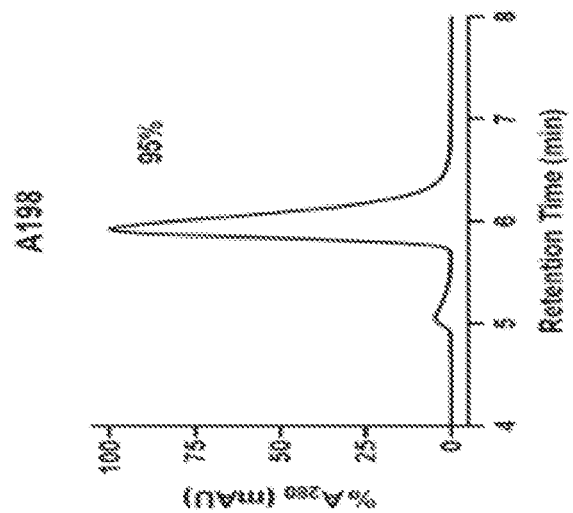
Figure 1B:
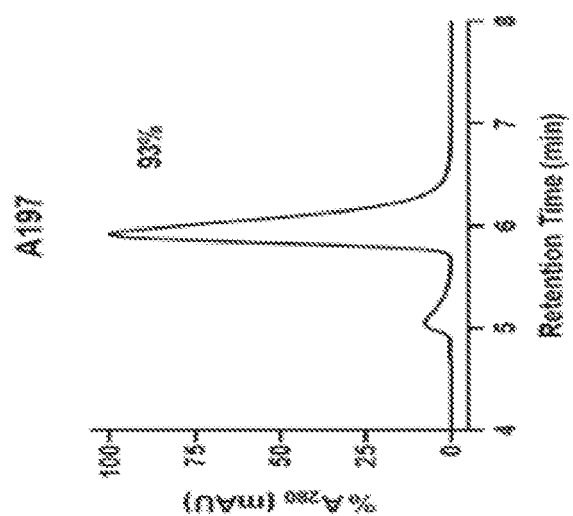
Figure 1B:
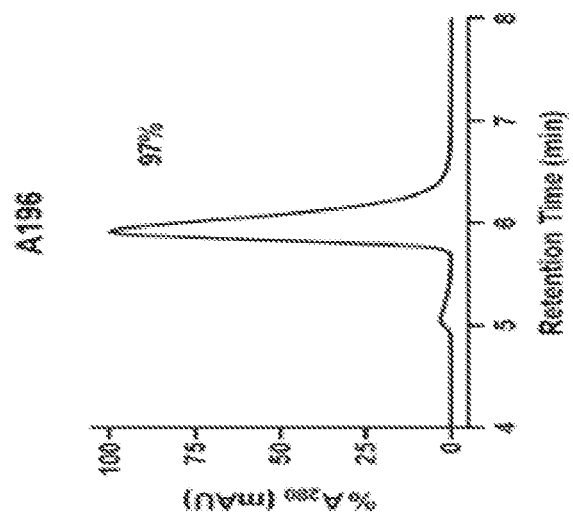
Figure 1C:
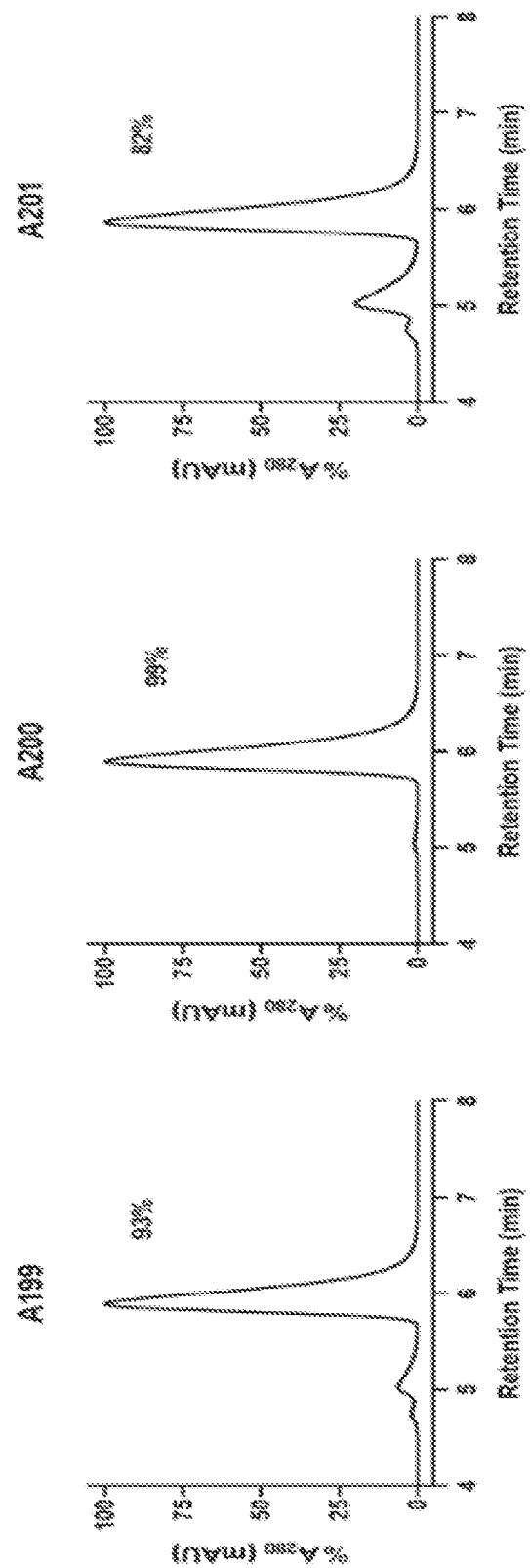

The antibodies were analyzed by size exclusion chromatography (SEC) to determine percent monomer and identify any large molecular weight aggregate contaminant species. A total volume of 15 µL of protein A purified antibodies at a concentration of 0.1-1 µg/µL were analyzed using a Waters SEC column (Acquity UPLC BEH SEC, 200 Å, 1.7 µm, 4.6×150 mm) on a Shimadzu UPLC instrument at a flow rate of 0.2 mL/min and a column oven temperature of 30° C. Standard PBS was used as the mobile phase and absorbance at 280 nm was used to monitor protein elution. For some antibody clones tested that demonstrated non-symmetrical elution profiles, PBS buffer supplemented with 350 mM NaCl at pH 6.0 was utilized to reduced non-specific interactions with the column matrix. The percent main peak (monomer) value was calculated using the Shimadzu software. Representative sample profiles are shown in FIGS. 1A-C. The monomeric content of purified antibody variants is shown in Table 2.

Example 3: Abrogation of Effector Function

In certain cases, it might be beneficial to reduce the potential effector function of the antibodies. Multiple strategies to diminish effector function have been described, including point mutations to ablate FcγR and C1q binding, cross-subclass Fc designs to eliminate FcγR and C1q binding, and glycoengineering to ablate FcγR and C1q binding. Representative examples are highlighted in Table 3.

TABLE 3

| Representative Approaches to Abrogating Effector Function | |
| --- | --- |
| Mutation(s) | Effect |
| E233P | Decreases binding to FcγRI, II, III |
| S228P, L235E SPLE in IgG4 | Decreases binding to FcγRI |
| L235E | Decreases binding to FcγRs |
| L234A, L235A | Decreases binding to FcγRI, II, III |
| L234A, L235A, G237A | Decreases binding to FcγRI, II, III, C1q |
| L234A, L235A, P329G | Decreases binding to FcγRI, II, III, C1q |
| L234F, L235E, P331S | Decreases binding to FcγRI, II, III, C1q |
| L234A, L235E, G237A | Decreases binding to FcγRI, II, III, C1q |
| L234A, L235E, G237A, P331S | Decreases binding to FcγRI, II, III, C1q |
| L234A, L235A, G237A, P238S, H268A, A330S, P331S (IgG1σ) | Decreases binding to FcγRI, IIa, IIb, IIIa |
| L234A, L235A, P329A | Decreases binding to FcγRI, II, III, C1q |
| G236R, L328R | Decreases binding to FcγRI, II, III |
| G237A | Decreases binding to FcγRII |
| F241A | Decreases binding to C1q |
| V264A | Decreases binding to C1q |
| D265A | Decreases binding to FcγRI, II, III |
| D265A, N297A | Decreases binding to FcγRI, II, III, C1q |
| D265A, N297G | Decreases binding to FcγRI, II, III, C1q |
| D270A | Decreases binding to C1q |
| N297A, G, D, Q | Elimination of N-linked glycosylation Decreases binding to FcγRI, II, III, C1q |
| P329A, G, R | Decreases binding to C1q |
| A330L | Decreases binding to C1q |
| P331A, S | Diminished C1q binding |
| IgG2 | Decreases binding to FcγRs |
| IgG4 | Decreases binding to FcγRs; Does not activate complement system |
| S228P | Prevent IgG4 Fab arm exchange |
| S228P, F234A, L235A (IgG4) | Decreases binding to FcγRI, IIa, IIIa |
| IgG2-IgG4 cross-subclass (IgG2/G4) | Decreases binding to FcγRI, II, III, C1q |
| IgG2-IgG3 cross-subclass | Decreases binding to FcγRs; Decreases binding to C1q |
| H268Q, V309L, A330S, P331S (IgG2m4) | Decreases binding to FcγRI, II, III, C1q |
| V234A, G237A, P238S, H268A, V309L, A330S, P331S (IgG2σ) | Decreases binding to FcγRI, IIa, IIb, IIIa, C1q |
| High mannose glycosylation | Decreases binding to C1q |

In order to express antibodies with abrogated effector function, the light chain variable regions of the antibodies disclosed in Example 2 and Table 1 are cloned with a kappa light chain constant region, while the heavy chain variable regions are cloned with a modified IgG1 heavy chain backbone, or a modified IgG2 backbone, or a modified IgG4 backbone, or an unmodified IgG2 or IgG4 backbone, such as those disclosed in Table 3, or elsewhere.

The impact of the various Fc engineering approaches on CDC activity can be assessed using C1q binding and C3 fixation assays. Purified antibodies are diluted in PBS and serial dilutions are plated on a microtiter plate for 12-18 h at 4° C. The plates are blocked with 5% gelatin/PBS containing 1% (v/v) Tween-20 for 1 h at 25° C. Subsequently, the plates are incubated with 10% (v/v) human sera in PBS and C1q binding is detected using 1:500 dilution of HRP-conjugated rabbit anti-C1q (Bioss Inc.) in PBS containing 1% (v/v) Tween-20. To test C3 fixation, a 1:1000 dilution of rabbit anti C3 (abcam) is used followed by a 1:2000 dilution of HRP-conjugated chicken anti-rabbit IgG (abcam). The plates are developed as described for antibody quantitation assays in Example 1. EC50 values are calculated by fitting the data to a log (agonist) vs. response-variable slope (four parameter) model using GraphPad Prism (Sunnyvale, Calif.).

Additionally, the variants may be characterized for the binding of isolated C1q. MaxiSorp 384-well plates (Thermo Scientific, Nunc) are coated with serially diluted antibodies in 50 mM carbonate buffer, pH 9.6 (coat buffer), for 12-18 h at 4° C. Plates are washed with phosphate buffered saline (PBS) containing 0.05% polysorbate 20, pH 7.4 and blocked with PBS containing 0.5% BSA, 0.05% polysorbate 20, 15 ppm Proclin and 10% Blocker Casein (ThermoScientific), pH 7.4. After 1-hour incubation at 25° C., plates are washed. Human C1q (Quidel, San Diego, Calif.) in the same buffer is added and incubated for 1.5 hour. Bound C1q is detected by adding 20 ng/mL biotinylated mouse anti-mouse C1q (Hycult biotech; cross reacting with human C1q) for 1.5 hour followed by horseradish peroxidase (HRP)-conjugated streptavidin (GE Healthcare Life Sciences) for 1 hour. To check for coating efficiency, some coated wells receive buffer only for the first two incubation steps and receive goat anti-human Fab'2-HRP when the wells used for measuring C1q binding received streptavidin-HRP. Plates are washed after each incubation step. Peroxidase activity is detected with substrate 3, 3', 5, 5'-tetramethyl benzidine (TMB) (Kirkegaard & Perry Laboratories). The reaction is stopped with 1M phosphoric acid and absorbance is measured at 450 nm. Dose-response binding curves are fitted with a four-parameter model and EC50 values are calculated using GraphPad Prism (Sunnyvale, Calif.).

The impact of the various Fc engineering approaches on ADCC activity is assessed using soluble FcγR receptor binding ELISAs. Soluble human FcγRI, FcγRIIb and FcγRIII (binding affinity to both the F158 and V158 polymorphic forms of FcγRIII is assessed) are expressed as recombinant fusion proteins with Gly-His6-glutathione-S-transferase (GST) at the C-terminus of the extracellular domain of the receptor. MaxiSorp 384-well plates are coated with 1 μg/ml human FcγR in coat buffer. Plates are washed and blocked with PBS containing 0.5% BSA, 15 ppm Proclin, pH 7.4. After a 1 h incubation, plates are washed and 3-fold serial dilution of antibodies in PBS containing 0.5% BSA, 0.05% polysorbate 20, 15 ppm Proclin, pH 7.4 is added to the plates and incubated for 2 h. For enhanced binding sensitivity due to avidity, immune complexes are formed using anti-human antibody. Bound antibody is detected with HRP-conjugated goat anti-human kappa (Southern Biotech) using Ultra TMB substrate as described in Example 1. The reaction is terminated and the plate is read as described above. The dose-dependent binding curve of the wild type antibody (no Fc modifications) is fitted with GraphPad Prism (Sunnyvale, Calif.) four parameter curve fitting program. The relative affinity of the variant vs. the wild type is estimated by dividing the equivalent ng/ml wild type concentration at the appropriate concentration.

In addition, the variants are tested directly in Fc effector bioassays (Promega) following manufacturer's directions. These assays include FcγRIIa-H ADCP Bioassay (Promega cat #G9901), ADCC Reporter Bioassays, FcγRIIIa F Variant (Promega, cat #G9798), ADCC Reporter Bioassays, FγRIIIa V Variant (Promega, cat. #G7015). The variants are tested both as monomeric Ig and as small immune complexes (ICs) by using an anti-hu Ig antibody to form small ICs.

A Europium based ADCC assay is performed. Briefly, peripheral blood lymphocytes (PBLs) are isolated by Ficoll Paque Plus gradient centrifugation. The PBLs are collected, washed with RPMI1640, 10% FCS and resuspended in cell culture medium. The cells are diluted to $2.5 \times 10^6$ cells/ml. Target cells are labelled with BADTA (2,2':6',2''-terpyridine-6,6''-dicarboxylic acid acetoxymethylester): Cells are harvested by adding Accutase (Millipore), washed once and diluted to $1 \times 10^6$ cells/ml. Next, 2.5 μL BADTA is added per $1 \times 10^6$ cells and incubated for 35 min at 37° C. with 5% $CO_2$. After labelling the cells are diluted with 10 ml culture medium, centrifuged at 200×g for 10 min and supernatant aspirated. This step is repeated 3× with culture medium/2 mM Probenicid and the sample is diluted to $1 \times 10^5$ cells/ml, centrifuged at 300×g for 5 min, supernatant taken off and 50 μL pipetted into the wells intended for the background controls. The final ratio of effector (PBL) to target cells is 25:1.

Controls include: (1) Background: the 50 μL aliquot, diluted with 100 μL medium, (2) Spontaneous lysis: 50 μL of the labelled target cell suspension plus 100 μL culture medium, incubated 2 h at 37° C., (3) Maximal lysis: 50 μL/well of the labelled target cell suspension plus 100 μL Triton X-100 (0.5% in PBS) incubated 2 h at 37° C., (4) Lysis control without antibodies: 50 μL/well of the labelled target cell suspension and 50 μL culture medium plus 50 μL of effector cells incubated 2 h at 37° C., (5) Lysis control without effector cells: 50 μL/well of the labelled target cell suspension; add 50 μL culture medium plus antibody at highest concentration used and incubate 2 h at 37° C.

At the end of the incubation period the 96 well plate is centrifuged at 100 rpm. 20 μL of each supernatant is transferred into an OptiPlate HTRF-96 (Packard) and 200 μL Europium solution is added and incubated for 15 min on a shaker. Fluorescence is measured as for time resolved fluorescence and spontaneous release and specific release are calculated.

A CDC assay is performed. Briefly, target cells are washed and diluted to $1 \times 10^5$ cells/ml and 100 μL/well ($10^4$ cells) are added to a 96-well flat bottom microtiter plate. A titration curve of the test antibody is created using serial dilutions, beginning at 1 μg/mL. Antibody is added to the plate, mixed gently, and is then placed at 37° C./5% CO2 incubator for 30 min. Next, 25 μL freshly dissolved baby rabbit complement (Cedarlane CL3441, 1 ml lyophilized, dilute freshly in 4 ml double distilled water) is added, mixed gently, and the plate is incubated at 37° C./5% CO2 incubator for 30 min. After the incubation period 50 μL supernatant is taken off and 100 μL Cell Titer Glo. reagent (Promega Corp.) is added to the remaining 100 μL supernatant. The plate is placed on an orbital shaker for 2 min, 100 µL/well is transferred into a black luminescence microtiter plate (Costar) and luminescence is measured.

Controls included: (1) medium control (target cells plus 50 µL medium), (2) maximal lysis control (target cells plus 50 µL 0.5% Triton X-100), (3) complement control (target cells plus 25 µL medium plus 25 µL complement).

Example 4: Characterization of Potency and Species Selectivity in Whole Blood Assay The relative potency of a panel of candidate antibodies was first assessed by determining the inhibition of interferon gamma release in human blood using the antibodies at 1 and 10 nM. All of the antibodies displayed potent activity, with A219 appearing to be one of the most potent candidates (Table 4).

TABLE 4

| Clone | % Inhibition at 1 nM Ig | % Inhibition at 10 nM Ig |
|---|---|---|
| A147 | 51.3 | 72.4 |
| A212 | 46.8 | 71.2 |
| A213 | 48.6 | 69.8 |
| A217 | 46.0 | 72.2 |
| A219 | 59.8 | 75.2 |
| A220 | 36.9 | 63.2 |

Figure 2:
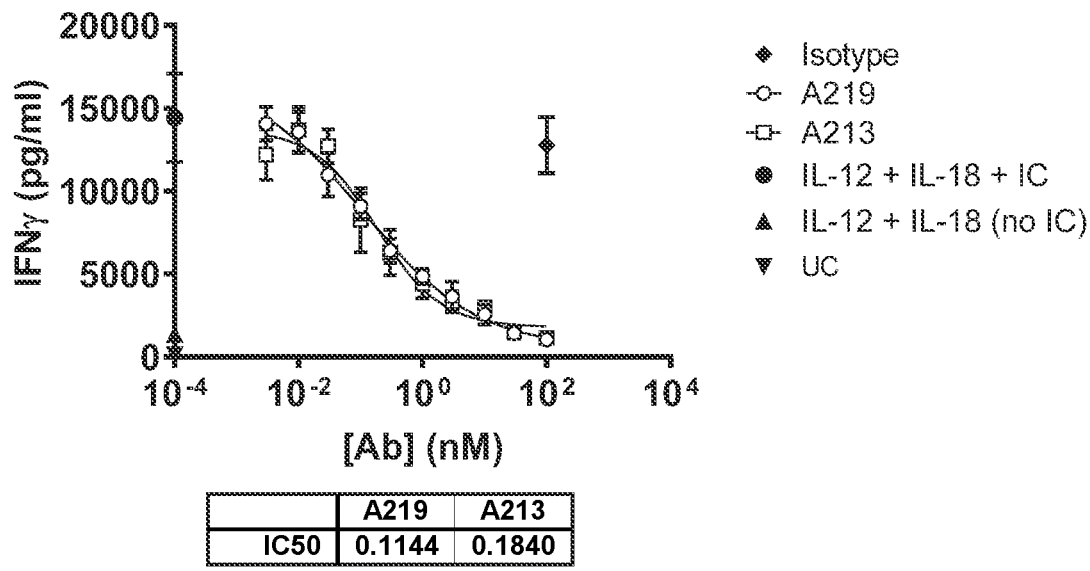
FIG. 2 depicts inhibition of interferon gamma in human blood with anti-TL1A antibodies.
Figure 2:
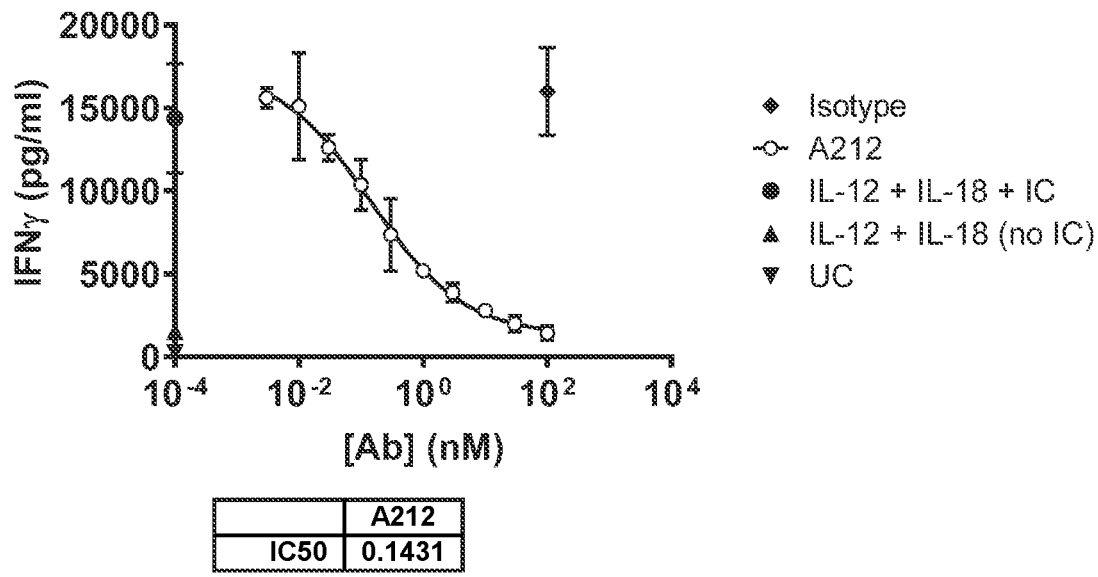

Next, three of the variants were characterized for inhibition of interferon gamma release in human blood using multiple human blood donors and testing the antibodies across a broader range of concentrations (0.01-100 nM). Representative inhibition profiles of variants A212, A213 and A219 are shown in FIG. 2. The mean IC50 values for these variants, and a control antibody termed 1D1, for the inhibition of interferon gamma release from multiple human donors is shown in Table 5.

TABLE 5

| Clone | Mean | SD |
|---|---|---|
| A212 | 51.3 | 72.4 |
| A213 | 46.8 | 71.2 |
| A219 | 48.6 | 69.8 |
| 1D1 | 46.0 | 72.2 |

Example 5: In Vivo Assessment of Anti-TL1A Efficacy

The efficacy of anti-TL1A antibodies in animal models of colitis is performed. Anti-TL1A antibodies are tested in rodent models of acute colitis induced by intrarectal administration of di- or tri-nitrobenzenesulfonic acid (D/TNBS) or oxazolone, and chronic colitis induced by administration of DSS in drinking water or transfer of CD45RB$^{hi}$ T cells. DNBS and oxazolone induce localized ulceration and inflammation. DSS administration induces robust generalized inflammation of the intestinal tract characterized by erosive lesions and inflammatory infiltrate. Symptoms of all these models usually include diarrhea, occult blood, weight loss and occasionally rectal prolapse. In a prophylactic model, antibody treatment begins at the start of administration of the colitis-inducing compound. In a therapeutic model, antibody treatment begins several days after commencement of induction. The effect of the treatment on weight, stool consistency and occult blood, as well as microscopic effects on epithelial integrity and degree of inflammatory infiltrate is determined. Daily clinical scoring is performed based on stool consistency and presence of occult blood giving a disease activity index (DAI) score.

Example 6: Phase 1 Clinical Trial

A phase 1 clinical trial is performed to evaluate the safety, tolerability, pharmacokinetics and pharmacodynamics of an anti-TL1A antibody provided herein in normal healthy volunteer subjects. A Synopsis is provided in Table 15.

TABLE 15

Synopsis of Phase 1, Single-Center, Double-Blind, Placebo-Controlled, Safety and Pharmacokinetics Study of anti-TL1A antibody in Healthy Volunteers

| | |
|---|---|
| OBJECTIVE: | To assess: Primary: The safety and tolerability of single and multiple doses of anti-TL1A antibody following administration. Secondary: The pharmacokinetics (PK) of anti-TL1A antibody after single and multiple doses. Exploratory: The effects of anti-TL1A antibody on tissue and serum pharmacodynamic (PD) markers. The exposure-response relationship of anti-TL1A antibody on PD markers. |
| STUDY DESIGN: | Single center, double-blind, randomized, placebo-controlled, single dose followed by multiple dose study of anti-TL1A antibody. |
| SAMPLE SIZE: | The study is planned to enroll: Single Dose Phase: Eight (8) subjects (6 active, 2 placebo) per dose level; up to 5 dose levels are planned (a total of 40 subjects if all 5 dose levels are completed). Multiple Dose Phase: Eight (8) subjects (6 active, 2 placebo) per dose level, up to 4 dose levels are planned (a total of 32 subjects if all 4 dose levels are completed). Subjects who discontinue the study prematurely may be replaced. |

TABLE 15-continued

Synopsis of Phase 1, Single-Center, Double-Blind, Placebo-Controlled, Safety and
Pharmacokinetics Study of anti-TL1A antibody in Healthy Volunteers

| | |
|---|---|
| SUBJECT TYPE: | Healthy, ambulatory, non-smoking, male or female volunteers aged 18 to 55 years. Female volunteers must be women of non-childbearing potential. |
| DOSAGE AND DOSE PROGRESSION: | Single Ascending Dose (SAD) Phase:<br>Placebo (matching volume of 0.9% normal saline [NS])<br>anti-TL1A antibody:<br>Dose Progression: second and higher dosing cohorts to be selected based on AEs and available PK and PD data<br>Multiple Ascending Dose (MAD) Phase<br>Placebo (matching volume of 0.9% NS)<br>anti-TL1A antibody on Day 1/Weeks 0, Day 15/Week 2, and Day 29/Week 4<br>Dosing Progression: second and higher dosing cohorts to be selected based on AEs and available PK and PD data. |
| STUDY PARAMETERS: | Primary objectives by:<br>Adverse events, physical examinations, chest x-ray, vital signs, ECGs, clinical laboratory values, and anti-drug antibody levels in serum samples.<br>Secondary objectives by:<br>Pharmacokinetics: Concentrations of anti-TL1A antibody in serum samples will be determined by validated LCMS methods.<br>Exploratory objectives by:<br>Pharamcodynamics: Change from Baseline in serum and tissue (in the MAD cohorts where sigmoidoscopy will be performed) PD markers |
| INCLUSION CRITERIA: | Subjects are required to meet the following criteria in order to be included in the study:<br>1. Male or female (of non-childbearing potential only) between 18 and 55 years of age.<br>2. Females must be of non-childbearing potential and must have undergone one of the following sterilization procedures, and have official documentation, at least 6 months prior to the first dose:<br>a. hysteroscopic sterilization;<br>b. bilateral tubal ligation or bilateral salpingectomy;<br>c. hysterectomy;<br>d. bilateral oophorectomy, or;<br>e. be postmenopausal with amenorrhea for at least 1 year prior to the first dose and have FSH serum levels consistent with postmenopausal status as per investigator judgment.<br>Note: A female of non-childbearing potential who has undergone one of the sterilization procedures mentioned above, but could not provide official documentation, must be sexually inactive and remain inactive throughout the study, or must agree to use a physical (e.g., condom, diaphragm) and a chemical (e.g., spermicide) barrier method from the time of screening and throughout the study.<br>3. Male subjects must use reliable forms of contraception from screening to 30 days after the end of dosing.<br>Note: A non-vasectomized, male subject must agree to use a condom with spermicide or abstain from sexual intercourse during the study until 30 days beyond the last dose of study drug. (No restrictions are required for a vasectomized male provided his vasectomy has been performed 4 months or more prior to the first dose. A male who has been vasectomized less than 4 months prior to the first dose, or could not provide official documentation, must follow the same restrictions as a non-vasectomized male).<br>4. Continuous non-smoker who has not used tobacco or nicotine-containing products for a least 6 months prior to the first dose of study drug.<br>5. Good general health as determined by medical history, and by results of physical examination, chest x-ray, vital signs, ECG, and clinical laboratory tests obtained within 28 days (4 weeks) prior to study drug administration.<br>6. Subjects must have documentation of positive serology for varicella zoster virus (VZV) immunoglobulin G (IgG) antibody status.<br>7. Able to provide written informed consent and understand and comply with the requirements of the study. |
| EXCLUSION CRITERIA: | Subjects with the following characteristics will be excluded from the study:<br>1. Subject participation in more than one cohort.<br>2. History or presence of any clinically significant organ system disease that could interfere with the objectives of the study or the safety of the subjects.<br>3. Blood pressure and heart rate are outside the ranges 90-140 mmHg systolic, 40-90 mmHg diastolic, heart rate 60-100 beats/min.<br>4. 12-lead ECG with any abnormality judged by the Investigator to be clinically significant, QRS ≥110 milliseconds (msec), or QT/QTcF interval of >450 msec for men or >470 msec for women. |

TABLE 15-continued

Synopsis of Phase 1, Single-Center, Double-Blind, Placebo-Controlled, Safety and Pharmacokinetics Study of anti-TL1A antibody in Healthy Volunteers 5. Presence or history of any abnormality or illness, which in the opinion of the Investigator may affect absorption, distribution, metabolism or elimination of the study drug.
6. Any screening laboratory evaluation outside the laboratory reference range that is judged by the Investigator to be clinically significant.
7. History of or current active tuberculosis (TB) infection; history of latent TB that has not been fully treated or current latent TB infection.
8. History of more than one episode of herpes zoster infection or history of disseminated herpes zoster infection.
9. Positive serum test for HIV, hepatitis C or hepatitis B virus infection.
10. History of significant allergy to any medication.
11. History of alcohol or drug abuse within the past 24 months.
12. Administration of any prescription drug within 21 days of study drug administration; or over-the-counter drug (acetaminophen and ibuprofen ≤ 1 g/day permitted) or herbal, nutritional or vitamin supplement within 7 days of study drug administration.
13. Evidence of drug abuse on urine testing, or a positive test for alcohol.
14. Administration or use of any investigational drug or device within 30 days of study drug administration.
15. Blood or plasma donation within 60 days prior to dosing.

TABLE 6

CDR Amino Acid Sequences

| SEQ ID NO | Description | Sequence |
|---|---|---|
| 1 | HCDR1 | GFDIQDTYMH |
| 2 | HCDR2a | RIDPASGHTKYDPKFQV |
| 3 | HCDR2b | RIEPASGHIKYDPKFQG |
| 4 | HCDR2c | RIDPASGHIKYDPKFQG |
| 5 | HCDR2d | RIEPASGHIKYDPKFQV |
| 6 | HCDR3a | SGGLPDV |
| 7 | HCDR3b | ARSGGLPDV |
| 8 | HCDR3c | SGGLPDW |
| 9 | HCDR3d | ARSGGLPDW |
| 10 | LCDR1 | RASSSVSYMY |
| 11 | LCDR2 | ATSNLAS |
| 12 | LCDR3a | QQWEGNPRT |
| 13 | LCDR3b | QQWKGNPRT |
| 14 | LCDR3c | QQWSGNPRT |
| 15 | LCDR3d | QQWSRNPRT |

TABLE 7

Heavy Chain Variable Region Amino Acid Sequences

| SEQ ID NO | Description | Sequence |
|---|---|---|
| 101 | 217 VH, 158 VH | QVQLVQSGAEVKKPGASVKVSCKASGFDIQDTYMHWVKQ RPGQGLEWMGRIDPASGHTKYDPKFQVRVTITRDTSTSTV YMELSSLRSEDTAVYYCARSGGLPDVWGQGTTVTVSS |
| 102 | 220 VH, 160 VH | QVQLVQSGAEVKKPGASVKVSCKASGFDIQDTYMHWVKQ RPGQGLEWMGRIDPASGHTKYDPKFQVRVTMTRDTSTSTA YLELSSLRSEDTAVYYCARSGGLPDVWGQGTTVTVSS |
| 103 | 223 VH, 200 VH, 194 VL, 206 VH | EVQLVQSGAEVKKPGASVKVSCKASGFDIQDTYMHWVRQ RPGQGLEWIGRIDPASGHTKYDPKFQVRATITTDTSTAY LELSSLRSEDTAVYYCARSGGLPDVWGQGTTVTVSS |
| 104 | 219 VH, 157 VH | QVQLVQSGAEVKKPGASVKVSCKASGFDIQDTYMHWVKQ RPGQGLEWMGRIDPASGHTKYDPKFQVRVTITRDTSTSTV YLELSSLRSEDTAVYYCARSGGLPDVWGQGTTVTVSS |

TABLE 7-continued

Heavy Chain Variable Region Amino Acid Sequences

| SEQ ID NO | Description | Sequence |
|---|---|---|
| 105 | 221 VH, 125 VH | QVQLVQSGAEVKKPGASVKVSCKASGFDIQDTYMHWVKQRPGQGLEWMGRIDPASGHTKYDPKFQVRATITRDTSTSTAYLELSSLRSEDTAVYYCARSGGLPDVWGQGTTVTVSS |
| 106 | 213 VH, 162 VH | QVQLVQSGAEVKKPGASVKVSCKASGFDIQDTYMHWVRQRPGQGLEWMGRIDPASGHTKYDPKFQVRVTITTDTSTSTVYMELSSLRSEDTAVYYCARSGGLPDVWGQGTTVTVSS |
| 107 | 212 VH, 100 VH, 181 VH, 34 VH, 79 VH | QVQLVQSGAEVKKPGASVKVSCKASGFDIQDTYMHWVRQRPGQGLEWIGRIDPASGHTKYDPKFQVRATITTDTSTAYLELSSLRSEDTAVYYCARSGGLPDVWGQGTTVTVSS |
| 108 | 107 VH, 211 VH, 15 VH, 30 VH, 29 VH, 48 VH, 49 VH, 50 VH, 51 VH, 52 VH, 56 VH | QVQLVQSGAEVKKPGASVKVSCKASGFDIQDTYMHWVKQRPGQGLEWIGRIDPASGHTKYDPKFQVRATITTDTSTAYLELSSLRSEDTAVYYCARSGGLPDVWGQGTTVTVSS |
| 109 | 205 VH, 199 VH, 55 VH, 193 VH | EVQLVQSGAEVKKPGASVKVSCKASGFDIQDTYMHWVKQRPGQGLEWIGRIDPASGHTKYDPKFQVRATITTDTSTSTAYLELSSLRSEDTAVYYCARSGGLPDVWGQGTTVTVSS |
| 110 | 129 VH, 139 VH, 140 VH, 215 VH | QVQLVQSGAEVKKPGASVKVSCKASGFDIQDTYMHWVRQRPGQGLEWMGRIDPASGHTKYDPKFQVRVTITTDTSTSTAYLELSSLRSEDTAVYYCARSGGLPDVWGQGTTVTVSS |
| 111 | 214 VH, 128 VH, 141 VH, 142 VH, 144 VH | QVQLVQSGAEVKKPGASVKVSCKASGFDIQDTYMHWVRQRPGQGLEWMGRIDPASGHTKYDPKFQVRVTITRDTSTSTAYLELSSLRSEDTAVYYCARSGGLPDVWGQGTTVTVSS |
| 112 | 216 VH, 123 VH | QVQLVQSGAEVKKPGASVKVSCKASGFDIQDTYMHWVRQRPGQGLEWIGRIDPASGHTKYDPKFQVRVTITRDTSTSTAYLELSSLRSEDTAVYYCARSGGLPDVWGQGTTVTVSS |
| 113 | 122 VH | QVQLVQSGAEVKKPGASVKVSCKASGFDIQDTYMHWVRQRPGQGLEWIGRIDPASGHTKYDPKFQVRATITRDTSTSTAYLELSSLRSEDTAVYYCARSGGLPDVWGQGTTVTVSS |
| 114 | 222 VH, 126 VH | QVQLVQSGAEVKKPGASVKVSCKASGFDIQDTYMHWVKQRPGQGLEWMGRIDPASGHTKYDPKFQVRVTITRDTSTSTAYLELSSLRSEDTAVYYCARSGGLPDVWGQGTTVTVSS |
| 115 | 188 VH, 41 VH, 102 VH | QVQLVQSGAEVKKPGASVKVSCKASGFDIQDTYMHWVKQRPGQGLEWIGRIDPASGHTKYDPKFQVRVTITTDTSTSTAYLELSSLRSEDTAVYYCARSGGLPDVWGQGTTVTVSS |
| 116 | 203 VH, 197 VH, 209 VH, 224 VH | EVQLVQSGAEVKKPGASVKVSCKASGFDIQDTYMHWVKQAPGQGLEWMGRIEPASGHIKYDPKFQGRVTMTRDTSTSTVYMELSSLRSEDTAVYYCARSGGLPDWWGQGTTVTVSS |
| 117 | 147 VH, 112 VH, 59 VH | QVQLVQSGAEVKKPGASVKVSCKASGFDIQDTYMHWVKQRPGQGLEWMGRIEPASGHIKYDPKFQGRVTMTRDTSTSTVYMELSSLRSEDTAVYYCARSGGLPDWWGQGTTVTVSS |
| 118 | 127 VH | QVQLVQSGAEVKKPGASVKVSCKASGFDIQDTYMHWVKQRPGQGLEWMGRIDPASGHTKYDPKFQVRVTITTDTSTSTAYLELSSLRSEDTAVYYCARSGGLPDVWGQGTTVTVSS |
| 119 | 159 VH, 218 VH | QVQLVQSGAEVKKPGASVKVSCKASGFDIQDTYMHWVKQRPGQGLEWMGRIDPASGHTKYDPKFQVRVTITRDTSTSTAYMELSSLRSEDTAVYYCARSGGLPDVWGQGTTVTVSS |
| 120 | 103 VH, 45 VH, 167 VH, 187 VH | QVQLVQSGAEVKKPGASVKVSCKASGFDIQDTYMHWVKQRPGQGLEWIGRIDPASGHTKYDPKFQVRVTITRDTSTSTAYLELSSLRSEDTAVYYCARSGGLPDVWGQGTTVTVSS |
| 121 | 64 VH, 148 VH, 97 VH, 114 VH, 130 VH, 133 VH, 137 VH, 155 VH | QVQLVQSGAEVKKPGASVKVSCKASGFDIQDTYMHWVRQAPGQGLEWMGRIEPASGHIKYDPKFQVRVTMTRDTSTSTVYMELSSLRSEDTAVYYCARSGGLPDWWGQGTTVTVSS |

TABLE 7-continued

Heavy Chain Variable Region Amino Acid Sequences

| SEQ ID NO | Description | Sequence |
|---|---|---|
| 122 | 67 VH, 138 VH, 115 VH, 149 VH, 134 VH, 98 VH, 156 VH | QVQLVQSGAEVKKPGASVKVSCKASGFDIQDTYMHWVRQ APGQGLEWMGRIEPASGHIKYDPKFQVRATMTRDTSTSTV YMELSSLRSEDTAVYYCARSGGLPDWWGQGTTVTVSS |
| 123 | 68 VH, 99 VH, 116 VH | QVQLVQSGAEVKKPGASVKVSCKASGFDIQDTYMHWVRQ APGQGLEWMGRIEPASGHIKYDPKFQVRVTITRDTSTSTVY MELSSLRSEDTAVYYCARSGGLPDWWGQGTTVTVSS |
| 124 | 94 VH, 113 VH, 151 VH, 78 VH | QVQLVQSGAEVKKPGASVKVSCKASGFDIQDTYMHWVRQ APGQGLEWMGRIEPASGHIKYDPKFQVRATITRDTSTSTVY MELSSLRSEDTAVYYCARSGGLPDWWGQGTTVTVSS |
| 125 | 110 VH, 58 VH, 136 VH, 146 VH, 154 VH | QVQLVQSGAEVKKPGASVKVSCKASGFDIQDTYMHWVKQ APGQGLEWMGRIEPASGHIKYDPKFQGRVTMTRDTSTSTV YMELSSLRSEDTAVYYCARSGGLPDWWGQGTTVTVSS |
| 126 | 169 VH, 175 VH | QVQLVQSGAEVKKPGASVKVSCKASGFDIQDTYMHWVKQ APGQGLEWMGRIDPASGHIKYDPKFQGRVTMTRDTSTSTV YMELSSLRSEDTAVYYCARSGGLPDWWGQGTTVTVSS |
| 127 | 173 VH, 179 VH | QVQLVQSGAEVKKPGASVKVSCKASGFDIQDTYMHWVKQ APGQGLEWMGRIEPASGHIKYDPKFQGRATMTRDTSTSTV YMELSSLRSEDTAVYYCARSGGLPDWWGQGTTVTVSS |
| 128 | 96 VH, 132 VH, 65 VH, 150 VH | QVQLVQSGAEVKKPGASVKVSCKASGFDIQDTYMHWVRQ APGQGLEWMGRIEPASGHIKYDPKFQGRATMTRDTSTSTV YMELSSLRSEDTAVYYCARSGGLPDWWGQGTTVTVSS |
| 129 | 196 VH, 202 VH, 208 VH | EVQLVQSGAEVKKPGASVKVSCKASGFDIQDTYMHWVRQ APGQGLEWMGRIEPASGHIKYDPKFQGRATMTRDTSTSTV YMELSSLRSEDTAVYYCARSGGLPDWWGQGTTVTVSS |
| 130 | 172 VH, 178 VH | QVQLVQSGAEVKKPGASVKVSCKASGFDIQDTYMHWVRQ APGQGLEWMGRIDPASGHIKYDPKFQGRATMTRDTSTSTV YMELSSLRSEDTAVYYCARSGGLPDWWGQGTTVTVSS |
| 131 | 75 VH, 72 VH, 95 VH, 152 VH | QVQLVQSGAEVKKPGASVKVSCKASGFDIQDTYMHWVRQ APGQGLEWMGRIEPASGHIKYDPKFQGRATITTDTSTSTVY MELSSLRSEDTAVYYCARSGGLPDWWGQGTTVTVSS |
| 132 | 174 VH, 180 VH | QVQLVQSGAEVKKPGASVKVSCKASGFDIQDTYMHWVRQ APGQGLEWMGRIEPASGHIKYDPKFQGRATMTRDTSTSTA YMELSSLRSEDTAVYYCARSGGLPDWWGQGTTVTVSS |
| 133 | 109 VH, 91 VH, 135 VH, 145 VH, 153 VH | QVQLVQSGAEVKKPGASVKVSCKASGFDIQDTYMHWVRQ APGQGLEWMGRIEPASGHIKYDPKFQGRVTMTRDTSTSTA YMELSSLRSEDTAVYYCARSGGLPDWWGQGTTVTVSS |
| 134 | 198 VH, 204 VH, 210 VH | EVQLVQSGAEVKKPGASVKVSCKASGFDIQDTYMHWVRQ APGQGLEWMGRIEPASGHIKYDPKFQGRVTMTRDTSTSTA YMELSSLRSEDTAVYYCARSGGLPDWWGQGTTVTVSS |
| 135 | 170 VH, 176 VH | QVQLVQSGAEVKKPGASVKVSCKASGFDIQDTYMHWVRQ APGQGLEWMGRIDPASGHIKYDPKFQGRVTMTRDTSTSTA YMELSSLRSEDTAVYYCARSGGLPDWWGQGTTVTVSS |
| 136 | 31 VH, 85 VH, 86 VH, 87 VH, 88 VH, 89 VH, 90 VH, 143 VH | QVQLVQSGAEVKKPGASVKVSCKASGFDIQDTYMHWVRQ APGQGLEWMGRIEPASGHIKYDPKFQGRVTMTRDTSTSTV YMELSSLRSEDTAVYYCARSGGLPDWWGQGTTVTVSS |
| 137 | 32 VH, 33 VH | DVQLVQSGAEVKKPGASVKVSCKASGFDIQDTYMHWVRQ APGQGLEWMGRIEPASGHIKYDPKFQGRVTMTRDTSTSTV YMELSSLRSEDTAVYYCARSGGLPDWWGQGTTVTVSS |
| 138 | 35 VH, 182 VH | QVQLVQSGAEVKKPGASVKVSCKASGFDIQDTYMHWVKQ APGQGLEWIGRIDPASGHTKYDPKFQVRATITTDTSTSTAY LELSSLRSEDTAVYYCARSGGLPDVWGQGTTVTVSS |
| 139 | 36 VH, 81 VH, 104 VH, 165 VH, | QVQLVQSGAEVKKPGASVKVSCKASGFDIQDTYMHWVRQ APGQGLEWIGRIDPASGHTKYDPKFQVRATITTDTSTSTAY LELSSLRSEDTAVYYCARSGGLPDVWGQGTTVTVSS |

TABLE 7-continued

Heavy Chain Variable Region Amino Acid Sequences

| SEQ ID NO | Description | Sequence |
|---|---|---|
| 140 | 37 VH, 82 VH, 101 VH, 183 VH | QVQLVQSGAEVKKPGASVKVSCKASGFDIQDTYMHWVKQ RPGQGLEWMGRIDPASGHTKYDPKFQVRATITTDTSTSTAY LELSSLRSEDTAVYYCARSGGLPDVWGQGTTVTVSS |
| 141 | 38 VH, 190 VH | QVQLVQSGAEVKKPGASVKVSCKASGFDIQDTYMHWVKQ RPGQGLEWIGRIDPASGHTKYDPKFQVRATITTDTSTSTVY LELSSLRSEDTAVYYCARSGGLPDVWGQGTTVTVSS |
| 142 | 39 VH, 191 VH | QVQLVQSGAEVKKPGASVKVSCKASGFDIQDTYMHWVKQ RPGQGLEWIGRIDPASGHTKYDPKFQVRATITTDTSTSTAY MELSSLRSEDTAVYYCARSGGLPDVWGQGTTVTVSS |
| 143 | 40 VH, 105 VH, 192 VH | QVQLVQSGAEVKKPGASVKVSCKASGFDIQDTYMHWVKQ RPGQGLEWIGRIDPASGHTKYDPKFQVRATITTDTSTSTVY MELSSLRSEDTAVYYCARSGGLPDVWGQGTTVTVSS |
| 144 | 42 VH, 83 VH, 186 VH | QVQLVQSGAEVKKPGASVKVSCKASGFDIQDTYMHWVKQ RPGQGLEWIGRIDPASGHTKYDPKFQVRATMTTDTSTSTAY LELSSLRSEDTAVYYCARSGGLPDVWGQGTTVTVSS |
| 145 | 43 VH, 184 VH | QVQLVQSGAEVKKPGASVKVSCKASGFDIQDTYMHWVKQ RPGQGLEWIGRIDPASGHTKYDPKFQVRATITRDTSTSTAY LELSSLRSEDTAVYYCARSGGLPDVWGQGTTVTVSS |
| 146 | 44 VH, 53 VH, 166 VH, 189 VH | QVQLVQSGAEVKKPGASVKVSCKASGFDIQDTYMHWVKQ RPGQGLEWIGRIDPASGHTKYDPKFQVRVTMTTDTSTSTAY LELSSLRSEDTAVYYCARSGGLPDVWGQGTTVTVSS |
| 147 | 46 VH, 168 VH, 185 VH | QVQLVQSGAEVKKPGASVKVSCKASGFDIQDTYMHWVKQ RPGQGLEWIGRIDPASGHTKYDPKFQVRATMTRDTSTSTA YLELSSLRSEDTAVYYCARSGGLPDVWGQGTTVTVSS |
| 148 | 47 VH | QVQLVQSGAEVKKPGASVKVSCKASGFDIQDTYMHWVKQ RPGQGLEWIGRIDPASGHTKYDPKFQVRVTMTRDTSTSTA YLELSSLRSEDTAVYYCARSGGLPDVWGQGTTVTVSS |
| 149 | 54 VH | DVQLVQSGAEVKKPGASVKVSCKASGFDIQDTYMHWVKQ RPGQGLEWIGRIDPASGHTKYDPKFQVRATITTDTSTSTAY LELSSLRSEDTAVYYCARSGGLPDVWGQGTTVTVSS |
| 150 | 57 VH, 111 VH | QVQLVQSGAEVKKPGASVKVSCKASGFDIQDTYMHWVRQ RPGQGLEWMGRIEPASGHIKYDPKFQGRVTMTRDTSTSTV YMELSSLRSEDTAVYYCARSGGLPDWWGQGTTVTVSS |
| 151 | 60 VH, 117 VH | QVQLVQSGAEVKKPGASVKVSCKASGFDIQDTYMHWVRQ APGQGLEWMGRIDPASGHIKYDPKFQGRVTMTRDTSTSTV YMELSSLRSEDTAVYYCARSGGLPDWWGQGTTVTVSS |
| 152 | 61 VH | QVQLVQSGAEVKKPGASVKVSCKASGFDIQDTYMHWVRQ APGQGLEWIGRIEPASGHIKYDPKFQGRVTMTRDTSTSTVY MELSSLRSEDTAVYYCARSGGLPDWWGQGTTVTVSS |
| 153 | 62 VH, 118 VH | QVQLVQSGAEVKKPGASVKVSCKASGFDIQDTYMHWVRQ APGQGLEWIGRIDPASGHIKYDPKFQGRVTMTRDTSTSTVY MELSSLRSEDTAVYYCARSGGLPDWWGQGTTVTVSS |
| 154 | 63 VH, 120 VH | QVQLVQSGAEVKKPGASVKVSCKASGFDIQDTYMHWVRQ APGQGLEWMGRIEPASGHVKYDPKFQGRVTMTRDTSTSTV YMELSSLRSEDTAVYYCARSGGLPDWWGQGTTVTVSS |
| 155 | 66 VH | QVQLVQSGAEVKKPGASVKVSCKASGFDIQDTYMHWVRQ APGQGLEWMGRIEPASGHIKYDPKFQGRVTITRDTSTSTVY MELSSLRSEDTAVYYCARSGGLPDWWGQGTTVTVSS |
| 156 | 69 VH, 108 VH | EVQLVQSGAEVKKPGASVKVSCKASGFDIQDTYMHWVRQ APGQGLEWMGRIEPASGHIKYDPKFQGRVTMTRDTSTSTV YMELSSLRSEDTAVYYCARSGGLPDWWGQGTTVTVSS |
| 157 | 70 VH, 73 VH | QVQLVQSGAEVKKPGASVKVSCKASGFDIQDTYMHWVRQ APGQGLEWMGRIEPASGHIKYDPKFQGRVTMTTDTSTSTV YMELSSLRSEDTAVYYCARSGGLPDWWGQGTTVTVSS |

TABLE 7-continued

Heavy Chain Variable Region Amino Acid Sequences

| SEQ ID NO | Description | Sequence |
|---|---|---|
| 158 | 71 VH, 74 VH | QVQLVQSGAEVKKPGASVKVSCKASGFDIQDTYMHWVRQAPGQGLEWMGRIEPASGHIKYDPKFQGRVTITTDTSTSTVYMELSSLRSEDTAVYYCARSGGLPDWWGQGTTVTVSS |
| 159 | 76 VH, 119 VH | QVQLVQSGAEVKKPGASVKVSCKASGFDIQDTYMHWVRQAPGQGLEWMGRIEPASGHTKYDPKFQGRVTMTRDTSTSTVYMELSSLRSEDTAVYYCARSGGLPDWWGQGTTVTVSS |
| 160 | 77 VH | QVQLVQSGAEVKKPGASVKVSCKASGFDIQDTYMHWVRQAPGQGLEWMGRIEPASGHIKYDPKFQGRATITRDTSTSTVYMELSSLRSEDTAVYYCARSGGLPDWWGQGTTVTVSS |
| 161 | 92 VH | QVQLVQSGAEVKKPGASVKVSCKASGFDIQDTYMHWVRQAPGQGLEWMGRIEPASGHIKYDPKFQGRVTMTRDTSTSTVYLELSSLRSEDTAVYYCARSGGLPDWWGQGTTVTVSS |
| 162 | 93 VH | QVQLVQSGAEVKKPGASVKVSCKASGFDIQDTYMHWVRQAPGQGLEWMGRIEPASGHIKYDPKFQGRVTMTRDTSTSTAYLELSSLRSEDTAVYYCARSGGLPDWWGQGTTVTVSS |
| 163 | 121 VH | QVQLVQSGAEVKKPGASVKVSCKASGFDIQDTYMHWVRQRPGQGLEWMGRIDPASGHTKYDPKFQVRATITTDTSTSTAYLELSSLRSEDTAVYYCARSGGLPDVWGQGTTVTVSS |
| 164 | 124 VH | QVQLVQSGAEVKKPGASVKVSCKASGFDIQDTYMHWVRQRPGQGLEWIGRIDPASGHTKYDPKFQVRVTITTDTSTSTAYLELSSLRSEDTAVYYCARSGGLPDVWGQGTTVTVSS |
| 165 | 161 VH | QVQLVQSGAEVKKPGASVKVSCKASGFDIQDTYMHWVRQRPGQGLEWMGRIDPASGHTKYDPKFQVRVTITTDTSTSTVYLELSSLRSEDTAVYYCARSGGLPDVWGQGTTVTVSS |
| 166 | 163 VH | QVQLVQSGAEVKKPGASVKVSCKASGFDIQDTYMHWVRQRPGQGLEWMGRIDPASGHTKYDPKFQVRVTITTDTSTSTAYMELSSLRSEDTAVYYCARSGGLPDVWGQGTTVTVSS |
| 167 | 164 VH | QVQLVQSGAEVKKPGASVKVSCKASGFDIQDTYMHWVRQRPGQGLEWMGRIDPASGHTKYDPKFQVRVTMTTDTSTSTAYLELSSLRSEDTAVYYCARSGGLPDVWGQGTTVTVSS |
| 168 | 171 VH, 177 VH | QVQLVQSGAEVKKPGASVKVSCKASGFDIQDTYMHWVRQAPGQGLEWMGRIDPASGHIKYDPKFQGRATITTDTSTSTVYMELSSLRSEDTAVYYCARSGGLPDWWGQGTTVTVSS |
| 169 | 195 VH, 201 VH, 207 VH | EVQLVQSGAEVKKPGASVKVSCKASGFDIQDTYMHWVRQAPGQGLEWMGRIEPASGHIKYDPKFQGRATITTDTSTSTVYMELSSLRSEDTAVYYCARSGGLPDWWGQGTTVTVSS |

TABLE 8

Light Chain Variable Region Amino Acid Sequences

| SEQ ID NO | Description | Sequence |
|---|---|---|
| 201 | 217 VL, 219 VL, 221 VL, 200 VL, 213 VL, 212 VL, 211 VL, 199 VL, 214 VL, 216 VL, 222 VL, 203 VL, 147 VL, 218 VL, 179 VL, 148 VL, 149 VL, 151 VL, 180 VL, 175 VL, 178 VL, 145 VL, 146 VL, | EIVLTQSPGTLSLSPGERATLSCRASSSVSYMYWYQQKPGQAPRPLIYATSNLASGIPDRFSGSGSGTDFTLTISRLEPEDFAVYYCQQWEGNPRTFGGGTKLEIK |

TABLE 8-continued

Light Chain Variable Region Amino Acid Sequences

| SEQ ID NO | Description | Sequence |
|---|---|---|
| | 150 VL, 152 VL, 176 VL, 177 VL, 201 VL, 202 VL, 204 VL, 215 VL, 224 VL | |
| 202 | 223 VL, 107 VL, 205 VL, 181 VL, 188 VL, 64 VL, 67 VL, 68 VL, 94 VL, 33 VL, 57 VL, 58 VL, 59 VL, 60 VL, 61 VL, 62 VL, 63 VL, 65 VL, 66 VL, 69 VL, 70 VL, 71 VL, 72 VL, 76 VL, 77 VL, 78 VL, 91 VL, 92 VL, 93 VL, 97 VL, 98 VL, 99 VL, 140 VL, 142 VL, 143 VL, 182 VL, 183 VL, 184 VL, 185 VL, 186 VL, 187 VL, 189 VL, 190 VL, 191 VL, 192 VL, 206 VL, 207 VL, 208 VL, 209 VL, 210 VL | EIVLTQSPGTLSLSPGERATLSCRASSSVSYMYWYQQKPGQ APRLLIYATSNLASGIPDRFSGSGSGTDFTLTISRLEPEDFAV YYCQQWEGNPRTFGGGTKLEIK |
| 203 | 15 VL | EIVLTQSPGTLSLSPGERATLSCRASSSVSYMYWYQQKPGQ APRLLIYATSNLASGIPDRFSGSGSGTDFTLTISRLEPEDFAV YYCQQWSGNPRTFGGGTKLEIK |
| 204 | 30 VL, 100 VL, 129 VL, 122 VL, 127 VL, 126 VL, 160 VL, 157 VL, 159 VL, 158 VL, 125 VL, 103 VL, 101 VL, 102 VL, 104 VL, 105 VL, 121 VL, 123 VL, 124 VL, 128 VL, 144 VL, 161 VL, 162 VL, 163 VL, 164 VL | EIVLTQSPGTLSLSPGERATLSCRASSSVSYMYWYQQKPGQ APRLLIYATSNLASGIPDRFSGSGSGTDFTLTISRLEPEDFAV YYCQQWKGNPRTFGGGTKLEIK |
| 205 | 110 VL, 197 VL, 112 VL, 169 VL, 173 VL, 115 VL, 113 VL, 96 VL, 196 VL, 172 VL, 75 VL, 174 VL, 109 VL, 198 VL, 170 VL, 29 VL, 31 VL, 32 VL, 73 VL, 74 VL, 95 VL, 108 VL, 111 VL, 114 VL, 116 VL, 117 VL, 118 VL, 119 VL, 120 VL, 130 VL, 153 VL, 154 VL, 155 VL, 156 VL, 165 VL, 166 VL, 167 VL, 168 VL, 171 VL, 193 VL, 194 VL, 195 VL, 220 VL | EIVLTQSPGTLSLSPGERATLSCRASSSVSYMYWYQQKPGQ APRPWIYATSNLASGIPDRFSGSGSGTDFTLTISRLEPEDFAV YYCQQWEGNPRTFGGGTKLEIK |
| 206 | 134 VL, 132 VL, 133 VL, 135 VL, 136 VL | EIVLTQSPGTLSLSPGERATLSCRASSSVSYMYWYQQKPGQ APRPLIYATSNLASGIPDRFSGSGSGTDFTLTISRLEPEDFAV YYCQQWKGNPRTFGGGTKLEIK |

TABLE 8-continued

Light Chain Variable Region Amino Acid Sequences

| SEQ ID NO | Description | Sequence |
|---|---|---|
| 207 | 138 VL, 137 VL, 139 VL, 141 VL | EIVLTQSPGTLSLSPGERATLSCRASSSVSYMYWYQQKPGQAPRLLIYATSNLASGIPDRFSGSGSGTDFTLTISRLEPEDFAVYYCQQWSRNPRTFGGGTKLEIK |
| 208 | 34 VL, 35 VL, 36 VL, 37 VL, 38 VL, 39 VL, 40 VL, 41 VL, 42 VL, 43 VL, 44 VL, 45 VL, 46 VL, 47 VL, 53 VL, 54 VL, 55 VL, 79 VL, 81 VL, 82 VL, 83 VL | EIVLTQSPGTLSASPGERATMSCRASSSVSYMYWYQQKPGQAPRPWIYATSNLASGVPDRFSGSGSGTDYTLTISRVEPEDFAVYYCQQWSGNPRTFGGGTKLEIK |
| 209 | 85 VL | EIVLTQSPGTLSLSPGERATLSCRASSSVSYMYWYQQKPGQAPRLLIYATSNLASGVPDRFSGSGSGTDFTLTISRLEPEDFAVYYCQQWEGNPRTFGGGTKLEIK |
| 210 | 48 VL | EIVLTQSPGTLSASPGERATLSCRASSSVSYMYWYQQKPGQAPRPWIYATSNLASGVPDRFSGSGSGTDYTLTISRVEPEDFAVYYCQQWSGNPRTFGGGTKLEIK |
| 211 | 49 VL | EIVLTQSPGTLSASPGERATMSCRASSSVSYMYWYQQKPGQAPRLLIYATSNLASGVPDRFSGSGSGTDYTLTISRVEPEDFAVYYCQQWSGNPRTFGGGTKLEIK |
| 212 | 50 VL | EIVLTQSPGTLSASPGERATMSCRASSSVSYMYWYQQKPGQAPRPWIYATSNLASGVPDRFSGSGSGTDFTLTISRVEPEDFAVYYCQQWSGNPRTFGGGTKLEIK |
| 213 | 51 VL | EIVLTQSPGTLSASPGERATMSCRASSSVSYMYWYQQKPGQAPRPWIYATSNLASGVPDRFSGSGSGTDYTLTISRLEPEDFAVYYCQQWSGNPRTFGGGTKLEIK |
| 214 | 52 VL | EIVLTQSPGTLSASPGERATMSCRASSSVSYMYWYQQKPGQAPRPWIYATSNLASGVPDRFSGSGSGTDFTLTISRLEPEDFAVYYCQQWSGNPRTFGGGTKLEIK |
| 215 | 56 VL | EIVLTQSPGTLSASPGERATMSCRASSSVSYMYWYQQKPGQAPRPWIYATSNLASGIPDRFSGSGSGTDYTLTISRVEPEDFAVYYCQQWSGNPRTFGGGTKLEIK |
| 216 | 86 VL | EIVLTQSPGTLSLSPGERATLSCRASSSVSYMYWYQQKPGQAPRLLIYATSNLASGIPDRFSGSGSGTDYTLTISRLEPEDFAVYYCQQWEGNPRTFGGGTKLEIK |
| 217 | 87 VL | EIVLTQSPGTLSLSPGERATLSCRASSSVSYMYWYQQKPGQAPRLLIYATSNLASGIPDRFSGSGSGTDFTLTISRVEPEDFAVYYCQQWEGNPRTFGGGTKLEIK |
| 218 | 88 VL | EIVLTQSPGTLSLSPGERATLSCRASSSVSYMYWYQQKPGQAPRLLIYATSNLASGIPDRFSGSGSGTDYTLTISRVEPEDFAVYYCQQWEGNPRTFGGGTKLEIK |
| 219 | 89 VL | EIVLTQSPGTLSASPGERATLSCRASSSVSYMYWYQQKPGQAPRLLIYATSNLASGIPDRFSGSGSGTDFTLTISRLEPEDFAVYYCQQWEGNPRTFGGGTKLEIK |
| 220 | 90 VL | EIVLTQSPGTMSLSPGERATLSCRASSSVSYMYWYQQKPGQAPRLLIYATSNLASGIPDRFSGSGSGTDFTLTISRLEPEDFAVYYCQQWEGNPRTFGGGTKLEIK |

TABLE 9A

Additional Sequences

| SEQ ID NO | Description | Sequence |
|---|---|---|
| 301 | Variable Heavy 1 | X1VQLVQSGAEVKKPGASVKVSCKAS[HCDR1]WVX2QX3PGQGLEWX4G[HCDR2]RX5TX6TX7DTSTSTX8YX9ELSSLRSEDTAVYYCAR[HCDR3]WGQGTTVTVSS<br>wherein each of X1-X11 is independently selected from A, R, N, D, C, Q, E, G, H, I, L, K, M, F, P, S, T, W, Y, or V<br>In some cases, X1 = Q or E<br>In some cases, X2 = R or K<br>In some cases, X3 = A or R<br>In some cases, X4 = M or I<br>In some cases, X5 = V or A<br>In some cases, X6 = M or I<br>In some cases, X7 = R or T<br>In some cases, X8 = V or A<br>In some cases, X9 = M or L |
| 302 | Variable Heavy 2 | X1VQLVQSGAEVKKPGASVKVSCKAS[HCDR1]WVX2QX3PGQGLEWX4G[HCDR2]RX5TX6TX7DTSTSTX8YX9ELSSLRSEDTAVYYC[HCDR3]WGQGTIVIVSS<br>wherein each of X1-X11 is independently selected from A, R, N, D, C, Q, E, G, H, I, L, K, M, F, P, S, T, W, Y, or V<br>In some cases, X1 = Q or E<br>In some cases, X2 = R or K<br>In some cases, X3 = A or R<br>In some cases, X4 = M or I<br>In some cases, X5 = V or A<br>In some cases, X6 = M or I<br>In some cases, X7 = R or T<br>In some cases, X8 = V or A<br>In some cases, X9 = M or L |
| 303 | Variable Light | EIVLTQSPGTLSLSPGERATLSC[LCDR1]WYQQKPGQAPRX10X11IY[LCDR2]GIPDRFSGSGSGTDFTLTISRLEPEDFAVYYC[LCDR3] FGGGTKLEIK<br>wherein each of X10 and X11 is independently selected from A, R, N, D, C, Q, E, G, H, I, L, K, M, F, P, S, T, W, Y, or V<br>In some cases, X10 = L or P<br>In some cases, X11 = L or W |
| 1301 | Variable Heavy 3 | X1VQLVQSGAEVKKPGASVKVSCKAS[HCDR1]WVX2QRPGQGLEWX4G[HCDR2]RX5TX6TX7DTSTSTX8YX9ELSSLRSEDTAVYYCAR[HCDR3]WGQGTTVTVSS<br>wherein each of X1, X2, X4, X5, X6, X7, X8, X9, X10, and X11 is independently selected from A, R, N, D, C, Q, E, G, H, I, L, K, M, F, P, S, T, W, Y, or V<br>In some cases, X1 = Q or E<br>In some cases, X2 = R or K<br>In some cases, X4 = M or I<br>In some cases, X5 = V or A<br>In some cases, X6 = M or I<br>In some cases, X7 = R or T<br>In some cases, X8 = V or A<br>In some cases, X9 = M or L |
| 1302 | Variable Heavy 4 | X1VQLVQSGAEVKKPGASVKVSCKAS[HCDR1]WVX2QRPGQGLEWX4G[HCDR21RX5TX6TX7DTSTSTX8YX9ELSSLRSEDTAVYYC[HCDR3]WGQGTTVTVSS<br>wherein each of X1, X2, X4, X5, X6, X7, X8, X9, X10, and X11 is independently selected from A, R, N, D, C, Q, E, G, H, I, L, K, M, F, P, S, T, W, Y, or V<br>In some cases, X1 = Q or E<br>In some cases, X2 = R or K<br>In some cases, X4 = M or I<br>In some cases, X5 = V or A<br>In some cases, X6 = M or I<br>In some cases, X7 = R or T<br>In some cases, X8 = V or A<br>In some cases, X9 = M or L |
| 304 219 HCFR1, 212 HCFR1 | | QVQLVQSGAEVKKPGASVKVSCKAS |
| 305 219 HCFR2 | | WVKQRPGQGLEWMG |
| 306 219 HCFR3a | | RVTITRDTSTSTVYLELSSLRSEDTAVYYCAR |

TABLE 9A-continued

Additional Sequences

| SEQ ID NO | Description | Sequence |
|---|---|---|
| 307 | 219 HCFR3b | RVTITRDTSTSTVYLELSSLRSEDTAVYYC |
| 308 | 219 HCFR4, 212 HCFR4 | WGQGTTVTVSS |
| 309 | 219 LCFR1, 212 LCFR1 | EIVLTQSPGTLSLSPGERATLSC |
| 310 | 219 LCFR2, 212 LCFR2 | WYQQKPGQAPRPLIY |
| 311 | 219 LCFR3, 212 LCFR3 | GIPDRFSGSGSGTDFTLTISRLEPEDFAVYYC |
| 312 | 219 LCFR4, 212 LCFR4 | FGGGTKLEIK |
| 313 | 212 HCFR2 | WVRQRPGQGLEWIG |
| 314 | 212 HCFR3a | RATITTDTSTSTAYLELSSLRSEDTAVYYCAR |
| 315 | 212 HCFR3b | RATITTDTSTSTAYLELSSLRSEDTAVYYC |
| 316 | IGHV1-46*02 | QVQLVQSGAEVKKPGASVKVSCKASGYTFNSYYMHWVRQAPGQGLEWMGIINPSGGSTSYAQKFQGRVTMTRDTSTSTVYMELSSLRSEDTAVYYCAR |
| 317 | IGKV3-20*01 | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSP |
| 319 | Light Chain Constant | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 9B

Fc and Constant Regions

SEQ ID NO: 320 IgG1 Constant
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGNV
FSCSVMHEALHNHYTQKSLSLSPGK SEQ ID NO: 321 IgG1 Constant
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK SEQ ID NO: 322 IgG1 Constant
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK SEQ ID NO: 323 Fc1 (L235E)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELEGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGNV
FSCSVMHEALHNHYTQKSLSLSPGK TABLE 9B-continued Fc and Constant Regions SEQ ID NO: 324 Fc2 (L235E)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPELEGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK SEQ ID NO: 325 Fc3 (L235E)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELEGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK SEQ ID NO: 326 Fc4 (L234A, L235A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPEAAGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGNV
FSCSVMHEALHNHYTQKSLSLSPGK SEQ ID NO: 327 Fc5 (L234A, L235A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPEAAGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK SEQ ID NO: 328 Fc6 (L234A, L235A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPEAAGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK SEQ ID NO: 329 Fc7 (L234A, L235A, G237A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPEAAGAPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGNV
FSCSVMHEALHNHYTQKSLSLSPG SEQ ID NO: 330 Fc8 (L234A, L235A, G237A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPEAAGAPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPG SEQ ID NO: 331 Fc9 (L234A, L235A, G237A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPEAAGAPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPG SEQ ID NO: 332 Fc10 (L234A, L235A, P329G)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPEAAGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALGAPIEKTISKAKGQPREPQVYTLPPSRDELTKN
QVSLTCLVKGFYPSDIAVEWESNGQPENNYKTTPPVLDSDGSFFLYSKLTVDKSRWQQGNV
FSCSVMHEALHNHYTQKSLSLSPGK SEQ ID NO: 333 Fc11 (L234A, L235A, P329G)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPEAAGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALGAPIEKTISKAKGQPREPQVYTLPPSREEMTKN TABLE 9B-continued Fc and Constant Regions QVSLTCLVKGFYPSDIAVEWESNGQPENNYKTTPPVLDSDGSFFLYSKLTVDKSRWQQGNV
FSCSVMHEALHNHYTQKSLSLSPGK SEQ ID NO: 334 Fc12 (L234A, L235A, P329G)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPEAAGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALGAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK SEQ ID NO: 335 Fc13 (L234F, L235E, P33 1S)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPEFEGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPASIEKTISKAKGQPREPQVYTLPPSRDELTKN
QVSLTCLVKGFYPSDIAVEWESNGQPENNYKTTPPVLDSDGSFFLYSKLTVDKSRWQQGNV
FSCSVMHEALHNHYTQKSLSLSPGK SEQ ID NO: 336 Fc14 (L234F, L235E, P331S)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPEFEGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPASIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK SEQ ID NO: 337 Fc15 (L234F, L235E, P33 1S)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPEFEGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPASIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK SEQ ID NO: 338 Fc16 (L234A, L235E, G237A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPEAEGAPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGNV
FSCSVMHEALHNHYTQKSLSLSPG SEQ ID NO: 339 Fc17 (L234A, L235E, G237A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPEAEGAPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPG SEQ ID NO: 340 Fc18 (L234A, L235E, G237A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPEAEGAPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPG SEQ ID NO: 341 Fc19 (L234A, L235E, G237A, P331S)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPEAEGAPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPASIEKTISKAKGQPREPQVYTLPPSRDELTKN
QVSLTCLVKGFYPSDIAVEWESNGQPENNYKTTPPVLDSDGSFFLYSKLTVDKSRWQQGNV
FSCSVMHEALHNHYTQKSLSLSPG SEQ ID NO: 342 Fc20 (L234A, L235E, G237A, P331S)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPEAEGAPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPASIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPG SEQ ID NO: 343 Fc21 (L234A, L235E, G237A, P331S)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPEAEGAPS TABLE 9B-continued Fc and Constant Regions

```
VFLFPPKPKDTLMISRTPEVTCVVVDVSHEDPEVKFNWYVDGVEVHNAKTKPREEQYNSTY
RVVSVLTVLHQDWLNGKEYKCKVSNKALPASIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPG

SEQ ID NO: 344 Fc22 (L234A, L235A, P329A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPEAAGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALAAPIEKTISKAKGQPREPQVYTLPPSRDELTKN
QVSLTCLVKGFYPSDIAVEWESNGQPENNYKTTPPVLDSDGSFFLYSKLTVDKSRWQQGNV
FSCSVMHEALHNHYTQKSLSLSPGK

SEQ ID NO: 345 Fc23 (L234A, L235A, P329A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPEAAGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALAAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK

SEQ ID NO: 346 Fc24 (L234A, L235A, P329A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPEAAGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALAAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK

SEQ ID NO: 347 Fc25 (D265A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVAVSHEDPEVKFNWYVDGVEVHNAKTKPREEQYNSTY
RVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGNV
FSCSVMHEALHNHYTQKSLSLSPGK

SEQ ID NO: 348 Fc26 (D265A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPELLGGPS
VFLFPPKPKDTLMISRTPEVTCVVVAVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK

SEQ ID NO: 349 Fc27 (D265A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVAVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK

SEQ ID NO: 350 Fc28 (N297G)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYGSTY
RVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGNV
FSCSVMHEALHNHYTQKSLSLSPGK

SEQ ID NO: 351 Fc29 (N297G)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYGSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK

SEQ ID NO: 352 Fc30 (N297G)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYGSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK
```

TABLE 9B-continued

Fc and Constant Regions

SEQ ID NO: 353 Fc31 (D265A, N297A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVAVSHEDPEVKFNWYVDGVEVHNAKTKPREEQYASTY
RVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGNV
FSCSVMHEALHNHYTQKSLSLSPGK

SEQ ID NO: 354 Fc32 (D265A, N297A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPELLGGPS
VFLFPPKPKDTLMISRTPEVTCVVVAVSHEDPEVKFNWYVDGVEVHNAKTKPREEQYASTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK

SEQ ID NO: 355 Fc33 (D265A, N297A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVAVSHEDPEVKFNWYVDGVEVHNAKTKPREEQYASTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK

SEQ ID NO: 356 Fc34 (D265A, N297G)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVAVSHEDPEVKFNWYVDGVEVHNAKTKPREEQYGSTY
RVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGNV
FSCSVMHEALHNHYTQKSLSLSPGK

SEQ ID NO: 357 Fc35 (D265A, N297G)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPELLGGPS
VFLFPPKPKDTLMISRTPEVTCVVVAVSHEDPEVKFNWYVDGVEVHNAKTKPREEQYGSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK

SEQ ID NO: 358 Fc36 (D265A, N297G)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVAVSHEDPEVKFNWYVDGVEVHNAKTKPREEQYGSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK

SEQ ID NO: 359 Fc37 (L235A, G237A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELAGAPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGNV
FSCSVMHEALHNHYTQKSLSLSPGK

SEQ ID NO: 360 Fc38 (L235A, G237A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPELAGAPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK

SEQ ID NO: 361 Fc39 (L235A, G237A)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELAGAPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNV
FSCSVMHEALHNHYTQKSLSLSPGK

TABLE 9B-continued

Fc and Constant Regions

SEQ ID NO: 362 Fc40 (IgG4)
ASTKGPSVFPLAPCSRSTSESTAALGCLVKDYFPEPVTVSWNSGALTSGVHTFPAVLQSSG
LYSLSSVVTVPSSSLGTKTYTCNVDHKPSNTKVDKRVESKYGPPCPSCPAPEFLGGPSVFL
FPPKPKDTLMISRTPEVTCVVVDVSQEDPEVQFNWYVDGVEVHNAKTKPREEQFNSTYRVV
SVLTVLHQDWLNGKEYKCKVSNKGLPSSIEKTISKAKGQPREPQVYTLPPSQEEMTKNQVS
LTCLVKGFYPSDIAVEWESNGQPENNYKTTPPVLDSDGSFFLYSRLTVDKSRWQEGNVFSC
SVMHEALHNHYTQKSLSLSLGK

SEQ ID NO: 401 (L234A, L235A)
ASTKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPEAAGGPSVFLFPPKPKD
TLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEALHNHYTQKSLSLSPGK

SEQ ID NO: 402 (L235E)
ASTKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELEGGPSVFLFPPKPKD
TLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEALHNHYTQKSLSLSPGK

SEQ ID NO: 403 (L234A, L235A, G237A)
ASTKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPEAAGAPSVFLFPPKPKD
TLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEALHNHYTQKSLSLSPGK

SEQ ID NO: 404 (L234A, L235E, G237A)
ASTKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPEAEGAPSVFLFPPKPKD
TLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEALHNHYTQKSLSLSPGK

SEQ ID NO: 405 (L234A, L235A, P329A)
ASTKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPEAAGGPSVFLFPPKPKD
TLMISRTPEVTCVVVDVSHEDPEVKFNWYVDGVEVHNAKTKPREEQYNSTYRVVSVLTVLHQDWLN
GKEYKCKVSNKALAAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEALHNHYTQKSLSLSPGK

SEQ ID NO: 406 (L234A, L235A, P329G)
ASTKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPEAAGGPSVFLFPPKPKD
TLMISRTPEVTCVVVDVSHEDPEVKFNWYVDGVEVHNAKTKPREEQYNSTYRVVSVLTVLHQDWLN
GKEYKCKVSNKALAAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEALHNHYTQKSLSLSPGK

SEQ ID NO: 407 (P329A)
ASTKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPEAAGGPSVFLFPPKPKD
TLMISRTPEVTCVVVDVSHEDPEVKFNWYVDGVEVHNAKTKPREEQYNSTYRVVSVLTVLHQDWLN
GKEYKCKVSNKALAAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEALHNHYTQKSLSLSPGK

SEQ ID NO: 408 (L234E, L235F, P331S)
ASTKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPEEFGGPSVFLFPPKPKD
TLMISRTPEVTCVVVDVSHEDPEVKFNWYVDGVEVHNAKTKPREEQYNSTYRVVSVLTVLHQDWLN
GKEYKCKVSNKALPASIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEALHNHYTQKSLSLSPGK

SEQ ID NO: 409 (D265A, N297G)
ASTKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKPKD
TLMISRTPEVTCVVVAVSHEDPEVKFNWYVDGVEVHNAKTKPREEQYGSTYRVVSVLTVLHQDWLN
GKEYKCKVSNKALPAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEALHNHYTQKSLSLSPGK

SEQ ID NO: 410 (N297G)
ASTKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKPKD
TLMISRTPEVTCVVVDVSHEDPEVKFNWYVDGVEVHNAKTKPREEQYGSTYRVVSVLTVLHQDWLN
GKEYKCKVSNKALPAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEALHNHYTQKSLSLSPGK

TABLE 9B-continued

Fc and Constant Regions

SEQ ID NO: 411 (S228P)
ASTKGPSVFPLAPCSRSTSESTAALGCLVKDYFPEPVTVSWNSGALTSGVHTFPAVLQSSGLYSLS
SVVTVPSSSLGTKTYTCNVDHKPSNTKVDKRVESKYGPPCPPCPAPEFLGGPSVFLFPPKPKDTLM
ISRTPEVTCVVVDVSQEDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHNHYTQKSLSLSLGK

SEQ ID NO: 412 (S228P, L235E)
ASTKGPSVFPLAPCSRSTSESTAALGCLVKDYFPEPVTVSWNSGALTSGVHTFPAVLQSSGLYSLS
SVVTVPSSSLGTKTYTCNVDHKPSNTKVDKRVESKYGPPCPPCPAPEFEGGPSVFLFPPKPKDTLM
ISRTPEVTCVVVDVSQEDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHNHYTQKSLSLSLGK

SEQ ID NO: 413 (S228P, F234A, L235A)
ASTKGPSVFPLAPCSRSTSESTAALGCLVKDYFPEPVTVSWNSGALTSGVHTFPAVLQSSGLYSLS
SVVTVPSSSLGTKTYTCNVDHKPSNTKVDKRVESKYGPPCPPCPAPEAAGGPSVFLFPPKPKDTLM
ISRTPEVTCVVVDVSQEDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHNHYTQKSLSLSLGK

SEQ ID NO: 501 (L234A, L235A)
QVQLVQSGAEVKKPGASVKVSCKASGFDIQDTYMHWVKQRPGQGLEWMGRIDPASGHTKYDPKFQV
RVTITRDTSTSTVYLELSSLRSEDTAVYYCARSGGLPDVWGQGTTVTVSSASTKGPSVFPLAPSSK
STSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK

SEQ ID NO: 502 (L235E)
QVQLVQSGAEVKKPGASVKVSCKASGFDIQDTYMHWVKQRPGQGLEWMGRIDPASGHTKYDPKFQV
RVTITRDTSTSTVYLELSSLRSEDTAVYYCARSGGLPDVWGQGTTVTVSSASTKGPSVFPLAPSSK
STSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELEGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK

SEQ ID NO: 503 (L234A, L235A, G237A)
QVQLVQSGAEVKKPGASVKVSCKASGFDIQDTYMHWVKQRPGQGLEWMGRIDPASGHTKYDPKFQV
RVTITRDTSTSTVYLELSSLRSEDTAVYYCARSGGLPDVWGQGTTVTVSSASTKGPSVFPLAPSSK
STSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGAPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK

SEQ ID NO: 504 (L234A, L235E, G237A)
QVQLVQSGAEVKKPGASVKVSCKASGFDIQDTYMHWVKQRPGQGLEWMGRIDPASGHTKYDPKFQV
RVTITRDTSTSTVYLELSSLRSEDTAVYYCARSGGLPDVWGQGTTVTVSSASTKGPSVFPLAPSSK
STSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAEGAPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK

SEQ ID NO: 505 (L234A, L235A, P329A)
QVQLVQSGAEVKKPGASVKVSCKASGFDIQDTYMHWVKQRPGQGLEWMGRIDPASGHTKYDPKFQV
RVTITRDTSTSTVYLELSSLRSEDTAVYYCARSGGLPDVWGQGTTVTVSSASTKGPSVFPLAPSSK
STSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALAAP
IEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK

SEQ ID NO: 506 (L234A, L235A, P329G)
QVQLVQSGAEVKKPGASVKVSCKASGFDIQDTYMHWVKQRPGQGLEWMGRIDPASGHTKYDPKFQV
RVTITRDTSTSTVYLELSSLRSEDTAVYYCARSGGLPDVWGQGTTVTVSSASTKGPSVFPLAPSSK
STSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALAAP
IEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK

SEQ ID NO: 507 (P329A)
QVQLVQSGAEVKKPGASVKVSCKASGFDIQDTYMHWVKQRPGQGLEWMGRIDPASGHTKYDPKFQV
RVTITRDTSTSTVYLELSSLRSEDTAVYYCARSGGLPDVWGQGTTVTVSSASTKGPSVFPLAPSSK

TABLE 9B-continued

Fc and Constant Regions

STSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALAAP
IEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK

SEQ ID NO: 508 (L234E, L235F, P331S)
QVQLVQSGAEVKKPGASVKVSCKASGFDIQDTYMHWVKQRPGQGLEWMGRIDPASGHTKYDPKFQV
RVTITRDTSTSTVYLELSSLRSEDTAVYYCARSGGLPDVWGQGTTVTVSSASTKGPSVFPLAPSSK
STSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEEFGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAS
IEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK

SEQ ID NO: 509 (D265A, N297G)
QVQLVQSGAEVKKPGASVKVSCKASGFDIQDTYMHWVKQRPGQGLEWMGRIDPASGHTKYDPKFQV
RVTITRDTSTSTVYLELSSLRSEDTAVYYCARSGGLPDVWGQGTTVTVSSASTKGPSVFPLAPSSK
STSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVA
VSHEDPEVKFNWYVDGVEVHNAKTKPREEQYGSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK

SEQ ID NO: 510 (N297G)
QVQLVQSGAEVKKPGASVKVSCKASGFDIQDTYMHWVKQRPGQGLEWMGRIDPASGHTKYDPKFQV
RVTITRDTSTSTVYLELSSLRSEDTAVYYCARSGGLPDVWGQGTTVTVSSASTKGPSVFPLAPSSK
STSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYGSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK

SEQ ID NO: 511 (S228P)
QVQLVQSGAEVKKPGASVKVSCKASGFDIQDTYMHWVKQRPGQGLEWMGRIDPASGHTKYDPKFQV
RVTITRDTSTSTVYLELSSLRSEDTAVYYCARSGGLPDVWGQGTTVTVSSASTKGPSVFPLAPCSR
STSESTAALGCLVKDYFPEPVTVSWNSGALTSGVHTFPAVLQSSGLYSLSSVVTVPSSSLGTKTYT
CNVDHKPSNTKVDKRVESKYGPPCPPCPAPEFLGGPSVFLFPPKPKDTLMISRTPEVTCVVVDVSQ
EDPEVQFNWYVDGVEVHNAKTKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWESNGQPENNYKTTPPVLDS
DGSFFLYSRLTVDKSRWQEGNVFSCSVMHEALHNHYTQKSLSLSLGK

SEQ ID NO: 512 (S228P, L235E)
QVQLVQSGAEVKKPGASVKVSCKASGFDIQDTYMHWVKQRPGQGLEWMGRIDPASGHTKYDPKFQV
RVTITRDTSTSTVYLELSSLRSEDTAVYYCARSGGLPDVWGQGTTVTVSSASTKGPSVFPLAPCSR
STSESTAALGCLVKDYFPEPVTVSWNSGALTSGVHTFPAVLQSSGLYSLSSVVTVPSSSLGTKTYT
CNVDHKPSNTKVDKRVESKYGPPCPPCPAPEFEGGPSVFLFPPKPKDTLMISRTPEVTCVVVDVSQ
EDPEVQFNWYVDGVEVHNAKTKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWESNGQPENNYKTTPPVLDS
DGSFFLYSRLTVDKSRWQEGNVFSCSVMHEALHNHYTQKSLSLSLGK

SEQ ID NO: 513 (S228P, F234A, L235A)
QVQLVQSGAEVKKPGASVKVSCKASGFDIQDTYMHWVKQRPGQGLEWMGRIDPASGHTKYDPKFQV
RVTITRDTSTSTVYLELSSLRSEDTAVYYCARSGGLPDVWGQGTTVTVSSASTKGPSVFPLAPCSR
STSESTAALGCLVKDYFPEPVTVSWNSGALTSGVHTFPAVLQSSGLYSLSSVVTVPSSSLGTKTYT
CNVDHKPSNTKVDKRVESKYGPPCPPCPAPEAAGGPSVFLFPPKPKDTLMISRTPEVTCVVVDVSQ
EDPEVQFNWYVDGVEVHNAKTKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWESNGQPENNYKTTPPVLDS
DGSFFLYSRLTVDKSRWQEGNVFSCSVMHEALHNHYTQKSLSLSLGK

SEQ ID NO: 514
EIVLTQSPGTLSLSPGERATLSCRASSSVSYMYWYQQKPGQAPRPLIYATSNLASGIPDRFSGSGS
GTDFTLTISRLEPEDFAVYYCQQWEGNPRTFGGGTKLEIKRTVAAPSVFIFPPSDEQLKSGTASVV
CLLNNFYPREAKVQWKVDNALQSGNSQESVTEQDSKDSTYSLSSTLTLSKADYEKHKVYACEVTHQ
GLSSPVTKSFNRGEC

TABLE 10

Select Antibodies

| Antibody | Heavy Chain CDR SEQ ID NOS (CDR1, CDR2, CDR3) | Light Chain CDR SEQ ID NOS (CDR1, CDR2, CDR3) |
|---|---|---|
| A | 1, 2, 6 | 10, 11, 12 |
| B | 1, 3, 8 | 10, 11, 12 |
| C | 1, 4, 8 | 10, 11, 12 |
| D | 1, 2, 6 | 10, 11, 13 |
| E | 1, 2, 6 | 10, 11, 14 |
| F | 1, 5, 8 | 10, 11, 12 |
| G | 1, 5, 8 | 10, 11, 13 |
| H | 1, 3, 8 | 10, 11, 13 |
| A2 | 1, 2, 7 | 10, 11, 12 |
| B2 | 1, 3, 9 | 10, 11, 12 |
| C2 | 1, 4, 9 | 10, 11, 12 |
| D2 | 1, 2, 7 | 10, 11, 13 |
| E2 | 1, 2, 7 | 10, 11, 14 |
| F2 | 1, 5, 9 | 10, 11, 12 |
| G2 | 1, 5, 9 | 10, 11, 13 |
| H2 | 1, 3, 9 | 10, 11, 13 |
| I | 1, 5, 8 | 10, 11, 15 |
| I2 | 1, 5, 9 | 10, 11, 15 |

TABLE 11

Select Antibodies - Variable Regions

| Antibody | Heavy Chain Variable Region SEQ ID NO | Light Chain Variable Region SEQ ID NOS |
|---|---|---|
| 15 | 108 | 203 |
| 30 | 108 | 204 |
| 64 | 121 | 202 |
| 67 | 122 | 202 |
| 68 | 123 | 202 |
| 75 | 131 | 205 |
| 94 | 124 | 202 |
| 96 | 128 | 205 |
| 100 | 107 | 204 |
| 103 | 120 | 204 |
| 107 | 108 | 202 |
| 109 | 133 | 205 |
| 110 | 125 | 205 |
| 112 | 117 | 205 |
| 113 | 124 | 205 |
| 115 | 122 | 205 |
| 122 | 113 | 204 |
| 125 | 105 | 204 |
| 126 | 114 | 204 |
| 127 | 118 | 204 |
| 129 | 110 | 204 |
| 132 | 128 | 206 |
| 134 | 122 | 206 |
| 138 | 122 | 204 |
| 147 | 117 | 201 |
| 148 | 121 | 201 |
| 149 | 122 | 201 |
| 151 | 124 | 201 |
| 157 | 104 | 204 |
| 158 | 101 | 204 |
| 159 | 119 | 204 |
| 160 | 102 | 204 |
| 169 | 126 | 205 |
| 170 | 135 | 205 |
| 172 | 130 | 205 |
| 173 | 127 | 205 |
| 174 | 132 | 205 |
| 175 | 126 | 201 |
| 178 | 130 | 201 |
| 179 | 127 | 201 |
| 180 | 132 | 201 |
| 181 | 107 | 202 |
| 188 | 115 | 202 |
| 196 | 129 | 205 |
| 197 | 116 | 205 |
| 198 | 134 | 205 |
| 199 | 109 | 201 |
| 200 | 103 | 201 |
| 203 | 116 | 201 |
| 205 | 109 | 202 |
| 211 | 108 | 201 |
| 212 | 107 | 201 |
| 213 | 106 | 201 |
| 214 | 111 | 201 |
| 216 | 112 | 201 |
| 217 | 101 | 201 |
| 218 | 119 | 201 |
| 219 | 104 | 201 |
| 220 | 102 | 201 |
| 221 | 105 | 201 |
| 222 | 114 | 201 |
| 223 | 103 | 202 |
| 500 | 301 | 303 |
| 501 | 302 | 303 |

Example 7: Design of Humanized Anti-TL1A Antibodies with Reduced Cell-Mediated Cytotoxicity As provided and described herein, Fc variants (e.g. SEQ ID NOs: 401-413) were designed to diminish effector function and subsequently tested for the ability to (i) effectively be purified/manufactured (Table 12), (ii) reduce antibody-dependent cell-mediated cytotoxicity (ADCC), and (iii) reduce complement-dependent cytotoxicity. Test articles tested comprise heavy chain SEQ ID NOs: 501-513, comprising Fc regions that comprises SEQ ID NOs: 401-413, respectively. Heavy chains used were paired with a light chain comprising SEQ ID NO: 514. ELISA titration profiles and EC50s were generated against recombinant TL1A antigen ("EC50", Table 13). Interestingly, Fc mutations did affect purity, as measured by monomer content, for select mutations/Fc variants (Table 12, wild-type IgG1 control).

Reduction of CDC Activity

Test articles were evaluated for CDC activity, compared to negative control Human IgG4 isotype control, on TL1A-expressing HEK293 target cells. Rituxan (anti-CD20) was used as a positive technical control on CD20-expressing Raji cell. All test articles were used at a final top concentration of 10 µg/mL followed by a five-fold dilution series (7 points total), in addition to a no treatment control, in triplicate. Cells were incubated with test articles for 15 minutes at 37 C, then treated with human complement, at a final concentration of 25%, for 3 hours at 37 C, 5% CO2. Following incubation, cells were washed and resuspended in Propidium Iodide (P.I.) at a final concentration of 5 µg/mL prior to flow cytometry analysis. Total cells were examined by flow cytometry during sample acquisition. Data were plotted on an XY chart, graphing percentage P.I. positive cells against the log of the concentration and fit to a non-linear regression curve. Cell cytotoxicity in the presence of all test articles was not distinguishable from cell cytotoxicity in the presence of isotype control (Table 13). CDC bioactivity was observed on Raji target cells with Rituxan treatment.

Reduction of CDC Activity

An antibody-dependent cell-mediated cytotoxicity (ADCC) reporter assay was performed for the characterization of test articles and IgG4 Isotype control on HEK 293

TL1A cells. A reporter cell line engineered to express human Fc-gamma-RIIIa V158 (high affinity) served as effector cells.

Prometheus test articles were evaluated with a top concentration of 10 ug/mL (log dilution for 7 points total, in addition to no test article control). Treatment conditions were tested in triplicate, effector and target cells were co-cultured for 6 hours at 37 C with 5% CO2. Raji target cells were used as a positive control, with Rituxan treatment at a top concentration of 10 ug/mL, 7-point log dilution series, and no treatment control. Test article 502 treatment resulted in dose-dependent increase in luciferase reporter gene activity, and 5044 treatment resulted in increase of reporter activity at the highest tested concentration. The rest of the test articles did not induce reporter activity (Table 13).

TABLE 12

| Class | Fc SEQ ID NO | Heavy Chain SEQ ID NO | mg/mL | mg | SDS-PAGE | SEC-HPLC (Purity) |
|---|---|---|---|---|---|---|
| IgG1, protein variants | 401 | 501 | 2.65 | 10.60 | 95% | 90% |
|  | 402 | 502 | 1.15 | 12.65 | 95% | 92% |
|  | 403 | 503 | 3.22 | 10.62 | 90% | 89% |
|  | 404 | 504 | 1.61 | 11.27 | 95% | 92% |
|  | 405 | 505 | 3.43 | 10.29 | 95% | 91% |
|  | 406 | 506 | 1.51 | 15.10 | 95% | 93% |
|  | 407 | 507 | 2.85 | 11.40 | 95% | 92% |
|  | 408 | 508 | 1.55 | 10.85 | 95% | 92% |
| IgG1, glycan knock-out | 409 | 509 | 2.33 | 9.32 | 90% | 90% |
|  | 410 | 510 | 1.36 | 12.24 | 95% | 92% |
| IgG4 | 411 | 511 | 1.78 | 19.58 | 95% | 82% |
|  | 412 | 512 | 2.33 | 18.64 | 90% | 81% |
|  | 413 | 513 | 5.08 | 15.24 | 95% | 90% |
| Control | — | — | 3.70 | 5.55 | 95% | 97% |

TABLE 13

| Class | Fc SEQ ID NO | Heavy Chain SEQ ID NO | EC50 (nM) | ADCC | CDC |
|---|---|---|---|---|---|
| IgG1, protein variants | 401 | 501 | 0.222 | ND | ND |
|  | 402 | 502 | 0.215 | 100 ng/mL | ND |
|  | 403 | 503 | 0.188 | ND | ND |
|  | 404 | 504 | 0.220 | 10 µg/mL | ND |
|  | 405 | 505 | 0.346 | ND | ND |
|  | 406 | 506 | 0.347 | ND | ND |
|  | 407 | 507 | 0.329 | ND | ND |
|  | 408 | 508 | 0.330 | ND | ND |
| IgG1, glycan knock-out | 409 | 509 | 0.340 | ND | ND |
|  | 410 | 510 | 0.293 | ND | ND |
| IgG4 | 411 | 511 | 0.299 | ND | ND |
|  | 412 | 512 | 0.324 | ND | ND |
|  | 413 | 513 | 0.252 | ND | ND |

Example 8: Biophysical Properties of Anti-TL1A Antibodies at High Concentrations The data for A219 anti-TL1A antibody properties in solution were analyzed together using a chemometric method termed partial least squares (PLS). Detailed descriptions of PLS modeling have been published in, for example, Katz, M. H. *Multivariate Analysis: A Practice Guide for Clinicians*. Cambridge University Press, New York, pp. 158-162 (1999); Stahle, L., Wold, K., Multivariate data analysis and experimental design in biomedical research. *Prog. Med Chem.* 1988, 25: 291-338; Wold S. PLS-regression: a basic tool of chemometrics. *Chemom. Intell. Lab. Syst.* 2001, 58: 109-130; and Martens, H.; Martens, M. *Multivariate Analysis of Quality: An Introduction*, Wiley and Sons, Chichester, UK (2001).

FIGS. 3A-C demonstrate viscosity as a function of antibody concentration and pH. Antibody concentration ranged from greater than about 125 mg/mL to greater than about 170 mg/mL. pH ranged from less than 5.0 to about 7.5. Concentration dependence is evident, with very low viscosities (e.g. as indicated by a viscosity less than 5 mPa-s or 7 mPa-s). The viscosity was measured using an m-VROC™ viscometer by Rheosense with an A10 chip. The shear rates employed were about 1820 s−1. The viscometer was temperature controlled using a ThermoCube thermoelectric chiller and the samples were delivered using a Hamilton 100 µL syringe (81060). The accuracy of the instrument was verified using neat Isopropyl alcohol and measured at 25° C. Furthermore, across the concentration range tested, the percent increase in the HMW fraction as measured by size exclusion chromatography ranged from 0% to a 1.3% increase. HMW as used herein refers to high molecule weight antibody fraction, e.g., aggregated protein, and which excludes monomeric antibody.

The foregoing description of various embodiments known to the applicant at this time of filing the application has been presented and is intended for the purposes of illustration and description. The present description is not intended to be exhaustive nor limited to the precise form disclosed and many modifications and variations are possible in the light of the above teachings. The embodiments described serve to explain principles and practical applications, and to enable others skilled in the art to utilize the various embodiments, optionally with various modifications, as are suited to the particular use contemplated. Therefore, it is intended that the disclosure not be limited to the particular embodiments disclosed.

What is claimed is:

1. An antibody or antigen binding fragment thereof that binds to tumor necrosis factor-like ligand 1A (TL1A), comprising a heavy chain variable framework region comprising a human IGHV1-46*02 framework (SEQ ID NO: 316) or a modified human IGHV1-46*02 framework, and a light chain variable framework region comprising a human IGKV3-20 framework (SEQ ID NO: 317) or a modified human IGKV3-20 framework; wherein the heavy chain variable framework region and the light chain variable framework region collectively comprise one to eight amino acid modification(s) from the human IGHV1-46*02 framework and the human IGKV3-20 framework, wherein the amino acid modification(s) comprise: (a) a modification at amino acid position 45 in the heavy chain variable region; (b) a modification at amino acid position 47 in the heavy chain variable region; (c) a modification at amino acid position 55 in the heavy chain variable region; (d) a modification at amino acid position 78 in the heavy chain variable region; (e) a modification at amino acid position 80 in the heavy chain variable region; (f) a modification at amino acid position 82 in the heavy chain variable region; (g) a modification at amino acid position 89 in the heavy chain variable region; or (h) a modification at amino acid position 91 in the heavy chain variable region, per Aho numbering; (i) or a combination of two or more modifications selected from (a) to (h).

2. The antibody or antigen binding fragment of claim 1, comprising at least about 80% monomeric fraction as determined by size exclusion chromatography.

3. The antibody or antigen binding fragment of claim 1, wherein the amino acid modification(s) comprise (a) R45K in the heavy chain variable region, (b) A47R in the heavy chain variable region, (c) M55I in the heavy chain variable region, (d) V78A in the heavy chain variable region, (e) M80I in the heavy chain variable region, (f) R82T in the heavy chain variable region, (g) V89A in the heavy chain variable region, or (h) M91L in the heavy chain variable region, per Aho numbering; (i) or a combination of two or more modifications selected from (a) to (h).

4. The antibody or antigen binding fragment of claim 3, wherein the amino acid modification(s) comprise: the A47R.

5. The antibody or antigen binding fragment of claim 4, wherein the amino acid modification(s) comprise: the A47R, M55I, V78A, M80I, R82T, V89A, and M91L; the A47R, M80I, and R82T; the A47R, M80I, R82T, V89A, and M91L; or the A47R, M55I, V78A, M80I, V89A, and M91L.

6. The antibody or antigen binding fragment of claim 4, wherein the amino acid modification(s) comprise: the R45K and A47R.

7. The antibody or antigen binding fragment of claim 6, wherein the amino acid modification(s) comprise: the R45K, A47R, V89A, and M91L.

8. The antibody or antigen binding fragment of claim 6, wherein the amino acid modification(s) comprise: the R45K and A47R, and M80I.

9. The antibody or antigen binding fragment of claim 8, wherein the amino acid modification(s) comprise: the R45K, A47R, M80I, and M91L; the R45K, A47R, V78A, M80I, V89A, and M91L; the R45K, A47R, M55I, V78A, M80I, R82T, V89A, and M91L; the R45K, A47R, M80I, V89A, and M91L; the R45K, A47R, M55I, M80I, R82T, V89A, and M91L; the R45K, A47R, M80I, and V89A; the R45K, A47R, M80I, R82T, V89A, M91L; or the R45K, A47R, M55I, M80I, V89A, and M91L.

10. The antibody or antigen binding fragment of claim 8, wherein the amino acid modification(s) comprise: the R45K, A47R, M80I, and M91L.

11. The antibody or antigen binding fragment of claim 3, wherein the amino acid modification(s) comprise: the R45K.

12. The antibody or antigen binding fragment of claim 11, wherein the amino acid modification(s) comprise: the R45K and V78A.

13. The antibody or antigen binding fragment of claim 3, wherein the amino acid modification(s) comprise: the V78A.

14. The antibody or antigen binding fragment of claim 13, wherein the amino acid modification(s) comprise: the V78A and V89A; the V78A and M80I; or the V78A, M80I, and R82T.

15. The antibody or antigen binding fragment of claim 3, wherein the amino acid modification(s) comprise: the V89A.

16. The antibody or antigen binding fragment of claim 3, wherein the amino acid modification(s) comprise: the M80I.

17. An antibody or antigen binding fragment thereof that binds to tumor necrosis factor-like ligand 1A (TL1A), comprising a heavy chain variable framework region comprising a human IGHV1-46*02 framework (SEQ ID NO: 316) or a modified human IGHV1-46*02 framework, and a light chain variable framework region comprising a human IGKV3-20 framework (SEQ ID NO: 317) or a modified human IGKV3-20 framework; wherein the heavy chain variable framework region and the light chain variable framework region collectively comprise one to eight amino acid modification(s) from the human IGHV1-46*02 framework and the human IGKV3-20 framework, wherein the amino acid modification(s) comprises: (a) a modification at amino acid position 54 in the light chain variable region; and/or (b) a modification at amino acid position 55 in the light chain variable region, per Aho numbering.

18. The antibody or antigen binding fragment of claim 17, wherein the amino acid modification comprises L54P in the light chain variable region, per Aho numbering.

19. The antibody or antigen binding fragment of claim 17, wherein the amino acid modification comprises L55W in the light chain variable region, per Aho numbering.

20. The antibody or antigen binding fragment of claim 17, comprising at least about 80% monomeric fraction as determined by size exclusion chromatography.

* * * * *